(12) United States Patent
Glueck et al.

(10) Patent No.: US 9,308,250 B2
(45) Date of Patent: *Apr. 12, 2016

(54) COMBINED MEASLES-MALARIA VACCINE

(71) Applicant: CADILA HEALTHCARE LIMITED, Ahmedabad, Gujarat (IN)

(72) Inventors: Reinhard Glueck, Gujarat (IN); Agata Fazio, Catania (IT); Viviana Gianino, Catania (IT); Martin A. Billeter, Zurich (CH)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/486,578

(22) Filed: Sep. 15, 2014

(65) Prior Publication Data

US 2015/0071876 A1 Mar. 12, 2015

Related U.S. Application Data

(62) Division of application No. 13/318,701, filed as application No. PCT/IN2010/000287 on May 3, 2010.

(30) Foreign Application Priority Data

May 5, 2009 (IN) .......................... 1181/MUM/2009

(51) Int. Cl.
| | |
|---|---|
| C12N 15/00 | (2006.01) |
| A61K 39/165 | (2006.01) |
| A61K 38/20 | (2006.01) |
| A61K 39/00 | (2006.01) |
| A61K 39/015 | (2006.01) |
| A61K 39/12 | (2006.01) |
| C12N 7/00 | (2006.01) |
| A61K 35/13 | (2015.01) |

(52) U.S. Cl.
CPC ........... *A61K 39/165* (2013.01); *A61K 38/2013* (2013.01); *A61K 39/0015* (2013.01); *A61K 39/015* (2013.01); *A61K 39/12* (2013.01); *C12N 7/00* (2013.01); *A61K 35/13* (2013.01); *A61K 2039/5256* (2013.01); *A61K 2039/53* (2013.01); *A61K 2039/54* (2013.01); *A61K 2039/55566* (2013.01); *A61K 2039/55588* (2013.01); *A61K 2039/575* (2013.01); *A61K 2039/70* (2013.01); *C12N 2760/18421* (2013.01); *C12N 2760/18434* (2013.01); *C12N 2760/18442* (2013.01); *C12N 2760/18443* (2013.01)

(58) Field of Classification Search
CPC .................................................. A61K 39/165
See application file for complete search history.

(56) References Cited

U.S. PATENT DOCUMENTS

| | | | |
|---|---|---|---|
| 5,112,749 A | 5/1992 | Brey, III et al. | |
| 5,756,101 A | 5/1998 | Paoletti et al. | |
| 6,214,353 B1 | 4/2001 | Paoletti et al. | |
| 2005/0208078 A1* | 9/2005 | Hoffman et al. | 424/272.1 |
| 2005/0265974 A1* | 12/2005 | Pau et al. | 424/93.2 |
| 2005/0266017 A1* | 12/2005 | Druilhe et al. | 424/191.1 |
| 2006/0127413 A1 | 6/2006 | Sutter et al. | |
| 2007/0071726 A1 | 3/2007 | Pau et al. | |
| 2007/0088156 A1 | 4/2007 | Pau et al. | |

FOREIGN PATENT DOCUMENTS

| | | |
|---|---|---|
| AU | 701825 B2 | 1/1995 |
| AU | 709479 B2 | 6/1997 |
| CA | 2 507 915 A1 | 7/2004 |
| WO | 94/28930 A1 | 12/1994 |
| WO | 97/06270 A1 | 2/1997 |

OTHER PUBLICATIONS

Li et al (Vaccine vol. 25, pp. 2567-2574, 2007).*
Fowkes et al (PLOS Medicine vol. 7, Issue 1, pp. 1-19, Jan. 2010).*

* cited by examiner

*Primary Examiner* — Albert Navarro
(74) *Attorney, Agent, or Firm* — Ladas & Parry LLP

(57) ABSTRACT

A combined measles-malaria vaccine containing different attenuated recombinant measles-malaria vectors comprising a heterologous nucleic acid encoding several *Plasmodium falciparum* antigens is described. Preferably, it relates to viral vectors that comprise nucleic acids encoding the circumsporozoite (CS) protein of *P. falciparum*, the merozoite surface protein 1 (MSP-1) of *P. falciparum*, and its derivatives (p-42; p-83-30-38) in its glycosylated and secreted forms, and apical membrane antigen1 (AMA1) of *P. falciparum*, in its anchored or secreted form. The viral vector stems from an attenuated measles virus, based on a strain that is used as a vaccine and is efficient in delivering the gene of interest and that binds to and infects the relevant immune cells efficiently.

19 Claims, 58 Drawing Sheets

MSP-1 3D7 gene p(+)MV₃-EZ-d-83-30-38/ d-83-30-38*-3D7

CS gene

```
        MluI      SgrAI    HindIII                                                              XbaI
BssHII
    acgcgtATCTTcaccggtgTGGaagcttGCCACCATGATGAGGAAACTGGCC.................................. GTGAACTCCTGA............ tctagagcgcgc
                                        M   R   K   L   A                          V   N   S   *
```

Figure 15 p(+)MV₃-EZ-CS p(+)MV₃-EZ-DiCo1 complete

```
       |   10     |   20     |   30     |   40     |   50     |   60     |   70     |
  80   |   90     |  100
   1 CACCTAAATT GTAAGCGTTA ATATTTTGTT AAAATTCGCG TTAAATTTTT GTTAAATCAG CTCATTTTTT
AACCAATAGG CCGAAATCGG CAAAATCCCT 100
 101 TATAAATCAA AAGAATAGAC CGAGATAGGG TTGAGTGTTG TTCCAGTTTG GAACAAGAGT CCACTATTAA
AGAACGTGGA CTCCAACGTC AAAGGGCGAA 200
 201 AAACCGTCTA TCAGGGCGAT GGCCCACTAC GTGAACCATC ACCCTAATCA AGTTTTTTGG GGTCGAGGTG
CCGTAAAGCA CTAAATCGGA ACCCTAAAGG 300
 301 GAGCCCCCGA TTTAGAGCTT GACGGGGAAA GCCggccatt taggccaTAG GGCGCTGGCA AGTGTAGCGG
TCACGCTGCG CGTAACCACC ACACCCGCCG 400
 401 CGCTTAATGC GCCGCTACAG GGCGCGTCCC ATTCGCCATT CAGGCTGCGC AACTGTTGGG AAGGGCGATC
GGTGCGGGCC TCTTCGCTAT TACGCCAGCT 500
 501 GGCGAAAGGG GGATGTGCTG CAAGGCGATT AAGTTGGGTA ACGCCAGGGT TTTCCCAGTC ACGACGTTGT
AAAACGACGG CCAGTGAATT Gtaatacgac 600
 601 tcactataAC CAAACAAAGT TGGGTAAGGA TAGTTCAATC AATGATCATC TTCTAGTGCA CTTAGGATTC
AAGATCCTAT TATCAGGGAC AAGAGCAGGA 700
 701 TTAGGGATAT CTGAGATGGC CACACTTTTA AGGAGCTTAG CATTGTTCAA AAGAAACAAG GACAAACCAC
CCATTACATC AGGATCCGGT GGAGCCATCA 800
 801 GAGGAATCAA ACACATTATT ATAGTACCAA TCCCTGGAGA TTCCTCAATT ACCACTCGAT CCAGACTTCT
GGACCGGTTG GTCAGGTTAA TTGGAAACCC 900
 901 GGATGTGAGC GGGCCCAAAC TAACAGGGGC ACTAATAGGT ATATTATCCT TATTTGTGGA GTCTCCAGGT
CAATTGATTC AGAGGATCAC CGATGACCCT 1000
1001 GACGTTAGCA TAAGGCTGTT AGAGGTTGTC CAGAGTGACC AGTCACAATC TGGCCTTACC TTCGCATCAA
GAGGTACCAA CATGGAGGAT GAGGCGGACC 1100
1101 AATACTTTTC ACATGATGAT CCAATTAGTA GTGATCAATC CAGGTTCGGA TGGTTCGAGA ACAAGGAAAT
CTCAGATATT GAAGTGCAAG ACCCTGAGGG 1200
1201 ATTCAACATG ATTCTGGGTA CCATCCTAGC CCAAATTTGG GTCTTGCTCG CAAAGGCGGT TACGGCCCCA
GACACGGCAG CTGATTCGGA GCTAAGAAGG 1300
1301 TGGATAAAGT ACACCCAACA AAGAAGGGTA GTTGGTGAAT TTAGATTGGA GAGAAAATGG TTGGATGTGG
TGAGGAACAG GATTGCCCAG GACCTCTCCT 1400
1401 TACGCCGATT CATGGTCGCT CTAATCCTGG ATATCAAGAG AACACCCGGA AACAAACCCA GGATTGCTGA
AATGATATGT GACATTGATA CATATATCGT 1500
1501 AGAGGCAGGA TTAGCCAGTT TTATCCTGAC TATTAAGTTT GGGATAGAAA CTATGTATCC TGCTCTTGGA
CTGCATGAAT TTGCTGGTGA GTTATCCACA 1600
1601 CTTGAGTCCT TGATGAACCT TTACCAGCAA ATGGGGGAAA CTGCACCCTA CATGGTAATC CTGGAGAACT
CAATTCAGAA CAAGTTCAGT GCAGGATCAT 1700
1701 ACCCTCTGCT CTGGAGCTAT GCCATGGGAG TAGGAGTGGA ACTTGAAAAC TCCATGGGGG GTTTGAACTT
TGGCCGATCT TACTTTGATC CAGCATATTT 1800
1801 TAGATTAGGG CAAGAGATGG TAAGGAGGTC AGCTGGAAAG GTCAGTTCCA CATTGGCATC TGAACTCGGT
ATCACTGCCG AGGATGCAAG CTTGTTTCA 1900
1901 GAGATTGCAA TGCATACTAC TGAGGACAAG ATCAGTAGAG CGGTTGGACC CAGACAAGCC CAAGTATCAT
TTCTACACGG TGATCAAAGT GAGAATGAGC 2000
2001 TACCGAGATT GGGGGGCAAG GAAGATAGGA GGGTCAAACA GAGTCGAGGA GAAGCAGGG AGAGCTACAG
AGAAACCGGG CCCAGCAGAG CAAGTGATGC 2100
2101 GAGAGCTGCC CATCTTCCAA CCGGCACACC CCTAGACATT GACACTGCAT CGGAGTCCAG CCAAGATCCG
CAGGACAGTC GAAGGTCAGC TGACGCCCTG 2200
2201 CTTAGGCTGC AAGCCATGGC AGGAATCTCG GAAGAACAAG GCTCAGACAC GGACACCCCT ATAGTGTACA
ATGACAGAAA TCTTCTAGAC TAGGTGCGAG 2300
2301 AGGCCGAGGG CCAGAACAAC ATCCGCCTAC CCTCCATCAT TGTTATAAAA AACTTAGGAA CCAGGTCCAC
ACAGCCGCCA GCCCATCAAC CATCCACTCC 2400
2401 CACGATTGGA GCCAATGGTA GAAGAGCAGG CACGCCATGT CAAAAACGGA CTGGAATGCA TCCGGGCTCT
CAAGGCCGAG CCCATCGGCT CACTGGCCAT 2500
2501 CGAGGAAGCT ATGGCAGCAT GGTCAGAAAT ATCAGACAAC CCAGGACAGG AGCGAGCCAC CTGCAGGGAA
GAGAAGGCAG GCAGTTCGGG TCTCAGAAAA 2600
2601 CCATGCCTCT CAGCAATTGG ATCAACTGAA GGCGGTGCAC CTCGCATCCG CGGTCAGGGA CCTGGAGAGA
GCGATGACGA CGCTGAAACT TTGGGAATCC 2700
2701 CCCCAAGAAA TCTCCAGGCA TCAAGCACTG GGTTACAGTG TTATTACGTT TATGATCACA GCGGTGAAGC
GGTTAAGGGA ATCCAAGATG CTGACTCTAT 2800
2801 CATGGTTCAA TCAGGCCTTG ATGGTGATAG CACCCTCTCA GGAGGAGACA ATGAATCTGA AAACAGCGAT
GTGGATATTG GCGAACCTGA TACCGAGGGA 2900
2901 TATGCTATCA CTGACCGGGG ATCTGCTCCC ATCTCTATGG GGTTCAGGGC TTCTGATGTT GAAACTGCAG
AAGGAGGGGA GATCCACGAG CTCCTGAGAC 3000
3001 TCCAATCCAG AGGCAACAAC TTTCCGAAGC TTGGGAAAAC TCTCAATGTT CCTCCGCCCC GGACCCCGG
TAGGGCCAGC ACTTCCGGGA CACCCATTGA 3100
3101 AAAGGGCACA GACGCGAGAT TAGCCTCATT TGGAACGGAG ATCGCGTCTT TATTGACAGG TGGTGCAACC
CAATGTGCTC GAAAGTCACC CTCGGAACCA 3200
3201 TCAGGGCCAG GTGCACCTGC GGGGAATGTC CCCGAGTGTG TGAGCAATGC CGCACTGATA CAGGAGTGGA
CACCCGAATC TGGTACCACA ATCTCCCCGA 3300
3301 GATCCCAGAA TAATGAAGAA GGGGAGACT ATTATGATGA TGAGCTGTTC TCTGATGTCC AAGATATTAA
AACAGCCTTG GCCAAAATAC ACGAGGATAA 3400
```

Figure 24

```
3401 TCAGAAGATA ATCTCCAAGC TAGAATCACT GCTGTTATTG AAGGGAGAAG TTGAGTCAAT TAAGAAGCAG
ATCAACAGGC AAAATATCAG CATATCCACC 3500
3501 CTGGAAGGAC ACCTCTCAAG CATCATGATC GCCATTCCTG GACTTGGGAA GGATCCCAAC GACCCCACTG
CAGATGTCGA AATCAATCCC GACTTGAAAC 3600
3601 CCATCATAGG CAGAGATTCA GGCCGAGCAC TGGCCGAAGT TCTCAAGAAA CCCGTTGCCA GCCGACAACT
CCAAGGAATG ACAAATGGAC GGACCAGTTC 3700
3701 CAGAGGACAG CTGCTGAAGG AATTTCAGCT AAAGCCGATC GGGAAAAAGA TGAGCTCAGC CGTCGGGTTT
GTTCCTGACA CCGGCCCTGC ATCACGCAGT 3800
3801 GTAATCGGCT CCATTATAAA ATCCAGCCGG CTAGAGGAGG ATCGGAAGCG TTACCTGATG ACTCTCCTTG
ATGATATCAA AGGAGCCAAT GATCTTGCCA 3900
3901 AGTTCCACCA GATGCTGATG AAGATAATAA TGAAGTAGCT ACAGCTCAAC TTACCTGCCA ACCCCATGCC
AGTCGACCCA actagtctac cctccatcat 4000
4001 tgttataaaa aacttaggaa ccaggtccac acagccgcca gcccatcaAc gcgTATCTTc accggtgATC
TATacgtagc gcgcATGagt aaaggagaag 4100
4101 aactttcac tggagttgtc ccaattcttg ttgaattaga tggtgatgtt aatgggcaca aattttctgt
cagtggagag ggtgaaggtg atgcaacata 4200
4201 cggaaaactt acccttaaat ttatttgcac tactggaaaa ctacctgttc catggccaac acttgtcact
actttcacct atggtgttca atgcttttca 4300
4301 agatacccag atcatatgaa acggcatgac ttttttcaaga gtgccatgcc cgaaggttac gtacaggaaa
gaactatatt tttcaaagat gacgggaact 4400
4401 acaagacacg tgctgaagtc aagtttgaag gtgataccct tgttaataga atcgagttaa aaggtattga
tttttaaagaa gatggaaaca ttcttggaca 4500
4501 caaattggaa tacaactata actcacacaa tgtatacatc atggcagaca aacaaaagaa tggaatcaga
gttaacttca aaattagaca caacattgaa 4600
4601 gatggaagcg ttcaactagc agaccattat caacaaaata ctccaattgg cgatggccct gtcctttac
cagacaacca ttacctgtcc acacaatctg 4700
4701 cccttcgaa agatcccaac gaaaagagag accacatggt ccttcttgag tttgtaacag ctgctgggat
tacacatggc atggatgaac tatacaaata 4800
4801 gtgagcgcgc agcgctgacg tctcgcgatg atactagtAC AACCTAAATC CATCATAAAA AACTTAGGAG
CAAAGTGATT GCCTCCCAAG TTCCACAATG 4900
4901 ACAGAGATCT ACGACTTCGA CAAGTCGGCA TGGGACATCA AAGGGTCGAT CGCTCCGATA CAACCCACCA
CCTACAGTGA TGGCAGGCTG GTGCCCCAGG 5000
5001 TCAGAGTCAT AGATCCTGGT CTAGGCGACA GGAAGGATGA ATGCTTTATG TACATGTTTC TGCTGGGGGT
TGTTGAGGAC AGGGATTCCC TAGGGCCTCC 5100
5101 AATCGGGCGA GCATTTGGGT CCCTGCCCTT AGGTGTTGGC AGATCCACAG CAAAGCCCGA AAAACTCCTC
AAAGAGGCCA CTGAGCTTGA CATAGTTGTT 5200
5201 AGACGTACAG CAGGGCTCAA TGAAAAACTG GTGTTCTACA ACAACACCCC ACTAACTCTC CTCACACCTT
GGAGAAAGGT CCTAACAACA GGGAGTGTCT 5300
5301 TCAACGCAAA CCAAGTGTGC AATGCGGTTA ATCTGATACC GCTCGATACC CCGCAGAGGT TCCGTGTTGT
TTATATGAGC ATCACCCGTC TTTCGGATAA 5400
5401 CGGGTATTAC ACCGTTCCTA GAAGAATGCT GGAATTCAGA TCGGTCAATG CAGTGGCCTT CAACCTGCTG
GTGACCCTTA GGATTGACAA GGCGATAGGC 5500
5501 CCTGGGAAGA TCATCGACAA TACAGAGCAA CTTCCTGAGG CAACATTTAT AGTCCACATC GGGAACTTCA
GGAGAAAGAA GAGTGAAGTC TACTCTGCCG 5600
5601 ATTATTGCAA AATGAAAATC GAAAAGATGG GCCTGGTTTT TGCACTTGGT GGGATAGGGG GCACCAGTCT
TCACATTAGA AGCACAGGCA AAATGAGCAA 5700
5701 GACTCTCAAT GCACAACTCG GGTTCAAGAA GACCTTATGT TACCCGCTGA TGGATATCAA TGAAGACCTT
AATCGATTAC TCTGAGGAG CAGATGCAAG 5800
5801 ATAGTAAGAA TCCAGGCAGT TTTGCAGCCA TCAGTTCCTC AAGAATTCCG CATTTACGAC GACGTGATCA
TAAATGATGA CCAAGGACTA TTCAAAGTTC 5900
5901 TGTAGACCGT AGTGCCCAGC AATGCCCGAA AACGACCCCC CTCACAATGA CAGCCAGAAG GCCCGGACAA
AAAAGCCCCC TCCGAAAGAC TCCACGGACC 6000
6001 AAGCGAGAGG CCAGCCAGCA GCCGACGGCA AGCGCGAACA CCAGGCGGCC CCAGCACAGA ACAGCCCTGA
CACAAGGCCA CCACCAGCCA CCCCAATCTG 6100
6101 CATCCTCCTC GTGGGACCCC CGAGGACCAA CCCCCAAGGC TGCCCCCGAT CCAAACCACC AACCGCATCC
CCACCACCCC CGGGAAAGAA ACCCCCAGCA 6200
6201 ATTGGAAGGC CCCTCCCCCT CTTCCTCAAC ACAAGAACTC CACAACCGAA CCGCACAAGC GACCGAGGTG
ACCCAACCGC AGGCATCCGA CTCCCTAGAC 6300
6301 AGATCCTCTC TCCCCGGCAA ACTAAACAAA ACTTAGGGCC AAGGAACATA CACACCCAAC AGAACCCAGA
CCCCGGCCCA CGGCGCCGCG CCCCCAACCC 6400
6401 CCGACAACCA GAGGGAGCCC CCAACCAATC CCGCCGGCTC CCCCGGTGCC CACAGGCAGG GACACCAACC
CCCGAACAGA CCCAGCACCC AACCATCGAC 6500
6501 AATCCAAGAC GGGGGGGCCC CCCCAAAAAA AAGCCCCCAG GGGCCGACAG CCAGCACCGC GAGGAAGCCC
ACCCACCCCA CACACGACCA CGGCAACCAA 6600
6601 ACCAGAACCC AGACCACCCT GGGCCACCAG CTCCCAGACT CGGCCATCAC CCCGCAGAAA GGAAAGGCCA
CAACCCGCGC ACCCCAGCCC CGATCCGGCG 6700
6701 GGGAGCCACC CAACCCGAAC CAGCACCCAA GAGCGATCCC CGAAGGACCC CCGAACCGCA AAGGACATCA
GTATCCCACA GCCTCTCCAA GTCCCCCGGT 6800
```

Figure 24 (Contd..)

```
6801 CTCCTCCTCT TCTCGAAGGG ACCAAAAGAT CAATCCACCA CACCCGACGA CACTCAACTC CCCACCCCTA
AAGGAGACAC CGGGAATCCC AGAATCAAGA 6900
6901 CTCATCCAAT GTCCATCATG GGTCTCAAGG TGAACGTCTC TGCCATATTC ATGGCAGTAC TGTTAACTCT
CCAAACACCC ACCGGTCAAA TCCATTGGGG 7000
7001 CAATCTCTCT AAGATAGGGG TGGTAGGAAT AGGAAGTGCA AGCTACAAAG TTATGACTCG TTCCAGCCAT
CAATCATTAG TCATAAAATT AATGCCCAAT 7100
7101 ATAACTCTCC TCAATAACTG CACGAGGGTA GAGATTGCAG AATACAGGAG ACTACTGAGA ACAGTTTTGG
AACCAATTAG AGATGCACTT AATGCAATGA 7200
7201 CCCAGAATAT AAGACCGGTT CAGAGTGTAG CTTCAAGTAG GAGACACAAG AGATTTGCGG GAGTAGTCCT
GGCAGGTGCG GCCCTAGGCG TTGCCACAGC 7300
7301 TGCTCAGATA ACGGCCGGCA TTGCACTTCA CCAGTCCATG CTGAACTCTC AAGCCATCGA CAATCTGAGA
GCGAGCCTGG AAACTACTAA TCAGGCAATT 7400
7401 GAGGCAATCA GACAAGCAGG GCAGGAGATG ATATTGGCTG TTCAGGGTGT CCAAGACTAC ATCAATAATG
AGCTGATACC GTCTATGAAC CAACTATCTT 7500
7501 GTGATTTAAT CGGCCAGAAG CTCGGGCTCA AATTGCTCAG ATACTATACA GAAATCCTGT CATTATTTGG
CCCCAGTTTA CGGGACCCCA TATCTGCGGA 7600
7601 GATATCTATC CAGGCTTTGA GCTATGCGCT TGGAGGAGAC ATCAATAAGG TGTTAGAAAA GCTCGGATAC
AGTGGAGGTG ATTTACTGGG CATCTTAGAG 7700
7701 AGCAGAGGAA TAAAGGCCCG GATAACTCAC GTCGACACAG AGTCCTACTT CATTGTCCTC AGTATAGCCT
ATCCGACGCT GTCCGAGATT AAGGGGGTGA 7800
7801 TTGTCCACCG GCTAGAGGGG GTCTCGTACA ACATAGGCTC TCAAGAGTGG TATACCACTG TGCCCAAGTA
TGTTGCAACC CAAGGGTACC TTATCTCGAA 7900
7901 TTTTGATGAG TCATCGTGTA CTTTCATGCC AGAGGGGACT GTGTGCAGCC AAAATGCCTT GTACCCGATG
AGTCCTCTGC TCCAAGAATG CCTCCGGGGG 8000
8001 TACACCAAGT CCTGTGCTCG TACACTCGTA TCCGGGTCTT TTGGGAACCG GTTCATTTTA TCACAAGGGA
ACCTAATAGC CAATTGTGCA TCAATCCTTT 8100
8101 GCAAGTGTTA CACAACAGGA ACGATCATTA ATCAAGACCC TGACAAGATC CTAACATACA TTGCTGCCGA
TCACTGCCCG GTAGTCGAGG TGAACGGCGT 8200
8201 GACCATCCAA GTCGGGACAG GGAGGTATCC AGACGCTGTG TACTTGCACA GAATTGACCT CGGTCCTCCC
ATATCATTGG AGAGGTTGGA CGTAGGGACA 8300
8301 AATCTGGGGA ATGCAATTGC TAAGTGGAG GATGCCAAGG AATTGTTGGA GTCATCGGAC CAGATATTGA
GGAGTATGAA AGGTTTATCG AGCACTAGCA 8400
8401 TAGTCTACAT CCTGATTGCA GTGTGTCTTG GAGGGTTGAT AGGGATCCCC GCTTTAATAT GTTGCTGCAG
GGGCGTTGT AACAAAAAGG GAGAACAAGT 8500
8501 TGGTATGTCA AGACCAGGCC TAAAGCCTGA TCTTACGGGA ACATCAAAAT CCTATGTAAG GTCGCTCTGA
TCCTCTACAA CTCTTGAAAC ACAAATGTCC 8600
8601 CACAAGTCTC CTCTTCGTCA TCAAGCAACC ACCGCACCCA GCATCAAGCC CACCTGAAAT TATCTCCGGC
TTCCCTCTGG CCGAACAATA TCGGTAGTTA 8700
8701 ATTAAAACTT AGGGTGCAAA ATCATCCACA ATGTCACCAC AACGAGACCG GATAAATGCC TTCTACAAAG
ATAACCCCCA TCCCAAGGGA AGTAGGATAG 8800
8801 TCATTAACAG AGAACATCTT ATGATTGATA GACCTTATGT TTTGCTGGCT GTTCTGTTTG TCATGTTTCT
GAGCTTGATC GGGTTGCTAG CCATTGCAGG 8900
8901 CATTAGACTT CATCGGGCAG CCATCTACAC CGCAGAGATC CATAAAAGCC TCAGCACCAA TCTAGATGTA
ACTAACTCAA TCGAGCATCA GGTCAAGGAC 9000
9001 GTGCTGACAC CACTCTTCAA AATCATCGGT GATGAAGTGG GCCTGAGGAC ACCTCAGAGA TTCACTGACC
TAGTGAAATT CATCTCTGAC AAGATTAAAT 9100
9101 TCCTTAATCC GGATAGGGAG TACGACTTCA GAGATCTCAC TTGGTGTATC AACCCGCCAG AGAGAATCAA
ATTGGATTAT GATCAATACT GTGCAGATGT 9200
9201 GGCTGCTGAA GAGCTCATGA ATGCATTGGT GAACTCAACT CTACTGGAGA CCAGAACAAC CAATCAGTTC
CTAGCTGTCT CAAAGGGAAA CTGCTCAGGG 9300
9301 CCCACTACAA TCAGAGGTCA ATTCTCAAAC ATGTCGCTGT CCCTGTTAGA CTTGTATTTA GGTCGAGGTT
ACAATGTGTC ATCTATAGTC ACTATGACAT 9400
9401 CCCAGGGAAT GTATGGGGGA ACTTACCTAG TGGAAAAGCC TAATCTGAGC AGCAAAGGT CAGAGTTGTC
ACAACTGAGC ATGTACCGAG TGTTTGAAGT 9500
9501 AGGTGTTATC AGAAATCCGG GTTTGGGGGC TCCGGTGTTC CATATGACAA ACTATCTTGA GCAACCAGTC
AGTAATGATC TCAGCAACTG TATGGTGGCT 9600
9601 TTGGGGGAGC TCAAACTCGC AGCCCTTTGT CACGGGGAAG ATTCTATCAC AATTCCCTAT CAGGGATCAG
GGAAGGTGT CAGCTTCCAG CTCGTCAAGC 9700
9701 TAGGTGTCTG GAAATCCCCA ACCGACATGC AATCCTGGGT CCCCTTATCA ACGGATGATC CAGTGATAGA
CAGGCTTTAC CTCTCATCTC ACAGAGGTGT 9800
9801 TATCGCTGAC AATCAAGCAA AATGGGCTGT CCCGACAACA CGAACAGATG ACAAGTTGCG AATGGAGACA
TGCTTCCAAC AGGCGTGTAA GGGTAAAATC 9900
9901 CAAGCACTCT GCGAGAATCC CGAGTGGGCA CCATTGAAGG ATAACAGGAT TCCTTCATAC GGGGTCTTGT
CTGTTGATCT GAGTCTGACA GTTGAGCTTA 10000
10001 AAATCAAAAT TGCTTCGGGA TTCGGGCCAT TGATCACACA CGGTTCAGGG ATGGACCTAT ACAAATCCAA
CCACAACAAT GTGTATTGGC TGACTATCCC 10100
10101 GCCAATGAAG AACCTAGCCT TAGGTGTAAT CAACACATTG GAGTGGATAC CGAGATTCAA GGTTAGTCCC
TACCTCTTCA CTGTCCCAAT TAAGGAAGCA 10200
```

Figure 24 (contd..)

```
10201 GGCGAAGACT GCCATGCCCC AACATACCTA CCTGCGGAGG TGGATGGTGA TGTCAAACTC AGTTCCAATC
TGGTGATTCT ACCTGGTCAA GATCTCCAAT 10300
10301 ATGTTTTGGC AACCTACGAT ACTTCCAGGG TTGAACATGC TGTGGTTTAT TACGTTTACA GCCCAGGCCG
CTCATTTTCT TACTTTTATC CTTTTAGGTT 10400
10401 GCCTATAAAG GGGGTCCCCA TCGAATTACA AGTGGAATGC TTCACATGGG ACCAAAAACT CTGGTGCCGT
CACTTCTGTG TGCTTGCGGA CTCAGAATCT 10500
10501 GGTGGACATA TCACTCACTC TGGGATGGTG GGCATGGGAG TCAGCTGCAC AGTCACCCGG GAAGATGGAA
CCAATCGCAG ATAGGGCTGC TAGTGAACCA 10600
10601 ATCACATGAT GTCACCCAGA CATCAGGCAT ACCCACTAGT GTGAAATAGA CATCAGAATT AAGAAAAACG
TAGGGTCCAA GTGGTtCCCC GTTATGGACT 10700
10701 CGCTATCTGT CAACCAGATC TTATACCCTG AAGTTCACCT AGATAGCCCG ATAGTTACCA ATAAGATAGT
AGCCATCCTG GAGTATGCTC GAGTCCCTCA 10800
10801 CGCTTACAGC CTGGAGGACC CTACACTGTG TCAGAACATC AAGCACCGCC TAAAAACGG ATTTTCCAAC
CAAATGATTA TAAACAATGT GGAAGTTGGG 10900
10901 AATGTCATCA AGTCCAAGCT TAGGAGTTAT CCGGCCCACT CTCATATTCC ATATCCAAAT TGTAATCAGG
ATTTATTTAA CATAGAAGAC AAAGAGTCAA 11000
11001 CGAGGAAGAT CCGTGAACTC CTCAAAAAGG GGAATTCGCT GTACTCCAAA GTCAGTGATA AGGTTTTCCA
ATGCTTAAGG GACACTAACT CACGGCTTGG 11100
11101 CCTAGGCTCC GAATTGAGGG AGGACATCAA GGAGAAAGTT ATTAACTTGG GAGTTTACAT GCACAGCTCC
CAGTGGTTTG AGCCCTTTCT GTTTTGGTTT 11200
11201 ACAGTCAAGA CTGAGATGAG GTCAGTGATT AAATCACAAA CCCATACTTG CCATAGGAGG AGACACACAC
CTGTATTCTT CACTGGTAGT TCAGTTGAGT 11300
11301 TGCTAATCTC TCGTGACCTT GTTGCTATAA TCAGTAAAGA GTCTCAACAT GTATATTACC TGACATTTGA
ACTGGTTTTG ATGTATTGTG ATGTCATAGA 11400
11401 GGGGAGGTTA ATGACAGAGA CCGCTATGAC TATTGATGCT AGGTATACAG AGCTTCTAGG AAGAGTCAGA
TACATGTGGA AACTGATAGA TGGTTTCTTC 11500
11501 CCTGCACTCG GGAATCCAAC TTATCAAATT GTAGCAATGC TGGAGCCTCT TTCACTTGCT TACCTGCAGC
TGAGGGATAT AACAGTAGAA CTCAGAGGTG 11600
11601 CTTTCCTTAA CCACTGCTTT ACTGAAATAC ATGATGTTCT TGACCAAAAC GGGTTTTCTG ATGAAGGTAC
TTATCATGAG TTAATTGAAG CTCTAGATTA 11700
11701 CATTTTCATA ACTGATGACA TACATCTGAC AGGGGAGATT TTCTCATTTT TCAGAAGTTT CGGCCACCCC
AGACTTGAAG CAGTAACGGC TGCTGAAAAT 11800
11801 GTTAGGAAAT ACATGAATCA GCCTAAAGTC ATTGTGTATG AGACTCTGAT GAAAGGTCAT GCCATATTTT
GTGGAATCAT AATCAACGGC TATCGTGACA 11900
11901 GGCACGGAGG CAGTTGGCCA CCGCTGACCC TCCCCCTGCA TGCTGCAGAC ACAATCCGGA ATGCTCAAGC
TTCAGGTGAA GGGTTAACAC ATGAGCAGTG 12000
12001 CGTTGATAAC TGGAAATCTT TTGCTGGAGT GAAATTTGGC TGCTTTATGC CTCTTAGCCT GGATAGTGAT
CTGACAATGT ACCTAAAGGA CAAGGCACTT 12100
12101 GCTGCTCTCC AAAGGGAATG GGATTCAGTT TACCCGAAAG AGTTCCTGCG TTACGACCCT CCCAAGGGAA
CCGGGTCACG GAGGCTTGTA GATGTTTTC 12200
12201 TTAATGATTC GAGCTTTGAC CCATATGATG TGATAATGTA TGTTGTAAGT GGAGCTTACC TCCATGACCC
TGAGTTCAAC CTGTCTTACA GCCTGAAAGA 12300
12301 AAAGGAGATC AAGGAAACAG GTAGACTTTT TGCTAAAATG ACTTACAAAA TGAGGGCATG CCAAGTGATT
GCTGAAAATC TAATCTCAAA CGGGATTGGC 12400
12401 AAATATTTTA AGGACAATGG GATGGCCAAG GATGAGCACG ATTTGACTAA GGCACTCCAC ACTCTAGCTG
TCTCAGGAGT CCCCAAAGAT CTCAAAGAA 12500
12501 GTCACAGGGG GGGGCCAGTC TTAAAAACCT ACTCCCGAAG CCCAGTCCAC ACAAGTACCA GGAACGTGAG
AGCAGCAAAA GGGTTTATAG GGTTCCCTCA 12600
12601 AGTAATTCGG CAGGACCAAG ACACTGATCA TCCGGAGAAT ATGGAAGCTT ACGAGACAGT CAGTGCATTT
ATCACGACTG ATCTCAAGAA GTACTGCCTT 12700
12701 AATTGGAGAT ATGAGACCAT CAGCTTGTTT GCACAGAGGC TAAATGAGAT TTACGGATTG CCCTCATTTT
TCCAGTGGCT GCATAAGAGG CTTGAGACCT 12800
12801 CTGTCCTGTA TGTAAGTGAC CCTCATTGCC CCCCCGACCT TGACGCCCAT ATCCCGTTAT ATAAAGTCCC
CAATGATCAA ATCTTCATTA AGTACCCTAT 12900
12901 GGGAGGTATA GAAGGGTATT GTCAGAAGCT GTGGACCATC AGCACCATTC CCTATCTATA CCTGGCTGCT
TATGAGAGCG GAGTAAGGAT TGCTTCGTTA 13000
13001 GTGCAAGGGG ACAATCAGAC CATAGCCGTA ACAAAAGGG TACCCAGCAC ATGGCCCTAC AACCTTAAGA
AACGGGAAGC TGCTAGAGTA ACTAGAGATT 13100
13101 ACTTTGTAAT TCTTAGGCAA AGGCTACATG ATATTGGCCA TCACCTCAAG GCAAATGAGA CAATTGTTTC
ATCACATTTT TTTGTCTATT CAAAAGGAAT 13200
13201 ATATTATGAT GGGCTACTTG TGTCCCAATC ACTCAAGAGC ATCGCAAGAT GTGTATTCTG GTCAGAGACT
ATAGTTGATG AAACAAGGGC AGCATGCAGT 13300
13301 AATATTGCTA CAACAATGGC TAAAAGCATC GAGAGAGGTT ATGACCGTTA CCTTGCATAT TCCCTGAACG
TCCTAAAAGT GATACAGCAA ATTCTGATCT 13400
13401 CTCTTGGCTT CACAATCAAT TCAACCATGA CCCGGGATGT AGTCATACCC CTCCTCACAA ACAACGACCT
CTTAATAAGG ATGGCACTGT TGCCCGCTCC 13500
13501 TATTGGGGGG ATGAATTATC TGAATATGAG CAGGCTGTTT GTCAGAAACA TCGGTGATCC AGTAACATCA
TCAATTGCTG ATCTCAAGAG AATGATTCTC 13600
13601 GCCTCACTAA TGCCTGAAGA GACCCTCCAT CAAGTAATGA CACAACAACC GGGGGACTCT TCATTCCTAG
```

Figure 24 (Contd..)

ACTGGGCTAG CGACCCTTAC TCAGCAAATC 13700
13701 TTGTATGTGT CCAGAGCATC ACTAGACTCC TCAAGAACAT AACTGCAAGG TTTGTCCTGA TCCATAGTCC
AAACCCAATG TTAAAAGGAT TATTCCATGA 13800
13801 TGACAGTAAA GAAGAGGACG AGGGACTGGC GGCATTCCTC ATGGACAGGC ATATTATAGT ACCTAGGGCA
GCTCATGAAA TCCTGGATCA TAGTGTCACA 13900
13901 GGGGCAAGAG AGTCTATTGC AGGCATGCTG GATACCACAA AAGGCTTGAT TCGAGCCAGC ATGAGGAAGG
GGGGGTTAAC CTCTCGAGTG ATAACCAGAT 14000
14001 TGTCCAATTA TGACTATGAA CAATTCAGAG CAGGGATGGT GCTATTGACA GGAAGAAAGA GAAATGTCCT
CATTGACAAA GAGTCATGTT CAGTGCAGCT 14100
14101 GGCGAGAGCT CTAAGAAGCC ATATGTGGGC GAGGCTAGCT CGAGGACGGC CTATTTACGG CCTTGAGGTC
CCTGATGTAC TAGAATCTAT GCGAGGCCAC 14200
14201 CTTATTCGGC GTCATGAGAC ATGTGTCATC TGCGAGTGTG GATCAGTCAA CTACGGATGG TTTTTTGTCC
CCTCGGGTTG CCAACTGGAT GATATTGACA 14300
14301 AGGAAACATC ATCCTTGAGA GTCCCATATA TTGGTTCTAC CACTGATGAG AGAACAGACA TGAAGCTTGC
CTTCGTAAGA GCCCCAAGTC GATCCTTGCG 14400
14401 ATCTGCTGTT AGAATAGCAA CAGTGTACTC ATGGGCTTAC GGTGATGATG ATAGCTCTTG GAACGAAGCC
TGGTTGTTGG CTAGGCAAAG GGCCAATGTG 14500
14501 AGCCTGGAGG AGCTAAGGGT GATCACTCCC ATCTCAACTT CGACTAATTT AGCGCATAGG TTGAGGGATC
GTAGCACTCA AGTGAAATAC TCAGGTACAT 14600
14601 CCCTTGTCCG AGTGGCGAGG TATACCACAA TCTCCAACGA CAATCTCTCA TTTGTCATAT CAGATAAGAA
GGTTGATACT AACTTTATAT ACCAACAAGG 14700
14701 AATGCTCCTA GGGTTGGGTG TTTTAGAAAC ATTGTTTCGA CTCGAGAAAG ATACCGGATC ATCTAACACG
GTATTACATC TTCACGTCGA AACAGATTGT 14800
14801 TGCGTGATCC CGATGATAGA TCATCCCAGG ATACCCAGCT CCCGCAAGCT AGAGCTGAGG GCAGAGCTAT
GTACCAACCC ATTGATATAT GATAATGCAC 14900
14901 CTTTAATTGA CAGAGATGCA ACAAGGCTAT ACACCCAGAG CCATAGGAGG CACCTTGTGG AATTTGTTAC
ATGGTCCACA CCCCAACTAT ATCACATTTT 15000
15001 AGCTAAGTCC ACAGCACTAT CTATGATTGA CCTGGTAACA AAATTTGAGA AGGACCATAT GAATGAAATT
TCAGCTCTCA TAGGGGATGA CGATATCAAT 15100
15101 AGTTTCATAA CTGAGTTTCT GCTCATAGAG CCAAGATTAT TCACTATCTA CTTGGGCCAG TGTGCGGCCA
TCAATTGGGC ATTTGATGTA CATTATCATA 15200
15201 GACCATCAGG GAAATATCAG ATGGGTGAGC TGTTGTCATC GTTCCTTTCT AGAATGAGCA AAGGAGTGTT
TAAGGTGCTT GTCAATGCTC TAAGCCACCC 15300
15301 AAAGATCTAC AAGAAATTCT GGCATTGTGG TATTATAGAG CCTATCCATG GTCCTTCACT TGATGCTCAA
AACTTGCACA CAACTGTGTG CAACATGGTT 15400
15401 TACACATGCT ATATGACCTA CCTCGACCTG TTGTTGAATG AAGAGTTAGA AGAGTTCACA TTTCTCTTGT
GTGAAAGCGA CGAGGATGTA GTACCGGACA 15500
15501 GATTCGACAA CATCCAGGCA AAACACTTAT GTGTTCTGGC AGATTTGTAC TGTCAACCAG GGACCTGCCC
ACCAATTCGA GGTCAAGAC CGGTAGAGAA 15600
15601 ATGTGCAGTT CTAACCGACC ATATCAAGGC AGAGGCTATG TTATCTCCAG CAGGATCTTC GTGGAACATA
AATCCAATTA TTGTAGACCA TTACTCATGC 15700
15701 TCTCTGACTT ATCTCCGGCG AGGATCGATC AAACAGATAA GATTGAGAGT TGATCCAGGA TTCATTTTCG
ACGCCCTCGC TGAGGTAAAT GTCAGTCAGC 15800
15801 CAAAGATCGG CAGCAACAAC ATCTCAAATA TGAGCATCAA GGCTTTCAGA CCCCCACACG ATGATGTTGC
AAAATTGCTC AAAGATATCA ACACAAGCAA 15900
15901 GCACAATCTT CCCATTTCAG GGGGCAATCT CGCCAATTAT GAAATCCATG CTTTCCGCAG AATCGGGTTG
AACTCATCTG CTTGCTACAA AGCTGTTGAG 16000
16001 ATATCAACAT TAATTAGGAG ATGCCTTGAG CCAGGGGAGG ACGGCTTGTT CTTGGGTGAG GGATCGGGTT
CTATGTTGAT CACTTATAAG GAGATACTTA 16100
16101 AACTAAACAA GTGCTTCTAT AATAGTGGGG TTTCCGCCAA TTCTAGATCT GGTCAAAGGG AATTAGCACC
CTATCCCTCC GAAGTTGGCC TTGTCGAACA 16200
16201 CAGAATGGGA GTAGGTAATA TTGTCAAAGT GCTCTTTAAC GGGAGGCCCG AAGTCACGTG GGTAGGCAGT
GTAGATTGCT TCAATTTCAT AGTTAGTAAT 16300
16301 ATCCCTACCT CTAGTGTGGG GTTTATCCAT TCAGATATAG AGACCTTGCC TGACAAAGAT ACTATAGAGA
AGCTAGAGGA ATTGGCAGCC ATCTTATCGA 16400
16401 TGGCTCTGCT CCTGGGCAAA ATAGGATCAA TACTGGTGAT TAAGCTTATG CCTTTCAGCG GGGATTTTGT
TCAGGGATTT ATAAGTTATG TAGGGTCTCA 16500
16501 TTATAGAGAA GTGAACCTTG TATACCCTAG ATACAGCAAC TTCATATCTA CTGAATCTTA TTTGGTTATG
ACAGATCTCA AGGCTAACCG GCTAATGAAT 16600
16601 CCTGAAAAGA TTAAGCAGCA GATAATTGAA TCATCTGTGA GGACTTCACC TGGACTTATA GGTCACATCC
TATCCATTAA GCAACTAAGC TGCATACAAG 16700
16701 CAATTGTGGG AGACGCAGTT AGTAGAGGTA ATATCAATCC TACTCTGAAA AAACTTACAC CTATAGAGCA
GGTGCTGATC AATTGCGGGT TGGCAATTAA 16800
16801 CGGACCTAAG CTGTGCAAAG AATTGATCCA CCATGATGTT GCCTCAGGGC AAGATGGATT GCTTAATTCT
ATACTCATCC TCTACAGGGA GTTGGCAAGA 16900
16901 TTCAAAGACA ACCAAAGAAG TCAACAAGGG ATGTTCCACG CTTACCCCGT ATTGGTAAGT AGCAGGCAAC
GAGAACTTAT ATCTAGGATC ACCCGCAAAT 17000
17001 TTTGGGGCA CATTCTTCTT TACTCCGGGA ACAGAAAGTT GATAAATAAG TTTATCCAGA ATCTCAAGTC
CGGCTATCTG ATACTAGACT TACACCAGAA 17100

Figure 24(Contd..)

```
17101 TATCTTCGTT AAGAATCTAT CCAAGTCAGA GAAACAGATT ATTATGACGG GGGGTTTGAA ACGTGAGTGG
GTTTTTAAGG TAACAGTCAA GGAGACCAAA 17200
17201 GAATGGTATA AGTTAGTCGG ATACAGTGCC CTGATTAAGG ACTAATTGGT TGAACTCCGG AACCCTAATC
CTGCCCTAGG TGGTTAGGCA TTATTTGCAA 17300
17301 TATATTAAAG AAAACTTTGA AAATACGAAG TTTCTATTCC CAGCTTTGTC TGGTggccgg catggtccca
gcctcctcgc tggcgccggc tgggcaacat 17400
17401 tccgagggga ccgtcccctc ggtaatggcg aatgggacGC GGCCgatccg gctgctaaca aagcccgaaa
ggaagctgag ttggctgctg ccaccgctga 17500
17501 gcaataacta gcataacccc ttggggcctc taaacgggtc ttgaggggtt ttttgctgaa aggaggaact
atatccggat GCGGCCGCaG GTACCCAGCT 17600
17601 TTTGTTCCCt ttagtgaggg ttaattTCGA GCTTGGCGTA ATCATGGTCA TAGCTGTTTC CTGTGTGAAA
TTGTTATCCG CTCACAATTC CACACAACAT 17700
17701 ACGAGCCGGA AGCATAAAGT GTAAAGCCTG GGGTGCCTAA TGAGTGAGCT AACTCACATT AATTGCGTTG
CGCTCACTGC CCGCTTTCCA GTCGGGAAAC 17800
17801 CTGTCGTGCC AGCTGCATTA ATGAATCGGC CAACGCGCGG GGAGAGGCGG TTTGCGTATT GGGCGCTCTT
CCGCTTCCTC GCTCACTGAC TCGCTGCGCT 17900
17901 CGGTCGTTCG GCTGCGGCGA GCGGTATCAG CTCACTCAAA GGCGGTAATA CGGTTATCCA CAGAATCAGG
GGATAACGCA GGAAAGAACA TGTGAGCAAA 18000
18001 AGGCCAGCAA AAGGCCAGGA ACCGTAAAAA GGCCGCGTTG CTGGCGTTTT TCCATAGGCT CCGCCCCCCT
GACGAGCATC ACAAAAATCG ACGCTCAAGT 18100
18101 CAGAGGTGGC GAAACCCGAC AGGACTATAA AGATACCAGG CGTTTCCCCC TGGAAGCTCC CTCGTGCGCT
CTCCTGTTCC GACCCTGCCG CTTACCGGAT 18200
18201 ACCTGTCCGC CTTTCTCCCT TCGGGAAGCG TGGCGCTTTC TCATAGCTCA CGCTGTAGGT ATCTCAGTTC
GGTGTAGGTC GTTCGCTCCA AGCTGGGCTG 18300
18301 TGTGCACGAA CCCCCCGTTC AGCCCGACCG CTGCGCCTTA TCCGGTAACT ATCGTCTTGA GTCCAACCCG
GTAAGACACG ACTTATCGCC ACTGGCAGCA 18400
18401 GCCACTGGTA ACAGGATTAG CAGAGCGAGG TATGTAGGCG GTGCTACAGA GTTCTTGAAG TGGTGGCCTA
ACTACGGCTA CACTAGAAGG ACAGTATTTG 18500
18501 GTATCTGCGC TCTGCTGAAG CCAGTTACCT TCGGAAAAAG AGTTGGTAGC TCTTGATCCG GCAAACAAAC
CACCGCTGGT AGCGGTGGTT TTTTGTTTG 18600
18601 CAAGCAGCAG ATTACGCGCA GAAAAAAAGG ATCTCAAGAA GATCCTTTGA TCTTTTCTAC GGGGTCTGAC
GCTCAGTGGA ACGAAAACTC ACGTTAAGGG 18700
18701 ATTTTGGTCA TGAGATTATC AAAAAGGATC TTCACCTAGA TCCTTTTAAA TTAAAAATGA AGTTTTAAAT
CAATCTAAAG TATATATGAG TAAACTTGGT 18800
18801 CTGACAGTTA CCAATGCTTA ATCAGTGAGG CACCTATCTC AGCGATCTGT CTATTTCGTT CATCCATAGT
TGCCTGACTC CCCGTCGTGT AGATAACTAC 18900
18901 GATACGGGAG GGCTTACCAT CTGGCCCCAG TGCTGCAATG ATACCGCGAG ACCCACGCTC ACCGGCTCCA
GATTTATCAG CAATAAACCA GCCAGCCGGA 19000
19001 AGGGCCGAGC GCAGAAGTGG TCCTGCAACT TTATCCGCCT CCATCCAGTC TATTAATTGT TGCCGGGAAG
CTAGAGTAAG TAGTTCGCCA GTTAATAGTT 19100
19101 TGCGCAACGT TGTTGCCATT GCTACAGGCA TCGTGGTGTC ACGCTCGTCG TTTGGTATGG CTTCATTCAG
CTCCGGTTCC CAACGATCAA GGCGAGTTAC 19200
19201 ATGATCCCCC ATGTTGTGCA AAAAAGCGGT TAGCTCCTTC GGTCCTCCGA TCGTTGTCAG AAGTAAGTTG
GCCGCAGTGT TATCACTCAT GGTTATGGCA 19300
19301 GCACTGCATA ATTCTCTTAC TGTCATGCCA TCCGTAAGAT GCTTTTCTGT GACTGGTGAG TACTCAACCA
AGTCATTCTG AGAATAGTGT ATGCGGCGAC 19400
19401 CGAGTTGCTC TTGCCCGGCG TCAATACGGG ATAATACCGC GCCACATAGC AGAACTTTAA AAGTGCTCAT
CATTGGAAAA CGTTCTTCGG GGCGAAAACT 19500
19501 CTCAAGGATC TTACCGCTGT TGAGATCCAG TTCGATGTAA CCCACTCGTG CACCCAACTG ATCTTCAGCA
TCTTTTACTT TCACCAGCGT TTCTGGGTGA 19600
19601 GCAAAACAG GAAGGCAAAA TGCCGCAAAA AAGGGAATAA GGGCGACACG GAAATGTTGA ATACTCATAC
TCTTCCTTTT TCAATATTAT TGAAGCATTT 19700
19701 ATCAGGGTTA TTGTCTCATG AGCGGATACA TATTTGAATG TATTTAGAAA AATAAACAAA TAGGGGTTCC
GCGCACATTT CCCCGAAAAG TGC    19793
              | 10       | 20       | 30       | 40       | 50       | 60       | 70
  | 80       | 90       | 100
```

Figure 24 (contd..)

```
        |   10      |   20      |  30      |  40      |   50      |  60      |   70
|  80   |   90      |  100
      1 CACCTAAATT GTAAGCGTTA ATATTTTGTT AAAATTCGCG TTAAATTTTT GTTAAATCAG CTCATTTTTT
AACCAATAGG CCGAAATCGG CAAAATCCCT 100
    101 TATAAATCAA AAGAATAGAC CGAGATAGGG TTGAGTGTTG TTCCAGTTTG GAACAAGAGT CCACTATTAA
AGAACGTGGA CTCCAACGTC AAAGGGCGAA 200
    201 AAACCGTCTA TCAGGGCGAT GGCCCACTAC GTGAACCATC ACCCTAATCA AGTTTTTTGG GGTCGAGGTG
CCGTAAAGCA CTAAATCGGA ACCCTAAAGG 300
    301 GAGCCCCCGA TTTAGAGCTT GACGGGGAAA GCCggccatt taggccaTAG GGCGCTGGCA AGTGTAGCGG
TCACGCTGCG CGTAACCACC ACACCCGCCG 400
    401 CGCTTAATGC GCCGCTACAG GGCGCGTCCC ATTCGCCATT CAGGCTGCGC AACTGTTGGG AAGGGCGATC
GGTGCGGGCC TCTTCGCTAT TACGCCAGCT 500
    501 GGCGAAAGGG GGATGTGCTG CAAGGCGATT AAGTTGGGTA ACGCCAGGGT TTTCCCAGTC ACGACGTTGT
AAAACGACGG CCAGTGAATT Gtaatacgac 600
    601 tcactataAC CAAACAAAGT TGGGTAAGGA TAGTTCAATC AATGATCATC TTCTAGTGCA CTTAGGATTC
AAGATCCTAT TATCAGGGAC AAGAGCAGGA 700
    701 TTAGGGATAT CTGAGATGGC CACACTTTTA AGGAGCTTAG CATTGTTCAA AAGAAACAAG GACAAACCAC
CCATTACATC AGGATCCGGT GGAGCCATCA 800
    801 GAGGAATCAA ACACATTATT ATAGTACCAA TCCCTGGAGA TTCCTCAATT ACCACTCGAT CCAGACTTCT
GGACCGGTTG GTCAGGTTAA TTGGAAACCC 900
    901 GGATGTGAGC GGGCCCAAAC TAACAGGGGC ACTAATAGGT ATATTATCCT TATTTGTGGA GTCTCCAGGT
CAATTGATTC AGAGGATCAC CGATGACCCT 1000
   1001 GACGTTAGCA TAAGGCTGTT AGAGGTTGTC CAGAGTGACC AGTCACAATC TGGCCTTACC TTCGCATCAA
GAGGTACCAA CATGGAGGAT GAGGCGGACC 1100
   1101 AATACTTTTC ACATGATGAT CCAATTAGTA GTGATCAATC CAGGTTCGGA TGGTTCGAGA ACAAGGAAAT
CTCAGATATT GAAGTGCAAG ACCCTGAGGG 1200
   1201 ATTCAACATG ATTCTGGGTA CCATCCTAGC CCAAATTTGG GTCTTGCTCG CAAAGGCGGT TACGGCCCCA
GACACGGCAG CTGATTCGGA GCTAAGAAGG 1300
   1301 TGGATAAAGT ACACCCAACA AAGAAGGGTA GTTGGTGAAT TTAGATTGGA GAGAAAATGG TTGGATGTGG
TGAGGAACAG GATTGCCGAG GACCTCTCCT 1400
   1401 TACGCCGATT CATGGTCGCT CTAATCCTGG ATATCAAGAG AACACCCGGA AACAAACCCA GGATTGCTGA
AATGATATGT GACATTGATA CATATATCGT 1500
   1501 AGAGGCAGGA TTAGCCAGTT TTATCCTGAC TATTAAGTTT GGGATAGAAA CTATGTATCC TGCTCTTGGA
CTGCATGAAT TTGCTGGTGA GTTATCCACA 1600
   1601 CTTGAGTCCT TGATGAACCT TTACCAGCAA ATGGGGGAAA CTGCACCCTA CATGGTAATC CTGGAGAACT
CAATTCAGAA CAAGTTCAGT GCAGGATCAT 1700
   1701 ACCCTCTGCT CTGGAGCTAT GCCATGGGAG TAGGAGTGGA ACTTGAAAAC TCCATGGGGG GTTTGAACTT
TGGCCGATCT TACTTTGATC CAGCATATTT 1800
   1801 TAGATTAGGG CAAGAGATGG TAAGGAGGTC AGCTGGAAAG GTCAGTTCCA CATTGGCATC TGAACTCGGT
ATCACTGCCG AGGATGCAAG GCTTGTTTCA 1900
   1901 GAGATTGCAA TGCATACTAC TGAGGACAAG ATCAGTAGAG CGGTTGGACC CAGACAAGCC CAAGTATCAT
TTCTACACGG TGATCAAAGT GAGAATGAGC 2000
   2001 TACCGAGATT GGGGGGCAAG GAAGATAGGA GGGTCAAACA GAGTCGAGGA GAAGCCAGGG AGAGCTACAG
AGAAACCGGG CCCAGCAGAG CAAGTGATGC 2100
   2101 GAGAGCTGCC CATCTTCCAA CCGGCACACC CCTAGACATT GACACTGCAT CGGAGTCCAG CCAAGATCCG
CAGGACAGTC GAAGGTCAGC TGACGCCCTG 2200
   2201 CTTAGGCTGC AAGCCATGGC AGGAATCTCG GAAGAACAAG GCTCAGACAC GGACACCCCT ATAGTGTACA
ATGACAGAAA TCTTCTAGAC TAGGTGCGAG 2300
   2301 AGGCCGAGGG CCAGAACAAC ATCCGCCTAC CCTCCATCAT TGTTATAAAA AACTTAGGAA CCAGGTCCAC
ACAGCCGCCA GCCCATCAAC CATCCACTCC 2400
   2401 CACGATTGGA GCCAATGGTA GAAGAGCAGG CACGCCATGT CAAAAACGGA CTGGAATGCA TCCGGGCTCT
CAAGGCCGAG CCCATCGGCT CACTGGCCAT 2500
   2501 CGAGGAAGCT ATGGCAGCAT GGTCAGAAAT ATCAGACAAC CCAGGACAGG AGCGAGCCAC CTGCAGGGAA
GAGAAGGCAG GCAGTTCGGG TCTCAGAAAA 2600
   2601 CCATGCCTCT CAGCAATTGG ATCAACTGAA GGCGGTGCAC CTCGCATCCG CGGTCAGGGA CCTGGAGAGA
GCGATGCGA CGCTGAAACT TTGGGAATCC 2700
   2701 CCCCAAGAAA TCTCCAGGCA TCAAGCACTG GGTTACAGTG TTATTACGTT TATGATCACA GCGGTGAAGC
GGTTAAGGGA ATCCAAGATG CTGACTCTAT 2800
   2801 CATGGTTCAA TCAGGCCTTG ATGGTGATAG CACCCTCTCA GGAGGAGACA ATGAATCTGA AAACAGCGAT
GTGGATATTG GCGAACCTGA TACCGAGGGA 2900
   2901 TATGCTATCA CTGACCGGGG ATCTGCTCCC ATCTCTATGG GGTTCAGGGC TTCTGATGTT GAAACTGCAG
AAGGAGGGGA GATCCACGAG CTCCTGAGAC 3000
   3001 TCCAATCCAG AGGCAACAAC TTTCCGAAGC TTGGGAAAAC TCTCAATGTT CCTCCGCCCC CGGACCCCGG
TAGGGCCAGC ACTTCCGGGA CACCCATTAA 3100
   3101 AAAGGGCACA GACGCGAGAT TAGCCTCATT TGGAACGGAG ATCGCGTCTT TATTGACAGG TGGTGCAACC
CAATGTGCTC GAAAGTCACC CTCGGAACCA 3200
   3201 TCAGGGCCAG GTGCACCTGC GGGGAATGTC CCCGAGTGTG TGAGCAATGC CGCACTGATA CAGGAGTGGA
CACCCGAATC TGGTACCACA ATCTCCCCGA 3300
   3301 GATCCCAGAA TAATGAAGAA GGGGAGACT ATTATGATGA TGAGCTGTTC  TCTGATGTCC AAGATATTAA
```

Figure 25

```
AACAGCCTTG GCCAAAATAC ACGAGGATAA 3400
    3401 TCAGAAGATA ATCTCCAAGC TAGAATCACT GCTGTTATTG AAGGGAGAAG TTGAGTCAAT TAAGAAGCAG
ATCAACAGGC AAAATATCAG CATATCCACC 3500
    3501 CTGGAAGGAC ACCTCTCAAG CATCATGATC GCCATTCCTG GACTTGGGAA GGATCCCAAC GACCCCACTG
CAGATGTCGA AATCAATCCC GACTTGAAAC 3600
    3601 CCATCATAGG CAGAGATTCA GGCCGAGCAC TGGCCGAAGT TCTCAAGAAA CCCGTTGCCA GCCGACAACT
CCAAGGAATG ACAAATGGAC GGACCAGTTC 3700
    3701 CAGAGGACAG CTGCTGAAGG AATTTCAGCT AAAGCCGATC GGGAAAAAGA TGAGCTCAGC CGTCGGGTTT
GTTCCTGACA CCGGCCCTGC ATCACGCAGT 3800
    3801 GTAATCCGCT CCATTATAAA ATCCAGCCGG CTAGAGGAGG ATCGGAAGCG TTACCTGATG ACTCTCCTTG
ATGATATCAA AGGAGCCAAT GATCTTGCCA 3900
    3901 AGTTCCACCA GATGCTGATG AAGATAATAA TGAAGTAGCT ACAGCTCAAC TTACCTGCCA ACCCCATGCC
AGTCGACCCA actagtACAA CCTAAATCCA 4000
    4001 TCATAAAAAA CTTAGGAGCA AAGTGATTGC CTCCCAAGTT CCACAATGAC AGAGATCTAC GACTTCGACA
AGTCGGCATG GGACATCAAA GGGTCGATCG 4100
    4101 CTCCGATACA ACCCACCACC TACAGTGATG GCAGGCTGGT GCCCCAGGTC AGAGTCATAG ATCCTGGTCT
AGGCGACAGG AAGGATGAAT GCTTTATGTA 4200
    4201 CATGTTTCTG CTGGGGGTTG TTGAGGACAG GGATTCCCTA GGGCCTCCAA TCGGGCGAGC ATTTGGGTCC
CTGCCCTTAG GTGTTGGCAG ATCCACAGA 4300
    4301 AAGCCCGAAA AACTCCTCAA AGAGGCCACT GAGCTTGACA TAGTTGTTAG ACGTACAGCA GGGCTCAATG
AAAAACTGGT GTTCTACAAC AACACCCCAC 4400
    4401 TAACTCTCCT CACACCTTGG AGAAAGGTCC TAACAACAGG GAGTGTCTTC AACGCAAACC AAGTGTGCAA
TGCGGTTAAT CTGATACCGC TCGATACCCC 4500
    4501 GCAGAGGTTC CGTGTTGTTT ATATGAGCAT CACCCGTCTT TCGGATAACG GGTATTACAC CGTTCCTAGA
AGAATGCTGG AATTCAGTCA GGTCAATGCA 4600
    4601 GTGGCCTTCA ACCTGCTGGT GACCCTTAGG ATTGACAAGG CGATAGGCCC TGGGAAGATC ATCGACAATA
CAGAGCAACT TCCTGAGGCA ACATTTATAG 4700
    4701 TCCACATCGG GAACTTCAGG AGAAAGAAGA GTGAAGTCTA CTCTGCCGAT TATTGCAAAA TGAAAATCGA
AAAGATGGGC CTGGTTTTTG CACTCGGTGG 4800
    4801 GATAGGGGC ACCAGTCTTC ACATTAGAAG CACAGGCAAA ATGAGCAAGA CTCTCAATGC ACAACTCGGG
TTCAAGAAGA CCTTATGTTA CCCGCTGATG 4900
    4901 GATATCAATG AAGACCTTAA TCGATTACTC TGGAGGAGCA GATGCAAGAT AGTAAGAATC CAGGCAGTTT
TGCAGCCATC AGTTCCTCAA GAATTCCGCA 5000
    5001 TTTACGACGA CGTGATCATA AATGATGACC AAGGACTATT CAAAGTTCTG TAGACCGTAG TGCCCAGCAA
TGCCCGAAAA CGACCCCCCT CACAATGACA 5100
    5101 GCCAGAAGGC CCGGACAAAA AAGCCCCCTC CGAAAGACTC CACGGACCAA GCGAGAGGCC AGCCAGCAGC
CGACGGCAAG CGCGAACACC AGGCGGCCCC 5200
    5201 AGCACAGAAC AGCCCTGACA CAAGGCCACC ACCAGCCACC CCAATCTGCA TCCTCCTCGT GGGACCCCCG
AGGACCAACC CCCAAGGCTG CCCCCGATCC 5300
    5301 AAACCACCAA CCGCATCCCC ACCACCCCCG GGAAAGAAAC CCCCAGCAAT TGGAAGGCCC CTCCCCCTCT
TCCTCAACAC AAGAACTCCA CAACCGAACC 5400
    5401 GCACAAGCGA CCGAGGTGAC CCAACCGCAG GCATCCGACT CCCTAGACAG ATCCTCTCTC CCCGGCAAAC
TAAACAAAAC TTAGGGCCAA GGAACATACA 5500
    5501 CACCCAACAG AACCCAGACC CCGGCCCACG GCGCCGCGCC CCCAACCCCC GACAACCAGA GGGAGCCCCC
AACCAATCCC GCCGGCTCCC CCGGTGCCCA 5600
    5601 CAGGCAGGGA CACCAACCCC CGAACAGACC CAGCACCCAA CCATCGACAA TCCAAGACGG GGGGCCCCC
CCAAAAAAAA GCCCCAGGG GCCGACAGCC 5700
    5701 AGCACCGCGA GGAAGCCCAC CCACCCCACA CACGACCACG GCAACCAAAC CAGAACCCAG ACCACCCTGG
GCCACCAGCT CCCAGACTCG GCCATCACCC 5800
    5801 CGCAGAAAGG AAAGGCCACA ACCCGCGCAC CCCAGCCCCG ATCCGGCGGG GAGCCACCCA ACCCGAACCA
GCACCCAAGA GCGATCCCCG AAGGACCCCC 5900
    5901 GAACCGCAAA GGACATCAGT ATCCCACAGC CTCTCCAAGT CCCCCGGTCT CCTCCTCTTC TCGAAGGGAC
CAAAAGATCA ATCCACCACA CCCGACGACA 6000
    6001 CTCAACTCCC CACCCCTAAA GGAGACACCG GGAATCCCAG AATCAAGACT CATCCAATGT CCATCATGGG
TCTCAAGGTG AACGTCTCTG CCATATTCAT 6100
    6101 GGCAGTACTG TTAACTCTCC AAACACCCAC CGGTCAAATC CATTGGGGCA ATCTCTCTAA GATAGGGGTG
GTAGGAATAG GAAGTGCAAG CTACAAAGTT 6200
    6201 ATGACTCGTT CCAGCCATCA ATCATTAGTC ATAAAATTAA TGCCCAATAT AACTCTCCTC AATAACTGCA
CGAGGGTAGA GATTGCAGAA TACAGGAGAC 6300
    6301 TACTGAGAAC AGTTTTGGAA CCAATTAGAG ATGCACTTAA TGCAATGACC CAGAATATAA GACCGGTTCA
GAGTGTAGCT TCAAGTAGGA GACACAAGAG 6400
    6401 ATTTGCGGGA GTAGTCCTGG CAGGTGCGGC CCTAGGCGTT GCCACAGCTG CTCAGATAAC GGCCGGCATT
GCACTTCACC AGTCCATGCT GAACTCTCAA 6500
    6501 GCCATCGACA ATCTGAGAGC GAGCCTGGAA ACTACTAATC AGGCAATTGA GGCAATCAGA CAAGCAGGGC
AGGAGATGAT ATTGGCTGTT CAGGGTGTCC 6600
    6601 AAGACTACAT CAATAATGAG CTGATACCGT CTATGAACCA ACTATCTTGT GATTTAATCG GCCAGAAGCT
CGGGCTCAAA TTGCTCAGAT ACTATACAGA 6700
    6701 AATCCTGTCA TTATTTGGCC CCAGTTTACG GGACCCCATA TCTGCGGAGA TATCTATCCA GGCTTTGAGC
```

Figure 25(Contd..)

```
TATGCGCTTG GAGGAGACAT CAATAAGGTG 6800
   6801 TTAGAAAAGC TCGGATACAG TGGAGGTGAT TTACTGGGCA TCTTAGAGAG CAGAGGAATA AAGGCCCGGA
TAACTCACGT CGACACAGAG TCCTACTTCA 6900
   6901 TTGTCCTCAG TATAGCCTAT CCGACGCTGT CCGAGATTAA GGGGGTGATT GTCCACCGGC TAGAGGGGGT
CTCGTACAAC ATAGGCTCTC AAGAGTGGTA 7000
   7001 TACCACTGTG CCCAAGTATG TTGCAACCCA AGGGTACCTT ATCTCGAATT TTGATGAGTC ATCGTGTACT
TTCATGCCAG AGGGGACTGT GTGCAGCCAA 7100
   7101 AATGCCTTGT ACCCGATGAG TCCTCTGCTC CAAGAATGCC TCCGGGGGTA CACCAAGTCC TGTGCTCGTA
CACTCGTATC CGGGTCTTTT GGGAACCGGT 7200
   7201 TCATTTTATC ACAAGGGAAC CTAATAGCCA ATTGTGCATC AATCCTTTGC AAGTGTTACA CAACAGGAAC
GATCATTAAT CAAGACCCTG ACAAGATCCT 7300
   7301 AACATACATT GCTGCCGATC ACTGCCCGGT AGTCGAGGTG AACGGCGTGA CCATCCAAGT CGGGAGCAGG
AGGTATCCAG ACGCTGTGTA CTTGCACAGA 7400
   7401 ATTGACCTCG GTCCTCCCAT ATCATTGGAG AGGTTGGACG TAGGGACAAA TCTGGGGAAT GCAATTGCTA
AGTTGGAGGA TGCCAAGGAA TTGTTGGAGT 7500
   7501 CATCGGACCA GATATTGAGG AGTATGAAAG GTTTATCGAG CACTAGCATA GTCTACATCC TGATTGCAGT
GTGTCTTGGA GGGTTGATAG GGATCCCCGC 7600
   7601 TTTAATATGT TGCTGCAGGG GGCGTTGTAA CAAAAAGGGA GAACAAGTTG GTATGTCAAG ACCAGGCCTA
AAGCCTGATC TTACGGGAAC ATCAAAATCC 7700
   7701 TATGTAAGGT CGCTCTGATC CTCTACAACT CTTGAAACAC AAATGTCCCA CAAGTCTCCT CTTCGTCATC
AAGCAACCAC CGCACCCAGC ATCAAGCCCA 7800
   7801 CCTGAAATTA TCTCCGGCTT CCTCTGGCC GAACAATATC GGTAGTTAAT TAAAACTTAG GGTGCAAGAT
CATCCACAAT GTCACCACAA CGAGACCGGA 7900
   7901 TAAATGCCTT CTACAAAGAT AACCCCCATC CCAAGGGAAG TAGGATAGTC ATTAACGAG AACATCTTAT
GATTGATAGA CCTTATGTTT TGCTGGCTGT 8000
   8001 TCTGTTTGTC ATGTTTCTGA GCTTGATCGG GTTGCTAGCC ATTGCAGGCA TTAGACTTCA TCGGGCAGCC
ATCTACACCG CAGAGATCCA TAAAAGCCTC 8100
   8101 AGCACCAATC TAGATGTAAC TAACTCAATC GAGCATCAGG TCAAGGACGT GCTGACACCA CTCTTCAAAA
TCATCGGTGA TGAAGTGGGC CTGAGGACAC 8200
   8201 CTCAGAGATT CACTGACCTA GTGAAATTCA TCTCTGACAA GATTAAATTC CTTAATCCGG ATAGGGAGTA
CGACTTCAGA GATCTCACTT GGTGTATCAA 8300
   8301 CCCGCCAGAG AGAATCAAAT TGGATTATGA TCAATACTGT GCAGATGTGG CTGCTGAAGA GCTCATGAAT
GCATTGGTGA ACTCAACTGT ACTGGAGACC 8400
   8401 AGAACAACCA ATCAGTTCCT AGCTGTCTCA AAGGGAAACT GCTCAGGGCC CACTACAATC AGAGGTCAAT
TCTCAAACAT GTCGCTGTCC CTGTTAGACT 8500
   8501 TGTATTTAGG TCGAGGTTAC AATGTGTCAT CTATAGTCAC TATGACATCC CAGGGAATGT ATGGGGGAAC
TTACCTAGTG GAAAAGCCTA ATCTGAGCAG 8600
   8601 CAAAAGGTCA GAGTTGTCAC AACTGAGCAT GTACCGAGTG TTTGAAGTAG GTGTTATCAG AAATCCGGGT
TTGGGGGCTC CGGTGTTCCA TATGACAAAC 8700
   8701 TATCTTGAGC AACCAGTCAG TAATGATCTC AGCAACTGTA TGGTGGCTTT GGGGGAGCTC AAACTCGCAG
CCCTTTGTCA CGGGGAAGAT TCTATCACAA 8800
   8801 TTCCCTATCA GGGATCAGGG AAAGGTGTCA GCTTCCAGCT CGTCAAGCTA GGTGTCTGGA AATCCCCAAC
CGACATGCAA TCCTGGGTCC CCTTATCAAC 8900
   8901 GGATGATCCA GTGATAGACA GGCTTTACCT CTCATCTCAC AGAGGTGTTA TCGCTGACAA TCAAGCAAAA
TGGGCTGTCC CGACAACACG AACAGATGAC 9000
   9001 AAGTTGCGAA TGGAGACATG CTTCCAACAG GCGTGTAAGG GTAAAATCCA AGCACTCTGC GAGAATCCCG
AGTGGGCACC ATTGAAGGAT AACAGGATTC 9100
   9101 CTTCATACGG GGTCTTGTCT GTTGATCTGA GTCTGACAGT TGAGCTTAAA ATCAAAATTG CTTCGGGATT
CGGGCCATTG ATCACACACG GTTCAGGGAT 9200
   9201 GGACCTATAC AAATCCAACC ACAACAATGT GTATTGGCTG ACTATCCCGC CAATGAAGAA CCTAGCCTTA
GGTGTAATCA ACACATTGGA GTGGATACCG 9300
   9301 AGATTCAAGG TTAGTCCCTA CCTCTTCACT GTCCCAATTA AGGAAGCAGG CGAAGACTGC CATGCCCCAA
CATACCTACC TGCGGAGGTG GATGGTGATG 9400
   9401 TCAAACTCAG TTCCAATCTG GTGATTCTAC CTGGTCAAGA TCTCCAATAT GTTTTGGCAA CCTACGATAC
TTCCAGGGTT GAACATGCTG TGGTTTATTA 9500
   9501 CGTTTACAGC CCAGGCCGCT CATTTTCTTA CTTTTATCCT TTTAGGTTGC CTATAAAGGG GGTCCCCATC
GAATTACAAG TGGAATGCTT CACATGGGAC 9600
   9601 CAAAAACTCT GGTGCCGTCA CTTCTGTGTG CTTGCGGACT CAGAATCTGG TGGACATATC ACTCACTCTG
GGATGGTGGG CATGGGAGTC AGCTGCACAG 9700
   9701 TCACCCGGGA AGATGGAACC AATGCAGAT AGGGCTGCTA GTGAACCAAT CACATGATGT CACCCAGACA
TCAGGCATAC CCactagtct accctccatc 9800
   9801 attgttataa aaaacttagg aaccaggtcc acacagccgc cagcccatca AcgcgTATCT TCACCGGTGA
TCTATCGCGt acgtagcgcg catgagtaaa 9900
   9901 ggagaagaac ttttcactgg agttgtccca attcttgttg aattagatgg tgatgttaat gggcacaaat
tttctgtcag tggagagggt gaaggtgatg 10000
  10001 caacatacgg aaaacttacc cttaaattta tttgcactac tggaaaacta cctgttccat ggccaacact
tgtcactact ttcacctatg gtgttcaatg 10100
  10101 cttttcaaga tacccagatc atatgaaacg gcatgacttt ttcaagagtg ccatgcccga aggttacgta
caggaaagaa ctatattttt caaagatgac 10200
```

Figure 25(Contd..)

```
10201 gggaactaca agacacgtgc tgaagtcaag tttgaaggtg ataccttgt taatagaatc gagttaaaag
gtattgattt taaagaagat ggaaacattc 10300
10301 ttggacacaa attggaatac aactataact cacacaatgt atacatcatg gcagacaaac aaaagaatgg
aatcagagtt aacttcaaaa ttagacacaa 10400
10401 cattgaagat ggaagcgttc aactagcaga ccattatcaa caaaatactc caattggcga tggccctgtc
cttttaccag acaaccatta cctgtccaca 10500
10501 caatctgccc tttcgaaaga tcccaacgaa aagagagacc acatggtcct tcttgagttt gtaacagctg
ctgggattac acatggcatg gatgaactat 10600
10601 acaaatagtg agcgcgcagc gctgacgtct cgcgatgata ctagtGTGAA ATAGACATCA GAATTAAGAA
AAACGTAGGG TCCAAGTGGT TCCCCGTTAT 10700
10701 GGACTCGCTA TCTGTCAACC AGATCTTATA CCCTGAAGTT CACCTAGATA GCCCGATAGT TACCAATAAG
ATAGTAGCCA TCCTGGAGTA TGCTCGAGTC 10800
10801 CCTCACGCTT ACAGCCTGGA GGACCCTACA CTGTGTCAGA ACATCAAGCA CCGCCTAAAA AACGGATTTT
CCAACCAAAT GATTATAAAC AATGTGGAAG 10900
10901 TTGGGAATGT CATCAAGTCC AAGCTTAGGA GTTATCCGGC CCACTCTCAT ATTCCATATC CAAATTGTAA
TCAGGATTTA TTTAACATGA AAGACAAAGA 11000
11001 GTCAACGAGG AAGATCCGTG AACTCCTCAA AAAGGGGAAT TCGCTGTACT CCAAAGTCAG TGATAAGGTT
TTCCAATGCT TAAGGACAC TAACTCACGG 11100
11101 CTTGGCCTAG GCTCCGAATT GAGGGAGGAC ATCAAGGAGA AAGTTATTAA CTTGGGAGTT TACATGCACA
GCTCCCAGTG GTTTGAGCCC TTTCTGTTTT 11200
11201 GGTTTACAGT CAAGACTGAG ATGAGGTCAG TGATTAAATC ACAAACCCAT ACTTGCCATA GGAGGAGACA
CACACCTGTA TTCTTCACTG GTAGTTCAGT 11300
11301 TGAGTTGCTA ATCTCTCGTG ACCTTGTTGC TATAATCAGT AAAGAGTCTC AACATGTATA TTACCTGACA
TTTGAACTGG TTTTGATGTA TTGTGATGTC 11400
11401 ATAGAGGGGA GGTTAATGAC AGAGACCGCT ATGACTATTG ATGCTAGGTA TACAGAGCTT CTAGGAAGAG
TCAGATACAT GTGGAAACTG ATAGATGGTT 11500
11501 TCTTCCCTGC ACTCGGGAAT CCAACTTATC AAATTGTAGC AATGCTGGAG CCTCTTTCAC TTGCTTACCT
GCAGCTGAGG GATATAACAG TAGAACTCAG 11600
11601 AGGTGCTTTC CTTAACCACT GCTTTACTGA AATACATGAT GTTCTTGACC AAAACGGGTT TTCTGATGAA
GGTACTTATC ATGAGTTAAT TGAAGCTCTA 11700
11701 GATTACATTT TCATAACTGA TGACATACAT CTGACAGGGG AGATTTTCTC ATTTTTCAGA AGTTTCGGCC
ACCCCAGACT TGAAGCAGTA ACGGCTGCTG 11800
11801 AAAATGTTAG GAAATACATG AATCAGCCTA AAGTCATTGT GTATGAGACT CTGATGAAAG GTCATGCCAT
ATTTTGTGGA ATCATAATCA ACGGCTATCG 11900
11901 TGACAGGCAC GGAGGCAGTT GGCCACCGCT GACCCTCCCC CTGCATGCTG CAGACACAAT CCGGAATGCT
CAAGCTTCAG GTGAAGGGTT AACACATGAG 12000
12001 CAGTGCGTTG ATAACTGGAA ATCTTTTGCT GGAGTGAAAT TTGGCTGCTT TATGCCTCTT AGCCTGGATA
GTGATCTGAC AATGTACCTA AAGGACAAGG 12100
12101 CACTTGCTGC TCTCCAAAGG GAATGGGATT CAGTTTACCC GAAAGAGTTC CTGCGTTACG ACCCTCCCAA
GGGAACCGGG TCACGGAGGC TTGTAGATGT 12200
12201 TTTCCTTAAT GATTCGAGCT TTGACCCATA TGATGTGATA ATGTATGTTG TAAGTGGAGC TTACCTCCAT
GACCCTGAGT TCAACCTGTC TTACAGCCTG 12300
12301 AAAGAAAAGG AGATCAAGGA AACAGGTAGA CTTTTTGCTA AAATGACTTA CAAAATGAGG GCATGCCAAG
TGATTGCTGA AAATCTAATC TCAAACGGGA 12400
12401 TTGGCAAATA TTTTAAGGAC AATGGGATGG CCAAGGATGA GCACGATTTG ACTAAGGCAC TCCACACTCT
AGCTGTCTCA GGAGTCCCCA AAGATCTCAA 12500
12501 AGAAAGTCAC AGGGGGGGGC CAGTCTTAAA AACCTACTCC CGAAGCCCAG TCCACACAAG TACCAGGAAC
GTGAGAGCAG CAAAAGGGTT TATAGGGTTC 12600
12601 CCTCAAGTAA TTCGGCAGGA CCAAGACACT GATCATCCGG AGAATATGGA AGCTTACGAG ACAGTCAGTG
CATTTATCAC GACTGATCTC AAGAAGTACT 12700
12701 GCCTTAATTG GAGATATGAG ACCATCAGCT TGTTTGCACA GAGGCTAAAT GAGATTTACG GATTGCCCTC
ATTTTTCCAG TGGCTGCATA AGAGGCTTGA 12800
12801 GACCTCTGTC CTGTATGTAA GTGACCCTCA TTGCCCCCCC GACCTTGACG CCCATATCCC GTTATATAAA
GTCCCCAATG ATCAAATCTT CATTAAGTAC 12900
12901 CCTATGGGAG GTATAGAAGG GTATTGTCAG AAGCTGTGGA CCATCAGCAC CATTCCCTAT CTATACCTGG
CTGCTTATGA GAGCGGAGTA AGGATTGCTT 13000
13001 CGTTAGTGCA AGGGGACAAT CAGACCATAG CCGTAACAAA AAGGGTACCC AGCACATGGC CCTACAACCT
TAAGAAACGG GAAGCTGCTA GAGTAACTAG 13100
13101 AGATTACTTT GTAATTCTTA GGCAAAGGCT ACATGATATT GGCCATCACC TCAAGGCAAA TGAGACAATT
GTTTCATCAC ATTTTTTGT CTATTCAAAA 13200
13201 GGAATATATT ATGATGGGCT ACTTGTGTCC CAATCACTCA AGAGCATCGC AAGATGTGTA TTCTGGTCAG
AGACTATAGT TGATGAAACA AGGGCAGCAT 13300
13301 GCAGTAATAT TGCTACAACA ATGGCTAAAA GCATCGAGAG AGGTTATGAC CGTTACCTTG CATATTCCCT
GAACGTCCTA AAAGTGATAC AGCAAATTCT 13400
13401 GATCTCTCTT GGCTTCACAA TCAATTCAAC CATGACCCGG GATGTAGTCA TACCCCTCCT CACAAACAAC
GACCTCTTAA TAAGGATGGC ACTGTTGCCC 13500
13501 GCTCCTATTG GGGGATGAA TTATCTGAAT ATGAGCAGGC TGTTTGTCAG AAACATCGGT GATCCAGTAA
CATCATCAAT TGCTGATCTC AAGAGAATGA 13600
```

Figure 25 (Contd..)

```
13601 TTCTCGCCTC ACTAATGCCT GAAGAGACCC TCCATCAAGT AATGACACAA CAACCGGGGG ACTCTTCATT
CCTAGACTGG GCTAGCGACC CTTACTCAGC 13700
13701 AAATCTTGTA TGTGTCCAGA GCATCACTAG ACTCCTCAAG AACATAACTG CAAGGTTTGT CCTGATCCAT
AGTCCAAACC CAATGTTAAA AGGATTATTC 13800
13801 CATGATGACA GTAAAGAAGA GGACGAGGGA CTGGCGGCAT TCCTCATGGA CAGGCATATT ATAGTACCTA
GGGCAGCTCA TGAAATCCTG GATCATAGTG 13900
13901 TCACAGGGGC AAGAGAGTCT ATTGCAGGCA TGCTGGATAC CACAAAAGGC TTGATTCGAG CCAGCATGAG
GAAGGGGGGG TTAACCTCTC GAGTGATAAC 14000
14001 CAGATTGTCC AATTATGACT ATGAACAATT CAGAGCAGGG ATGGTGCTAT TGACAGGAAG AAAGAGAAAT
GTCCTCATTG ACAAAGAGTC ATGTTCAGTG 14100
14101 CAGCTGGCGA GAGCTCTAAG AAGCCATATG TGGGCGAGGC TAGCTCGAGG ACGGCCTATT TACGGCCTTG
AGGTCCCTGA TGTACTAGAA TCTATGCGAG 14200
14201 GCCACCTTAT TCGGCGTCAT GAGACATGTG TCATCTGCGA GTGTGGATCA GTCAACTACG GATGGTTTTT
TGTCCCCTCG GGTTGCCAAC TGGATGATAT 14300
14301 TGACAAGGAA ACATCATCCT TGAGAGTCCC ATATATTGGT TCTACCACTG ATGAGAGAAC AGACATGAAG
CTTGCCTTCG TAAGAGCCCC AAGTCGATCC 14400
14401 TTGCGATCTG CTGTTAGAAT AGCAACAGTG TACTCATGGG CTTACGGTGA TGATGATAGC TCTTGGAACG
AAGCCTGGTT GTTGGCTAGG CAAAGGGCCA 14500
14501 ATGTGAGCCT GGAGGAGCTA AGGGTGATCA CTCCCATCTC AACTTCGACT AATTTAGCGC ATAGGTTGAG
GGATCGTAGC ACTCAAGTGA AATACTCAGG 14600
14601 TACATCCCTT GTCCGAGTGG CGAGGTATAC CACAATCTCC AACGACAATC TCTCATTTGT CATATCAGAT
AAGAAGGTTG ATACTAACTT TATATACCAA 14700
14701 CAAGGAATGC TCCTAGGGTT GGGTGTTTTA GAAACATTGT TTCGACTCGA GAAAGATACC GGATCATCTA
ACACGGTATT ACATCTTCAC GTCGAAACAG 14800
14801 ATTGTTGCGT GATCCCGATG ATAGATCATC CCAGGATACC CAGCTCCCGC AAGCTAGAGC TGAGGGCAGA
GCTATGTACC AACCCATTGA TATATGATAA 14900
14901 TGCACCTTTA ATTGACAGAG ATGCAACAAG GCTATACACC CAGAGCCATA GGAGGCACCT TGTGGAATTT
GTTACATGGT CCACACCCCA ACTATATCAC 15000
15001 ATTTTAGCTA AGTCCACAGC ACTATCTATG ATTGACCTGG TAACAAAATT TGAGAAGGAC CATATGAATG
AAATTTCAGC TCTCATAGGG GATGACGATA 15100
15101 TCAATAGTTT CATAACTGAG TTTCTGCTCA TAGAGCCAAG ATTATTCACT ATCTACTTGG GCCAGTGTGC
GGCCATCAAT TGGGCATTTG ATGTACATTA 15200
15201 TCATAGACCA TCAGGGAAAT ATCAGATGGG TGAGCTGTTG TCATCGTTCC TTTCTAGAAT GAGCAAAGGA
GTGTTTAAGG TGCTTGTCAA TGCTCTAAGC 15300
15301 CACCCAAAGA TCTACAAGAA ATTCTGGCAT TGTGGTATTA TAGAGCCTAT CCATGGTCCT TCACTTGATG
CTCAAAACTT GCACACAACT GTGTGCAACA 15400
15401 TGGTTTACAC ATGCTATATG ACCTACCTCG ACCTGTTGTT GAATGAAGAG TTAGAAGAGT TCACATTTCT
CTTGTGTGAA AGCGACGAGG ATGTAGTACC 15500
15501 GGACAGATTC GACAACATCC AGGCAAAACA CTTATGTGTT CTGGCAGATT TGTACTGTCA ACCAGGGACC
TGCCCACCAA TTCGAGGTCT AAGACCGGTA 15600
15601 GAGAAATGTG CAGTTCTAAC CGACCATATC AAGGCAGAGG CTATGTTATC TCCAGCAGGA TCTTCGTGGA
ACATAAATCC AATTATTGTA GACCATTACT 15700
15701 CATGCTCTCT GACTTATCTC CGGCGAGGAT CGATCAAACA GATAAGATTG AGAGTTGATC CAGGATTCAT
TTTCGACGCC CTCGCTGAGG TAAATGTCAG 15800
15801 TCAGCCAAAG ATCGGCAGCA ACAACATCTC AAATATGAGC ATCAAGGCTT TCAGACCCCC ACACGATGAT
GTTGCAAAAT TGCTCAAAGA TATCAACACA 15900
15901 AGCAAGCACA ATCTTCCCAT TTCAGGGGGC AATCTCGCCA ATTATGAAAT CCATGCTTTC CGCAGAATCG
GGTTGAACTC ATCTGCTTGC TACAAAGCTG 16000
16001 TTGAGATATC AACATTAATT AGGAGATGCC TTGAGCCAGG GGAGGACGGC TTGTTCTTGG GTGAGGGATC
GGGTTCTATG TTGATCACTT ATAAGGAGAT 16100
16101 ACTTAAACTA AACAAGTGCT TCTATAATAG TGGGGTTTCC GCCAATTCTA GATCTGGTCA AAGGGAATTA
GCACCCTATC CCTCCGAAGT TGGCCTTGTC 16200
16201 GAACACAGAA TGGGAGTAGG TAATATTGTC AAAGTGCTCT TTAACGGGAG GCCCGAAGTC ACGTGGGTAG
GCAGTGTAGA TTGCTTCAAT TTCATAGTTA 16300
16301 GTAATATCCC TACCTCTAGT GTGGGGTTTA TCCATTCAGA TATAGAGACC TTGCCTGACA AAGATACTAT
AGAGAAGCTA GAGGAATTGG CAGCCATCTT 16400
16401 ATCGATGGCT CTGCTCCTGG GCAAAATAGG ATCAATACTG GTGATTAAGC TTATGCCTTT CAGCGGGGAT
TTTGTTCAGG GATTTATAAG TTATGTAGGG 16500
16501 TCTCATTATA GAGAAGTGAA CCTTGTATAC CCTAGATACA GCAACTTCAT ATCTACTGAA TCTTATTTGG
TTATGACAGA TCTCAAGGCT AACCGGCTAA 16600
16601 TGAATCCTGA AAAGATTAAG CAGCAGATAA TTGAATCATC TGTGAGGACT TCACCTGGAC TTATAGGTCA
CATCCTATCC ATTAAGCAAC TAAGCTGCAT 16700
16701 ACAAGCAATT GTGGGAGCG CAGTTAGTAG AGGTGATATC AATCCTACTC TGAAAAACT TACACCTATA
GAGCAGGTGC TGATCAATTG CGGGTTGCAA 16800
16801 ATTAACGGAC CTAAGCTGTG CAAAGAATTG ATCCACCATG ATGTTGCCTC AGGGCAAGAT GGATTGCTTA
ATTCTATACT CATCCTCTAC AGGGAGTTGG 16900
16901 CAAGATTCAA AGACAACCAA AGAAGTCAAC AAGGGATGTT CCACGCTTAC CCCGTATTGG TAAGTAGCAG
GCAACGAGAA CTTATATCTA GGATCACCCG 17000
```

Figure 25(Contd..)

```
17001 CAAATTTTGG GGGCACATTC TTCTTTACTC CGGGAACAGA AAGTTGATAA ATAAGTTTAT CCAGAATCTC
AAGTCCGGCT ATCTGATACT AGACTTACAC 17100
17101 CAGAATATCT TCGTTAAGAA TCTATCCAAG TCAGAGAAAC AGATTATTAT GACGGGGGGT TTGAAACGTG
AGTGGGTTTT TAAGGTAACA GTCAAGGAGA 17200
17201 CCAAAGAATG GTATAAGTTA GTCGGATACA GTGCCCTGAT TAAGGACTAA TTGGTTGAAC TCCGGAACCC
TAATCCTGCC CTAGGTGGTT AGGCATTATT 17300
17301 TGCAATATAT TAAAGAAAAC TTTGAAAATA CGAAGTTTCT ATTCCCAGCT TTGTCTGGTg gccggcatgg
tcccagcctc ctcgctggcg ccggctgggc 17400
17401 aacattccga ggggaccgtc ccctcggtaa tggcgaatgg gacGCGGCCg atccggctgc taacaaagcc
cgaaaggaag ctgagttggc tgctgccacc 17500
17501 gctgagcaat aactagcata accccttggg gcctctaaac gggtcttgag gggttttttg ctgaaaggag
gaactatatc cggatGCGGC CGCaGGTACC 17600
17601 CAGCTTTTGT TCCCtttagt gagggttaat tTCGAGCTTG GCGTAATCAT GGTCATAGCT GTTTCCTGTG
TGAAATTGTT ATCCGCTCAC AATTCCACAC 17700
17701 AACATACGAG CCGGAAGCAT AAAGTGTAAA GCCTGGGGTG CCTAATGAGT GAGCTAACTC ACATTAATTG
CGTTGCGCTC ACTGCCCGCT TTCCAGTCGG 17800
17801 GAAACCTGTC GTGCCAGCTG CATTAATGAA TCGGCCAACG CGCGGGGAGA GGCGGTTTGC GTATTGGGCG
CTCTTCCGCT TCCTCGCTCA CTGACTCGCT 17900
17901 GCGCTCGGTC GTTCGGCTGC GGCGAGCGGT ATCAGCTCAC TCAAAGGCGG TAATACGGTT ATCCACAGAA
TCAGGGGATA ACGCAGGAAA GAACATGTGA 18000
18001 GCAAAAGGCC AGCAAAAGGC CAGGAACCGT AAAAAGGCCG CGTTGCTGGC GTTTTTCCAT AGGCTCCGCC
CCCCTGACGA GCATCACAAA AATCGACGCT 18100
18101 CAAGTCAGAG GTGGCGAAAC CCGACAGGAC TATAAAGATA CCAGGCGTTT CCCCCTGGAA GCTCCCTCGT
GCGCTCTCCT GTTCCGACCC TGCCGCTTAC 18200
18201 CGGATACCTG TCCGCCTTTC TCCCTTCGGG AAGCGTGGCG CTTTCTCATA GCTCACGCTG TAGGTATCTC
AGTTCGGTGT AGGTCGTTCG CTCCAAGCTG 18300
18301 GGCTGTGTGC ACGAACCCCC CGTTCAGCCC GACCGCTGCG CCTTATCCGG TAACTATCGT CTTGAGTCCA
ACCCGGTAAG ACACGACTTA TCGCCACTGG 18400
18401 CAGCAGCCAC TGGTAACAGG ATTAGCAGAG CGAGGTATGT AGGCGGTGCT ACAGAGTTCT TGAAGTGGTG
GCCTAACTAC GGCTACACTA GAAGGACAGT 18500
18501 ATTTGGTATC TGCGCTCTGC TGAAGCCAGT TACCTTCGGA AAAAGAGTTG GTAGCTCTTG ATCCGGCAAA
CAAACCACCG CTGGTAGCGG TGGTTTTTTT 18600
18601 GTTTGCAAGC AGCAGATTAC GCGCAGAAAA AAAGGATCTC AAGAAGATCC TTTGATCTTT TCTACGGGGT
CTGACGCTCA GTGGAACGAA AACTCACGTT 18700
18701 AAGGGATTTT GGTCATGAGA TTATCAAAAA GGATCTTCAC CTAGATCCTT TTAAATTAAA AATGAAGTTT
TAAATCAATC TAAAGTATAT ATGAGTAAAC 18800
18801 TTGGTCTGAC AGTTACCAAT GCTTAATCAG TGAGGCACCT ATCTCAGCGA TCTGTCTATT TCGTTCATCC
ATAGTTGCCT GACTCCCCGT CGTGTAGATA 18900
18901 ACTACGATAC GGGAGGGCTT ACCATCTGGC CCCAGTGCTG CAATGATACC GCGAGACCCA CGCTCACCGG
CTCCAGATTT ATCAGCAATA AACCAGCCAG 19000
19001 CCGGAAGGGC CGAGCGCAGA AGTGGTCCTG CAACTTTATC CGCCTCCATC CAGTCTATTA ATTGTTGCCG
GGAAGCTAGA GTAAGTAGTT CGCCAGTTAA 19100
19101 TAGTTTGCGC AACGTTGTTG CCATTGCTAC AGGCATCGTG GTGTCACGCT CGTCGTTTGG TATGGCTTCA
TTCAGCTCCG GTTCCCAACG ATCAAGGCGA 19200
19201 GTTACATGAT CCCCCATGTT GTGCAAAAAA GCGGTTAGCT CCTTCGGTCC TCCGATCGTT GTCAGAAGTA
AGTTGGCCGC AGTGTTATCA CTCATGGTTA 19300
19301 TGGCAGCACT GCATAATTCT CTTACTGTCA TGCCATCCGT AAGATGCTTT TCTGTGACTG GTGAGTACTC
AACCAAGTCA TTCTGAGAAT AGTGTATGCG 19400
19401 GCGACCGAGT TGCTCTTGCC CGGCGTCAAT ACGGGATAAT ACCGCGCCAC ATAGCAGAAC TTTAAAAGTG
CTCATCATTG GAAAACGTTC TTCGGGGCGA 19500
19501 AAACTCTCAA GGATCTTACC GCTGTTGAGA TCCAGTTCGA TGTAACCCAC TCGTGCACCC AACTGATCTT
CAGCATCTTT TACTTTCACC AGCGTTTCTG 19600
19601 GGTGAGCAAA AACAGGAAGG CAAAATGCCG CAAAAAAGGG AATAAGGGCG ACACGGAAAT GTTGAATACT
CATACTCTTC CTTTTTCAAT ATTATTGAAG 19700
19701 CATTTATCAG GGTTATTGTC TCATGAGCGG ATACATATTT GAATGTATTT AGAAAAATAA ACAAATAGGG
GTTCCGCGCA CATTTCCCCG AAAAGTGC  19798
```

Figure 25(Contd..)

```
          |   10       |   20       |   30       |   40       |   50       |   60       |
70        |   80       |   90       |  100
    1 ATGaccgtcg  cgcggccgag  cgtgcccgcg  gcgctgcccc  tcctcgggga  gctgcccgg
ctgctgctgc tggtgctgtt gtgcctgccg gccgtgtggG 100
  101 GATCCGTGAC  CCACGAATCC  TATCAGGAGC  TGGTTAAGAA  ACTGGAAGCT  TTAGAGGACG
CCGTATTGAC AGGTTACTCC CTATTCCAGA AAGAAAAGAT 200
  201 GGTTTTAAAC  GAAGAAGAAA  TTACCACAAA  GGGAGCATCC  GCCCAGTCTG  GAGCATCTGC
TCAGAGCGGA GCATCTGCTC AGAGTGGAGC AAGCGCCCAA 300
  301 AGTGGAGCGT  CTGCCCAGTC  AGGCGCCTCA  GCTCAATCTG  GAACCTCTGG  GCCGAGTGGT
CCTAGCGGTA CTTCTCCAAG TAGCCGGTCT AATACACTCC 400
  401 CACGTTCCAA  CACCTCCAGT  GGAGCCTCCC  CACCCGCCGA  CGCATCCGAC  TCAGACGCTA
AGAGTTATGC AACCTGAAG CACCGCGTGA GGAACTACCT 500
  501 TTTCACTATC  AAAGAGTTGA  AGTACCCTGA  ATTGTTCGAT  TTGACCAACC  ATATGCTGAC
ACTCTGTGAC AACATACATG GTTTCAAGTA TCTGATAGAT 600
  601 GGGTATGAAG  AAATTAACGA  GCTGCTCTAT  AAACTCAACT  TTTACTTCGA  CCTGCTGCGT
GCCAAGCTGA ACGATGTCTG TGCAAACGAT TACTGCCAGA 700
  701 TCCCATTCAA  CCTAAAGATA  CGTGCGAACG  AGCTGGATGT  TCTGAAGAAA  CTCGTGTTCG
GGTATCGGAA ACCCTTGGAC AACATTAAGG ACAATGTGGG 800
  801 GAAGATGGAG  GATTACATTA  AGAAAAATAA  AACAACAATC  GCTAACATAA  ATGAGCTTAT
CGAGGGGAGC AAAAAGACCA TCGACCAGAA CAAGAATGCC 900
  901 GACAATGAAG  AGGGAAAAAA  GAAACTATAC  CAAGCCCAGT  ATGATTTGAG  CATCTACAAT
    AAGCAACTAG AGGAAGCTCA CAACCCTCATC AGCGTACTGG 1000
 1001 AAAAGAGAAT  TGACACCCTG  AAAAAGAATG  AAAACATTAA  GAAACTCCTG  GACAAGATTA
ACGAAATTAA AAACCCaCCt CCaGCGAATA GCGGAAATAC 1100
 1101 CCCGAATACC  CTGCTGGATA  AGAACAAAAA  GATTGAAGAG  CACGAAGAGA  AAATCAAGGA
AATCGCCAAG ACTATTAAGT TCAATATAGA TTCTCTGTTC 1200
 1201 ACAGACCCtC  TGGAGCTGGA  ATACTACCTG  CGCGAGAAGA  ATAAGAAGGT  CGACGTGACC
CCAAAGAGCC AAGACCCAAC AAAGTCCGTG CAGATCCCCA 1300
 1301 AAGTGCCCTA  CCCCAAACGGC  ATCGTGTATC  CCCTGCCTCT  TACCGACATC  CACAACTCTC
TGGCAGCCGA TAACGACAAA AACAGCTATG GAGACCTGAT 1400
 1401 GAACCCCAC  ACTAAGGAAA  AGATAAACGA  GAAGATCATT  ACCGATAATA  AGGAGCGGAA
GATTTTTATC AACAACATCA AGAAGAAAAT CGACCTGGAA 1500
 1501 GAGAAAAATA  TCAATCACAC  CAAAGAGCAA  AACAAGAAAT  TACTGGAGGA  CTATGAGAAG
AGCAAAAAGG ATTATGAGGA ACTGTTAGAG AAGTTCTATG 1600
 1601 AAATGAAATT  CAACAACAAT  TTCGATAAGG  ATGTGGTCGA  TAAAATTTTC  AGCGCCCGGT
ACACCTACAA CGTGGAGAAG CAGCGGTACA ACAATAAGTT 1700
 1701 CAGCAGCTCC  AATAACTCGG  TCTACAATGT  GCAGAAGCTG  AAGAAAGCTC  TGAGCTATCT
GGAAGACTAC TCGCTGAGGA AAGGGATTTC TGAGAAGGAT 1800
 1801 TTCAACCACT  ACTACACCCT  CAAAACCGGC  CTGGAAGCTG  ACATCAAGAA  ACTCACTGAA
GAGATCAAAA GTTCTGAGAA TAAGATACTG GAGAAGAACT 1900
 1901 TCAAGGGACT  AACGCACTCT  GCAAACGGCT  CCCTGGAAGT  CTCTGACATC  GTGAAACTGC
AAGTCCAAAA GGTGCTGCTC ATCAAAAAAA TCGAGGATCT 2000
 2001 GCGAAAGATC  GAGCTGTTTC  TTAAGAACGC  CCAACTGAAA  GACTCAATCC  ACGTGCCTAA
CATTTACAAA CCGCAGAACA AACCAGAACC ATATTATCTG 2100
 2101 ATCGTGCTGA  AGAAGGAGG  GGATAAGCTG  AAGGAATTCA  TCCCAAAAGT  GAAAGATATG
TTAAAGAAAG AGCAAGCCGT GCTGAGCAGC ATAACGCAGC 2200
 2201 CTCTGGTGGC  CGCAAGCGAG  ACAACCGAAG  ATGGCGGGCA  CAGCACCCAC  ACCCTGTCTC
AGTCTGGCGA AACAGAGGTG ACAGAAGAGA CAGAAGAGAC 2300
 2301 CGAAGAAACA  GTGGGCACA   CCACTACTGT  GACCATCACT  TTGCCCCCTA  CGCAGCCATC
TCCCCCAAAA GAGGTCAAAG TCGTGGAAAA CTCCATTGAA 2400
 2401 CAGAAGTCCA  ACGACAACTC  ACAGGCTCTG  ACGAAGACCG  TCTATCTGAA  GAAACTGGAC
GAGTTCCTGA CCAAAAGCTA CATCTGCCAT AAATACATCC 2500
 2501 TCGTGTCTAA  CAGCAGCATG  GATCAGAAGC  TGTTGGAGGT  GTACAACCTA  ACGCCCGAAG
AAGAGAACGA GTTAAAATCC TGTGATCCCT TAGACCTACT 2600
 2601 GTTTAACATT  CAGAACAACA  TCCCCGCTAT  GTACAGCTTA  TATGATTCCA  TGAATAACGA
CCTCCAGCAC CTGTTCTTCG AGCTGTACCA GAAAGAGATG 2700
 2701 ATCTACTATC  TGCATAAGCT  GAAAGAGGAG  AATCACATCA  AAAAGTTGCT  GGAAGAGCAG
AAACAGATAA CTGGGACGTC CAGCACATCG TCACCTGGCA 2800
 2801 ACACGACAGT  AAATACCGCC  CAGTCTGCTA  CACACTCCAA  CTCCCAGAAC  CAGCAGAGCA
ACGCTTCTAG CACCAACACC CAGAATGGGG TAGCAGTTAG 2900
 2901 TAGCGGCCCT  GCTGTGGTGG  AGGAATCGCA  TGACCCCCTC  ACTGTATTAT  CTATTTCAAA
CGACCTAAAA GGGATTGTGT CCCTCCTCAA TTTAGGTAAT 3000
```

Figure 26

```
3001 AAGACCAAGG TCCCTAACCC CTTGACTATC AGCACTACGG AAATGGAGAA GTTTTATGAA
AACATCCTGA AGAACAACGA CACCTATTTT AACGACGACA 3100
3101 TAAAGCAGTT CGTGAAGAGT AACAGTAAAG TGATTACCGG GCTGACAGAA ACCCAGAAAA
ATGCTTTAAA TGATGAGATC AAGAAACTGA AAGACACACT 3200
3201 CCAGCTCTCC TTCGATCTGT ACAACAAGTA CAAACTAAAG CTGGACAGAT TATTCAATAA
GAAGAAGGAG CTTGGGCAAG ATAAGATGCA GATTAAGAAG 3300
3301 CTAACTTTAC TGAAGGAGCA GCTCGAGAGC AAGCTCAACT CCCTGAATAA TCCACATAAT
GTGCTCCAGA ACTTTTCCGT ATTCTTCAAT AAGAAGAAAG 3400
3401 AAGCAGAGAT TGCCGAGACG GAAAATACCC TCGAAAACAC TAAGATATTA CTGAAACACT
ATAAAGGGCT GGTGAAGTAT TACAACGGAG AGTCTAGCCC 3500
3501 ATTGAAGACT CTTTCAGAAG TGTCAATTCA AACCGAGGAT AACTACGCAA ACCTAGAAAA
GTTCAGAGTG CTGAGCAAAA TCGACGGCAA ACTCAATGAT 3600
3601 AACCTACACC TCGGAAAAAA AAAGCTGAGC TTCCTGTCCA GTGGACTTCA TCATTTAATT
ACCGAATTGA AAGAAGTTAT CAAAAACAAA AACTACACTG 3700
3701 GGAACAGCCC ATCTGAAAAT AATAAAAAGG TCAACGAGGC CCTCAAGTCT TATGAAAATT
TCCTTCCAGA AGCAAAAGTG ACAACCGTCG TGACCCCCCC 3800
3801 CCAGCCCGAT GTCACCCCCA GCCCTCTAAG CGTGAGAGTG TCTGGATCAA GTGGCTCCAC
AAAAGAAGAA ACCCAGATCC CCACATCAGG ATCTCTACTG 3900
3901 ACCGAGTTGC AGCAGGTCGT CCAACTCCAG AATTATGACG AGGAAGACGA CAGCCTCGTG
GTTTTGCCAA TCTTCGGCGA ATCAGAAGAC AACGACGAGT 4000
4001 ACCTAGACCA AGTGGTCACC GGGGAAGCGA TTAGTGTCAC TATGGACAAT ATCCTCAGCG
GCTTCGAGAA CGAGTATGAC GTGATCTACC TCAAACCACT 4100
4101 AGCCGGAGTT TACAGAAGTC TCAAGAAGCA GATCGAAAAG AACATCTTCA CCTTTAATCT
AAACCTAAAC GACATCTTGA ATTCCCGGCT GAAAAGCCG 4200
4201 AAATACTTCC TCGACGTACT GGAGTCGGAT TTGATGCAGT TTAAGCACAT CTCCAGCAAC
GAATACATTA TCGAGGACTC GTTCAAACTG TTAAACTCCG 4300
4301 AGCAGAAGAA CACCCTGCTG AAGTCCTACA AATATATCAA AGAGTCAGTC GAGAACGATA
TTAAATTCGC CCAAGAAGGC ATAAGCTACT ACGAAAAGGT 4400
4401 CCTCGCCAAA TACAAGGACG ATCTGGAGTC TATCAAAAAG GTCATCAAAG AAGAGAAAGA
GAAATTTCCC AGTTCTCCCC CTACAACGCC GCCCTCTCCA 4500
4501 GCCAAGACTG ATGAACAGAA AAAAGAGTCT AAGTTCCTCC CTTTCCTCAC TAATATCGAG
ACTCTCTACA ATAACCTAGT GAACAAGATT GACGACTACC 4600
4601 TGATCAACCT TAAAGCCAAG ATAAACGACT GCAATGTCGA GAAGGATGAG GCTCATGTTA
AGATCACCAA ACTGTCCGAT CTGAAAGCCA TCGACGACAA 4700
4701 GATCGACTTA TTTAAAAACC CATACGATTT CGAGGCTATC AAAAAGCTGA TCAATGATGA
CACCAAGAAA GATATGCTCG GCAAGCTGCT GAGCACGGGT 4800
4801 CTGGTGCAGA ACTTCCCTAA CACCATCATA TCAAAGCTCA TAGAGGGCAA GTTCCAAGAC
ATGCTGAATA TTTCACAGCA TCAGTGCGTC AAGAAGCAGT 4900
4901 GCCCCGAAAA TTCTGGATGC TTCCGGCACC TGGATGAGCG AGAAGAGTGC AAGTGCCTGC
TTAACTATAA ACAGGAGGGC GACAAATGTG TGGAGAACCC 5000
5001 AAATCCGACG TGCAACGAGA CAACGGTGG CTGCGATGCC GACGCGACTT GTACAGAGGA
AGACTCGGGG AGTTCTCGGA AAAAAATCAC GTGCGAGTGC 5100
5101 ACCAAACCCG ACAGTTATCC TCTGTTCGAT GGGATATTCT GCTCCTCCAG CaacgttACT
ACTTCCGGCA CTACCCGTCT TCTATCTGGT CACACGTGTT 5200
5201 TCACGTTGAC AGGTTTGCTT GGGACGCTAG TAACCATGGG CTTGCTGACT            TAA
5253
       |   10   |   20   |   30   |   40   |   50   |   60   |
  70   |   80   |   90   |  100
```

Figure 26 (Contd..)

```
       |   10       |   20       |   30       |   40       |   50       |   60       |   70
   |   80       |   90       |  100
       1 ATGaccgtcg cgcggccgag cgtgcccgcg gcgctgcccc tcctcgggga gctgcccgg
ctgctgctgc tggtgctgtt gtgcctgccg gccgtgtggg 100
     101 gatcCGTGAC CCACGAATCC TATCAGGAGC TGGTTAAGAA ACTGGAAGCT TTAGAGGACG
CCGTATTGAC AGGTTACTCC CTATTCCAGA AAGAAAGAT 200
     201 GGTTTTAAAC GAAGAAGAAA TTACCACAAA GGGAGCATCC GCCCAGTCTG GAGCATCTGC
TCAGAGCGGA GCATCTGCTC AGAGTGGAGC AAGCGCCCAA 300
     301 AGTGGAGCGT CTGCCCAGTC AGGCGCCTCA GCTCAATCTG GAACCTCTGG GCCGAGTGGT
CCTAGCGGTA CTTCTCCAAG TAGCCGGTCT AATACACTCC 400
     401 CACGTTCCAA CACCTCCAGT GGAGCCTCCC CACCCGCCGA CGCATCCGAC TCAGACGCTA
AGAGTTATGC AGACCTGAAG CACCGCGTGA GGAACTACCT 500
     501 TTTCACTATC AAAGAGTTGA AGTACCCTGA ATTGTTCGAT TTGACCAACC ATATGCTGAC
ACTCTGTGAC AACATACATG GTTTCAAGTA TCTGATAGAT 600
     601 GGGTATGAAG AAATTAACGA GCTGCTCTAT AAACTCAACT TTTACTTCGA CCTGCTGCGT
GCCAAGCTGA ACGATGTCTG TGCAAACGAT TACTGCCAGA 700
     701 TCCCATTCAA CCTAAAGATA CGTGCGAACG AGCTGGATGT TCTGAAGAAA CTCGTGTTCG
GGTATCGGAA ACCCTTGGAC AACATTAAGG ACAATGTGGG 800
     801 GAAGATGGAG GATTACATTA AGAAAAATAA AACAACAATC GCTAACATAA ATGAGCTTAT
CGAGGGGAGC AAAAAGACCA TCGACCAGAA CAAGAATGCC 900
     901 GACAATGAAG AGGGAAAAAA GAAACTATAC CAAGCCCAGT ATGATTTGAG CATCTACAAT
AAGCAACTAG AGGAAGCTCA CAACCTCATC AGCGTACTGG 1000
    1001 AAAAGAGAAT TGACACCCTG AAAAAGAATG AAAACATTAA GAAACTCCTG GACAAGATTA
ACGAAATTAA AAACCCaCCt CCaGCGAATA GCGGAAATAC 1100
    1101 CCCGAATACC CTGCTGGATA GAACAAAAA GATTGAAGAG CACGAAGAGA AAATCAAGGA
AATCGCCAAG ACTATTAAGT TCAATATAGA TTCTCTGTTC 1200
    1201 ACAGACCCtC TGGAGCTGGA ATACTACCTG CGCGAGAAGA ATAAGAAGGT CGACGTGACC
CCAAAGAGCC AAGACCCAAC AAAGTCCGTG CAGATCCCCA 1300
    1301 AAGTGCCCTA CCCAAACGGC ATCGTGTATC CCCTGCCTCT TACCGACATC CACAACTCTC
TGGCAGCCGA TAACAGCTATG GAGACCTGAT 1400
    1401 GAACCCCCAC ACTAAGGAAA AGATAAACGA GAAGATCATT ACCGATAATA AGGAGCGGAA
GATTTTTATC AACAACATCA AGAAGAAAAT CGACCTGGAA 1500
    1501 GAGAAAAATA TCAATCACAC CAAAGAGCAA AACAAGAAAT TACTGGAGGA CTATGAGAAG
AGCAAAAAGG ATTATGAGGA ACTGTTAGAG AAGTTCTATG 1600
    1601 AAATGAAATT CAACAACAAT TTCGATAAGG ATGTGGTCGA TAAAATTTTC AGCGCCCGGT
ACACCTACAA CGTGGAGAAG CAGCGGTACA ACAATAAGTT 1700
    1701 CAGCAGCTCC AATAACTCGG TCTACAATGT GCAGAAGCTG AAGAAAGCTC TGAGCTATCT
GGAAGACTAC TCGCTGAGGA AAGGGATTTC TGAGAAGGAT 1800
    1801 TTCAACCACT ACTACACCCT CAAAACCGGC CTGGAAGCTG ACATCAAGAA ACTCACTGAA
GAGATCAAAA GTTCTGAGAA TAAGATACTG GAGAAGAACT 1900
    1901 TCAAGGGACT AACGCACTCT GCAAACGGCT CCCTGGAAGT CTCTGACATC GTGAAACTGC
AAGTCCAAAA GGTGCTGCTC ATCAAAAAAA TCGAGGATCT 2000
    2001 GCGAAAGATC GAGCTGTTTC TTAAGAACGC CCAACTGAAA GACTCAATCC ACGTGCCTAA
CATTTACAAA CCGCAGAACA AACCAGAACC ATACTATCTG 2100
    2101 ATCGTGCTGA AGAAGGAGGT GGATAAGCTG AAGGAATTCA TCCCAAAAGT GAAAGATATG
TTAAAGAAAG AGCAAGCCGT GCTGAGCAGC ATAACGCAGC 2200
    2201 CTCTGGTGGC CGCAAGCGAG ACAACCGAAG ATGGCGGGCA CAGCACCCAC ACCCTGTCTC
AGTCTGGCGA AACAGAGGTG ACAGAAGAGA CAGAAGAGAC 2300
    2301 CGAAGAAACA GTGGGGCACA CCACTACTGT GACCATCACT TTGCCCCCTA CGCAGCCATC
TCCCCCAAAA GAGGTCAAAG TCGTGGAAAA CTCCATTGAA 2400
    2401 CAGAAGTCCA ACGACAACTC ACAGGCTCTG ACGAAGACCG TCTATCTGAA GAAACTGGAC
GAGTTCCTGA CCAAAAGCTA CATCTGCCAT AAATACATCC 2500
    2501 TCGTGTCTAA CAGCAGCATG GATCAGAAGC TGTTGGAGGT GTACAACCTA ACGCCCGAAG
AAGAGAACGA GTTAAAATCC TGTGATCCCT TAGACCTACT 2600
    2601 GTTTAACATT CAGAACAACA TCCCCGCTAT GTACAGCTTA TATGATTCCA TGAATAACGA
CCTCCAGCAC CTGTTCTTCG AGCTGTACCA GAAAGAGATG 2700
    2701 ATCTACTATC TGCATAAGCT GAAAGAGGAG AATCACATCA AAAGTTGCT GGAAGAGCAG
AAACAGATAA CTGGGACGTC CAGCACATCG TCACCTGGCA 2800
    2801 ACACGACAGT AAATACCGCC CAGTCTGCTA CACACTCCAA CTCCCAGAAC CAGCAGAGCA
ACGCTTCTAG CACCAACACC CAGAATGGGG TAGCAGTTAG 2900
    2901 TAGCGGCCCT GCTGTGGTGG AGGAATCGCA TGACCCCCTC ACTGTATTAT CTATTTCAAA
CGACCTAAAA GGGATTGTGT CCCTCCTCAA TTTAGGTAAT 3000
```

Figure 27

```
3001  AAGACCAAGG  TCCCTAACCC  CTTGACTATC  AGCACTACGG  AAATGGAGAA  GTTTTATGAA
AACATCCTGA AGAACAACGA CACCTATTTT AACGACGACA 3100
3101  TAAAGCAGTT  CGTGAAGAGT  AACAGTAAAG  TGATTACCGG  GCTGACAGAA  ACCCAGAAAA
ATGCTTTAAA TGATGAGATC AAGAAACTGA AAGACACACT 3200
3201  CCAGCTCTCC  TTCGATCTGT  ACAACAAGTA  CAAACTAAAG  CTGGACAGAT  TATTCAATAA
GAAGAAGGAG CTTGGGCAAG ATAAGATGCA GATTAAGAAG 3300
3301  CTAACTTTAC  TGAAGGAGCA  GCTCGAGAGC  AAGCTCAACT  CCCTGAATAA  TCCACATAAT
GTGCTCCAGA ACTTTTCCGT ATTCTTCAAT AAGAAGAAAG 3400
3401  AAGCAGAGAT  TGCCGAGACG  GAAAATACCC  TCGAAAACAC  TAAGATATTA  CTGAAACACT
ATAAAGGGCT GGTGAAGTAT TACAACGGAG AGTCTAGCCC 3500
3501  ATTGAAGACT  CTTTCAGAAG  TGTCAATTCA  AACCGAGGAT  AACTACGCAA  ACCTAGAAAA
GTTCAGAGTG CTGAGCAAAA TCGACGGCAA ACTCAATGAT 3600
3601  AACCTACACC  TCGGAAAAAA  AAAGCTGAGC  TTCCTGTCCA  GTGGACTTCA  TCATTTAATT
ACCGAATTGA AAGAAGTTAT CAAAAACAAA AACTACACTG 3700
3701  GGAACAGCCC  ATCTGAAAAT  AATAAAAAGG  TCAACGAGGC  CCTCAAGTCT  TATGAAAATT
TCCTTCCAGA AGCAAAAGTG ACAACCGTCG TGACCCCCCC 3800
3801  CCAGCCCGAT  GTCACCCCCA  GCCCTCTAAG  CGTGAGAGTG  TCTGGATCAA  GTGGCTCCAC
AAAAGAAGAA ACCCAGATCC CCACATCAGG ATCTCTACTG 3900
3901  ACCGAGTTGC  AGCAGGTCGT  CCAACTCCAG  AATTATGACG  AGGAAGACGA  CAGCCTCGTG
GTTTTGCCAA TCTTCGGCGA ATCAGAAGAC AACGACGAGT 4000
4001  ACCTAGACCA  AGTGGTCACC  GGGGAAGCGA  TTAGTGTCAC  TATGGACAAT  ATCCTCAGCG
GCTTCGAGAA CGAGTATGAC GTGATCTACC TCAAACCACT 4100
4101  AGCCGGAGTT  TACAGAAGTC  TCAAGAAGCA  GATCGAAAAG  AACATCTTCA  CCTTTAATCT
AAACCTAAAC GACATCTTGA ATTCCCGGCT GAAAAAGCGG 4200
4201  AAATACTTCC  TCGACGTACT  GGAGTCGGAT  TTGATGCAGT  TTAAGCACAT  CTCCAGCAAC
GAATACATTA TCGAGGACTC GTTCAAACTG TTAAACTCCG 4300
4301  AGCAGAAGAA  CACCCTGCTG  AAGTCCTACA  AATATATCAA  AGAGTCAGTC  GAGAACGATA
TTAAATTCGC CCAAGAAGGC ATAAGCTACT ACGAAAAGGT 4400
4401  CCTCGCCAAA  TACAAGGACG  ATCTGGAGTC  TATCAAAAAG  GTCATCAAAG  AAGAGAAAGA
GAAATTTCCC AGTTCTCCCC CTACAACGCC GCCCTCTCCA 4500
4501  GCCAAGACTG  ATGAACAGAA  AAAAGAGTCT  AAGTTCCTCC  CTTTCCTCAC  TAATATCGAG
ACTCTCTACA ATAACCTAGT GAACAAGATT GACGACTACC 4600
4601  TGATCAACCT  TAAAGCCAAG  ATAAACGACT  GCAATGTCGA  GAAGGATGAG  GCTCATGTTA
AGATCACCAA ACTGTCCGAT CTGAAAGCCA TCGACGACAA 4700
4701  GATCGACTTA  TTTAAAAACC  CATACGATTT  CGAGGCTATC  AAAAAGCTGA  TCAATGATGA
CACCAAGAAA GATATGCTCG GCAAGCTGCT GAGCACGGGT 4800
4801  CTGGTGCAGA  ACTTCCCTAA  CACCATCATA  TCAAAGCTCA  TAGAGGGCAA  GTTCCAAGAC
ATGCTGAATA TTTCACAGCA TCAGTGCGTC AAGAAGCAGT 4900
4901  GCCCCGAAAA  TTCTGGATGC  TTCCGGCACC  TGGATGAGCG  AGAAGAGTGC  AAGTGCCTGC
TTAACTATAA ACAGGAGGGC GACAAATGTG TGGAGAACCC 5000
5001  AAATCCGACG  TGCAACGAGA  ACAACGGTGG  CTGCGATGCC  GACGCGACTT  GTACAGAGGA
AGACTCGGGG AGTTCTCGGA AAAAAATCAC GTGCGAGTGC 5100
5101  ACCAAACCCG  ACAGTTATCC  TCTGTTCGAT  GGGATATTCT  GCTCCTCCAG  CAACGTTTAG
5160
        |   10    |   20    |   30    |   40    |   50    |   60    |
70      |   80    |   90    |  100
```

Figure 27 (Contd..)

```
       |   10        |   20        |   30        |   40        |   50        |   60        |   70
   |   80        |   90        |  100
       1 ATGaccgtcg  cgcggccgag   cgtgcccgcg   gcgctgcccc   tcctcgggga   gctgcccgg
   ctgctgctgc tggtgctgtt  gtgcctgccg  gccgtgtgG 100
     101 GATCCGTGAC  CCACGAATCC   TATCAGGAGC   TGGTTAAGAA   ACTGGAAGCT   TTAGAGGACG
   CCGTATTGAC AGGTTACTCC  CTATTCCAGA  AAGAAAGAT 200
     201 GGTTTTAAAC  GAAGAAGAAA   TTACCACAAA   GGGAGCATCC   GCCCAGTCTG   GAGCATCTGC
   TCAGAGCGGA GCATCTGCTC  AGAGTGGAGC  AAGCGCCCAA 300
     301 AGTGGAGCGT  CTGCCCAGTC   AGGCGCCTCA   GCTCAATCTG   GAACCTCTGG   GCCGAGTGGT
   CCTAGCGGTA CTTCTCCAAG  TAGCCGGTCT  AATACACTCC 400
     401 CACGTTCCAA  CACCTCCAGT   GGAGCCTCCC   CACCCGCCGA   CGCATCCGAC   TCAGACGCTA
   AGAGTTATGC AGACCTGAAG  CACCGCGTGA  GGAACTACCT 500
     501 TTTCACTATC  AAAGAGTTGA   AGTACCCTGA   ATTGTTCGAT   TTGACCAACC   ATATGCTGAC
   ACTCTGTGAC AACATACATG  GTTTCAAGTA  TCTGATAGAT 600
     601 GGGTATGAAG  AAATTAACGA   GCTGCTCTAT   AAACTCAACT   TTTACTTCGA   CCTGCTGCGT
   GCCAAGCTGA ACGATGTCTG  TGCAAACGAT  TACTGCCAGA 700
     701 TCCCATTCAA  CCTAAAGATA   CGTGCGAACG   AGCTGGATGT   TCTGAAGAAA   CTCGTGTTCG
   GGTATCGGAA ACCCTTGGAC  AACATTAAGG  ACAATGTGGG 800
     801 GAAGATGGAG  GATTACATTA   AGAAAATAA    AACAACAATC   GCTAACATAA   ATGAGCTTAT
   CGAGGGGAGC AAAAAGACCA  TCGACCAGAA  CAAGAATGCC 900
     901 GACAATGAAG  AGGGAAAAAA   GAAACTATAC   CAAGCCCAGT   ATGATTTGAG   CATCTACAAT
   AAGCAACTAG AGGAAGCTCA  CAACCTCATC  AGCGTACTGG 1000
    1001 AAAAGAGAAT  TGCACCCTG    AAAAAGAATG   AAAACATTAA   GAAACTCCTG   GACAAGATTA
   ACGAAATTAA AAACCCaCCt  CCaGCGAATA  GCGGAAATAA 1100
    1101 CCCGAATACC  CTGCTGGATA   AGAACAAAAA   GATTGAAGAG   CACGAAGAGA   AAATCAAGGA
   AATCGCCAAG ACTATTAAGT  TCAATATAGA  TTCTCTGTTC 1200
    1201 ACAGACCCtC  TGGAGCTGGA   ATACTACCTG   CGCGAGAAGA   ATAAGAAGGT   CGACGTGACC
   CCAAAGAGCC AAGACCCAAC  AAAGTCCGTG  CAGATCCCCA 1300
    1301 AAGTGCCCTA  CCCAAACGGC   ATCGTGTATC   CCCTGCCTCT   TACCGACATC   CACAACTCTC
   TGGCAGCCGA TAACGACAAA  AACAGCTATG  AGACCTGAT 1400
    1401 GAACCCCCAC  ACTAAGGAAA   AGATAAACGA   GAAGATCATT   ACCGATAATA   AGGAGCGGAA
   GATTTTTATC AACAACATCA  AGAAGAAAAT  CGACCTGGAA 1500
    1501 GAGAAAAATA  TCAATCACAC   CAAAGAGCAA   AACAAGAAAT   TACTGGAGGA   CTATGAGAAG
   AGCAAAAAGG ATTATGAGGA  ACTGTTAGAG  AAGTTCTATG 1600
    1601 AAATGAAATT  CAACAACAAT   TTCGATAAGG   ATGTGGTCGA   TAAAATTTTC   AGCGCCCGGT
   ACACCTACAA CGTGGAGAAG  CAGCGGTACA  ACAATAAGTT 1700
    1701 CAGCAGCTCC  AATAACTCGG   TCTACAATGT   GCAGAAGCTG   AAGAAAGCTC   TGAGCTATCT
   GGAAGACTAC TCGCTGAGGA  AAGGGATTTC  TGAGAAGGAT 1800
    1801 TTCAACCACT  ACTACACCCT   CAAAACCGGC   CTGGAAGCTG   ACATCAAGAA   ACTCACTGAA
   GAGATCAAAA GTTCTGAGAA  TAAGATACTG  GAGAAGAACT 1900
    1901 TCAAGGGACT  AACGCACTCT   GCAACGGCT    CCCTGGAAGT   CTCTGACATC   GTGAAACTGC
   AAGTCCAAAA GGTGCTGCTC  ATCAAAAAAA  TCGAGGATCT 2000
    2001 GCGAAAGATC  GAGCTGTTTC   TTAAGAACGC   CCAACTGAAA   GACTCAATCC   ACGTGCCTAA
   CATTTACAAA CCGCAGAACA  AACCAGAACC  ATACTATCTG 2100
    2101 ATCGTGCTGA  AGAAGGAGGT   GGATAAGCTG   AAGGAATTCA   TCCCAAAAGT   GAAAGATATG
   TTAAAGAAAG AGCAAGCCGT  GCTGAGCAGC  ATAACGCAGC 2200
    2201 CTCTGGTGGC  CGCAAGCGAG   ACAACCGAAG   ATGGCGGGCA   CAGCACCCAC   ACCCTGTCTC
   AGTCTGGCGA AACAGAGGTG  ACAGAAGAGA  CAGAAGAGAC 2300
    2301 CGAAGAAACA  GTGGGGCACA   CCACTACTGT   GACCATCACT   TTGCCCCCTA   CGCAGCCATC
   TCCCCCAAAA GAGGTCAAAG  TCGTGGAAAA  CTCCATTGAA 2400
    2401 CAGAAGTCCA  ACGACAACTC   ACAGGCTCTG   ACGAAGACCG   TCTATCTGAA   GAAACTGGAC
   GAGTTCCTGA CCAAAAGCTA  CATCTGCCAT  AAATACATCC 2500
    2501 TCGTGTCTAA  CAGCAGCATG   GATCAGAAGC   TGTTGGAGGT   GTACAACCTA   ACGCCCGAAG
   AAGAGAACGA GTTAAAATCC  TGTGATCCCT  TAGACCTACT 2600
    2601 GTTTAACATT  CAGAACAACA   TCCCCGCTAT   GTACAGCTTA   TATGATTCCA   TGAATAACGA
   CCTCCAGCAC CTGTTCTTCG  AGCTGTACCA  GAAAGAGATG 2700
    2701 ATCTACTATC  TGCATAAGCT   GAAAGAGGAG   AATCACATCA   AAAGTTGCT    GGAAGAGCAG
   AAACAGATAA CTGGGACGTC  CAGCACATCG  TCACCTGGCA 2800
    2801 ACACGACAGT  AAATACCGCC   CAGTCTGCTA   CACACTCCAA   CTCCCAGAAC   CAGCAGAGCA
   ACGCTTCTAG CACCAACACC  CAGAATGGGG  TAGCAGTTAG 2900
    2901 TAGCGGCCCT  GCTGTGGTGG   AGGAATCGCA   TGACCCCTC    ACTGTATTAT   CTATTTCAAA
   CGACCTAAAA GGGATTGTGT  CCCTCCTCAA  TTTAGGTAAT 3000
```

Figure 28

```
3001  AAGACCAAGG  TCCCTAACCC  CTTGACTATC  AGCACTACGG  AAATGGAGAA  GTTTTATGAA
AACATCCTGA AGAACAACGA CACCTATTTT AACGACGACA 3100
3101  TAAAGCAGTT  CGTGAAGAGT  AACAGTAAAG  TGATTACCGG  GCTGACAGAA  ACCCAGAAAA
ATGCTTTAAA TGATGAGATC AAGAAACTGA AAGCACACT 3200
3201  CCAGCTCTCC  TTCGATCTGT  ACAACAAGTA  CAAACTAAAG  CTGGACAGAT  TATTCAATAA
GAAGAAGGAG CTTGGGCAAG ATAAGATGCA GATTAAGAAG 3300
3301  CTAACTTTAC  TGAAGGAGCA  GCTCGAGAGC  AAGCTCAACT  CCCTGAATAA  TCCACATAAT
GTGCTCCAGA ACTTTTCCGT ATTCTTCAAT AAGAAGAAAG 3400
3401  AAGCAGAGAT  TGCCGAGACG  GAAAATACCC  TCGAAAACAC  TAAGATATTA  CTGAAACACT
ATAAAGGGCT GGTGAAGTAT TACAACGGAG AGTCTAGCCC 3500
3501  ATTGAAGACT  CTTTCAGAAG  TGTCAATTCA  AACCGAGGAT  AACTACGCAA  ACCTAGAAAA
GTTCAGAGTG CTGAGCAAAA TCGACGGCAA ACTCAATGAT 3600
3601  AACCTACACC  TCGGAAAAAA  AAAGCTGAGC  TTCCTGTCCA  GTGGACTTCA  TCATTTAATT
ACCGAATTGA AAGAAGTTAT CAAAAACAAA AACTACACTG 3700
3701  GGAACAGCCC  ATCTGAAAAT  AATAAAAAGG  TCAACGAGGC  CCTCAAGTCT  TATGAAAATT
TCCTTCCAGA AGCAAAAGTG ACAACCGTCG TGACCCCCCC 3800
3801  CCAGCCCGAT  GTCACCCCCA  GCCCTCTAAG  CGTGAGAGTG  TCTGGATCAA  GTGGCTCCAC
AAAAGAAGAA ACCCAGATCC CCACATCAGG ATCTCTACTG 3900
3901  ACCGAGTTGC  AGCAGGTCGT  CCAACTCCAG  AATTATGACG  AGGAAGACGA  CAGCCTCGTG
GTTTTGCCAA TCTTCGGCGA ATCAGAAGAC AACGACGAGT 4000
4001  ACCTAGACCA  AGTGgtcacC  aacgttACTA  CTTCCGGCAC  TACCCGTCTT  CTATCTGGTC
ACACGTGTTT CACGTTGACA GGTTTGCTTG GGACGCTAGT 4100
4101              AACCATGGGC              TTGCTGACTT              AA
4122
     |    10   |    20   |    30   |    40   |    50   |    60   |
70   |    80   |    90   |   100
```

Figure 28 (Contd..)

```
         |   10      |   20      |   30      |   40      |   50      |   60      |   70      |
                                         |   80      |   90      |  100
   1 ATGaccgtcg  cgcggccgag  cgtgcccgcg  gcgctgcccc  tcctcgggga  gctgcccgg
ctgctgctgc  tggtgctgtt  gtgcctgccg  gccgtgtggG 100
 101 GATCCGTGAC  CCACGAATCC  TATCAGGAGC  TGGTTAAGAA  ACTGGAAGCT  TTAGAGGACG
CCGTATTGAC  AGGTTACTCC  CTATTCCAGA  AAGAAAAGAT 200
 201 GGTTTTAAAC  GAAGAAGAAA  TTACCACAAA  GGGAGCATCC  GCCCAGTCTG  GAGCATCTGC
TCAGAGCGGA  GCATCTGCTC  AGAGTGGAGC  AAGCGCCCAA 300
 301 AGTGGAGCGT  CTGCCCAGTC  AGGCGCCTCA  GCTCAATCTG  GAACCTCTGG  GCCGAGTGGT
CCTAGCGGTA  CTTCTCCAAG  TAGCCGGTCT  AATACACTCC 400
 401 CACGTTCCAA  CACCTCCAGT  GGAGCCTCCC  CACCCGCCGA  CGCATCCGAC  TCAGACGCTA
AGAGTTATGC  AGACCTGAAG  CACCGCGTGA  GGAACTACCT 500
 501 TTTCACTATC  AAAGAGTTGA  AGTACCCTGA  ATTGTTCGAT  TTGACCAACC  ATATGCTGAC
ACTCTGTGAC  AACATACATG  GTTTCAAGTA  TCTGATAGAT 600
 601 GGGTATGAAG  AAATTAACGA  GCTGCTCTAT  AAACTCAACT  TTTACTTCGA  CCTGCTGCGT
GCCAAGCTGA  ACGATGTCTG  TGCAAACGAT  TACTGCCAGA 700
 701 TCCCATTCAA  CCTAAAGATA  CGTGCGAACG  AGCTGGATGT  TCTGAAGAAA  CTCGTGTTCG
GGTATCGGAA  ACCCTTGGAC  AACATTAAGG  ACAATGTGGG 800
 801 GAAGATGGAG  GATTACATTA  AGAAAAATAA  AACAACAATC  GCTAACATAA  ATGAGCTTAT
CGAGGGGAGC  AAAAAGACCA  TCGACCAGAA  CAAGAATGCC 900
 901 GACAATGAAG  AGGGAAAAAA  GAAACTATAC  CAAGCCCAGT  ATGATTTGAG  CATCTACAAT
AAGCAACTAG  AGGAAGCTCA  CAACCTCATC  AGCGACTAGG 1000
1001 AAAAGAGAAT  TGACACCCTG  AAAAAGAATG  AAAACATTAA  GAAACTCCTG  GACAAGATTA
ACGAAATTAA  AAACCcACCt  CCaGCGAATA  GCGGAAATAC 1100
1101 CCCGAATACC  CTGCTGGATA  AGAACAAAAA  GATTGAAGAG  CACGAAGAGA  AAATCAAGGA
AATCGCCAAG  ACTATTAAGT  CAATATAGA  TTCTCTGTTC 1200
1201 ACAGACCCtC  TGGAGCTGGA  ATACTACCTG  CGCGAGAAGA  ATAAGAAGGT  CGACGTGACC
CCAAAGAGCC  AAGACCCAAC  AAAGTCCGTG  CAGATCCCCA 1300
1301 AAGTGCCCTA  CCCAAACGGC  ATCGTGTATC  CCCTGCCTCT  TACCGACATC  CACAACTCTC
TGGCAGCCGA  TAACGACAAA  AACAGCTATG  AGACCTGAT 1400
1401 GAACCCCCAC  ACTAAGGAAA  AGATAAACGA  GAAGATCATT  ACCGATAATA  AGGAGCGGAA
GATTTTTATC  AACAACATCA  AGAAGAAAAT  CGACCTGGAA 1500
1501 GAGAAAAATA  TCAATCACAC  CAAAGAGCAA  AACAAGAAAT  TACTGGAGGA  CTATGAGAAG
AGCAAAAAGG  ATTATGAGGA  ACTGTTAGAG  AAGTTCTATG 1600
1601 AAATGAAATT  CAACAACAAT  TTCGATAAGG  ATGTGGTCGA  TAAAATTTTC  AGCGCCCGGT
ACACCTACAA  CGTGGAGAAG  CAGCGGTACA  ACAATAAGTT 1700
1701 CAGCAGCTCC  AATAACTCGG  TCTACAATGT  GCAGAAGCTG  AAGAAAGCTC  TGAGCTATCT
GGAAGACTAC  TCGCTGAGGA  AAGGGATTTC  TGAGAAGGAT 1800
1801 TTCAACCACT  ACTACACCCT  CAAAACCGGC  CTGGAAGCTG  ACATCAAGAA  ACTCACTGAA
GAGATCAAAA  GTTCTGAGAA  TAAGATACTG  GAGAAGAACT 1900
1901 TCAAGGGACT  AACGCACTCT  GCAAACGGCT  CCCTGGAAGT  CTCTGACATC  GTGAAACTGC
AAGTCCAAAA  GGTGCTGCTC  ATCAAAAAAA  TCGAGGATCT 2000
2001 GCGAAAGATC  GAGCTGTTTC  TTAAGAACGC  CCAACTGAAA  GACTCAATCC  ACGTGCCTAA
CATTTACAAA  CCGCAGAACA  AACCAGAACC  ATACTATCTG 2100
2101 ATCGTGCTGA  AGAAGGAGGT  GGATAAGCTG  AAGGAATTCA  TCCCAAAAGT  GAAAGATATG
TTAAAGAAAG  AGCAAGCCGT  GCTGAGCAGC  ATAACGCAGC 2200
2201 CTCTGGTGGC  CGCAAGCGAG  ACAACCGAAG  ATGGCGGGCA  CAGCACCCAC  ACCCTGTCTC
AGTCTGGCGA  AACAGAGGTG  ACAGAAGAGA  CAGAAGAGAC 2300
2301 CGAAGAAACA  GTGGGGCACA  CCACTACTGT  GACCATCACT  TTGCCCCCTA  CGCAGCCATC
TCCCCCAAAA  GAGGTCAAAG  TCGTGGAAAA  CTCCATTGAA 2400
2401 CAGAAGTCCA  ACGACAACTC  ACAGGCTCTG  ACGAAGACCG  TCTATCTGAA  GAAACTGGAC
GAGTTCCTGA  CCAAAAGCTA  CATCTGCCAT  AAATACATCC 2500
2501 TCGTGTCTAA  CAGCAGCATG  GATCAGAAGC  TGTTGGAGGT  GTACAACCTA  ACGCCCGAAG
AAGAGAACGA  GTTAAAATCC  TGTGATCCCT  TAGACCTACT 2600
2601 GTTTAACATT  CAGAACGAAA  TCCCCGCTAT  GTACAGCTTA  TATGATTCCA  TGAATAACGA
CCTCCAGCAC  CTGTTCTTCG  AGCTGTACCA  GAAAGAGATG 2700
2701 ATCTACTATC  TGCATAAGCT  GAAAGAGGAG  AATCACATCA  AAAAGTTGCT  GGAAGAGCAG
AAACAGATAA  CTGGGACGTC  CAGCACATCG  TCACCTGGCA 2800
2801 ACACGACAGT  AAATACCGCC  CAGTCTGCTA  CACACTCCAA  CTCCCAGAAC  CAGCAGAGCA
ACGCTTCTAG  CACCAACACC  CAGAATGGGG  TAGCAGTTAG 2900
2901 TAGCGGCCCT  GCTGTGGTGG  AGGAATCGCA  TGACCCCCTC  ACTGTATTAT  CTATTTCAAA
CGACCTAAAA  GGGATTGTGT  CCCTCCTCAA  TTTAGGTAAT 3000
```

Figure 29

```
3001  AAGACCAAGG  TCCCTAACCC  CTTGACTATC  AGCACTACGG  AAATGGAGAA  GTTTTATGAA
AACATCCTGA AGAACAACGA CACCTATTTT AACGACGACA 3100
3101  TAAAGCAGTT  CGTGAAGAGT  AACAGTAAAG  TGATTACCGG  GCTGACAGAA  ACCCAGAAAA
ATGCTTTAAA TGATGAGATC AAGAAACTGA AAGACACACT 3200
3201  CCAGCTCTCC  TTCGATCTGT  ACAACAAGTA  CAAACTAAAG  CTGGACAGAT  TATTCAATAA
GAAGAAGGAG CTTGGGCAAG ATAAGATGCA GATTAAGAAG 3300
3301  CTAACTTTAC  TGAAGGAGCA  GCTCGAGAGC  AAGCTCAACT  CCCTGAATAA  TCCACATAAT
GTGCTCCAGA ACTTTTCCGT ATTCTTCAAT AAGAAGAAAG 3400
3401  AAGCAGAGAT  TGCCGAGACG  GAAAATACCC  TCGAAAACAC  TAAGATATTA  CTGAAACACT
ATAAAGGGCT GGTGAAGTAT TACAACGGAG AGTCTAGCCC 3500
3501  ATTGAAGACT  CTTTCAGAAG  TGTCAATTCA  AACCGAGGAT  AACTACGCAA  ACCTAGAAAA
GTTCAGAGTG CTGAGCAAAA TCGACGGCAA ACTCAATGAT 3600
3601  AACCTACACC  TCGGAAAAAA  AAAGCTGAGC  TTCCTGTCCA  GTGGACTTCA  TCATTTAATT
ACCGAATTGA AAGAAGTTAT CAAAAACAAA AACTACACTG 3700
3701  GGAACAGCCC  ATCTGAAAAT  AATAAAAAGG  TCAACGAGGC  CCTCAAGTCT  TATGAAAATT
TCCTTCCAGA AGCAAAAGTG ACAACCGTCG TGACCCCCCC 3800
3801  CCAGCCCGAT  GTCACCCCCA  GCCCTCTAAG  CGTGAGAGTG  TCTGGATCAA  GTGGCTCCAC
AAAAGAAGAA ACCCAGATCC CCACATCAGG ATCTCTACTG 3900
3901  ACCGAGTTGC  AGCAGGTCGT  CCAACTCCAG  AATTATGACG  AGGAAGACGA  CAGCCTCGTG
GTTTTGCCAA TCTTCGGCGA ATCAGAAGAC AACGACGAGT 4000
 4001              ACCTAGACCA              AGTGGTCACC              GGGGAATAA
4029
        |    10    |    20    |    30    |    40    |    50    |    60    |
70      |    80    |    90    |   100
```

Figure 29 (Contd..)

```
       |   10      |   20      |   30      |   40      |   50      |   60      |   70
|   80      |   90      |  100
     1 ATGaccgtcg cgcggccgag cgtgcccgcg gcgctgcccc tcctcgggga gctgccccgg
ctgctgctgc tggtgctgtt gtgcctgccg gccgtgtggG 100
   101 GATCCGTGGT CACCGGGGAA GCGATTAGTG TCACTATGGA CAATATCCTC AGCGGCTTCG
AGAACGAGTA TGACGTGATC TACCTCAAAC CACTAGCCGG 200
   201 AGTTTACAGA AGTCTCAAGA AGCAGATCGA AAAGAACATC TTCACCTTTA ATCTAAACCT
AAACGACATC TTGAATTCCC GGCTGAAAAA GCGGAAATAC 300
   301 TTCCTCGACG TACTGGAGTC GGATTTGATG CAGTTTAAGC ACATCTCCAG CAACGAATAC
ATTATCGAGG ACTCGTTCAA ACTGTTAAAC TCCGAGCAGA 400
   401 AGAACACCCT GCTGAAGTCC TACAAATATA TCAAAGAGTC AGTCGAGAAC GATATTAAAT
TCGCCCAAGA AGGCATAAGC TACTACGAAA AGGTCCTCGC 500
   501 CAAATACAAG GACGATCTGG AGTCTATCAA AAAGGTCATC AAAGAAGAGA AAGAGAAATT
TCCCAGTTCT CCCCCTACAA CGCCGCCCTC TCCAGCCAAG 600
   601 ACTGATGAAC AGAAAAAAGA GTCTAAGTTC CTCCCTTTCC TCACTAATAT CGAGACTCTC
TACAATAACC TAGTGAACAA GATTGACGAC TACCTGATCA 700
   701 ACCTTAAAGC CAAGATAAAC GACTGCAATG TCGAGAAGGA TGAGGCTCAT GTTAAGATCA
CCAAACTGTC CGATCTGAAA GCCATCGACG ACAAGATCGA 800
   801 CTTATTTAAA AACCCATACG ATTTCGAGGC TATCAAAAAG CTGATCAATG ATGACACCAA
GAAAGATATG CTCGGCAAGC TGCTGAGCAC GGGTCTGGTG 900
   901 CAGAACTTCC CTAACACCAT CATATCAAAG CTCATAGAGG GCAAGTTCCA AGACATGCTG
AATATTTCAC AGCATCAGTG CGTCAAGAAG CAGTGCCCCG 1000
  1001 AAAATTCTGG ATGCTTCCGG CACCTGGATG AGCGAGAAGA GTGCAAGTGC CTGCTTAACT
ATAAACAGGA GGGCGACAAA TGTGTGGAGA ACCCAAATCC 1100
  1101 GACGTGCAAC GAGAACAACG TGGCTGCGA TGCCGACGCG ACTTGTACAG AGGAAGACTC
GGGGAGTTCT CGGAAAAAAA TCACGTGCGA GTGCACCAAA 1200
  1201 CCCGACAGTT ATCCTCTGTT CGATGGGATA TTCTGCTCCT CCAGCaacgt tACTACTTCC
GGCACTACCC GTCTTCTATC TGGTCACACG TGTTTCACGT 1300
  1301      TGACAGGTTT     GCTTGGGACG      CTAGTAACCA     TGGGCTTGCT       GACTTAA
1347
       |   10      |   20      |   30      |   40      |   50      |   60      |
    70     |   80      |   90      |  100
```

Figure 30

```
    |   10      |   20      |   30      |   40      |   50      |   60      |   70
|   80      |   90      |  100
    1 ATGaccgtcg cgcggccgag cgtgcccgcg gcgctgcccc tcctcgggga gctgcccggg
ctgctgctgc tggtgctgtt gtgcctgccg gccgtgtggg 100
  101 gatcCGTGGT CACCGGGGAA GCGATTAGTG TCACTATGGA CAATATCCTC AGCGGCTTCG
AGAACGAGTA TGACGTGATC TACCTCAAAC CACTAGCCGG 200
  201 AGTTTACAGA AGTCTCAAGA AGCAGATCGA AAAGAACATC TTCACCTTTA ATCTAAACCT
AAACGACATC TTGAATTCCC GGCTGAAAAA GCGGAAATAC 300
  301 TTCCTCGACG TACTGGAGTC GGATTTGATG CAGTTTAAGC ACATCTCCAG CAACGAATAC
ATTATCGAGG ACTCGTTCAA ACTGTTAAAC TCCGAGCAGG 400
  401 AGAACACCCT GCTGAAGTCC TACAAATATA TCAAAGAGTC AGTCGAGAAC GATATTAAAT
TCGCCCAAGA AGGCATAAGC TACTACGAAA AGGTCCTCGC 500
  501 CAAATACAAG GACGATCTGG AGTCTATCAA AAAGGTCATC AAAGAAGAGA AAGAGAAATT
TCCCAGTTCT CCCCCTACAA CGCCGCCCTC TCCAGCCAAG 600
  601 ACTGATGAAC AGAAAAAAGA GTCTAAGTTC CTCCCTTTCC TCACTAATAT CGAGACTCTC
TACAATAACC TAGTGAACAA GATTGACGAC TACCTGATCA 700
  701 ACCTTAAAGC CAAGATAAAC GACTGCAATG TCGAGAAGGA TGAGGCTCAT GTTAAGATCA
CCAAACTGTC CGATCTGAAA GCCATCGACG ACAAGATCGA 800
  801 CTTATTTAAA AACCCATACG ATTTCGAGGC TATCAAAAAG CTGATCAATG ATGACACCAA
GAAAGATATG CTCGGCAAGC TGCTGAGCAC GGGTCTGGTG 900
  901 CAGAACTTCC CTAACACCAT CATATCAAAG CTCATAGAGG GCAAGTTCCA AGACATGCTG
AATATTTCAC AGCATCAGTG CGTCAAGAAG CAGTGCCCCG 1000
 1001 AAAATTCTGG ATGCTTCCGG CACCTGGATG AGCGAGAAGA GTGCAAGTGC CTGCTTAACT
ATAAACAGGA GGGCGACAAA TGTGTGGAGA ACCCAAATCC 1100
 1101 GACGTGCAAC GAGAACAACG GTGGCTGCGA TGCCGACGCG ACTTGTACAG AGGAAGACTC
GGGGAGTTCT CGGAAAAAAA TCACGTGCGA GTGCACCAAA 1200
 1201 CCCGACAGTT ATCCTCTGTT CGATGGGATA TTCTGCTCCT CCAGCAACGT      TTAG
1254
            |   10      |   20      |   30      |   40      |   50      |   60      |
 70      |   80      |   90      |  100
```

Figure 31

```
         |    10        |    20        |    30        |    40        |    50        |    60        |    70
                        |    80        |    90        |   100
       1 ATGaccgtcg     cgcggccgag     cgtgcccgcg     gcgctgcccc     tcctcgggga     gctgcccgg
   ctgctgctgc tggtgctgtt gtgcctgccg gccgtgtggG 100
     101 GATCCGTGAC     CCACGAATCC     TATCAGGAGC     TGGTTAAGAA     ACTGGAAGCT     TTGGAAGATG
   CCGTCCTTAC CGGATACAGC CTGTTCCAGA AGGAGAAGAT 200
     201 GGTGCTGAAT     GAAGGGACGA     GTGGCACGGC     CGTTACAACC     AGCACACCCG     GTTCTAAAGG
   GTCTGTGGCT AGCGGTGGCT CCGGTGGGTC TGTGGCCTCT 300
     301 GGGGGTTCCG     TCGCCTCCGG     CGGCAGCGTG     GCATCAGGTG     GCTCAGTGGC     AAGCGGCGGT
   TCCGGGAACA GTCGAAGAAC CAATCCATCT GACAACTCTA 400
     401 GCGATTCCGA     CGCCAAGTCC     TACGCCGACC     TCAAGCACCG     AGTGAGAAAC     TATCTCCTCA
   CTATCAAGGA GCTGAAGTAC CCACAGTTGT TCGACCTCAC 500
     501 TAATCATATG     CTGACACTGT     GTGATAACAT     TCATGGCTTC     AAATATCTGA     TTGACGGTTA
   CGAAGAGATC AATGAACTCC TGTACAAGTT GAATTTCTAC 600
     601 TTCGACTTGC     TAAGGGCCAA     ACTGAATGAC     GTTTGCGCCA     ATGACTATTG     TCAAATTCCA
   TTCAATTTGA AGATCAGAGC CAACGAGTTG GACGTATTGA 700
     701 AGAAGTTGGT     CTTCGGATAT     CGCAAGCCTC     TCGACAACAT     CAAGGACAAT     GTGGGAAAGA
   TGGAAGATTA TATTAAAAAG AATAAGAAGA CCATCGAGAA 800
     801 CATTAACGAG     CTGATCGAAG     AATCCAAAAA     GACCATAGAC     AAAAATAAGA     ATGCAACCAA
   GGAGGAAGAA AAGAAGAAGT TGTACCAGGC CCAGTACGAC 900
     901 CTGTCCATCT     ATAACAAACA     GCTTGAAGAA     GCCCATAACC     TCATCAGCGT     ACTGGAGAAG
   CGCATAGACA CCCTCAAGAA GAATGAAAAT ATCAAAGAAC 1000
    1001 TGCTCGACAA     GATTAATGAA     ATTAAGAATC     CTCCGCCAGC     CAACTCTGGG     AACACCCCTA
   ACACGCTGCT GGACAAGAAC AAGAAGATAG AGGAGCACGA 1100
    1101 GAAAGAGATC     AAAGAGATCG     CCAAAACCAT     TAAGTTCAAC     ATAGATTCTC     TCTTTACTGA
   TCCCCTTGAG CTGGAGTACT ACTTGAGAGA GAAGAATAAG 1200
    1201 AATATAGACA     TCTCCGCCAA     AGTCGAGACA     AAGGAATCAA     CCGAACCTAA     TGAATATCCC
   AAtGGTGTGA CGTACCCTCT GTCTTATAAC GATATCAACA 1300
    1301 ACGCTCTCAA     CGAGCTCAAT     AGCTTCGGTG     ACTTGATTAA     CCCCTTCGAT     TATACGAAAG
   AACCCTCTAA GAATATCTAC ACAGACAATG AGAGAAAGAA 1400
    1401 GTTTATCAAC     GAAATCAAGG     AGAAGATCAA     AATTGAGAAG     AAGAAAATTG     AGAGTGACAA
   GAAAAGTTAC GAAGACCGCA GCAAAAGTCT AAACGATATC 1500
    1501 ACTAAAGAGT     ATGAAAAGCT     GCTGAACGAG     ATCTATGATT     CCAAATTCAA     CAATAACATC
   GACCTGACCA ACTTCGAGAA AATGATGGGA AAACGGTACT 1600
    1601 CTTACAAAGT     GGAGAAACTG     ACACACCATA     ATACCTTTGC     ATCCTATGAG     AATTCTAAGC
   ATAAtCTTGA GAAGCTCACC AAAGCTCTTA AGTATATGGA 1700
    1701 GGACTATTCT     CTGCGGAACA     TTGTTGTGGA     GAAAGAACTA     AAGTATTACA     AGAATCTCAT
   AAGTAAGATC GAAAACGAGA TCGAGACGCT TGTTGAGAAC 1800
    1801 ATTAAGAAGG     ATGAAGAACA     GTTGTTTGAG     AAGAAGATTA     CAAAAGACGA     gAATAAgCCA
   GAcGAaAAGA TCCTGGAGGT CTCCGAcATc GTTAAAGTCC 1900
    1901 AAGTGCAaAA     aGTaCTCCTC     ATGACAAGA     TTGATGAACT     CAAGAAGACT     CAACTCATTC
   TGAAGAACGT GGAGTTAAAA CATAATATAC ATGTGCCGAA 2000
    2001 TAGTTATAAG     CAGGAGAATA     AGCAGGAACC     ATACTACCTC     ATCGTACTCA     AGAAAGAGAT
   AGACAAACTG AAAGTGTTCA TGCCcAAaGT cGAGAGCCTG 2100
    2101 ATCAACGAAG     AGAAGAAGAA     CATTAAaACT     GAaGGACAGT     CaGATAACTC     cGAGCCTTCc
   ACAGAAGGAG AGATAACCGG aCAGGCTACC ACCAAGCCcG 2200
    2201 GaCAaCAGGC     CGGTTCaGCt     CTCGAaGGCG     ATAGCGTGCA     AGCtCAAGCA     CAAGAGCAGA
   AGCAGGCACA GCCtCCAGTG CCAGTgCCcG TtCCAGAGGC 2300
    2301 TAAaGCtCAA     GTGCCtACAC     CACCAGCtCC     tGTGAATAAC     AAGACCGAGA     ATGTCAGCAA
   aCTGGACTAC CTtGAGAAGC TCTATGAGTT CCTGAATACa 2400
    2401 TCCTACATCT     GCCACAAaTA     TATCCTCGTC     TCtCACAGCA     CTATGAACGA     GAAGATTCTt
   AAaCAGTACA AGAtAACCAA GGAAGAGGAG AGTAAaCTGT 2500
    2501 CCTCTTGTGA     tCCActgGAC     CTGCTGTTCA     ATATCCAGAA     CAACATtCCc     GTtATGTATT
   CTATGTTcGA TAGCCTCAAC AATTCtCTCT CTCAActgTT 2600
    2601 CATGGAGATa     TATGAGAAGG     AGATGGTcTG     CAACCTGTAT     AAaCTCAAaG     ACAACGACAA
   GATTAAGAAC cttctgGAGG AAGCTAAGAA GGTCTCCACC 2700
    2701 TCtGTtAAaA     CTCTCTCTTC     CAGcTCCATG     CAACCACTGT     CtCTCACACC     tCAAGACAAG
   CCcGAAGTgA GCGCTAACGA CGACACCTCT CACTCgACCA 2800
    2801 ACCTtAATAA     CTCaCTGAAa     CTGTTtGAGA     ACATCCTgTC     tCTcGGcAAG     AATAAGAACA
   TCTACCAAGA aCTtATTGGA CAGAAaTCgT CCGAGAACTT 2900
    2901 CTACGAGAAG     ATACTGAAaG     CAGCGACAC     ATTCTATAAC     GAGAGcTTcA     CTAAcTTcGT
   gAAaTCTAAa GCCGATGATA TcAACTCtCT tAACGATGAa 3000
```

Figure 32

```
3001 TCTAAaCGtA AGAAgCTGGA aGAGGACATC AATAAgctgA AgAAGACaCT gCAaCTGagc
TTCGACcTGT AcAACAAGTA cAAaCTGAAa CTGGAGAGAC 3100
3101 TCTTCGACAA GAAgAAGACA GTCGGCAAGT ATAAGATGCA GATCAAGAAG tTGACTCTGC
TCAAGGAGCA GCTtGAaAGC AAaCTCAACt caCTGAACAA 3200
3201 TCCgAAaCAC GTaCTGCAgA ACTTCtcaGT GTTCTTCAAC AAGAAGAAGG AaGCCGAGAT
CGCCGAGACA GAGAACACTC TGGAGAACAC CAAGATTCTt 3300
3301 CTCAAaCACT ACAAaGGCCT CGTCAAGTAT TATAATGGCG AGTCTTCTCC TCTGAAGACT
CTCTCCGAGG AGAGCATCCA GACCGAGGAT AACTACGCCA 3400
3401 GCCTCGAGAA CTTCAAGGTC CTGTCTAAGC TCGAAGGCAA GCTGAAGGAC AACCTGAACC
TGGAGAAGAA GAAGCTCAGC TACCTCTCTA GCGGACTGCA 3500
3501 TCACCTGATC GCCGAGCTCA AGGAAGTCAT TAAGAACAAG AACTACACCG GCAATAGCCC
AAGCGAGAAT AATACAGACG TGAATAACGC ACTGGAATCT 3600
3601 TAtAAGAAGT TCCTGCCTGA AGGAACAGAT GTCGCCACTG TGGTGTCTGA ATCTGGCTCC
GACACACTGG AGCAGTCTCA ACCTAAGAAG CCTGCATCTA 3700
3701 CTCATGTCGG AGCCGAGTCC AATACAATTA CCACATCTCA GAACGTCGAC GATGAGGTCG
ATGACGTCAT CATTGTGCCT ATCTTCGGCG AGAGCGAGGA 3800
3801 GGACTACGAT GACCTCGGCC AGGTGGTCAC CGGAGAGGCT GTCACTCCTT CCGTGATTGA
TAACATTCTG TCCAAAATCG AGAACGAATA CGAAGTGCTC 3900
3901 TATCTGAAAC CTCTGGCAGG CGTCTATAGG TCTCTCAAGA AACAGCTGGA GAATAACGTG
ATGACCTTCA ATGTCAACGT GAAGGACATT CTGAACAGCC 4000
4001 GCTTTAATAA GAGAGAAAAT TTCAAGAACG TCTTGGAGAG CGACTTGATT CCCTATAAAG
ACCTGACCTC CTCTAACTAt GTTGTCAAGG ACCCATACAA 4100
4101 GTTCCTCAAT AAAGAGAAGA GGGATAAATT TCTGTCTAGc TACAACTATA TCAAGGACTC
CATCGCACCC GATATCAATT TCGCTAATGA TGTGCTGGGG 4200
4201 TATTACAAGA TCCTGAGCGA AAAATACAAG TCTGACCTTG ACTCTATTAA AAAGTATATC
AACGATAAGC AAGGCGAGAA TGAAAAATAT CTGCCCTTCC 4300
4301 TGAATAACAT CGAAACCCTG TACAAGACAG TGAACGACAA AATCGACCTC TTCGTaATTC
ACCTGGAGGC CAAGGTCCTC AACTATACTT ACGAGAAGAG 4400
4401 CAATGTGGAA GTTAAAATCA AGGAGCTGAA CTACCTCAAA ACAATCCAAG ACAAGCTGGC
AGATTTCAAG AAAAATAACA ATTTCGTCGG AATTGCAGAC 4500
4501 CTGTCtACCG ATTATAACCA CAACAATCTC CTGACCAAGT TTCTGTCCAC TGGCATGGTG
TTCGAAAACC TCGCCAAAAC AGTGCTGAGC AATCTGCTCG 4600
4601 ACGGCAACCT GCAGGGCATG CTGAACATCT CCCAGCACCA ATGCGTGAAG AAACAGTGCC
CCCAGAATAG CGGCTGTTTC AGGCATCTGG ACGAGCGCGA 4700
4701 AGAGTGCAAG TGTCTCCTGA ACTACAAACA AGAAGGAGAT AAGTGCGTGG AGAACCCAAA
CCCTACCTGC AATGAAAACA ATGGCGGGTG TGACGCCGAT 4800
4801 GCTAAATGCA CCGAGGAAGA CAGCGGCTCT AACGAAAGA AAATCACATG CGAGTGTACT
AAGCCCGACT CCTATCCACT CTTcgacggg atCttCtgct 4900
4901 ccagctctAG CAAcgttACT ACTTCCGGCA CTACCCGTCT TCTATCTGGT CACACGTGTT
TCACGTTGAC AGGTTTGCTT GGGACGCTAG TAACCATGGG 5000
5001                    CTTGCTGACT                                  TAA
5013
    |   10    |   20    |   30    |   40    |   50    |   60    |
 70     |   80    |   90    |  100
```

Figure 32 (Contd..)

```
        |    10    |    20    |    30    |    40    |    50    |    60    |    70
             |    80    |    90    |   100
    1  atgatgagga  aactggccat  cctgagcgtg  agcagcttcc  tgttcgtgga  ggccctgttt
caggagtacc  agtgctacgg  cagcagcagc  aacacccggg  100
  101  tgctgaacga  gctgaactac  gacaacgccg  gcaccaacct  gtacaacgag  ctggagatga
actactacgg  caagcaggag  aactggtaca  gcctgaagaa  200
  201  gaacagccgg  tctctgggcg  agaacgacga  cggcaacaac  aacaacggcg  acaacggccg
ggagggcaag  gacgaggaca  agcgggacgg  caacaacgag  300
  301  gacaacgaga  agctgcggaa  gcccaagcac  aagaaactta  agcagcccgc  cgacggcaac
cccgacccca  acgccaaccc  caacgtggac  cccaacgcca  400
  401  atcctaatgt  cgacccaat   gccaatccga  acgttgatcc  caatgcgaat  cctaacgcta
accccaatgc  caacccaaat  gccaatccaa  atgcaaatcc  500
  501  caacgccaat  ccaaacgcaa  accctaatgc  taatccaaac  gctaatccta  atgccaatcc
caatgctaac  ccaaacgtcg  atcctaacgc  aaatccgaac  600
  601  gctaaccca   acgcaaatcc  caacgctaac  ccgaacgcaa  accctaacgc  caatccgaat
gccaacccaa  acgccaaccc  gaacgctaat  ccgaatgcta  700
  701  acccgaatgc  taatcctaac  gcaaacccaa  aCgcaaaccc  caatgcaaac  ccAaaTgcca
atcccaacgc  caatcctaat  gccaacaaga  acaatcaggg  800
  801  caacggccag  ggccacaaca  tgcccaacga  ccccaaccgg  aacgtggacg  agaacgccaa
cgccaacagc  gccgtgaaga  acaacaacaa  cgaggagccc  900
  901  agcgacaagc  acatcaagga  gtacctgaac  aagatccaga  acagcctgag  caccgagtgg
agccctgca   gcgtgacctg  cggcaacggc  attcaggtgc  1000
 1001  ggatcaagcc  cggcagcgcc  aacaagccca  aggacgagct  ggactacgcc  aatgacatcg
agaagaagat  ctgcaagatg  gagaagtgca  gcagcgtgtt  1100
 1101                        caacgtggtg                        aactcctga
1119
             |    10    |    20    |    30    |    40    |    50    |    60    |
  70     |    80    |    90    |   100
```

Figure 33

```
       |          10    |    20    |    30    |    40    |    50    |    60    |
70     |    80    |    90    |    100
     1 GGTACCGTCA CGCGTCACCG GTGTCATCAT GACCGTGGCC AGGCCCTCTG TGCCTGCCGC
CCTGCCCCTG CTGGGCGAGC TGCCCCGGCT GCTGCTCCTG 100
   101 GTGCTGCTGT GCCTGCCCGC CGTGTGGGGA TCCGTGATCG AGATCGTGGA GCGGAGCAAC
TACATGGGCA ACCCCTGGAC CGAGTACATG GCCAAGTACG 200
   201 ACATCGAGGA AGTGCACGGC AGCGGCATCC GGGTGGACCT GGGCGAGGAC GCCGAGGTGG
CCGGCACCCA GTACAGGCTG CCCAGCGGCA AGTGCCCCGT 300
   301 GTTCGGCAAG GGCATCATCA TCGAGAACAG CCAGACCACC TTCCTGACCC CCGTGGCCAC
CGAGAACCAG GACCTGAAGG ACGGCGGCTT CGCCTTCCCC 400
   401 CCCACCAAGC CCCTGATGAG CCCCATGACC CTGGACCAGA TGCGGCACTT CTACAAGGAC
AACGAGTACG TGAAGAACCT GGACGAGCTG ACCCTGTGCA 500
   501 GCCGGCACGC CGGCAACATG AACCCCGACA ACGACAAGAA CAGCAACTAC AAGTACCCG
CCGTGTACGA CGACAAGGAT AAGAAGTGCC ACATCCTGTA 600
   601 TATCGCCGCC CAGGAAAACA ACGGCCCAG GTACTGCAAC AAGGACGAGA GCAAGCGGAA
CAGCATGTTC TGCTTCAGAC CCGCCAAGGA CAAGAGCTTC 700
   701 CAGAACTACG TGTACCTGAG CAAGAACGTG GTGGACAACT GGGAGAAAGT GTGCCCCGG
AAGAATCTGG AAAACGCCAA GTTCGGCCTG TGGGTGGACG 800
   801 GCAACTGCGA GGACATCCCC CACGTGAACG AGTTCAGCGC CAACGACCTG TTCGAGTGCA
ACAAGCTGGT GTTCGAGCTG TCCGCCAGCG ACCAGCCCAA 900
   901 GCAGTACGAG CAGCACCTGA CCGACTACGA GAAGATCAAA GAGGGCTTCA AGAACAAGAA
CGCCGACATG ATCAAGAGCG CCTTTCTGCC AACTGGCGCC 1000
  1001 TTCAAGGCCG ACAGATACAA GAGCCACGGC AAGGGCTACA ACTGGGGCAA CTACAACAGA
AAGACCCAGA AGTGCGAGAT CTTCAACGTG AAGCCCACCT 1100
  1101 GCCTGATCAA CGACAAGTCC TATATCGCCA CCACCGCCCT GAGCCACCCC ATCGAGGTGG
AGCACAACTT CCCTTGCAGC CTGTACAAGG ATGAGATCAA 1200
  1201 GAAAGAGATC GAGCGGGAGA GCAAGAGGAT CAAGCTGAAC GACAACGACG ACGAGGGCAA
CAAGAAGATC ATTGCCCCCA GGATCTTCAT CAGCGACGAT 1300
  1301 AAGGACAGCC TGAAGTGCCC CTGCGACCCC GAGATCGTGT CCCAGAGCAC CTGCAATTTC
TTCGTGTGCA AATGCGTGGA GAAGCGGGCC GAAGTGACCA 1400
  1401 GCAACAACGA GGTGGTGGTG AAAGAGGAAT ATAAGGACGA GTACGCCGAC ATCCCCGAGC
ACAAGCCCAC CTACGACAAG ATGAAGATCA TCATTGCCAG 1500
  1501 CTCTGCCGCC GTGGCCGTGC TGGCCACCAT CCTGATGGTG TACCTGTACA AGCGGAAGGG
CAACGCCGAG AAGTACGATA AGATGGACCA GCCTCAGCAC 1600
  1601 TACGGCAAGA GCACCAGCCG GAACGACGAG ATGCTGGACC CCGAGGCCAG CTTCTGGGGC
GAGGAAAAGA GAGCTAGCCA CACCACCCCC GTGCTGATGG 1700
  1701           AAAAGCCCTA           CTACTGATGA           GCGCGCCTGA           GCTC
1734
       |    10    |    20    |    30    |    40    |    50    |    60    |
70     |    80    |    90    |    100
```

Figure 34

```
      |    10      |    20       |    30      |    40     |    50      |    60      |    70
                        |    80      |    90      |   100
   1  GGTACCGTCA   CGCGTCACCG   GTGTCATCAT   GACCGTGGCC   AGGCCCTCTG   TGCCTGCCGC
CCTGCCCCTG   CTGGGCGAGC   TGCCCCGGCT   GCTGCTCCTG   100
 101  GTGCTGCTGT   GCCTGCCCGC   CGTGTGGGGA   TCCGTGATCG   AGATCGTGGA   GCGGAGCAAC
TACATGGGCA   ACCCCTGGAC   CGAGTACATG   GCCAAGTACG   200
 201  ACATCGAGGA   AGTGCACGGC   AGCGGCATCC   GGGTGGACCT   GGGCGAGGAC   GCCGAGGTGG
CCGGCACCCA   GTACAGGCTG   CCCAGCGGCA   AGTGCCCCGT   300
 301  GTTCGGCAAG   GGCATCATCA   TCGAGAACAG   CCAGACCACC   TTCCTGACCC   CCGTGGCCAC
CGAGAACCAG   GACCTGAAGG   ACGGCGGCTT   CGCCTTCCCC   400
 401  CCCACCAAGC   CCCTGATGAG   CCCCATGACC   CTGGACCAGA   TGCGGCACTT   CTACAAGGAC
AACGAGTACG   TGAAGAACCT   GGACGAGCTG   ACCCTGTGCA   500
 501  GCCGGCACGC   CGGCAACATG   AACCCCGACA   ACGACAAGAA   CAGCAACTAC   AAGTACCCCG
CCGTGTACGA   CGACAAGGAT   AAGAAGTGCC   ACATCCTGTA   600
 601  TATCGCCGCC   CAGGAAAACA   ACGGCCCCAG   GTACTGCAAC   AAGGACGAGA   GCAAGCGGAA
CAGCATGTTC   TGCTTCAGAC   CCGCCAAGGA   CAAGAGCTTC   700
 701  CAGAACTACG   TGTACCTGAG   CAAGAACGTG   GTGGACAACT   GGGAGAAAGT   GTGCCCCCGG
AAGAATCTGG   AAAACGCCAA   GTTCGGCCTG   TGGGTGGACG   800
 801  GCAACTGCGA   GGACATCCCC   CACGTGAACG   AGTTCAGCGC   CAACGACCTG   TTCGAGTGCA
ACAAGCTGGT   GTTCGAGCTG   TCCGCCAGCG   ACCAGCCCAA   900
 901  GCAGTACGAG   CAGCACCTGA   CCGACTACGA   GAAGATCAAA   GAGGGCTTCA   AGAACAAGAA
CGCCGACATG   ATCAAGAGCG   CCTTTCTGCC   AACTGGCGCC   1000
1001  TTCAAGGCCG   ACAGATACAA   GAGCCACGGC   AAGGGCTACA   ACTGGGGCAA   CTACAACAGA
AAGACCCAGA   AGTGCGAGAT   CTTCAACGTG   AAGCCCACCT   1100
1101  GCCTGATCAA   CGACAAGTCC   TATATCGCCA   CCACCGCCCT   GAGCCACCCC   ATCGAGGTGG
AGCACAACTT   CCCTTGCAGC   CTGTACAAGG   ATGAGATCAA   1200
1201  GAAAGAGATC   GAGCGGGAGA   GCAAGAGGAT   CAAGCTGAAC   GACAACGACG   ACGAGGGCAA
CAAGAAGATC   ATTGCCCCCA   GGATCTTCAT   CAGCGACGAT   1300
1301  AAGGACAGCC   TGAAGTGCCC   CTGCGACCCC   GAGATCGTGT   CCCAGAGCAC   CTGCAATTTC
TTCGTGTGCA   AATGCGTGGA   GAAGCGGGCC   GAAGTGACCA   1400
1401  GCAACAACGA   GGTGGTGGTG   AAAGAGGAAT   ATAAGGACGA   GTACGCCGAC   ATCCCCGAGC
ACAAGCCCAC   CTACGACAAG   ATGTGATGAT   GAGCGCGCCT   1500
1501                                                                 GAGCTC
1506
      |    10      |    20       |    30      |    40     |    50      |    60      |    70
                        |    80      |    90      |   100
```

Figure 35

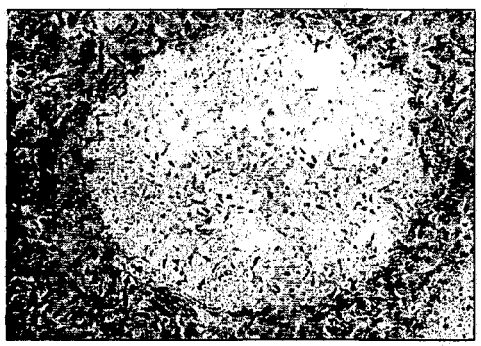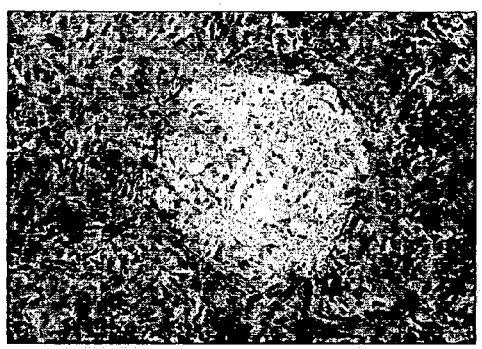
rMV3-d-42 3D7
Figure 36

Figure 42: Humoral response against Measles rMeV2EZ-d-p42-SgrAI    rMeV2EZ-d-p42*-SgrAI Blood was taken regularly and tested for Measles IgG Titers.

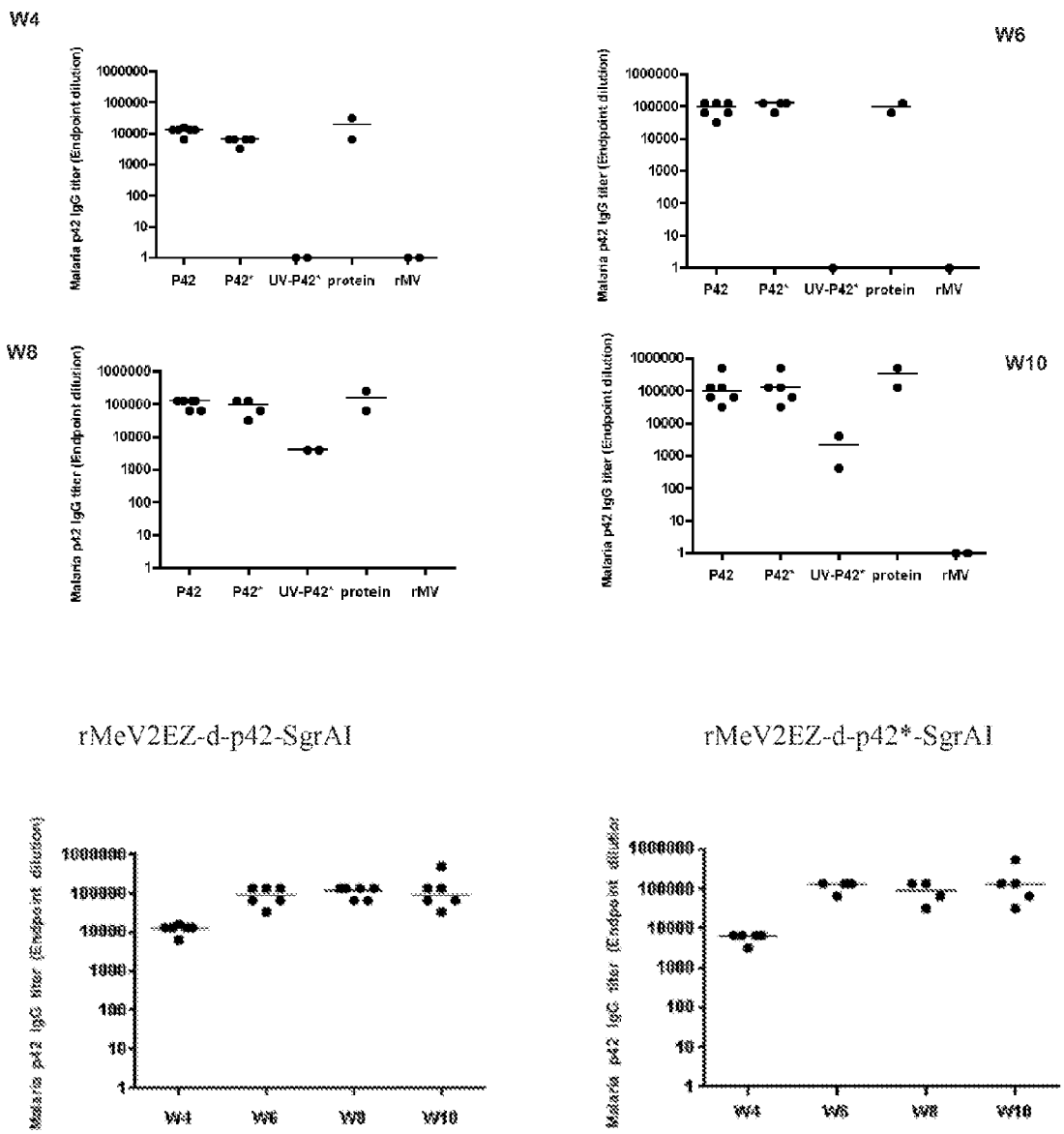
Figure 43: Humoral response against Malaria
Blood was taken regularly and tested for Malaria IgG Titers

COMBINED MEASLES-MALARIA VACCINE

CROSS REFERENCE APPLICATIONS

This application is a Divisional of application Ser. No. 13/318,701 filed on 23 Jan. 2012, which is a 371 of International Application PCT/IN10/00287 filed on 3 May 2010, which claims priority from Indian Patent Application Number 1181/MUM/2009 filed 5 May 2009, the content of which is incorporated herein by reference.

FIELD OF THE INVENTION

The present invention relates to a combined measles-malaria vaccine containing different attenuated recombinant measles-malaria vectors comprising a heterologous nucleic acid encoding several *Plasmodium falciparum* antigens. Preferably, it relates to viral vectors that comprise nucleic acids encoding the circumsporozoite (CS) protein of *P. falciparum*, the merozoite surface protein 1 (MSP-1) of *P. falciparum*, and its derivatives (p-42; p-83-30-38) in its glycosylated and secreted forms, and apical membrane antigen1 (AMA1) of *P. falciparum*, in its anchored or secreted form. The viral vector stems from an attenuated measles virus, based on a strain that is used as a vaccine and is efficient in delivering the gene of interest and that binds to and infects the relevant immune cells efficiently. In a preferred embodiment, the CS, the MSP1 and the AMA1 proteins are generated from the virus such that they will give rise to a potent immune response in mammals, preferably humans, the expression of the proteins is elevated due to human codon optimisation. Furthermore, the invention relates to the use of the recombinant vaccine in the prophylactic treatment of malaria.

BACKGROUND INFORMATION

Measles Virus

The invention relates to a vaccine containing recombinant attenuated measles viruses expressing antigens of *Plasmodium falciparum* (Pf) and to their use for the preparation of recombinant measles-malaria vaccine which will confer immunity against both Measles and Malaria antigens.

Measles virus (MV) is a member of the order Mononegavirales, i.e. viruses with a non-segmented negative-strand RNA genome. The non segmented genome of MV has an antimessage polarity; thus, the genomic RNA is not translated either in vivo or in vitro. Furthermore, it is biologically active only when it is very specifically associated with three viral proteins in the form of a ribonucleoprotein (RNP) complex (see below). Transcription and replication of non-segmented (−) strand RNA viruses and their assembly as virus particles have been reviewed extensively (1). Transcription and replication of measles virus do not involve the nucleus of the infected cells but rather take place in the cytoplasm of infected cells. The genome of the measles virus comprises genes encoding six major structural proteins from the six genes (designated N, P, M, F, H and L) and additionally two-non structural proteins derived from the P gene, C and V, involved in counteracting the constitutive immune responses and in regulation of transcription/replication. The gene order is 3' N, P (including C and V), M, F, H, and L 5'. In addition, from the 3'-terminal region a short leader RNA of about 50 nucleotides is transcribed. The cited genes respectively encode the proteins of the ribonucleocapsid (RNP) of the virus, i.e., the nucleoprotein (N), the phosphoprotein (P), and the large polymerase/replicase protein (L), which very tightly associate with the genome RNA, forming the RNP. The other genes encode the proteins of the viral envelope including the hemagglutinin (H), the fusion (F) and the matrix (M) proteins. The transcription of the MV genes follows a decreasing gradient: when the polymerase operates on the genomic template it synthesizes more RNA made from upstream genes than from downstream genes. In this discontinuous transcription mode the mRNAs are capped and polyadenylated. Conversely, in the replication mode, the L protein produces full length antigenomic and genomic RNA which are immediately covered with N, P and L proteins to form infectious progeny RNPs.

The measles virus has been isolated in 1954: Enders and Peebles inoculated primary human kidney cells with the blood of David Edmoston, a child affected by measles, and the resulting Edmoston strain of MV (2) was subsequently adapted to growth in a variety of cell lines. Adaptation to chicken embryos, chick embryo fibroblasts (CEF), and/or dog kidney cells and human diploid cells produced the attenuated Edmonston A and B (3), Zagreb (EZ) and AIK-C seeds. Edmonston B was licensed in 1963 as the first MV vaccine. Further passages of Edmonston A and B on CEF produced the more attenuated Schwarz and Moraten viruses (3) whose sequences have recently been shown to be identical (4; 5). Because Edmonston B vaccine was reactogenic, it was abandoned in 1975 and replaced by the Schwarz/Moraten vaccine. Several other vaccine strains are also used: AIK-C, Schwarz F88, CAM70, TD97 in Japan, Leningrad-16 in Russia, and Edmonston Zagreb. The CAM70 and TD97 Chinese strains were not derived from Edmonston. Schwarz/Moraten and AIK-C vaccines are produced on CEF. Zagreb vaccine is produced on human diploid cells (WI-38). Today, the Schwarz/Moraten, AIK-C and EZ vaccines are commonly used (6), but in principle, any one of these attenuated vaccine strains, which are all of the one unique MV serotype, proven to be safe and to induce long-lasting immune responses, can be used for the purposes of the invention.

MV vaccines induce life-long immunity after a single or two low-dose injections. Protection against measles is mediated both by antibodies and by CD4 and CD8 T cells. Persistence of MV-specific antibodies and CD8 cells has been shown for as long as 25 years after vaccination (7).

MV vaccine is easy to produce on a large scale in most countries and can be distributed at low cost. Because the attenuation of MV genome results from an advantageous combination of numerous mutations, the vaccine is very stable and reversion to pathogenicity has never been observed (6).

Regarding safety, MV replicates exclusively in the cytoplasm, ruling out the possibility of integration into host DNA. These characteristics make live attenuated MV vaccine an attractive candidate to be used as a multivalent vaccination vector. Such a vaccine may prove as efficient in eliciting long-lasting immune protection against other pathogenic agents as against the vector virus itself.

Martin Billeter and colleagues cloned cDNA corresponding to the antigenome of Edmonston MV, and established an original and efficient reverse genetics procedure to rescue the virus (8), as described in International Patent Application WO 97/06270. The recombinant measles virus is recovered from the helper cell line 293-3-46, stably transfected and expressing MV N an P proteins as well as bacteriophage T7 RNA polymerase. For rescue of any variant or recombinant MV the helper cell line is then transiently transfected with an expression plasmid encoding L protein, and most importantly with any antigenomic plasmid appropriately constructed to yield any mutated or recombinant antigenomic RNA compatible to give rise to progeny MV. The transient transfection step leads first to the transcription, preferably by the resident T7 RNA polymerase. The resulting antigenomic RNA is immediately (in statu nascendi) covered by the viral N, P and L proteins, to yield antigenomic RNP from which genomic RNP is produced. Second, the genomic RNP is transcribed by the attached L, to yield all viral mRNAs and the respective proteins. Finally, both genomic and antigenomic RNPs are amplified by replication.

In a slight variation of this procedure, rather than using stably transfected 293-3-46 helper cells, commercially available 293T cells have been transiently transfected, using simultaneously all 5 plasmids detailed in the original patent description, those encoding N, P and T7 polymerase (previously used to create the helper cell line) as well as the plasmid encoding L and the antigenomic plasmid. Note that in the "fully transient transfection" procedure it is possible to use also variant expression plasmids and to avoid the use of T7 RNA polymerase altogether, utilizing instead the resident RNA polymerase II to express also the L protein and the antigenome (9).

To rescue individual recombinant MVs the antigenomic plasmids utilized comprise the cDNA encoding the full length antigenomic (+)RNA of the measles virus recombined with nucleotide sequences encoding the heterologous antigen of interest (heterologous nucleotide sequence), flanked by MV-specific transcription start and termination sequences, thus forming additional transcription units (ATUs). This MV Edmonston strain vector has been developed by the original MV rescue inventors for the expression of foreign genes (10), demonstrating its large capacity of insertion (as much as 5 kb) and the high stability in the expression of transgenes (11; 12), such as Hepatitis B virus surface antigen, simian or human immunodeficiency viruses (SIV or HIV), mumps virus, and human IL-12. In particular, early on, recombinant measles virus expressing Hepatitis B virus surface and core antigens either individually or in combination have been produced and shown to induce humoral immune responses in genetically modified mice.

From the observation that the properties of the measles virus and especially its ability to elicit high titers of neutralizing antibodies in vivo and its property to be a potent inducer of long lasting cellular immune response, the inventors have proposed that it may be a good candidate for the production of recombinant viruses expressing antigens from *P. falciparum*, to induce neutralizing antibodies against said Malaria parasite which preferably could be suitable to achieve at least some degree of protection in animals and more preferably in human hosts.

Especially, MV strains and in particular vaccine strains have been elected in the present invention as candidate vectors to induce immunity against both measles virus and *P. falciparum* parasite whose constituent is expressed in the designed recombinant MV, in exposed infant populations because they are having no MV immunity.

Adult populations, even already MV immunized individuals, may however also benefit from MV recombinant immunization because re-administering MV virus under the recombinant form of the present invention results in a boost of anti-MV antibodies (13).

The invention relates in particular to the preparation of recombinant measles viruses bearing heterologous genes from *P. falciparum* parasites.

The advantageous immunological properties of the recombinant measles viruses according to the invention can be shown in an animal model which is chosen among animals susceptible to measles viruses, and wherein the humoral and/or cellular immune response against the heterologous antigen and/or against the measles virus is determined. Among such animals suitable to be used as model for the characterization of the immune response, the skilled person can especially use transgenic mice expressing CD46, one of the specific receptors for MV. The most promising recombinants can then be tested in monkeys.

The recombinant measles virus nucleotide sequence must comprise a total number of nucleotides which is a multiple of six. Adherence to this so-called "rule of six" is an absolute requirement not only for MV, but for all viruses belonging to the subfamily Paramyxovirinae. Apparently, the N protein molecules, each of which contacts six nucleotides, must cover the genomic and antigenomic RNAs precisely from the 5' to the 3' end.

It is of note that the location of the ATUs can vary along the antigenomic cDNA. Thus, taking advantage of the natural expression gradient of the mRNAs of MV mentioned above, the level of expression of inserted ATUs can be varied to appropriate levels. Preferred locations of ATUs are upstream of the L-gene, upstream from the M gene and upstream of the N gene, resulting in low, medium and strong expression, respectively, of heterologous proteins.

Malaria Parasite.

Malaria currently represents one of the most prevalent infectious diseases in the world, especially in tropical and subtropical areas. Per year, malaria infections lead to severe illnesses in hundreds of million individuals worldwide, killing between 1 and 3 million, primarily young infants in developing and emerging countries. The widespread occurrence and elevated incidence of malaria are a consequence of the widespread ban of DDT and the increasing numbers of drug-resistant parasites as well as insecticide-resistant parasite vectors. Other factors include environmental and climatic changes, civil disturbances, and increased mobility of populations.

Malaria is caused by the mosquito-borne hematoprotozoan parasites belonging to the genus *Plasmodium* from the phylum Apicomplexa. Four species of *Plasmodium* genus infect humans: *P. malariae*, responsible for Malaria quartana, *P. vivax* and *P. ovale*, both of which cause Malaria tertiana, and *P. falciparum*, the pathogen of Malaria tropica and responsible for almost all fatal infections. Many others cause disease in animals, such as *P. yoelii* and *P. berghei* in mice.

Malaria parasites have a life cycle consisting of several stages. Each stage is able to induce specific immune responses directed against the corresponding occurring stage-specific antigens. Malaria parasites are transmitted to man by several species of female *Anopheles* mosquitoes. Infected mosquitoes inject the "sporozoite" form of the malaria parasite into the mammalian bloodstream. Sporozoites remain for a few minutes in the circulation before invading hepatocytes. At this stage, the parasite is located in the extra-cellular environment and is exposed to antibody attack, mainly directed to the "circumsporozoite" (CS) protein, a major component of the sporozoite surface. Once in the liver, the parasites replicate and develop into so-called "schizonts." These schizonts occur in a ratio of up to 20,000 per infected cell. During this intra-cellular stage of the parasite, main players of the host immune response are T-lymphocytes, especially CD8+ T-lymphocytes. After about one week of liver infection, thousands of so-called "merozoites" are released into the bloodstream. Apical membrane antigen 1 (AMA1) and merozoite surface protein 1 (MSP1) are both present on merozoites that emerge from infected liver cells: they are essential components of the asexual blood-stage merozoite, responsible for invasion of erythrocytes. Once they enter red blood cells, they become targets of antibody-mediated immune response and T-cell secreted cytokines. After invading erythrocytes, the merozoites undergo several stages of replication, giving rise to so-called "trophozoites" and to schizonts and merozoites, which can infect new red blood cells. A limited amount of trophozoites may evolve into "gametocytes," which constitute the parasite's sexual stage. When susceptible mosquitoes ingest erythrocytes, gametocytes are released from the erythrocytes, resulting in several male gametocytes and one female gametocyte. The fertilization of these gametes leads to zygote formation and subsequent transformation into ookinetes, then into oocysts, and finally into salivary gland sporozoites. Targeting antibodies against gametocyte stage-specific surface antigens can block this cycle within the mosquito mid gut. Such antibodies will not protect the mammalian host but will reduce malaria transmission by decreasing the number of infected mosquitoes and their parasite load.

The MSP-1 is synthesised as 190-200 kDa (d-190) precursor which is proteolytically processed into fragments of 83, 30, 38 and 42 kDa (d-42) during schizogony (14). At the time of erythrocytic invasion the 42-kDa is further cleaved to yield a 33 kDa fragment which is shed with the rest of the complex, and a 19 kDa fragment, which contains two epidermal growth factor (EGF)-like domains, that remains associated with the merozoite membrane during invasion. This secondary cleavage is a pre-requisite for successfully erythrocyte invasion (15).

MSP-1 is an essentially dimorphic protein exhibiting high conservation within the dimorphic alleles characterised by the K1 and MAD20 prototypes.

AMA-1 (16) is a structurally conserved type I integral membrane protein, comprising 622 aa in *P. falciparum* (PfAMA-1), organised in a cytosolic region (50 aa), a transmembrane region, and an ectodomain, which folds as an a N-terminal pro-sequence and three domains (DI, DII, DIII) Expression of the protein is maximal in late schizogony: the precursor of AMA-1 (83 kDa) is processed proteolytically, to cleave away the pro-sequence, converting the protein into a 66 kDa form, which allows the merozoite relocalisation. Antibodies recognise mainly DI and DII, and appear to react equally well with several allelic variants. Antibody responses to DIII are generally low, levels increasing in adults (17, 18).

PfAMA-1 contains 64 polymorphic positions (9 in the pro-sequence, 52 in the ectodomain, 3 in the cytosolic region), most of them are dimorphic, which are important epitopes for host immune responses. To develop PfAMA-1-based vaccines it should be important to cover the polymorphisms: Diversity Covering (DiCo1, 2 and 3) PfAMA-1 are artificial sequences representing, to the greatest extent possible, the naturally occurring polymorphism of the PfAMA1 ectodomain. It has been shown that they induce immune responses which are functional against a range of parasites carrying diverse PfAMA1 alleles. This approach may offer a means by which vaccines targeting PfAMA1 can be produced such that a strong and a functional protection against the broad range of naturally occurring PfAMA1 alleles can be induced. (19).

The CS protein (CSP) has about 420 aa and a molecular weight of 58 kDa. It represents the major surface protein of sporozoites: its function is fundamental for the maturation of sporozoites from oocystis and for the invasion of hepatocytes, which is mediated from a conserved motif of positively charged aminoacids. CSP is organised into two non-repetitive regions at 5' and 3' ends, and a variable species-specific central region, consisting of multiple repeats of four-residues-long motifs, which represents the main epitope within the CSP. Since CSP continues to be detectable for at least the first 3 days of schizogony, it is considered an attractive vaccine target for both antibody-mediated immuno response, directed against extracellular sporozoites, and cell-mediated immuno responses, directed against schizonts (20).

Current approaches to malaria vaccine development can be classified according to the different stages in which the parasite can exist, as described above.

Three types of possible vaccines can be distinguished: i) pre-erythrocytic vaccines, which are directed against sporozoites and/or schizont-infected cells. These types of vaccines are primarily CS-based, and should ideally confer sterile immunity, mediated by humoral and cellular immune responses, preventing malaria infection; ii) asexual blood-stage vaccines, which are directed against merozoites-infected cells: MSP1 and AMA1 are leading malaria vaccine candidates, designed to minimize clinical severity. These vaccines should reduce morbidity and mortality and are meant to prevent the parasite from entering and/or developing in the erythrocytes; iii) transmission-blocking vaccines, which are designed to hamper the parasite development in the mosquito host. This type of vaccine should favour the reduction of population-wide malaria infection rates. Next to these vaccines, the feasibility of developing malaria vaccines that target multiple stages of the parasite life cycle is being pursued in so-called multi-component and/or multi-stage vaccines.

Today's global malaria vaccine portfolio looks promising with 47 new vaccine candidates, 31 in preclinical development, narrowing down to 16 in clinical trials. One of these, the RTS,S vaccine, being developed by GSK Biologicals and PATH-MVI, should enter final phase III clinical trials in 2008 (21). Other interesting vaccine candidates are those based on live recombinant viruses used as vector, such as Modified Vaccinia Ankara (MVA), as described in International Patent Application US2006127413, poxvirus (U.S. Pat. No. 6,214,353, AU7060294, AU1668197, WO9428930, and U.S. Pat. No. 5,756,101), adenovirus (US2007071726, US2005265974, US2007088156 and CA2507915), cold-adapted attenuated influenza virus, or based on yeasts, such as *Pichia pastoris* and *Saccharomyces* spp., or on bacterial expression systems, such as *Salmonella* spp. (U.S. Pat. No. 5,112,749) and *Escherichia coli* (EB0191748) (22).

Currently, no commercially available vaccine against malaria is available, although the development of vaccines against malaria has already been initiated more than 30 years ago. Many factors make malaria vaccine development difficult and challenging. First, the size and genetic complexity of the parasite mean that each infection presents thousands of antigens to the human immune system. Understanding which of these can be a useful target for vaccine development has been complicated, and to date at least 40 different promising antigens have been identified. Second, the parasite changes through several life stages even while in the human host, presenting, at each stage of the life cycle, a different subset of molecules to the immune system. Third, the parasite has evolved a series of strategies that allow it to confuse, hide, and misdirect the human immune system. Finally, it is possible to have multiple malaria infections of not only different species but also of different strains at the same time.

Hence the present invention fulfil the long felt need of prior art by providing combined measles-malaria vaccine containing different attenuated recombinant measles-malaria vectors comprising a heterologous nucleic acid encoding several *Plasmodium falciparum* antigens.

SUMMARY OF THE INVENTION

In one embodiment of the present invention provides a combined measles-malaria vaccine comprises a recombinant measles vaccine virus which express malaria antigens capable of eliciting immune response and protection both against measles and malaria.

In another embodiment, the present invention provides the recombinant measles vaccine virus having nucleotide sequence which expresses MSP1 malaria antigen. In preferred embodiment, recombinant measles vaccine virus having nucleotide sequence which expresses malaria antigen d190 or d83-30-38 or d42 in both anchored and secreted forms from 3D7 strain and the FCB1 strain.

In yet another embodiment, the present invention provides the recombinant measles vaccine virus having nucleotide sequence which expresses Diversity Covering (DiCo) AMA1 malaria antigen.

In yet another embodiment, the present invention provides the recombinant measles vaccine virus having nucleotide sequence which expresses CS malaria antigen.

DESCRIPTION OF THE FIGURES

FIG. 15: Representation of the CS synthetic gene. The coding nucleotides on the flanking regions of the CS gene and the corresponding amminoacids are shown. Unique restriction sites added for cloning procedures are in colours.

FIG. 24: Complete nucleotide sequence of p(+)MV$_2$EZ-GFP. The sequence can be described as follows with reference to the position of the nucleotides:
   592-608 T7 promoter
   609-17354 MV Edmoston Zagreb antigenome
   4049-4054 MluI restriction site
   4060-4067 SgrAI restriction site
   4079-4084 BssHII restriction site
   4085-4801 Green Fluorescent Protein (GFP) ORF
   4805-4810 BssHII restriction site
   4817-4822 AatII restriction site
   17355-17580 HDV ribozyme and T7 terminator FIG. 25: Complete nucleotide sequence of p(+)MV$_3$EZ-GFP. The sequence can be described as follows with reference to the position of the nucleotides:
   592608 T7 promoter
   60917359 MV Edmoston Zagreb antigenome
   98519856 MluI restriction site
   98629869 SgrAI restriction site
   98869891 BssHII restriction site
   989210608 Green Fluorescent Protein (GFP) ORF
   1061210617 BssHII restriction site
   1062410629 AatII restriction site
   1736017585 HDV ribozyme and T7 terminator FIG. 26: AN101TE: this is the MSP1 d-190 3D7 sequence ORF cloned by the inventors. The sequence can be described as follows with reference to the position of the nucleotides:
   1-3 Start codon
   4-99 d-1903D7 signal peptide
   100-105 BamHI restriction site
   4014-4020 BstEII restriction site
   5152-5157 AclI restriction site
   5158-5250 GPI sequence
   5251-5253 STOP codon FIG. 27: AN102TE: this is the MSP1 d-190* 3D7sequence ORF cloned by the inventors. The sequence can be described as follows with reference to the position of the nucleotides:
   1-3 Start codon
   4-99 d-190*3D7 signal peptide
   100-105 BamHI restriction site
   4014-4020 BstEII restriction site
   5152-5157 AclI restriction site
   5158-5160 STOP codon FIG. 28: AN103TE: this is the MSP1 d-83-30-38 3D7 sequence ORF cloned by the inventors. The sequence can be described as follows with reference to the position of the nucleotides:
   1-3 Start codon
   4-99 d-83-30-38 3D7 signal peptide
   100-105 BamHI restriction site
   4014-4020 BstEII restriction site
   4021-4026 AclI restriction site
   4027-4119 GPI sequence
   4120-4122 STOP codon FIG. 29: AN104TE: this is the MSP1 d-83-30-38* 3D7 sequence ORF cloned by the inventors. The sequence can be described as follows with reference to the position of the nucleotides:
   1-3 Start codon
   4-99 d-83-30-38* 3D7signal peptide
   100-105 BamHI restriction site
   4014-4020 BstEII restriction site
   4027-4029 STOP codon FIG. 30: AN105TE: this is the MSP1 d-42 3D7sequence ORF cloned by the inventors. The sequence can be described as follows with reference to the position of the nucleotides:
   1-3 Start codon
   4-99 d-42 3D7 signal peptide
   100-105 BamHI restriction site
   108-114 BstEII restriction site
   1246-1251 AclI restriction sites
   1252-1344 GPI sequence
   1345-1347 STOP codon FIG. 31: AN106TE: this is the MSP1 d-42* 3D7 sequence ORF cloned by the inventors. The sequence can be described as follows with reference to the position of the nucleotides:
   1-3 Start codon
   4-99 d-42* 3D7 signal peptide
   100-105 BamHI restriction site 108-114 BstEII restriction site
1246-1251 AcII restriction sites
1252-1254 STOP codon FIG. 32: AN107TE: this is the MSP1 d-190 FCB1 sequence ORF cloned by the inventors. The sequence can be described as follows with reference to the position of the nucleotides:
1-3 Start codon
4-99 d-190 FCB1 signal peptide
100-105 BamHI restriction site
146-151 HindIII restriction site
3825-3831 BstEII restriction site
4912-4917 AcII restriction sites
4918-5010 GPI sequence
5011-5013 STOP codon FIG. 33: AN108TE: this is the CS sequence ORF cloned by the inventors. The sequence can be described as follows with reference to the position of the nucleotides:
1-3 Start codon
4-1116 CS sequence
1117-1119 STOP codon FIG. 34: AN109TE: this is the DiCo1 complete sequence ORF cloned by the inventors. The sequence can be described as follows with reference to the position of the nucleotides:
1-3 Start codon
4-99 DiCo1 complete signal peptide
100-105 BamHI restriction site
106-1686 DiCo1 complete sequence ORF
1687-1689 STOP codon FIG. 35: AN110TE: this is the DiCo1 ecto sequence ORF cloned by the inventors. The sequence can be described as follows with reference to the position of the nucleotides:
1-3 Start codon
4-99 DiCo1 ecto signal peptide
100-105 BamHI restriction site
106-1455 DiCo1 ecto sequence ORF
1456-1458 STOP codon FIG. 36: Comparable cytopathic effects produced on Vero cells after infection with the recombinant Measles-p-42 Malaria virus MV virus vaccine.

FIG. 39: Growth kinetics curve of the recombinant Measles-p-42 Malaria virus compared with that of the MV virus vaccine.

Figure 41:
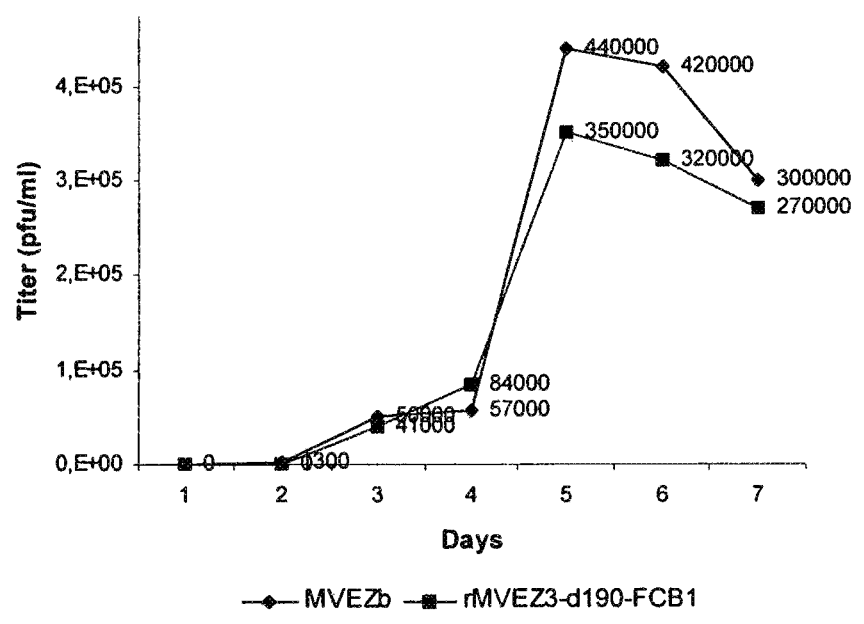

FIG. 41: Growth kinetics curve of the recombinant Measles-p-190-FCB1 Malaria virus compared with that of the MV virus vaccine.

FIG. 42: shows humoral response against measles.

FIG. 43: shows humoral immune responses against malaria.

DETAILED DESCRIPTION OF THE INVENTION

Figure 1:
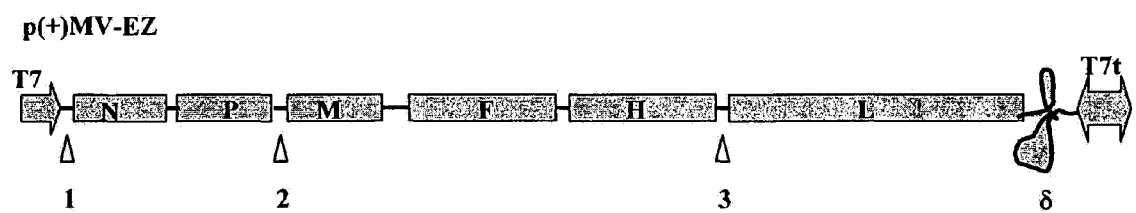
FIG. 1: Schematic representation of the antigenomic DNA p(+)MV-EZ of measles virus. p(+)MV-EZ is a plasmid derived from pBluescript containing the complete sequence of the measles virus (Edmoston Zagreb), under the control of the T7 RNA polymerase promoter (T7), containing three ATU respectively in position 1 (before the N gene of the measles virus), 2 (between the P and the M genes of the measles virus) and 3 (between the H and the L genes of the measles virus), and exactly terminated by the hepatitis delta ribozyme and T7 RNA polymerase terminator (δ T7t). The size of the plasmid is 18941 bp.

The object of the invention is the production of a combined measles-malaria vaccine from a recombinant Measles vectors capable of containing stably integrated DNA sequences which code for CS, MSP-1 or partial sections of it and AMA-1 or partial sections, in the secreted or surface anchored forms, of *P. falciparum*.

The invention shall also include the rescue of recombinant MV-Malaria viruses which are capable of infection, replication and expression of PfCS, PfMSP-1 and PfAMA-1 antigens in susceptible transgenic mice, monkeys and human host.

Furthermore, the invention intends to include the construction of multivalent recombinant measles-malaria vectors, in which two different antigens are simultaneously cloned and expressed in the same vector, conferring immunity against both of them.

Moreover, the invention relates to the combination of three different recombinant measles-malaria viruses, each carrying a different gene and expressing different antigens, in a manner to elicit immuno response in the host, directed against the different stages of the parasite's life-cycle.

In addition, the invention includes a process to produce recombinant measles-malaria viruses which are avoided of defective interfering particles (DIs). The DIs are known to significantly inhibit the growth of virus in any production system and to successfully suppress immune response in human individuals.

Furthermore, the invention comprises a method to produce a vaccine containing such recombinant viruses.

The examples below describe the preferred mode of carrying out the invention. It should be understood that these examples are provided for illustration and should not be construed as limiting the scope of the invention in any way.

Example 1

Construction of Recombinant MV-PfMSP-1 Plasmids

All cloning procedures were done as per the techniques described in Sambrook et al. (1989).

All the restriction enzymes were from New England BioLabs; the oligonucleotides PCR primers and DNA polylinkers were from Invitrogen.

PfMSP1 and its fragments (d-83-30-38 and d-42) either in the secreted and anchored form, have been chemically synthesized and human codon optimised. They have been cloned into the pZE21MV intermediate vector and have been slightly modified by adding SgrAI cloning site at the 5' end followed by an optimised Kozak sequence (TCATCA). These modifications have been checked by sequencing at MWG Biotech.

List of the recombinant MV-PfMSP-1 plasmids, GPI-anchored and secreted (*) forms, from 3D7 strain, which belongs to the MAD20 prototype, and from FCB1 strain, which belongs to the K1 prototype:
p(+)$MV_2EZ$-d-190-SgrAI (3D7)
p(+)$MV_3EZ$-d-190-SgrAI (3D7)
p(+)$MV_2EZ$-d-83-30-38-SgrAI (3 D7)
p(+)$MV_3EZ$-d-83-30-38-SgrAI (3D7)
p(+)$MV_2EZ$-d-42-SgrAI (3D7)
p(+)$MV_3EZ$-d-42-SgrAI (3D7)
p(+)$MV_2EZ$-d-190*-SgrAI (3D7)
p(+)$MV_3EZ$-d-190*-SgrAI (3D7)
p(+)$MV_2EZ$-d-83-30-38*-SgrAI (3D7)
p(+)$MV_3EZ$-d-83-30-38*-SgrAI (3D7)

p(+)MV₂EZ-d-42*-SgrAI (3D7)
p(+)MV₃EZ-d-42*-SgrAI (3D7)
p(+)MV₂EZ-d-190-SgrAI (FCB1)
p(+)MV₃EZ-d-190-SgrAI (FCB1)

1a) Construction of p(+)MV₂EZ-d-190-SgrAI (3D7, 24323 bp) and p(+)MV₃EZ-d-190-SgrAI (3D7, 24323 bp).

1 µg of MV plasmid DNA containing the green fluorescent protein (GFP) (p(+)MV₂₋₃EZ-GFP Berna strain, 19774 bp: FIGS. 24 and 25) was digested with one unit of both SgrAI and BssHII restriction enzymes, for two hours at their optimal temperature, in 50 µl final volume. All the digested DNA was loaded onto a 1% agarose gel, run at 80 Volt for about 2 hours. Then, the proper band (19048 bp) was excised from the gel, purified by QIAEX gel purification and the DNA concentration was calculated by absorbance at 260 nm and adjusted to 1 µg/ml.

Figure 37:
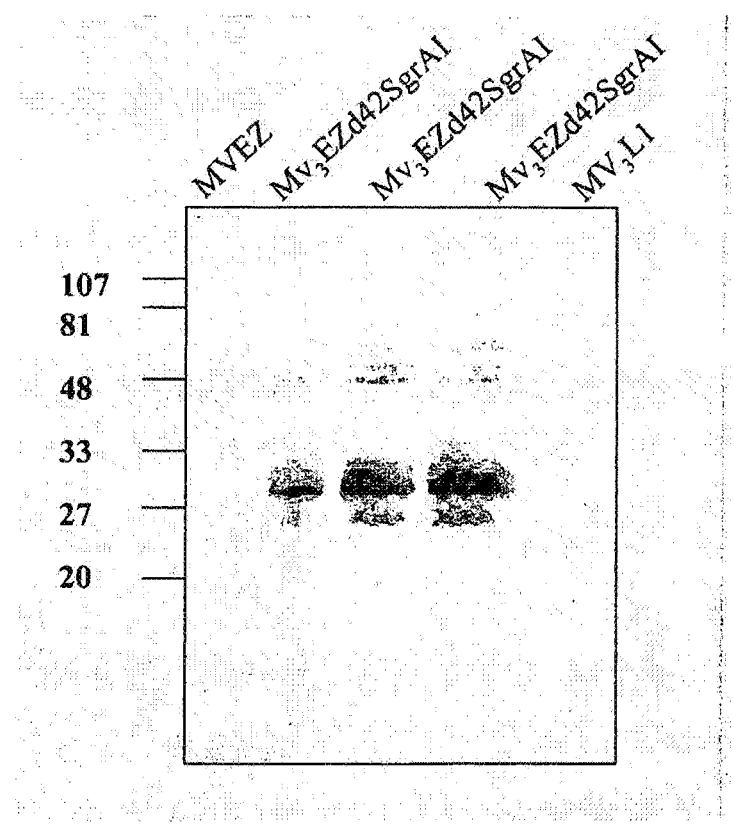
FIG. 37: Expression of the d-42 3D7 transgene inserted into position three of the Measles vector ($MV_3EZ$-d-42 SgrAI). Cell lysates from passage 1, 5 and 10 analysed by Western Blot against empty Measles vector (MVEZ) and a negative control ($MV_3L1$, a recombinant MV-Papilloma virus).
Figure 38:
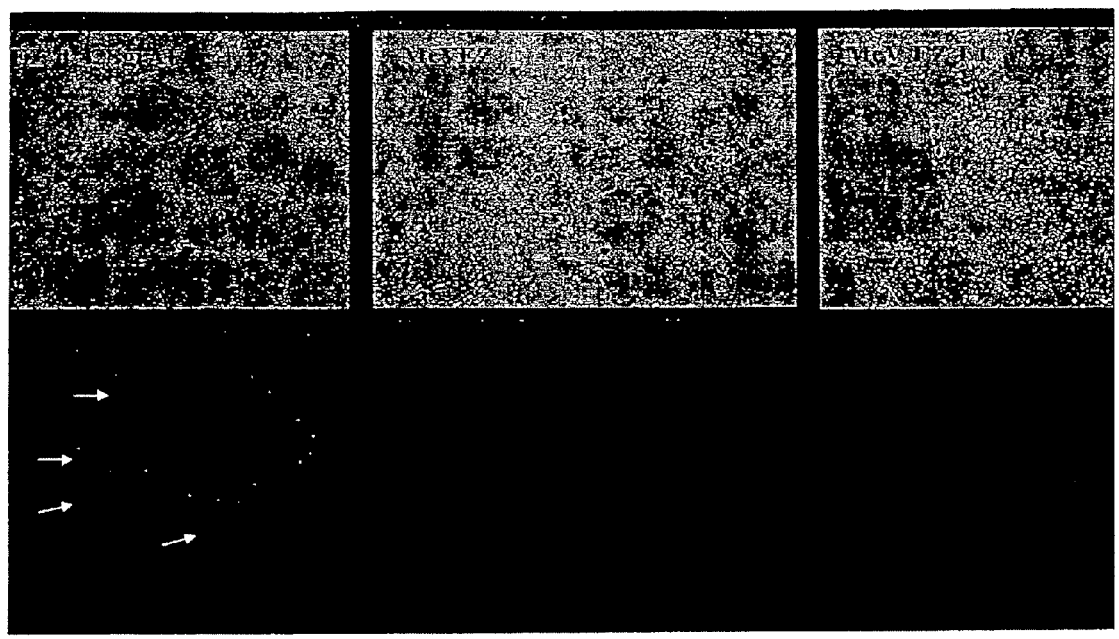
FIG. 38: Expression of the d-42 3D7 transgene inserted into position three of the Measles vector ($MV_3EZ$-d-42 SgrAI) analysed by immunofluorescence, compared with empty Measles vector (MVEZ) and a negative control (MV2EZL1, a recombinant MV-Papilloma virus). Arrows point to the same syncythia as they looked using an optical microscope before and after immunostaining.
Figure 40:
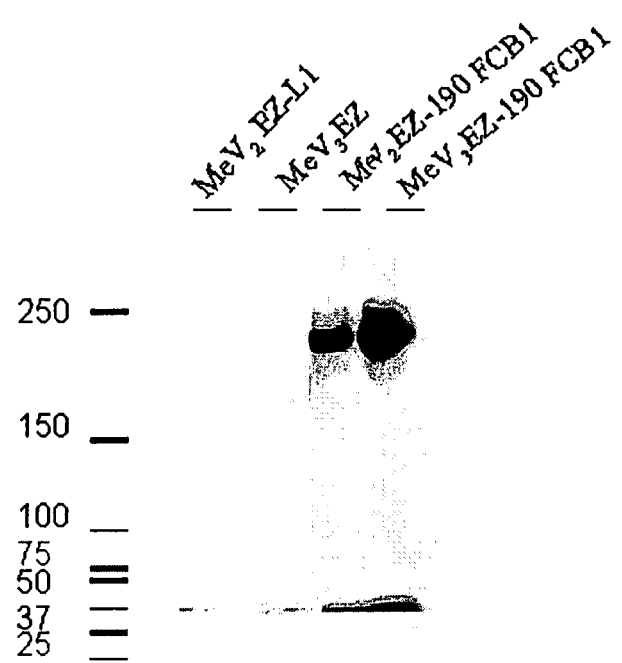
FIG. 40: Expression of the d-190 FCB1 transgene inserted into position two and three of the Measles vector ($MV_{2-3}EZ$-d-190 SgrAI FCB1). Cell lysates analysed by Western Blot against empty Measles vector (MVEZ) and a negative control (MV2EZL1, a recombinant MV-Papilloma virus).

1 µg of d-190 gene, inserted into an intermediate plasmid (pZE21MV-d-190 SgrAI, 7564 bp,) was taken out by SgrAI-BssHII digestion (one unit of each enzyme), for two hours at their optimal temperature, in 50 µl final volume. All the digested DNA was loaded onto a 1% agarose gel, run at 80 Volt for about 2 hours. Then, the proper band (5275 bp) was excised from the gel, purified by QIAEX gel purification kit and the DNA concentration was calculated by absorbance at 260 nm and adjusted to 1 μg/ml.

Thus, the vector (MV DNA: FIG. 1) and the insert (d-190 DNA: FIG. 2), were ligated in an equimolar ratio overnight at 16° C., using one unit of T4 DNA Ligase and its own reaction buffer in 10 μl final volume.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences, aligned with the assumed ones using a DNA Strider software, showed 100% identity.

The d-190-3D7 gene, inserted into position 2 of the MV vector (SgrAI, pos. 4060, and BssHII, pos. 9335) is represented in FIG. 4 and its Open Reading Frame (ORF) is listed in FIG. 26.

The d-190-3D7 gene, inserted into position 3 of the MV vector (SgrAI, pos. 9862, and BssHII, pos. 15137) is represented in FIG. 6.

The genome's length (starting at ACC, pos. 609, to GGT, pos. 21884) of the recombinant Measles-Malaria plasmids was a multiple of six, allowing the rescue of the recombinant $MV_{2-3}$-d-190-3D7 viruses.

1b) Construction of p(+)$MV_2$EZ-d-83-30-38-SgrAI (3D7, 23195 bp) and p(+)$MV_3$EZ-d-83-30-38-SgrAI (3D7, 23195 bp).

The measles vectors were prepared as detailed described in example 3a.

The pZE21MV-d-190 SgrAI was digested BstEII-AclI to cut out the d-42 fragment; a polylinker, with cohesive BstEII and AclI ends, had been ligated to obtain the intermediate plasmid pZE21MV-d-83-30-38-SgrAI (6436 bp).

The sequence of the polylinker was: 5'-GTCACCAGCG-GCCGCAA-3'.

1 μg of pZE21MV-d-83-30-38 SgrAI was digested SgrAI-BssHII (one unit of each enzyme), for two hours at their optimal temperature, in 50 μl final volume. All the digested DNA was loaded onto a 1% agarose gel, run at 80 Volt for about 2 hours. Then, the proper band (4147 bp) was excised from the gel, purified by QIAEX gel purification kit and the DNA concentration was calculated by absorbance at 260 nm and adjusted to 1 μg/ml.

Thus, the vector (MV DNA: FIG. 1) and the insert (d-83-30-38 DNA: FIG. 2), were ligated in an equimolar ratio overnight at 16° C., using one unit of T4 DNA Ligase and its own reaction buffer in 10 μl final volume.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences were then aligned with the assumed ones using a DNA Strider software.

The right clones were sent to MWG for sequencing: the sequences, aligned with the assumed ones using a DNA Strider software, showed 100% identity.

The d-83-30-38-3D7 gene, inserted into position 2 of the MV vector (SgrAI, pos. 4060, and BssHII, pos. 8207) is represented in FIG. 7 and its Open Reading Frame (ORF) is listed in FIG. 28.

The d-83-30-38-3D7 gene, inserted into position 3 of the MV vector (SgrAI, pos. 9862, and BssHII, pos. 14006) is represented in FIG. 9.

The genome's length (starting at ACC, pos. 609, to GGT, pos. 20756) of the recombinant Measles-Malaria plasmids was a multiple of six, allowing the rescue of the recombinant $MV_{2-3}$-d-83-30-38-3D7 viruses.

1c) Construction of p(+)$MV_2$EZ-d-42-SgrAI (3D7, 20417 bp) and p(+)$MV_3$EZ-d-42-SgrAI (3D7, 20417 bp).

The measles vectors were prepared as detailed described in example 3a.

1 μg of d-42gene, inserted into an intermediate plasmid (pZE21MV-d-42 SgrAI, 3658 bp) was taken out by SgrAI-BssHII digestion (one unit of each enzyme), for two hours at their optimal temperature, in 50 μl final volume. All the digested DNA was loaded onto a 1% agarose gel, run at 80 Volt for about 2 hours. Then, the proper band (1369 bp) was excised from the gel, purified by QIAEX gel purification kit and the DNA concentration was calculated by absorbance at 260 nm and adjusted to 1 μg/ml.

Thus, the vector (MV DNA: FIG. 1) and the insert (d-42 DNA: FIG. 2), were ligated in an equimolar ratio overnight at 16° C., using one unit of T4 DNA Ligase and its own reaction buffer in 10 μl final volume.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences, aligned with the assumed ones using a DNA Strider software, showed 100% identity.

The d-42-3D7 gene, inserted into position 2 of the MV vector (SgrAI, pos. 4060, and BssHII, pos. 5429) is represented in FIG. 10 and its Open Reading Frame (ORF) is listed in FIG. 30.

The d-42-3D7 gene, inserted into position 3 of the MV vector (SgrAI, pos. 9862, and BssHII, pos. 11231) is represented in FIG. 12.

The genome's length (starting at ACC, pos. 609, to GGT, pos. 17978) of the recombinant Measles-Malaria plasmids was a multiple of six, allowing the rescue of the recombinant $MV_{2-3}$-d-42-3D7 viruses.

The recombinant Measles-p-42 Malaria viruses and MV vaccine induced similar cytopathic effect (FIG. 36). The transgene is rather stably expressed: its expression was completely maintained in all analysed progeny clones derived from single original rescued clones after ten serial virus passages in human diploid cell MRC5 (FIG. 37-38).

Figure 39:
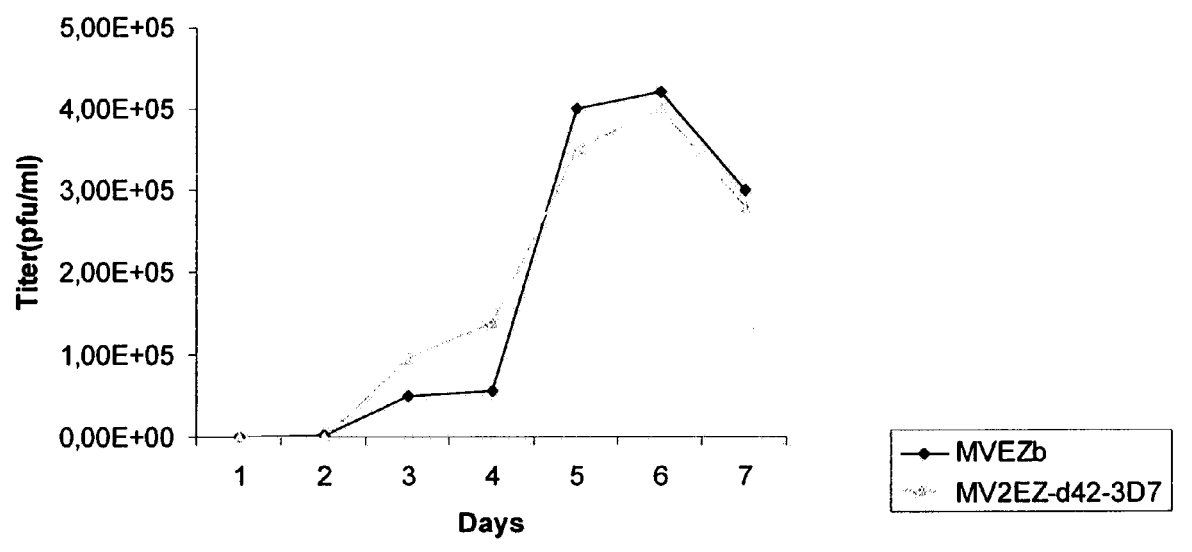

The growth curves of recombinant MV-Malaria virus and MV vaccine showed the same kinetics (FIG. 39).

1d) Construction of p(+)MV$_2$EZ-d-190*-SgrAI (3D7, 24227 bp) and p(+)MV$_3$EZ-d-190*-SgrAI (3D7, 24227 bp).

The measles vectors were prepared as detailed described in example 3a.

Using the intermediate vector pZE21MVd-190-SgrAI as template, a PCR reaction has been performed to delete the GPI anchor region, which is located between AclI (pos. 5434) and ClaI (pos. 5536) sites.

PCR amplifications were carried out using the proofreading Pfu DNA polymerase (Stratagene). DNA sequences of the synthetic oligonucleotides primers are given in lower case for the MV nucleotides and in upper case for non MV nucleotides; sequences of relevant restriction endonucleases recognition sites are underlined.

The following oligonucleotides primers have been used: For-ClaI, 5'-CCAATAAACGTTTAAT AGatcgattac gcgcgctctagc-3', and Rev-AvrII, 5'-gcctttgagtgagctgatacc-3'.

For-ClaI is homologous to the template at the level of the ClaI and BssHII sites and contains an overhang (in upper case) with two stop codons (TAATAG), the AclI site (AACGTT), and a 6 bp long-protection site for AclI (CCAATA). In the so-called PCR-GPI and in the final construct d-190*, AclI will become close to ClaI.

Rev-AvrII is homologous to the template (from pos. 5704 to 5724).

PCR product was 207 bp-long: its digestion with AclI+AvrII and ligation with the pre-digested AclI+AvrII intermediate vector pZE21MVd-190-SgrAI has produced pZE21 MVd-190*-SgrAI.

In detail, the digestion of the vector with AclI+AvrII has produced two bands of 7318 bp and 246 bp (containing the GPI region to delete): the 7.3 kb-fragment was purified from agarose gel by using QIAEX II purification kit (Qiagen) and was ligated to the digested AclI-AvrII PCR (insert) to obtain pZE21MVd-190*-SgrAI.

To screen for positive clones, NcoI digestion has be done, producing a single band of 7 kb from the d-190* intermediate vector, and two bands of 1.3 and 5.7 kb from the original GPI-anchor construct.

To construct the definitive recombinant p(+)MeV$_2$EZ-d190* and p(+)MeV$_3$EZ-d190* (FIG. 5 and FIG. 6), according to the "rule of six", MeV vectors and intermediate plasmid were digested with SgrAI+BssHII and afterwards ligated each other.

In detail, pZE21MVd-190*-SgrAI digested SgrAI+BssHII has produced three bands, 5.2 kb+1.3 kb+900 bp. D-190* sequence was contained in the 5.2 kb fragment, that has been cut, purified and ligated with MeV$_2$EZ and MeV$_3$EZ vectors SgrAI+BssHII digested (19 Kb in length), in an equimolar ratio overnight at 16° C., using one unit of T4 DNA Ligase.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences, aligned with the assumed ones using a DNA Strider software, showed 100% identity.

Figure 5:
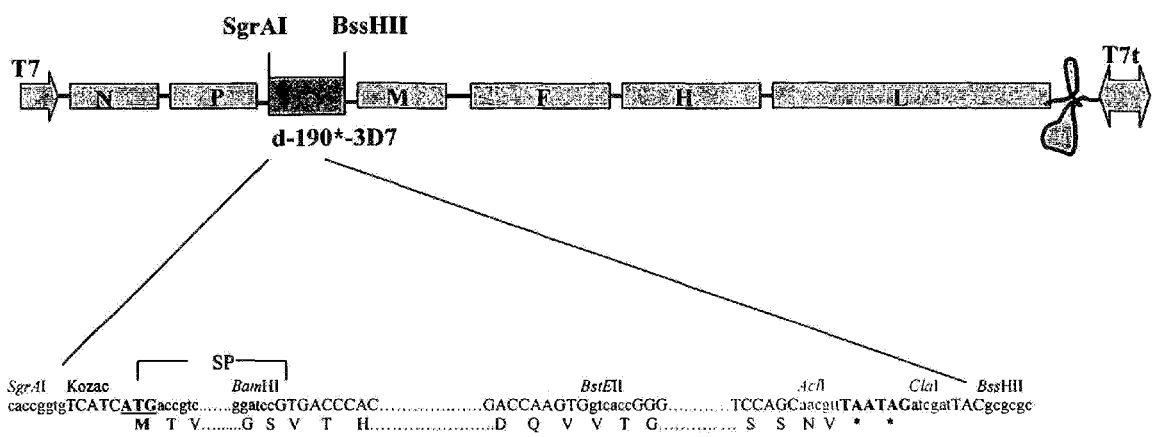
FIG. 5: Schematic representation of the recombinant measles-malaria plasmid, p(+)MV$_2$-EZ-d190*-3D7. It is a plasmid derived from p(+)MV-EZ containing d-190* malaria gene (3D7 strain), 5160 bp, coding the secreted form of the protein, cloned in position two of the measles genome by SgrAI-BssHII digestion. The size of the recombinant plasmid is 24227 bp.

The d-190*-3D7 gene, inserted into position 2 of the MV vector (SgrAI, pos. 4060, and BssHII, pos. 9239) is represented in FIG. 5 and its Open Reading Frame (ORF) is listed in FIG. 27.

Figure 6:
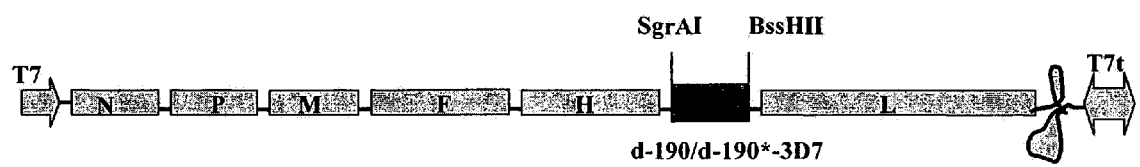
FIG. 6: Schematic representation of the recombinant measles-malaria plasmid, p(+)MV$_3$-EZ-d190-3D7 or p(+)MV$_3$-EZ-d190*-3D7. It is a plasmid derived from p(+)MV-EZ containing the d-190 malaria gene (3D7 strain), 5253 bp, coding the GPI-anchored form of the protein, or the d-190* malaria gene (3D7 strain), 5160 bp, coding the secreted form of the protein, cloned in position three of the measles genome by SgrAI-BssHII digestion. The recombinant plasmid p(+)MV$_3$-EZ-d190 is 24323 bp, and p(+)MV$_3$-EZ-d190* is 24227 bp
Figure 7:
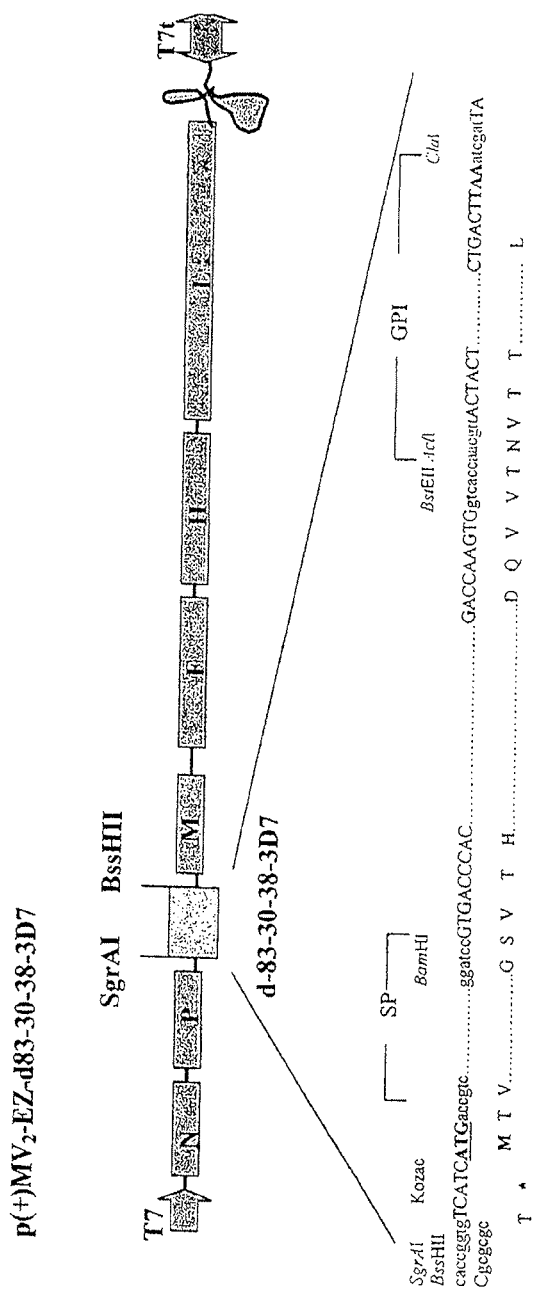
FIG. 7: Schematic representation of the recombinant measles-malaria plasmid, p(+)MV$_2$-EZ-d83-30-8-3D7. It is a plasmid derived from p(+)MV-EZ containing d-83-30-38 malaria gene (3D7 strain), 4122 bp, coding the GPI-anchored form of the protein, cloned in position two of the measles genome by SgrAI-BssHII digestion. The size of the recombinant plasmid is 23195 bp.

The d-190*-3D7 gene, inserted into position 3 of the MV vector (SgrAI, pos. 9862, and BssHII, pos. 15041) is represented in FIG. 6.

The genome's length (starting at ACC, pos. 609, to GGT, pos. 21788) of the recombinant Measles-Malaria plasmids was a multiple of six, allowing the rescue of the recombinant MV$_{2-3}$-d-90*-3 D7 viruses.

1e) Construction of p(+)MV$_2$EZ-d-83-30-38*-SgrAI (3D7, 23105 bp) and p(+)MV$_3$EZ-d-83-30-38*-SgrAI (3D7, 23105 bp).

The measles vectors were prepared as detailed described in example 3a.

The intermediate vector pZE21MVd-190-SgrAI was digested BstEII-ClaI to cut out the d-42 fragment and the GPI region, which is located between AclI (pos. 5434) and ClaI (pos. 5536) sites; a polylinker, with cohesive BstEII and ClaI ends, had been ligated to obtain the intermediate plasmid pZE21M V-d-83-30-38*-SgrAI (6346 bp).

The sequence of the polylinker was: 5'-GTCACCGGGGAATAATAGCGCAT-3'.

DNA sequence of the synthetic oligonucleotide polylinker is given in upper case for non MV nucleotides; sequences of relevant restriction endonucleases recognition sites are underlined.

Polylinker contains the BstEII (GTCACC) and ClaI (AT) sticky ends, two stop codons (TAATAG), and a triplet (GCG) to keep the rule of six.

1 μg of pZE21MV-d-83-30-38* SgrAI was digested SgrAI-BssHII (one unit of each enzyme), for two hours at their optimal temperature, in 50 μl final volume. All the digested DNA was loaded onto a 1% agarose gel, run at 80 Volt for about 2 hours. Then, the proper band (4057 bp) was excised from the gel, purified by QIAEX gel purification kit and the DNA concentration was calculated by absorbance at 260 nm and adjusted to 1 μg/ml.

Figure 2:
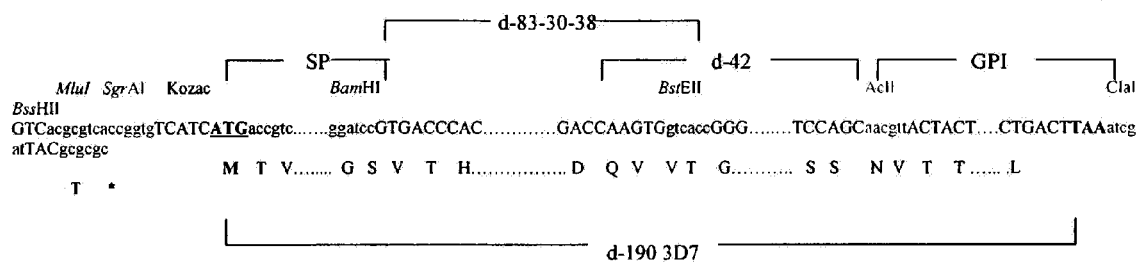
FIG. 2: Representation of the MSP-1 synthetic gene (d-190) from 3D7 strain. The coding nucleotides on the flanking regions of the d-190 gene fragments (d-83-30-38 and d-42) and the corresponding amminoacids are shown. Unique restriction sites added for cloning procedures are in colours; SP: signal peptide; GPI: glycosyl-phosphatidil-inositol sequence coded for membrane-anchored region.

Thus, the vector (MV DNA: FIG. 1) and the insert (d-83-30-38* DNA: FIG. 2), were ligated in an equimolar ratio overnight at 16° C., using one unit of T4 DNA Ligase and its own reaction buffer in 10 μl final volume.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences were then aligned with the assumed ones using a DNA Strider software. The right clones were sent to MWG for sequencing: the sequences, aligned with the assumed ones using a DNA Strider software, showed 100% identity.

Figure 8:
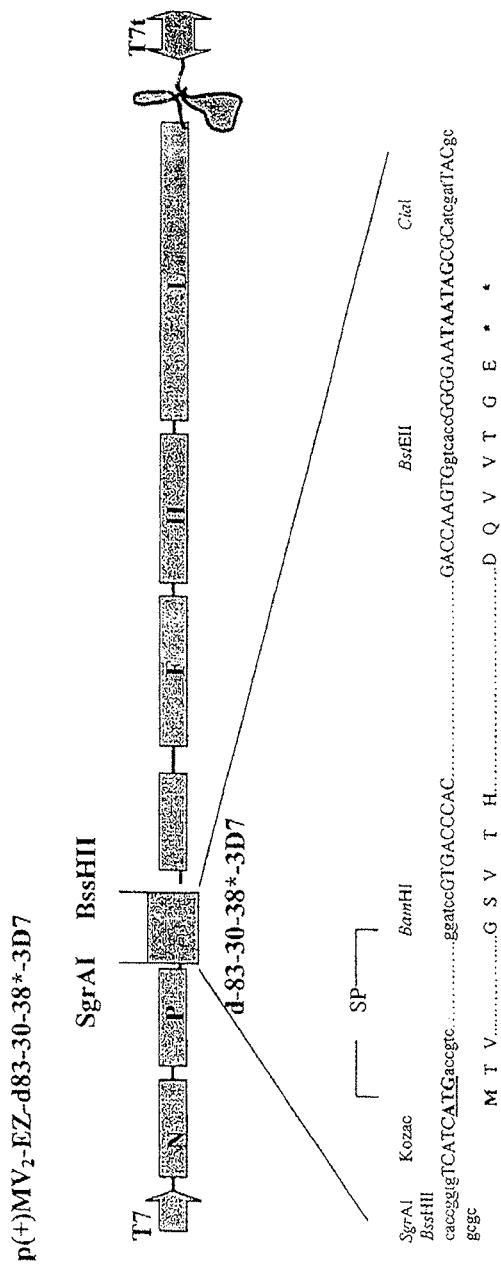
FIG. 8: Schematic representation of the recombinant measles-malaria plasmid, p(+)MV$_2$-EZ-d83-30-38*-3D7. It is a plasmid derived from p(+)MV-EZ containing d-83-30-38* malaria gene (3D7 strain), 4029 bp, coding the secreted form of the protein, cloned in position two of the measles genome by SgrAI-BssHII digestion. The size of the recombinant plasmid is 23105 bp.

The d-83-30-38*-3D7 gene, inserted into position 2 of the MV vector (SgrAI, pos. 4060, and BssHII, pos. 8117) is represented in FIG. 8 and its Open Reading Frame (ORF) is listed in FIG. 29.

Figure 9:
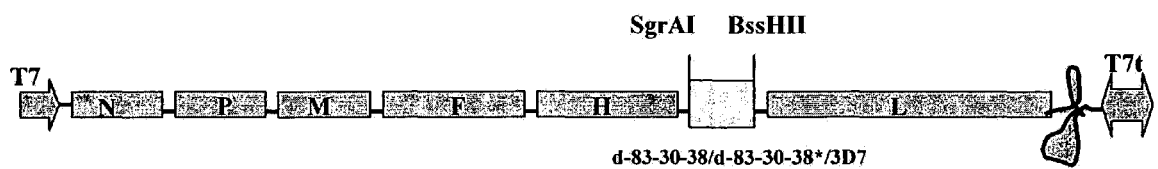
FIG. 9: Schematic representation of the recombinant measles-malaria plasmid, p(+)MV$_3$-EZ-d83-30-38-3D7 or p(+)MV$_3$-EZ-d83-30-38*-3D7. It is a plasmid derived from p(+)MV-EZ containing d-83-30-38 malaria gene (3D7 strain), 4122 bp, coding the GPI-anchored form of the protein, or the d-83-30-38* gene (3D7 strain), 4029 bp, coding the secreted form of the protein, cloned in position three of the measles genome by SgrAI-BssHII digestion. The recombinant plasmid p(+)MV$_3$-EZ-d83-30-38 is 23195 bp, p(+)MV$_3$-EZ-d83-30-38* is 23105 bp.
Figure 10:
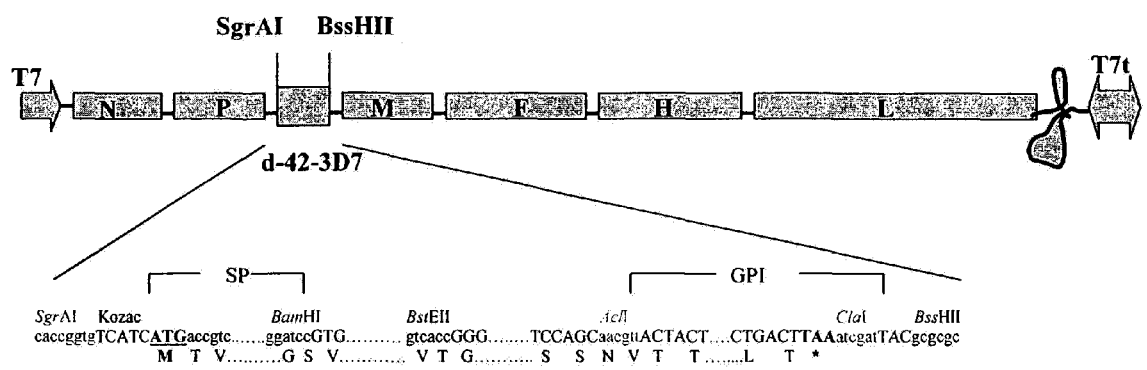
FIG. 10: Schematic representation of the recombinant measles-malaria plasmid, p(+)MV$_2$-EZ-d42-3D7. It is a plasmid derived from p(+)MV-EZ containing d-42 malaria gene (3D7 strain), 1347 bp, coding the GPI-anchored form of the protein, cloned in position two of the measles genome by SgrAI-BssHII digestion. The size of the recombinant plasmid is 20417 bp.

The d-83-30-38*-3D7 gene, inserted into position 3 of the MV vector (SgrAI, pos. 9862, and BssHII, pos. 13919) is represented in FIG. 9.

The genome's length (starting at ACC, pos. 609, to GGT, pos. 20666) of the recombinant Measles-Malaria plasmids was a multiple of six, allowing the rescue of the recombinant MV$_{2-3}$-d-83-30-38*-3D7 viruses.

1f) Construction of p(+)MV$_2$EZ-d-42*-SgrAI (3D7, 20345 bp) and p(+)MV$_3$EZ-d-42*-SgrAI (3D7, 20345 bp).

The measles vectors were prepared as detailed described in example 3a.

Using the intermediate vector pZE21MVd-42-SgrAI (3658 bp) as template, a PCR reaction has been performed to delete the GPI anchor region, which is located between AclI (pos. 1528) and ClaI (pos. 1630) sites.

PCR amplifications were carried out using the proofreading Pfu DNA polymerase (Stratagene). DNA sequences of the synthetic oligonucleotides primers are given in lower case for the MV nucleotides and in upper case for non MV nucleotides; sequences of relevant restriction endonucleases recognition sites are underlined.

The following oligonucleotides primers have been used: For-ClaI, 5'-CCAATAAACGTTTAAT AGatcgattac gcgcgctctagc-3', and Rev-AvrII, 5'-gccttgagtgagctgatacc-3'.

For-ClaI is homologous to the template at the level of the ClaI (pos. 1630) and BssHII (pos. 1639) sites and contains an overhang (in upper case) with two stop codons (TAATAG), the AclI site (AACGTT), and a 6 bp long-protection site for AclI (CCAATA). In the so-called PCR-GPI and in the final construct d-42*, AclI will become close to ClaI.

Rev-AvrII is homologous to the template (from pos. 1798 to 1818).

PCR product was 207 bp-long: its digestion with AclI+AvrII and ligation with the pre-digested AclI+AvrII intermediate vector pZE21MVd-42-SgrAI has produced pZE21 MVd-42*-SgrAI.

In detail, the digestion of the vector with AclI+AvrII has produced two bands of 3412 bp and 246 bp (containing the GPI region to delete): the 3.4 kb-fragment was purified from agarose gel by using QIAEX II purification kit (Qiagen) and was ligated to the digested AclI-AvrII PCR (insert) to obtain pZE21MVd-42*-SgrAI.

To screen for positive clones, NcoI digestion has be done, producing a single band of 3.4 kb from the d-42* intermediate vector, and two bands of 1.3 and 2.3 kb from the original GPI-anchor construct.

To construct the definitive recombinant p(+)MeV$_2$EZ-d42* and p(+)MeV$_3$EZ-d42*, according to the "rule of six", MeV vectors and intermediate plasmid were digested with SgrAI+BssHII and afterwards ligated each other.

In detail, pZE21MVd-42*-SgrAI digested SgrAI+ BssHII+SpeI has produced four bands, 1.3 kb+936 bp+800 bp+400 bp. D-42* sequence was contained in the 1.3 kb fragment, that has been cut, purified and ligated with MeV$_2$EZ and MeV$_3$EZ vectors SgrAI+BssHII digested (19 Kb in length), in an equimolar ratio overnight at 16° C., using one unit of T4 DNA Ligase.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences, aligned with the assumed ones using a DNA Strider software, showed 100% identity.

Figure 11:
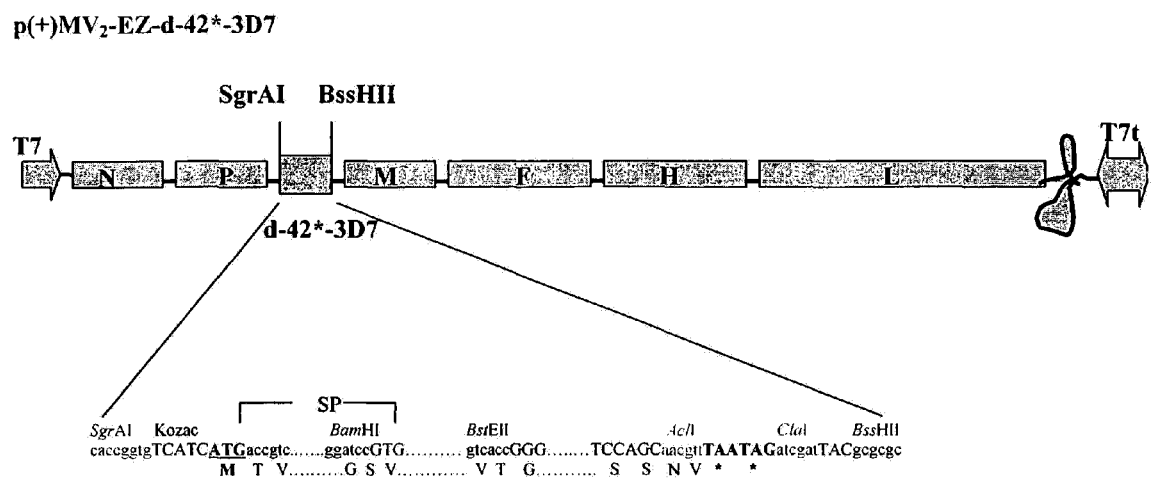
FIG. 11: Schematic representation of the recombinant measles-malaria plasmid, p(+)MV$_2$-EZ-d42*-3D7. It is a plasmid derived from p(+)MV-EZ containing d-42* malaria gene (3D7 strain), 1254 bp, coding the secreted form of the protein, cloned in position two of the measles genome by SgrAI-BssHII digestion. The size of the recombinant plasmid is 20345 bp.

The d-42*-3D7 gene, inserted into position 2 of the MV vector (SgrAI, pos. 4060, and BssHII, pos. 5357) is represented in FIG. 11 and its Open Reading Frame (ORF) is listed in FIG. 31.

Figure 12:
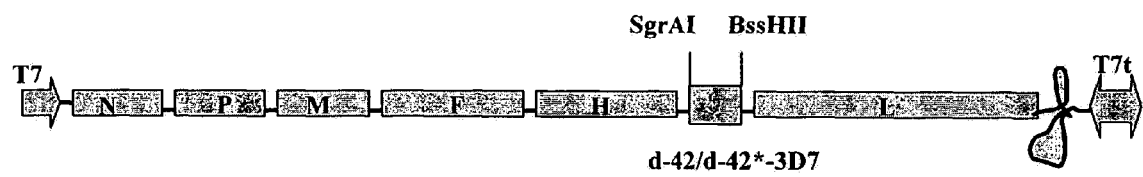
FIG. 12: Schematic representation of the recombinant measles-malaria plasmid, p(+)MV$_3$-EZ-d42-3D7 or p(+)MV$_3$-EZ-d42*-3D7. It is a plasmid derived from p(+)MV-EZ containing d-42 malaria gene (3D7 strain), 1347 bp, coding the GPI-anchored form of the protein, or the d-42* malaria gene (3D7 strain), 1254 bp, coding the secreted form of the protein, cloned in position three of the measles genome by SgrAI-BssHII digestion. The recombinant p(+)MV$_3$-EZ-d42 is 20417 bp, the p(+)MV$_3$-EZ-d42* is 20345 bp.
Figure 13:
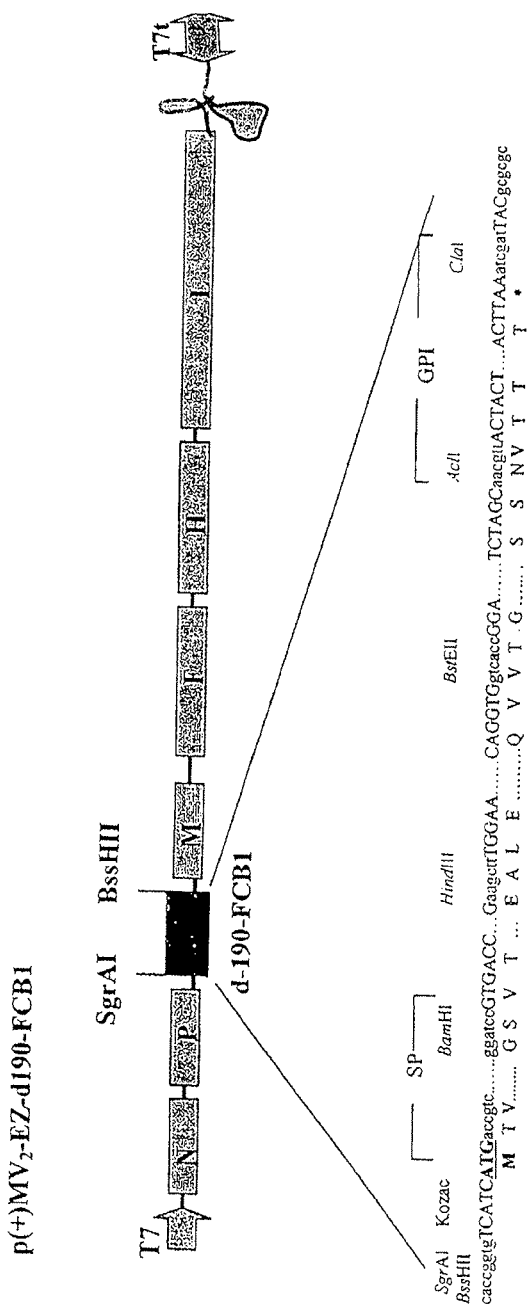
FIG. 13: Schematic representation of the recombinant measles-malaria plasmid, p(+)MV$_2$-EZ-d190-FCB1. It is a plasmid derived from p(+)MV-EZ containing d-190 malaria gene (FCB1 strain), 5013 bp, coding the GPI-anchored form of the protein, cloned in position two of the measles genome by SgrAI-BssHII digestion. The size of the recombinant plasmid is 24083 bp.
Figure 14:
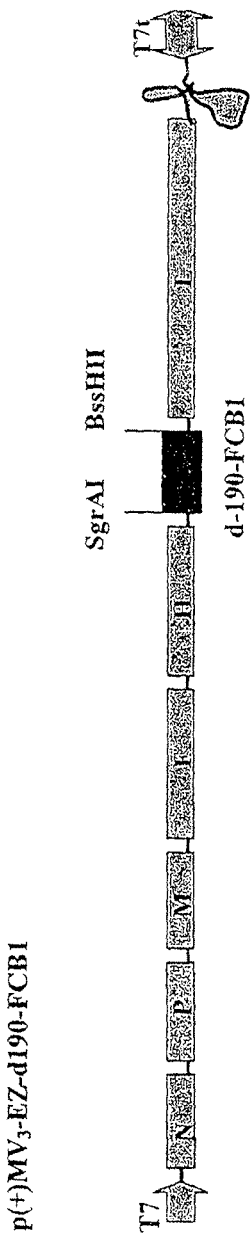
FIG. 14: Schematic representation of the recombinant measles-malaria plasmid, p(+)MV$_3$-EZ-d190-FCB1. It is a plasmid derived from p(+)MV-EZ containing the d-190 malaria gene (FCB1 strain), 5013 bp, coding the GPI-anchored form of the protein, cloned in position three of the measles genome by SgrAI-BssHII digestion. The recombinant plasmid p(+)MV$_3$-EZ-d190 is 24083 bp.

The d-42*-3D7 gene, inserted into position 3 of the MV vector (SgrAI, pos. 9862, and BssHII, pos. 11159) is represented in FIG. 12.

The genome's length (starting at ACC, pos. 609, to GGT, pos. 17906) of the recombinant Measles-Malaria plasmids was a multiple of six, allowing the rescue of the recombinant MV$_{2-3}$-d-42*-3D7 viruses.

1g) Construction of p(+)MV$_2$EZ-d-190-SgrAI (FCB1, 24083 bp) and p(+)MV$_3$EZ-d-190-SgrAI (FCB1, 24083 bp).

First of all, the cloning of the synthetic gene for MSP-1 of the FCB1 strain into the intermediate plasmid pZE21MV-SgrAI has been performed, keeping the signal peptide and the GPI-anchor region from MSP-1 of 3D7 strain. D-190 gene (FCB1) was obtained stepwise from an intermediate vector, called pZE23f-GX-190H, as follow:

i). 1 μg of the plasmid pZE21MV-d-190-SgrAI (3D7) was digested with HindIII+AclI restriction enzymes, for two hours at their optimal temperature, in 50l final volume. All the digested DNA was loaded onto a 1% agarose gel, run at 80 Volt for about 2 hours. Then, the proper band (2558 bp), corresponding to the vector, was excised from the gel, purified by QIAEX gel purification and the DNA concentration was calculated by absorbance at 260 nm.

ii). a PCR reaction was performed, using the pZE23f-GX-190H as template, in order to amplify and recover the d-42 portion of the MSP-1/FCB1. PCR amplification was carried out using the proofreading Pfu DNA polymerase (Stratagene). DNA sequences of the synthetic oligonucleotides primers are given in lower case for the MV nucleotides and in upper case for non MV nucleotides; sequences of relevant restriction endonucleases recognition sites are underlined.

The following oligonucleotides primers have been used, designed on the pZE23f-GX-190H sequence: For-1 FCB1, 5'-CCCAAGCTTccaggtggtcaccggAgagctgtcactcc-3', and Rev-1 FCB1, 5'-GCCTGC aacgttGCTagagctggagcaGaaGatcccgtcg-3'.

For-1 FCB1 is homologous to the template from pos. 4509 to pos. 4538, comprising the BstEII site (ggtcacc). The A (in upper case) was a t in the template, and it has been modified to eliminate a SgrAI site. It contains an overhang (in upper case) with the HindIII site (AAGCTT), after its 3 bp long-protection site (CCC).

Rev-1 FCB1 contains an AclI site (aacgtt), preceded by a 6-bp protection site (GCCTGC). It was introduced a triplet GCT, coding for a serine, to keep the rule of six; two a have been modified in G to avoid a poly(A) site.

The obtained PCR-HindIII-AclI (1.1 kb) has been digested HindIII+AclI and ligated, overnight at 16° C. in an equimolar ratio, to the pre-digested pZE21MV-d-190-SgrAI with HindIII+AclI (step i), obtaining the pZE21MV-d-42-SgrAI-FCB1 (3657 bp). XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and by restriction enzymes digestion with HindIII+AclI (expected fragments 2558 bp+1099 bp).

iii). the pZE21MV-d-42-SgrAI-FCB1, obtained as described in step ii, has been digested HindIII+BstEII (HindIII, pos. 428, and BstEII, pos. 440), and the proper band (3645 bp), corresponding to the opened vector, was loaded on a 1% agarose gel, excised from the gel, purified by QIAEX gel purification and the DNA concentration was calculated by absorbance at 260 nm.

iv). The pZE23f-GX-190H was digested HindIII+BstEII and the proper band of 3679 bp (insert), corresponding to the d-83-30-38/FCB1 fragment, was purified from the gel, as previously described.

v). the HindIII+BstEII digested fragment of 3657 bp (vector), obtained from pZE21MV-d-42-SgrAI-FCB1, has been ligated to the HindIII+BstEII fragment of 3679 bp (insert), containing the d-83-30-38/FCB1 and obtained by digestion from pZE23f-GX-190H. Ligation was done in an equimolar ratio overnight at 16° C., using one unit of T4 DNA Ligase, obtaining the pZE21MV-d-190-SgrAI-FCB1 (7324 bp).

Afterwards, XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion.

To construct the p(+)MV$_2$EZ-d-190-SgrAI-FCB1 and p(+)MV$_3$EZ-d-190-SgrAI-FCB1, the measles vectors were prepared as detailed described in example 3a.

1 µg of d-190/FCB1 gene, inserted into an intermediate plasmid (pZE21MV-d-190 SgrAI-FCB1, 7324 bp), was taken out by SgrAI-BssHII digestion (one unit of each enzyme), for two hours at their optimal temperature, in 50 µl final volume. All the digested DNA was loaded onto a 1% agarose gel, run at 80 Volt for about 2 hours. Then, the proper band (5035 bp) was excised from the gel, purified by QIAEX gel purification kit and the DNA concentration was calculated by absorbance at 260 nm and adjusted to 1 µg/ml.

Figure 3:
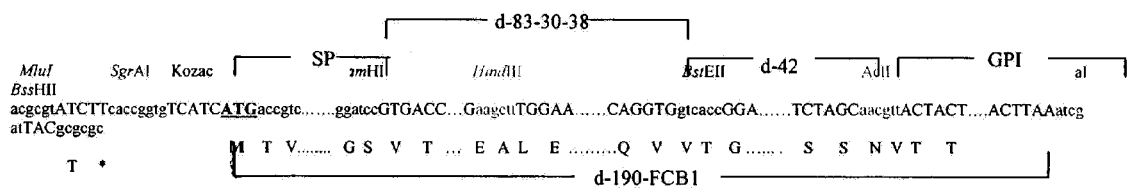
FIG. 3: Representation of the MSP-1 synthetic gene (d-190) from FCB1 strain. The coding nucleotides on the flanking regions of the d-190 gene fragments (d-83-30-38 and d-42) and the corresponding amminoacids are shown. Unique restriction sites added for cloning procedures are in colours; SP: signal peptide; GPI: glycosyl-phosphatidil-inositol sequence coded for membrane-anchored region. SP and GPI regions are from 3D7 strain.
Figure 4:
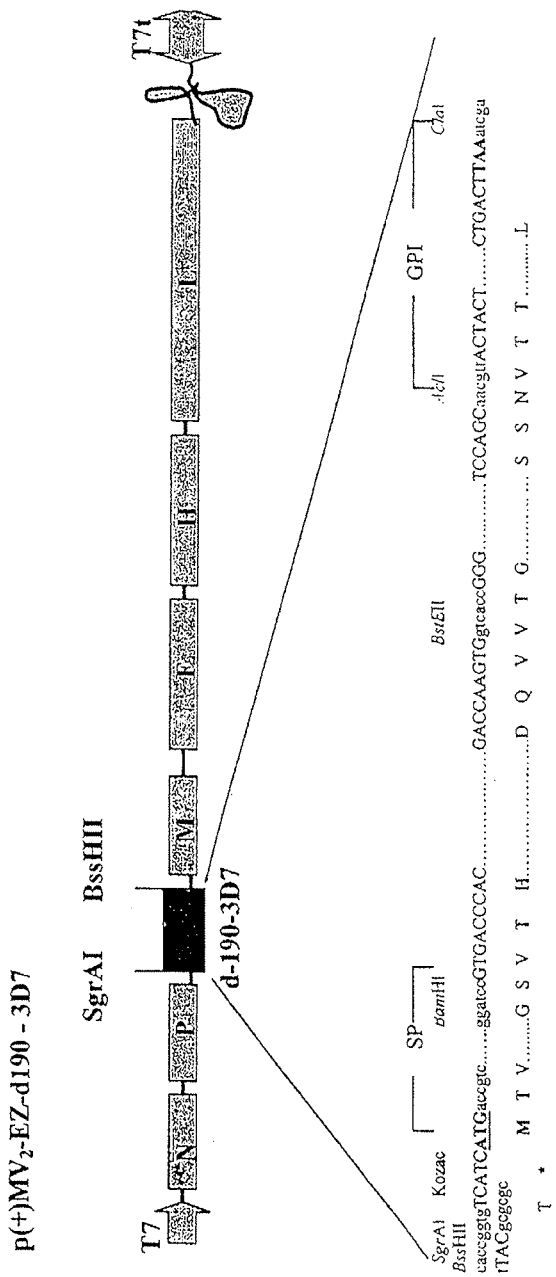
FIG. 4. Schematic representation of the recombinant measles-malaria plasmid, p(+)MV$_2$-EZ-d190-3D7. It is a plasmid derived from p(+)MV-EZ containing d-190 malaria gene (3D7 strain), 5253 bp, coding the GPI-anchored form of the protein, cloned in position two of the measles genome by SgrAI-BssHII digestion. The size of the recombinant plasmid is 24323 bp.

Thus, the vector (MV DNA: FIG. 1) and the insert (d-190/FCB1 DNA: FIG. 3), were ligated in an equimolar ratio overnight at 16° C., using one unit of T4 DNA Ligase and its own reaction buffer in 10 µl final volume.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences, aligned with the assumed ones using a DNA Strider software, showed 100% identity.

The d-190-FCB1 gene, inserted into position 2 of the MV vector (SgrAI, pos. 4060, and BssHII, pos. 9095) is represented in FIG. 13 and its Open Reading Frame (ORF) is listed in FIG. 32.

The d-190-FCB1 gene, inserted into position 3 of the MV vector (SgrAI, pos. 9862, and BssHII, pos. 14897) is represented in FIG. 14.

The genome's length (starting at ACC, pos. 609, to GGT, pos. 21884) of the recombinant Measles-Malaria plasmids was a multiple of six, allowing the rescue of the recombinant $MV_{2-3}$-d-190-FCB1 viruses.

The transgene is rather stably expressed: its expression was completely maintained in all analysed progeny clones derived from single original rescued clones after ten serial virus passages in human diploid cell MRC5 (FIG. 40).

The growth curves of recombinant MV-Malaria virus and MV vaccine showed the same kinetics (FIG. 41).

Example 2

Designing of DiCo1 Nucleic Acid Sequence

Starting from the aminoacidic DiCo1 sequence (ecto, trans and cytoplasmic domains: aa 97-622) and using the DNA Strider software, a correspondent nucleic acid sequence has been designed comparing the DiCo1 DNA degenerate sequence to a selected PfAMA1 gene (accession number AAG141.1), which represents the most similar sequence to the DiCo1 after BLAST alignment.

At the 5' end suitable unique restriction sites has been added (MluI and SgrAI) as cloning sites, followed by an optimal KOZAC sequence and a human optimised Signal Peptide (SP). At the 3' end, two stop codons and a BssHII cloning site have been added. Following this scheme, we designed two nucleotides sequences (respecting the "rule of six" for the further expression into the measles vector), encoding the anchored and the secreted forms of the DiCo1 protein: the first gene comprises the ectoplasmic, the transmembrane and cytoplasmic domains (FIG. 18), while the second one corresponds to the ectodomain alone (FIG. 19). The two sequences has been human codon optimised by GENEART, to reduce AT % content, to avoid poly(A) sequence and RNA instability motif.

DiCo1 complete ORF and DiCo1 ectodomain ORF are listed respectively in FIGS. 34 and 35.

Example 3

Construction of Recombinant MV-PfAMA-1 Plasmids

All cloning procedures were done as per techniques described in Sambrook et al. (1989).

PfAMA1, and in particular Diversity Covering sequences 1 (DiCo1) either in the secreted and anchored form, have been chemically synthesized and human codon optimised.

The codon optimised DiCo1 secreted and anchored forms were digested SgrAI+BssHII and ligated, overnight at 16° C. in an equimolar ratio, to the pre-digested $MeV_2$EZ and $MeV_3$EZ vectors (19 Kb in length), using one unit of T4 DNA Ligase, obtaining the following recombinant MV-PfAMA-1 plasmids: p(+)$MV_2$EZ-DiCo1-complete (FIG. 20), p(+)$MV_3$EZ-DiCo1-complete (FIG. 21), p(+)$MV_2$EZ-DiCo1-ecto (FIG. 22), and p(+)$MV_3$EZ-DiCo1-ecto (FIG. 23).

Example 4

Construction of Recombinant MV-PfCS Plasmids

Construction of p(+)$MV_2$EZ-CS-SgrAI (20219 bp) and p(+)$MV_3$EZ-CS-SgrAI (20219 bp)

All cloning procedures were basically as described in Sambrook et al. (1989).

PfCS1, cloned into an intermediate vector pAdApt35Bsu.CS.Pfalc.aa-sub.gcc, has been amplified by PCR, and directly cloned into the definitive MV vectors, obtaining two recombinant MV-PfCS plasmids: p(+)$MV_2$EZ-CS and p(+)$MV_3$EZ-CS.

In detail, a PCR reaction was performed, using the pAdApt35Bsu.CS.Pfalc.aa-sub.gcc as template, in order to amplify and recover the CS gene (FIG. 15). PCR amplification was carried out using the proofreading Pfu DNA polymerase (Stratagene). DNA sequences of the synthetic oligonucleotides primers are given in lower case for the MV nucleotides and in upper case for non MV nucleotides; sequences of relevant restriction endonucleases recognition sites are underlined.

The following oligonucleotides primers have been used, designed on the pAdApt35Bsu.CS.Pfalc.aa-sub.gcc sequence: For-SgrAI, 5'-ACTTTCTCACCGGTGTgg aagcttgccac catgat-3', and Rev-BssHII-CS 5'-TA GCGCGCtctagaggatccttatcagc-3'.

For-SgrAI is homologous to the template from pos. 1356 to pos. 1375, comprising the HindIII site (aagctt). It contains an overhang (in upper case) with SgrAI restriction site (CACCGGTG), after 6-bp long-protection site (ACTTCT).

Rev-BssHII-CS contains an overhang (in upper case) with BssHII restriction site (GCGCGC), which will be close to XbaI (tctaga) in the PCR-CS (1187 bp).

Figure 16:
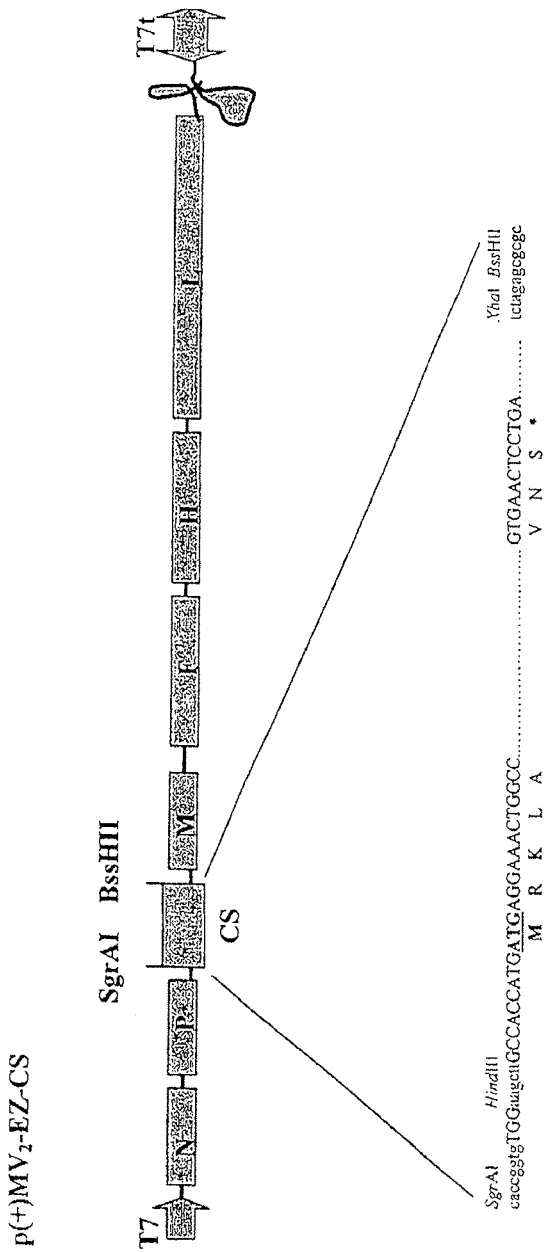
FIG. 16: Schematic representation of the recombinant measles-malaria plasmid, p(+)MV$_2$-EZ-CS. It is a plasmid derived from p(+)MV-EZ containing CS gene, 1119 bp, cloned in position two of the measles genome by SgrAI-BssHII digestion. The size of the recombinant plasmid is 20219 bp.
Figure 17:
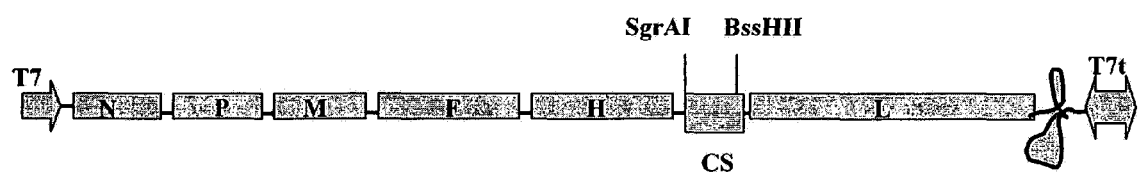
FIG. 17: Schematic representation of the recombinant measles-malaria plasmid, p(+)MV$_3$-EZ-CS. It is a plasmid derived from p(+)MV-EZ containing CS gene, 1119 bp, cloned in position three of the measles genome by SgrAI-BssHII digestion. The size of the recombinant plasmid is 20219 bp.
Figure 18:
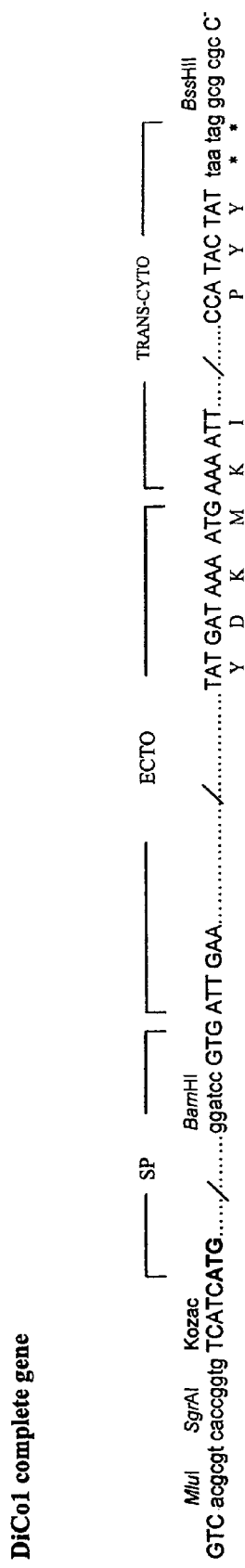
FIG. 18: Representation of the DiCo-1 complete synthetic gene. The coding nucleotides on the flanking regions of the DiCo1 complete gene domains (ecto and trans-cyto) and the corresponding amminoacids are shown. Unique restriction sites added for cloning procedures are in colours; SP: signal peptide human codon optimised.
Figure 19:
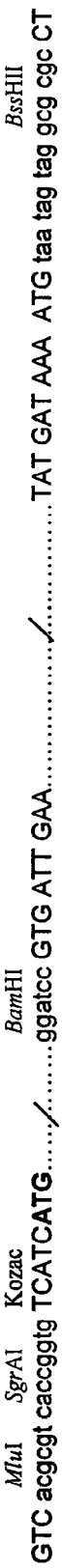
FIG. 19: Representation of the DiCo-1 ecto synthetic gene. The coding nucleotides on the flanking regions of the DiCo1 ecto domain and the corresponding amminoacids are shown. Unique restriction sites added for cloning procedures are in colours; SP: signal peptide (human codon optimised.
Figure 20:
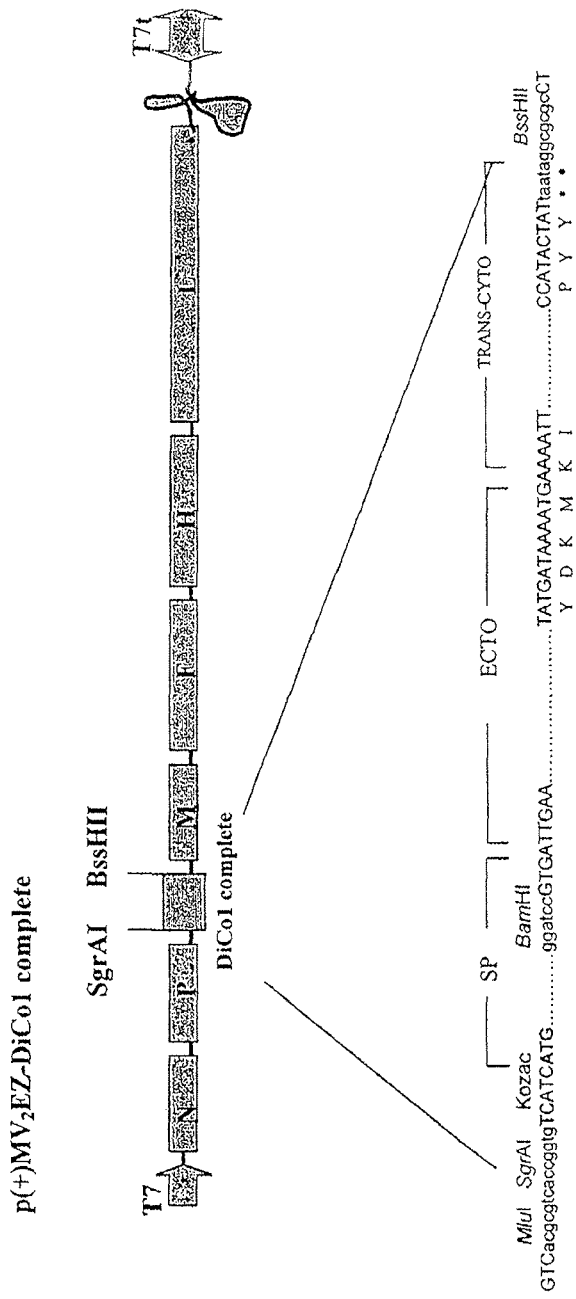
FIG. 20: Schematic representation of the recombinant measles-malaria plasmid, p(+)MV$_2$-EZ-DiCo1-complete. It is a plasmid derived from p(+)MV-EZ containing DiCo1 complete gene, 1689 bp, coding the transmembrane form of the protein, cloned in position two of the measles genome by SgrAI-BssHII digestion. The size of the recombinant plasmid is 20753 bp.
Figure 21:
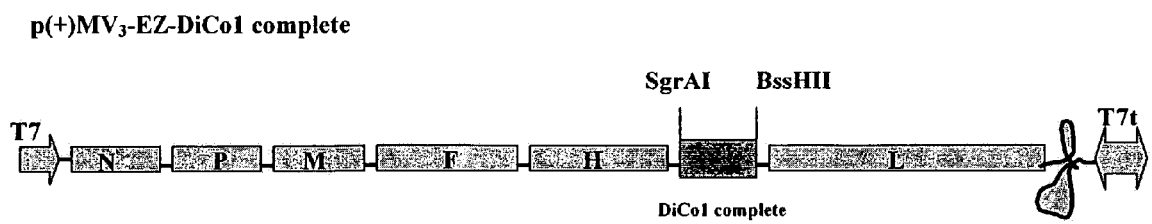
FIG. 21: Schematic representation of the recombinant measles-malaria plasmid, p(+)MV$_3$-EZ-DiCo1-complete. It is a plasmid derived from p(+)MV-EZ containing DiCo1 complete gene, 1689 bp, coding the transmembrane form of the protein, cloned in position three of the measles genome by SgrAI-BssHII digestion. The size of the recombinant plasmid is 20753 bp.
Figure 22:
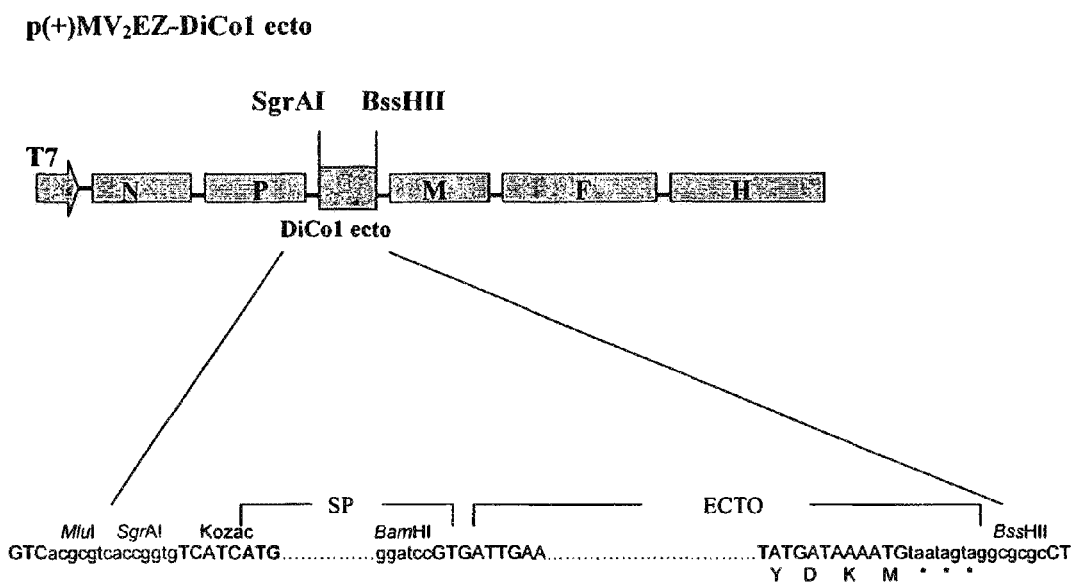
FIG. 22: Schematic representation of the recombinant measles-malaria plasmid, p(+)MV$_2$-EZ-DiCo1-ecto. It is a plasmid derived from p(+)MV-EZ containing DiCo1 ecto gene, 1458 bp, coding the secreted form of the protein, cloned in position two of the measles genome by SgrAI-BssHII digestion. The size of the recombinant plasmid is 20525 bp.
Figure 23:
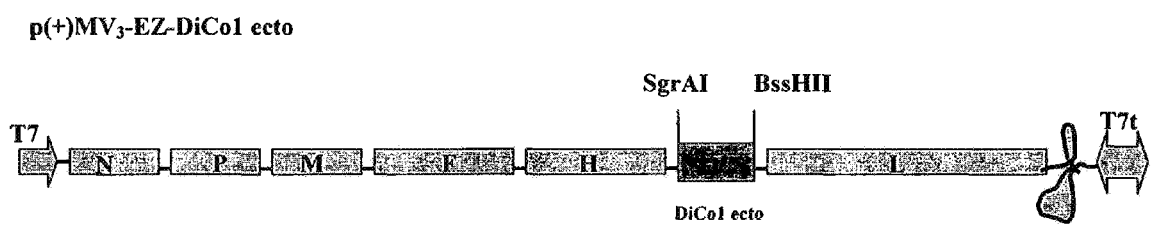
FIG. 23: Schematic representation of the recombinant measles-malaria plasmid, p(+)MV$_3$-EZ-DiCo1-ecto. It is a plasmid derived from p(+)MV-EZ containing DiCo1 ecto gene, 1458 bp, coding the secreted form of the protein, cloned in position three of the measles genome by SgrAI-BssHII digestion. The size of the recombinant plasmid is 20525 bp.

The obtained PCR-CS has been digested SgrAI+BssHII and ligated, overnight at 16° C. in an equimolar ratio, to the pre-digested MeV$_2$EZ and MeV$_3$EZ vectors SgrAI+BssHII (19 Kb in length), using one unit of T4 DNA Ligase, obtaining, respectively, p(+)MV$_2$EZ-CS-SgrAI (20219 bp, FIG. 16) and p(+)MV$_3$EZ-CS-SgrAI (20219 bp, FIG. 17). The CS ORF is listed in FIG. 33.

XL10 Gold chemical competent cell were then transformed with all ligation volume, following a standard transformation protocol (Sambrook et al. 1989), plated and selected on LB-Agar plates for ampicillin resistance. Colonies were screened by DNA plasmid preparation (QIAGEN, mini-midi and maxi kit) and restriction enzymes digestion. The right clones were sent to MWG for sequencing: the sequences, aligned with the assumed ones using a DNA Strider software, showed 100% identity.

Example 5

Cells and Viruses

Cells were maintained as monolayers in Dulbecco's Modified Eagles Medium (DMEM), supplemented with 5% Foetal Calf Serum (FCS) for Vero cells (African green monkey kidney) and with 10% FCS and 1% penicillin/streptomycin (P/S) for 293T cells (human embryonic kidney); DMEM supplemented with Glutamax (F12) and 10% FCS for MRC-5 (human foetal fibroblast); DMEM supplemented with 10% FCS and 1.2 mg/ml of G 418 for 293-3-46.

To grow MV virus stocks reaching titers of about $10^7$ pfu/ml, recombinant viruses and the vaccine strain Edmoston Zagreb were propagated in MRC-5 cells: plaque purification was carried out by transferring a syncythium to 35 mm MRC-5 cell culture which was expanded first to a 10 cm dish, and afterwards to a 175 cm flask. Virus stocks were made from 175 cm$^2$ cultures when syncythia formation was about 90% pronounced. Medium corresponding to the so-called "free-cell virus fraction" was collected, freeze and thawed three times and spun down to avoid cell debris. The medium was then stored at −80° C. Cells, which correspond to the so-called "cell-associated virus fraction", were scraped into 3 ml of OPTIMEM (Gibco BRL) followed by three rounds freezing and thawing, spun down and the cleared surnatant stored at −80° C.

Example 6

Transfection of Plasmids and Rescue of MV Viruses 293T cells were seeded into a 35 mm well to reach ~50-70% confluence when being transfected. 4 h before transfection, the medium was replaced with 3 ml DMEM containing 10% FCS. All recombinant plasmids were prepared according to the QIAGEN plasmid preparation kit. The kit for the Ca$^{2+}$ phosphate coprecipitation of DNA was from Invitrogen.

Cells were co-transfected with the plasmids in the follows final concentration: pCA-L 0.5 µg, pCA-N 0.5 µg, pCA-P 0.1 µg, pCA T7 1 µg and the recombinant Measles-Malaria plasmid 4 µg. All five plasmids, diluted in H$_2$O, were added in a Eppendorf tube containing 2M CaCl$_2$, the mix was added to another Eppendorf tube containing HEPES buffer under shaking conditions, and was incubated 30 min at room temperature (RT). Thus, the co-precipitates were added dropwise to the culture and the transfection was carried out at 37° C. and 5% CO$_2$ for about 18 h. Then, the transfection medium was replaced with 3 ml of DMEM containing 10% FCS.

Another way to obtain recombinant measles-malaria vaccine viruses is described hereafter, using the 293-3-46 helper cell (human embryonic kidney cells), stably expressing the measles N and P proteins as well as the T7 RNA polymerase. The viral RNA polymerase (large protein, L) was expressed by co-transfecting the cells with 15 ng of the plasmid peMCLa. To improve transfection efficiency 300 ng of pSC6-T7 Neo were added. Calcium-phosphate method was used for transfection.

First syncytia appeared 3-4 days after transfection when the cells were still subconfluent. To allow syncytia formation to progress more easily, almost confluent cell monolayer of each 35 mm well were then transferred to a 10 cm dish. Each syncytium was taken up in 300 μl of transfection medium and put in a sterile Eppendorf tube containing 700 μl of OPTIMEM, freeze and thaw for three rounds, and stored at −80° C.

Example 7

Virus Titration by Plaque Assay

Serial 10-times dilutions of virus preparations were carried out using OPTIMEM to a final volume of 0.5 ml. Each dilution was added on 35 mm Vero cell cultures. After 1 h of virus adsorption, the inoculum was removed and the infected cells were overlaid with 2 ml of DMEM containing 5% FCS and 1% low melting point agarose (LMP agarose). After 5 days of incubation at 37° C. and 5% $CO_2$, cultures were fixed with 1 ml of 10% TCA for 1 h, then UV cross-linked for 30 min. After removal of the agarose overlay, cell monolayers were stained with crystal violet dissolved in 4% ethanol, washed with water and the plaques were counted under the inverted microscope.

Example 8

MRC-5 Virus Serial Passages of Recombinant Viruses

Rescued viruses were serially passaged 10-times on MRC5 cells, seeded into 10 cm diameter plates, that were infected with the standard and the recombinant MV viruses at MOI of 0.01 PFU/cells. After monolayer was full infected, 1% surnatant of each culture was used to infect the subsequent MRC5 cells monolayer. To test transgene expression and stability, viruses from passage 1, 5, and 10 were used for further characterisation of expression by Western blot and immunofluorescence.

Example 9

Western Blot, Immunofluorescence

To analyse the expression either MV and Malaria, Western blot and immunofluorescence were carried out.

For Western blot, Vero cells seeded on 35 mm dish (1-5×$10^5$) were monitored the next day for 90% confluence and infected with cleared virus suspension from cell-associated virus fraction, using 0.1 MOI (Multiplicity Of Infection), including MVEZ as control. When about 80% syncythia formation was observed, cells were first washed with PBS and then scraped in 1 ml PBS and collected in an Eppendorf tube, and centrifuge at 2000 RPM/4 min. Cells were then lysated 5 min/RT with 70 μl of lysis buffer (1% NP-40, 50 mM Tris pH 8, 150 mM NaCl) supplemented with protease inhibitor cocktail (Complete Mini, Roche, 1 836 153). Surnatants were cleared by centrifuge at 13000 RPM/5 min, and transferred into a new tube: 30 µl of 4× loading buffer (Invitrogen) were added; samples were mixed and boiled at 95° C./2 min, spun down and stored at −20° C.

An SDS-PAGE migration was performed, running a NuPAGE 12% Bis-acrylamide gel in reducing conditions, using 1× Running Buffer, for 50 min at 200V (start 100-125 mA, end 60-80 mA).

Then, semi-dry method was used to transfer separated cell-proteins to Nitrocellulose Membrane, at 14V/1 h30.

As first antibodies, rabbit polyclonal against MSP1-p-83, diluted in PBST at least 1:30000, and against MSP1-p-42, diluted at least 1:50000, were used. The second antibody was a swine anti-rabbit antibody coupled to horse-radish peroxidase allowing the visualization of the bands by the enhanced chemiluminescence kit (ECL™, Amersham LifeScience).

For immunofluorescence, Vero cells were seeded on a 24 mm×24 mm glass cover slips in 35 mm wells, cultured overnight and infected with rescued recombinant virus. 3 days after infection cells on coverslips were fixed with 3.7% paraformaldehyde in PBS, and permeabilized with 0.1% TX-100, washed with blocking solution (PBS containing 1% BSA) for 1 h, and stained with the specific antibodies. Mouse hybridoma supernatant mAb 5.2, which recognises a EGF-like domain in the p-19 portion of p-42, was used in a dilution 1:100 followed by FITCH conjugated goat anti-mouse serum, diluted 1:250.

Example 10

Growth Kinetics Curve

MRC5 cells seeded on 35 mm dish (1-5×10$^5$) were monitored for 90% confluence and infected with cleared virus suspension from cell-associated virus fraction, using 0.1 MOI, including MVEZ as control. Samples, corresponding to the so-called "free-cell virus fraction" and to the so-called "cell-associated virus fraction", were collected daily for one week and titrated.

Example 11

Mice Immunisation

The immunogenic power of the rescued recombinant MV-Malaria viruses described was proven by immunisation tests performed on transgenic mice IFNAR/CD46, susceptible to MV infections. The animals were kept under optimal hygienic conditions and were immunized at 6-8 weeks of age. Below is provided an example of mice immunization with two recombinant Measles-Malaria virus: the MeV2EZ-d-p42-SgrAI (the GPI anchored form) and the MeV2EZ-d-p42* (the secreted form). Immunisation was performed intramuscularly using 10$^5$ PFU of each recombinant MV-Malaria in three injections at 0, 4 and 8 weeks. Mice immunized with recombinant-empty Measles (rMVEZ13—Empty cloned) served as negative control. UV inactivated rMV was used as a control to determine the effect of virus replication on activation of immune responses. The immune response of the MV vectored antigen was tested compared to the purified d-42 protein (0.5 mg/ml): mice were immunized sub cutaneously with 20 µg of protein in Incomplete Freund's Adjuvant.

The presence of MV-specific antibodies in the sera from the immunised IFNAR/CD46 mice (6 per test group and 3 for control group) was determined by ELISA using 96-microwell plates, coated with Measles virus EIA bulk (ATCC VR-24), for IgG antibody detection. Protein was diluted 0.6 µg/ml with 0.05 M carbonate buffer (pH 9.4), and 100 µl per well was added to 96-well-microtiter plates. The plates were incubated overnight at 4° C., washed with PBS/0.05% Tween 20 (PT) (ph 7.4), incubated with PT (0.1 ml/well)-10% BSA for 60 min at 37° C., and washed again with PT. Serial 2-folds dilutions of the tested sera were added (100 j/well), and the plates were incubated for 60 min at 37° C. The plates were washed with PT and were incubated with 100 µl of goat anti-mouse IgG HRP diluted 1:2000 in PT for 30 min at 37° C. The plates were washed with PT and incubated with 100 µl OPD (o-Phenylendiamin, Fluka 78411). The reaction was stopped after 3-4 min. Plates were read on a MicroElisa Reader at a wave length of 490 nm. Readings higher than three-folds negative controls were scored as positive reaction.

The presence of MV-Malaria-specific antibodies in the sera of immunised CD46 mice (at least 10 per test group) was determined by ELISA assay. Briefly, 96-microwell plates were coated 50 ng/well MSP-1-d42 3D7 strains, diluted with carbonate buffer pH 9.4. The plates were incubated overnight at 4° C., washed with PBS/0.05% Tween 20 (PT). Subsequently, unspecific interaction were blocked with 10% defatted milk dissolved in PT for 1 hour at 37° C. and wells were washed again with PT. The plates were consecutively incubated with various dilutions of mouse sera (starting at 1:200, followed by serial two-fold dilutions), peroxidase-conjugate goat anti-mouse IgG and with OPD substrate. Optical density values were measured at 490 nm. Values above the cut-off background level (mean value of sera from MV immunised mice multiplied by a factor of 2.1) were considered positive. Titres were depicted as reciprocal end-dilutions.

The humoral immune responses against Measles are shown in FIG. 42. The humoral immune responses against Malaria p42 are shown in FIG. 43.

Example 12

Purification of Recombinant Measles Virus Expressing Malaria Antigens from Defecting Interfering Particles (DIs) by Plaque Purification It is known from literature that after a certain number of passages with Paramyxoviruses, and in particular with measles virus, an accumulation of defective interfering particles (DIs) will occur (23, 24). It has been described that these DIs develop various defects: negative impact on vaccine safety, negative influence on virus yields in production, genome instability and suppression of immune reaction after vaccination. In order to avoid such DIs with our new recombinant viruses, we have applied the method of plaque purification as described in example 6 with the exception that we use MRC5 cell instead of 293T cells. After the formation of clear, well defined syncytia we aspirated under the microscope with a micropipette such material for further passaging in a fresh MRC5 tissue culture.

Example 13

Purification of Recombinant Measles Virus Expressing Malaria Antigens from Defecting Interfering Particles (DIs) by End Point Dilution The end point dilution technique was applied in microplates: in all wells a fresh monolayer of MRC5 cells had just developed. The virus suspension containing recombinant measles-malaria viruses was prepared in two fold dilutions.

From the well of the latest monolayer where a syncytia was detected the supernatant was aspirated with a pipette. The supernatant was mixed with a suspension containing MRC5 cells. This mixture was incubated at 4° C. for 1 hour. Finally, it was transferred in a small Costar flask and incubated at 35° C./5% $CO_2$ and harvested for purify recombinant measles-malaria virus after ten days.

Example 14

Production of a Combined Measles-Malaria Vaccine

The working seed of the described recombinant measles-malaria virus has been incubated on MRC5 cell monolayer in 1750 $cm^2$ roller bottles at 35° C. for ten days. The cells have been monitored every day for status of health and confluence. On day ten at highest level of syncytia formation, the supernatant was pumped in a steel cylinder for storage in liquid nitrogen. The same procedure was repeated two days later. After performing of all the tests (virus titer, genome stability, virus safety, cell safety, chemical analysis, sterility and others), the harvests have been thawed up and mixed with stabilizer containing gelatine, sorbitol, amminoacids and other sugars to final dilution of $10^5$. With a automated filling machine small lyo bottles (F3) have been inoculated with 0.5 ml each. A specially calculated lyophilisation program was used to guarantee maximal survival of the product during the freeze-drying process.

BIBLIOGRAPHY

1. Fields Virology, fifth edition (2007), eds.-in-chief Knipe, D. M. &. Howley, P. M. Lippincott Williams & Wilkins, Philadelphia Pa. 19106, USA.
2. Enders, J. F., and Peebles, T. C. (1954). Propagation in tissue cultures of cytopathogenic agents from patients with measles. Proc. Soc. Exp. Biol. Med., 86: 277-286.
3. Griffin, D. (2007) Measles virus. In: Fields Virology, fifth edition, eds.-in-chief Knipe, D. M. &. Howley, P. M. Lippincott Williams & Wilkins, Philadelphia Pa. 19106, USA.
4. Parks, C. L., Lerch, R. A., Walpita, P., Wang, H. P., Sidhu, M. S., and Udem, S. A. (2001). Analysis of the noncoding regions of measles virus strains in the Edmonston vaccine lineage. J. Virol., 75: 921-933.
5. Parks, C. L., Lerch, R. A., Walpita, P., Wang, H. P., Sidhu, M. S., and Udem, S. A. (2001). Comparison of predicted amino acid sequences of measles virus strains in the Edmonston vaccine lineage. J. Virol., 75: 910-920.
6. Hilleman, M. R. (2002). Current overview of the pathogenesis and prophylaxis of measles with focus on practical implications. Vaccine, 20: 651-665.
7. Ovsyannikova I G., Reid, K. C., Jacobson, R. M., Oberg, A. L., Klee, G. G., Poland, G. A. (2003). Cytokine production patterns and antibody response to measles vaccine. Vaccine, 21(25-26): 3946-53.
8. Radecke, F., P. Spielhofer, H. Schneider, K. Kaelin, M. Huber, K. Dötsch, G. Christiansen, and M. Billeter. (1995). Rescue of measles viruses from cloned DNA. EMBO Journal., 14: 5773-5784.
9. Martin, A., Staeheli, P. and Schneider, U. (2006). RNA polymerase II-controlled expression of antigenomic RNA enhances the rescue efficacies of two different members of the Mononegavirales independently of the site of viral genome replication. J. Virol., 80: 5708-5715.
10. Radecke, F., and M. Billeter. (1997). Reverse genetics meets the nonsegmented negative-strand RNA viruses. Rev. Med. Virol., 7: 49-63.
11. Singh M. R., Cattaneo, R., Billeter, M. A. (1999). A recombinant measles virus expressing hepatitis B virus surface antigen induces humoral immune responses in genetically modified mice. J. Virol., 73: 4823-4828.
12. Wang, Z. L., Hangartner, L., Cornu, T. I., Martin, L. R., Zuniga, A., and Billeter, M. (2001). Recombinant measles viruses expressing eterologous antigens of mumps and simian immunodeficiency viruses. Vaccine, 19: 2329-2336.
13. Dilraj, A., Cutts, F. T., de Castro, J. F., Wheeler, J. G., Brown, D., Roth, C., Coovadia, H. M., Bennett, J. V. (2000). Response to different measles vaccine strains given by aerosol and subcutaneous routes to schoolchildren: a randomised trial. Lancet, 355(9206): 798-803.
14. Holder A. A. and Freeman, R. R. (1984). The three major antigens on the surface of *Plasmodium falciparum* merozoites are derived from a single high molecular weight precursor. J. Exp. Med, 160(2): 624-9.
15. Blackman M. J., Whittle H., and Holder A. A. (1991). Processing of the *Plasmodium falciparum* major merozoite surface protein-1: identification of a 33-kilodalton secondary processing product which is shed prior to erythrocyte invasion. Mol. Biochem. Parasitol., 49(1): 35-44.
16. Remarque, E. J., Faber, B. W., Kocken, C. H. M., and Thomas, A. W. (2007). Apical membrane antigen 1: a malaria vaccine candidate in review. Trends Parasitol, 24: 74-83.
17. Polley, S. D., Mwangi, T., Kocken, C. H., Thomas, A. W., Dutta, S., Lanar, D. E., Remarque, E., Ross, A., Williams, T. N., Mwambingu, G., Lowe, B., Conway, D. J., and Marsh, K. (2004). Human antibodies to recombinant protein constructs of *Plasmodium falciparum* apical membrane antigen 1 (AMA1) and their association with protection from malaria. *Vaccine,* 23: 718-728.
18. Cortés, A., Mellombo, M., Masciantonio. R., Murphy, V. J., Reeder, J. C., and Anders, R. F. (2005). Allele specificity of naturally acquired antibody responses against *Plasmodium falciparum* apical membrane antigen1. *Infect. Immun.,* 73: 422-430.
19. Remarque, E. J., Faber, B. W., Kocken, C. H. M., and Thomas, A. W. (2008). A diversity-covering approach to immunisation with *Plasmodium falciparum* AMA1 induces broader allelic recognition and growth inhibition responses in rabbits. Infect. Immun.
20. Garcia, J. E., Puentes, A., and Patarroyo, M. E. (2006). Developmental biology of sporozoite-host interactions in *Plasmodium falciparum* malaria: implications for vaccine design. Clin. Microbiol. Rev., 19(4): 686-707.
21. Ballou, W. R., and Cahill, C. P. (2007). Two Decades of Commitment to Malaria Vaccine Development: GlaxoSmithKline Biologicals. Am. J. Trop. Med. Hyg., 77(6_Suppl): 289-295.
22. Girard, M. P, Reed, Z. H., Friede, M., and Kieny, M. P. (2007). A review of human vaccine research and development: Malaria. Vaccine, 25: 1567-1580.
23. Roux, L., Simon, A. E., Holland, J. J. (1991). Effects of Defective Interfering Viruses on virus replication and pathogenesis in vitro and in vivo. Adv. Virus Res., 40: 181-211.
24. Calain, P., and Roux, L. (1988). Generation of measles virus defective interfering particles and their presence in a preparation of attenuated live-virus vaccine. J. Virol., 62 (8):2859-2866.

The invention claimed is:

1. A combined measles-malaria immunogenic composition comprising a recombinant measles virus which expresses CS malaria antigens and measles antigens capable of eliciting immune response both against measles and CS malaria wherein the nucleotide sequence of CS malaria antigen is SEQ ID NO:10.

2. The combined measles-malaria immunogenic composition as claimed in claim 1, wherein the recombinant measles virus expresses single or different malaria antigens.

3. The combined measles-malaria immunogenic composition as claimed in claim 1, wherein the recombinant measles virus expresses CS malaria antigen in both anchored and secreted forms.

4. The combined measles-malaria immunogenic composition as claimed in claim 1, wherein the recombinant measles virus expresses CS malaria antigen in both anchored and secreted forms 3D7 strain and MAD 20.

5. The combined measles-malaria immunogenic composition as claimed in claim 1, wherein the recombinant measles virus expresses CS malaria antigen in both anchored and secreted forms FCBI strain.

6. The combined measles-malaria immunogenic composition as claimed in claim 1, wherein the malaria antigen is cloned between P and M or H and L protein of recombinant measles virus.

7. A measles vaccine virus vector comprising the nucleotide sequence of an antigen of malaria wherein the nucleotide sequence is SEQ ID NO: 10.

8. An isolated host cell comprising the vector of claim 7.

9. The host cell as claimed in claim 8, selected from *E. coli* or mammalian cell line.

10. The combined measles-malaria immunogenic composition as claimed in claim 1, wherein the recombinant measles virus originating from a vaccine strain is derived from Edmoston Zagreb.

11. The combined measles-malaria immunogenic composition as claimed in claim 1, wherein recombinant measles virus further encodes a protein with adjuvantic properties.

12. The immunogenic composition as claimed in claim 1, further comprising an interleukin.

13. The immunogenic composition as claimed in claim 1, which comprises one of the described recombinant measles malaria viruses or a mixture of two to several such viruses.

14. The immunogenic composition as claimed in claim 1, being a component of a combined vaccine where the other components are rubella, mumps, varicella or another life attenuated vaccine virus, naturally attenuated or recombinant, alone or in combination.

15. The immunogenic composition as claimed in claim 1, for parenteral administration comprising a suitable stabilizer.

16. The immunogenic composition as claimed in claim 1, comprising a suitable stabilizer, adjuvant or a combination thereof wherein the stabilizer and adjuvant are such that the vaccine can be administered parenterally, intranasally, by inhalation, orally, transdermally or in a suppository.

17. A composition comprising the combined measles-malaria composition as claimed in claim 1, comprising stabilizer, adjuvant or a combination thereof.

18. The composition as claimed in claim 12, wherein the interleukin is interleukin 2.

19. The immunogenic composition according to claim 15 wherein the stabilizer is gelatin, human serum, albumin, sorbitol or a combination thereof.

* * * * *

SEQUENCE LISTING

<160> NUMBER OF SEQ ID NOS: 12

<210> SEQ ID NO 1
<211> LENGTH: 19793
<212> TYPE: DNA
<213> ORGANISM: Artificial
<220> FEATURE:
<223> OTHER INFORMATION: Complete nucleotide sequence of p(+)MV2EZ-GFP

<400> SEQUENCE: 1

```
cacctaaatt gtaagcgtta atattttgtt aaaattcgcg ttaaattttt gttaaatcag     60
ctcatttttt aaccaatagg ccgaaatcgg caaaatccct tataaatcaa aagaatagac    120
cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca agttttttgg ggtcgaggtg ccgtaaagca ctaaatcgga accctaaagg    300
gagcccccga tttagagctt gacggggaaa gccggccatt taggccatag ggcgctggca    360
agtgtagcgg tcacgctgcg cgtaaccacc acacccgccg cgcttaatgc gccgctacag    420
ggcgcgtccc attcgccatt caggctgcgc aactgttggg aagggcgatc ggtgcgggcc    480
tcttcgctat tacgccagct ggcgaaaggg ggatgtgctg caaggcgatt aagttgggta    540
acgccagggt tttcccagtc acgacgttgt aaaacgacgg ccagtgaatt gtaatacgac    600
tcactataac caaacaaagt tgggtaagga tagttcaatc aatgatcatc ttctagtgca    660
cttaggattc aagatcctat tatcagggac aagagcagga ttagggatat ctgagatggc    720
cacactttta aggagcttag cattgttcaa aagaaacaag gacaaaccac ccattacatc    780
aggatccggt ggagccatca gaggaatcaa acacattatt atagtaccaa tccctggaga    840
ttcctcaatt accactcgat ccagacttct ggaccggttg gtcaggttaa ttggaaaccc    900
ggatgtgagc gggcccaaac taacaggggc actaataggt atattatcct tatttgtgga    960
gtctccaggt caattgattc agaggatcac cgatgaccct gacgttagca taaggctgtt   1020
agaggttgtc cagagtgacc agtcacaatc tggccttacc ttcgcatcaa gaggtaccaa   1080
catggaggat gaggcggacc aatacttttc acatgatgat ccaattagta gtgatcaatc   1140
caggttcgga tggttcgaga acaaggaaat ctcagatatt gaagtgcaag accctgaggg   1200
attcaacatg attctgggta ccatcctagc ccaaatttgg gtcttgctcg caaaggcggt   1260
tacggcccca gacacggcag ctgattcgga gctaagaagg tggataaagt acacccaaca   1320
aagaagggta gttggtgaat ttagattgga gagaaaatgg ttggatgtgg tgaggaacag   1380
gattgccgag gacctctcct tacgccgatt catggtcgct ctaatcctgg atatcaagag   1440
aacacccgga aacaaaccca ggattgctga aatgatatgt gacattgata catatatcgt   1500
agaggcagga ttagccagtt ttatcctgac tattaagttt gggatagaaa ctatgtatcc   1560
tgctcttgga ctgcatgaat ttgctggtga gttatccaca cttgagtcct tgatgaacct   1620
ttaccagcaa atgggggaaa ctgcacccta catggtaatc ctggagaact caattcagaa   1680
caagttcagt gcaggatcat accctctgct ctggagctat gccatgggag taggagtgga   1740
acttgaaaac tccatggggg gtttgaactt tggccgatct tactttgatc cagcatattt   1800
tagattaggg caagagatgg taaggaggtc agctggaaag gtcagttcca cattggcatc   1860
tgaactcggt atcactgccg aggatgcaag gcttgtttca gagattgcaa tgcatactac   1920
tgaggacaag atcagtagag cggttggacc cagacaagcc caagtatcat ttctacacgg   1980
tgatcaaagt gagaatgagc taccgagatt ggggggcaag gaagatagga gggtcaaaca   2040
```

```
gagtcgagga gaagccaggg agagctacag agaaaccggg cccagcagag caagtgatgc    2100
gagagctgcc catcttccaa ccggcacacc cctagacatt gacactgcat cggagtccag    2160
ccaagatccg caggacagtc gaaggtcagc tgacgccctg cttaggctgc aagccatggc    2220
aggaatctcg gaagaacaag gctcagacac ggacacccct atagtgtaca atgacagaaa    2280
tcttctagac taggtgcgag aggccgaggg ccagaacaac atccgcctac cctccatcat    2340
tgttataaaa aacttaggaa ccaggtccac acagccgcca gcccatcaac catccactcc    2400
cacgattgga gccaatggta aagagcagg cacgccatgt caaaaacgga ctggaatgca    2460
tccgggctct caaggccgag cccatcggct cactggccat cgaggaagct atggcagcat    2520
ggtcagaaat atcagacaac caggacagg agcgagccac ctgcagggaa gagaaggcag    2580
gcagttcggg tctcagaaaa ccatgcctct cagcaattgg atcaactgaa ggcggtgcac    2640
ctcgcatccg cggtcaggga cctggagaga gcgatgacga cgctgaaact tgggaatcc    2700 ccccaagaaa tctccaggca tcaagcactg ggttacagtg ttattacgtt tatgatcaca    2760
gcggtgaagc ggttaaggga atccaagatg ctgactctat catggttcaa tcaggccttg    2820
atggtgatag caccctctca ggaggagaca atgaatctga aaacagcgat gtggatattg    2880
gcgaacctga taccgaggga tatgctatca ctgaccgggg atctgctccc atctctatgg    2940
ggttcagggc ttctgatgtt gaaactgcag aaggagggga gatccacgag ctcctgagac    3000
tccaatccag aggcaacaac tttccgaagc ttgggaaaac tctcaatgtt cctccgcccc    3060
cggaccccgg tagggccagc acttccggga cacccattaa aaagggcaca gacgcgagat    3120
tagcctcatt tggaacggag atcgcgtctt tattgacagg tggtgcaacc caatgtgctc    3180
gaaagtcacc ctcggaacca tcagggccag gtgcacctgc ggggaatgtc cccgagtgtg    3240
tgagcaatgc cgcactgata caggagtgga cacccgaatc tggtaccaca atctccccga    3300
gatcccagaa taatgaagaa gggggagact attatgatga tgagctgttc tctgatgtcc    3360
aagatattaa aacagccttg gccaaaatac acgaggataa tcagaagata atctccaagc    3420
tagaatcact gctgttattg aagggagaag ttgagtcaat taagaagcag atcaacaggc    3480
aaaatatcag catatccacc ctggaaggac acctctcaag catcatgatc gccattcctg    3540
gacttgggaa ggatcccaac gaccccactg cagatgtcga aatcaatccc gacttgaaac    3600
ccatcatagg cagagattca ggccgagcac tggccgaagt tctcaagaaa cccgttgcca    3660
gccgacaact ccaaggaatg acaaatggac ggaccagttc cagaggacag ctgctgaagg    3720
aatttcagct aaagccgatc gggaaaaaga tgagctcagc cgtcgggttt gttcctgaca    3780
ccggccctgc atcacgcagt gtaatccgct ccattataaa atccagccgg ctagaggagg    3840
atcggaagcg ttacctgatg actctccttg atgatatcaa aggagccaat gatcttgcca    3900
agttccacca gatgctgatg aagataataa tgaagtagct acagctcaac ttacctgcca    3960
accccatgcc agtcgaccca actagtctac cctccatcat tgttataaaa aacttaggaa    4020
ccaggtccac acagccgcca gcccatcaac gcgtatcttc accggtgatc tatacgtagc    4080
gcgcatgagt aaaggagaag aacttttcac tggagttgtc ccaattcttg ttgaattaga    4140
tggtgatgtt aatgggcaca aattttctgt cagtggagag ggtgaaggtg atgcaacata    4200
cggaaaactt acccttaaat ttatttgcac tactggaaaa ctacctgttc catggccaac    4260
acttgtcact actttcacct atggtgttca atgcttttca agatacccag atcatatgaa    4320
acggcatgac ttttcaaga gtgccatgcc cgaaggttac gtacaggaaa gaactatatt    4380
tttcaaagat gacgggaact acaagacacg tgctgaagtc aagtttgaag gtgatacct    4440
```

```
tgttaataga atcgagttaa aaggtattga ttttaaagaa gatggaaaca ttcttggaca    4500
caaattggaa tacaactata actcacacaa tgtatacatc atggcagaca aacaaaagaa    4560
tggaatcaga gttaacttca aaattagaca caacattgaa gatggaagcg ttcaactagc    4620
agaccattat caacaaaata ctccaattgg cgatggccct gtccttttac cagacaacca    4680
ttacctgtcc acacaatctg ccctttcgaa agatcccaac gaaaagagag accacatggt    4740
ccttcttgag tttgtaacag ctgctgggat tacacatggc atggatgaac tatacaaata    4800
gtgagcgcgc agcgctgacg tctcgcgatg atactagtac aacctaaatc catcataaaa    4860
aacttaggag caaagtgatt gcctcccaag ttccacaatg acagagatct acgacttcga    4920
caagtcggca tgggacatca aagggtcgat cgctccgata caacccacca cctacagtga    4980
tggcaggctg gtgccccagg tcagagtcat agatcctggt ctaggcgaca ggaaggatga    5040
atgctttatg tacatgtttc tgctgggggt tgttgaggac agggattccc tagggcctcc    5100
aatcgggcga gcatttgggt ccctgccctt aggtgttggc agatccacag caaagcccga    5160
aaaactcctc aaagaggcca ctgagcttga catagttgtt agacgtacag cagggctcaa    5220
tgaaaaactg gtgttctaca acaacacccc actaactctc ctcacacctt ggagaaaggt    5280
cctaacaaca gggagtgtct tcaacgcaaa ccaagtgtgc aatgcggtta atctgatacc    5340
gctcgatacc ccgcagaggt tccgtgttgt ttatatgagc atcacccgtc tttcggataa    5400
cgggtattac accgttccta aagaatgct ggaattcaga tcggtcaatg cagtggcctt    5460
caacctgctg gtgaccctta ggattgacaa ggcgataggc cctgggaaga tcatcgacaa    5520
tacagagcaa cttcctgagg caacatttat agtccacatc gggaacttca ggagaaagaa    5580
gagtgaagtc tactctgccg attattgcaa aatgaaaatc gaaaagatgg gcctggtttt    5640
tgcacttggt gggataggg gcaccagtct tcacattaga agcacaggca aaatgagcaa    5700
gactctcaat gcacaactcg ggttcaagaa gaccttatgt tacccgctga tggatatcaa    5760
tgaagacctt aatcgattac tctggaggag cagatgcaag atagtaagaa tccaggcagt    5820
tttgcagcca tcagttcctc aagaattccg catttacgac gacgtgatca taaatgatga    5880
ccaaggacta ttcaaagttc tgtagaccgt agtgcccagc aatgcccgaa aacgaccccc    5940
ctcacaatga cagccagaag gcccggacaa aaaagccccc tccgaaagac tccacggacc    6000
aagcgagagg ccagccagca gccgacggca agcgcgaaca ccaggcggcc ccagcacaga    6060
acagccctga cacaaggcca ccaccagcca ccccaatctg catcctcctc gtgggacccc    6120
cgaggaccaa cccccaaggc tgcccccgat ccaaaccacc aaccgcatcc ccaccacccc    6180
cgggaaagaa accccagca attggaaggc ccctccccct cttcctcaac acaagaactc    6240
cacaaccgaa ccgcacaagc gaccgaggtg acccaaccgc aggcatccga ctccctagac    6300
agatcctctc tccccggcaa actaaacaaa acttagggcc aaggaacata cacacccaac    6360
agaacccaga ccccggccca cggcgccgcg ccccaacccc ccgacaacca gagggagccc    6420
ccaaccaatc ccgccggctc ccccggtgcc acaggcagg gacaccaacc cccgaacaga    6480
cccagcaccc aaccatcgac aatccaagac ggggggccc ccccaaaaaa aagcccccag    6540
gggccgacag ccagcaccgc gaggaagccc acccacccca cacgacca cggcaaccaa    6600 accagaaccc agaccaccct gggccaccag ctcccagact cggccatcac cccgcagaaa    6660
ggaaaggcca cacccgcgc accccagccc cgatccggcg gggagccacc caacccgaac    6720
cagcacccaa gagcgatccc cgaaggaccc ccgaaccgca aaggacatca gtatcccaca    6780
```

```
gcctctccaa gtcccccggt ctcctcctct tctcgaaggg accaaaagat caatccacca    6840
cacccgacga cactcaactc cccacccta aggagacac cgggaatccc agaatcaaga      6900
ctcatccaat gtccatcatg ggtctcaagg tgaacgtctc tgccatattc atggcagtac    6960
tgttaactct ccaaacaccc accggtcaaa tccattgggg caatctctct aagatagggg    7020
tggtaggaat aggaagtgca agctacaaag ttatgactcg ttccagccat caatcattag    7080
tcataaaatt aatgcccaat ataactctcc tcaataactg cacgagggta gagattgcag    7140
aatacaggag actactgaga acagttttgg aaccaattag agatgcactt aatgcaatga    7200
cccagaatat aagaccggtt cagagtgtag cttcaagtag gagacacaag agatttgcgg    7260
gagtagtcct ggcaggtgcg gccctaggcg ttgccacagc tgctcagata acggccggca    7320
ttgcacttca ccagtccatg ctgaactctc aagccatcga caatctgaga gcgagcctgg    7380
aaactactaa tcaggcaatt gaggcaatca gacaagcagg gcaggagatg atattggctg    7440
ttcagggtgt ccaagactac atcaataatg agctgataccc gtctatgaac caactatctt   7500
gtgatttaat cggccagaag ctcgggctca aattgctcag atactataca gaaatcctgt    7560
cattatttgg ccccagttta cgggaccccca tatctgcgga gatatctatc caggctttga   7620
gctatgcgct tggaggagac atcaataagg tgttagaaaa gctcggatac agtggaggtg    7680
atttactggg catcttagag agcagaggaa taaaggcccg gataactcac gtcgacacag    7740
agtcctactt cattgtcctc agtatagcct atccgacgct gtccgagatt aaggggtga    7800
ttgtccaccg gctagagggg gtctcgtaca acataggctc tcaagagtgg tataccactg    7860
tgcccaagta tgttgcaacc caagggtacc ttatctcgaa ttttgatgag tcatcgtgta    7920
ctttcatgcc agaggggact gtgtgcagcc aaaatgcctt gtacccgatg agtcctctgc    7980
tccaagaatg cctccggggg tacaccaagt cctgtgctcg tacactcgta tccgggtctt    8040
ttgggaaccg gttcatttta tcacaaggga acctaatagc caattgtgca tcaatccttt    8100
gcaagtgtta cacaacagga acgatcatta atcaagaccc tgacaagatc ctaacataca    8160
ttgctgccga tcactgcccg gtagtcgagg tgaacggcgt gaccatccaa gtcgggagca    8220
ggaggtatcc agacgctgtg tacttgcaca gaattgacct cggtcctccc atatcattgg    8280
agaggttgga cgtagggaca atctgggga atgcaattgc taagttggag gatgccaagg    8340
aattgttgga gtcatcggac cagatattga ggagtatgaa aggtttatcg agcactagca    8400
tagtctacat cctgattgca gtgtgtcttg gagggttgat agggatcccc gctttaatat    8460
gttgctgcag ggggcgttgt aacaaaaagg gagaacaagt tggtatgtca agaccaggcc    8520
taaagcctga tcttacggga acatcaaaat cctatgtaag gtcgctctga tcctctacaa    8580
ctcttgaaac acaaatgtcc cacaagtctc ctcttcgtca tcaagcaacc accgcaccca    8640
gcatcaagcc cacctgaaat tatctccggc ttccctctgg ccgaacaata tcggtagtta    8700
attaaaactt agggtgcaag atcatccaca atgtcaccac aacgagaccg gataaatgcc    8760
ttctacaaag ataacccca tcccaaggga agtaggatag tcattaacag agaacatctt     8820
atgattgata gaccttatgt tttgctggct gttctgtttg tcatgtttct gagcttgatc    8880
gggttgctag ccattgcagg cattagactt catcgggcag ccatctacac cgcagagatc    8940
cataaaagcc tcagcaccaa tctagatgta actaactcaa tcgagcatca ggtcaaggac    9000
gtgctgacac cactcttcaa aatcatcggt gatgaagtgg gcctgaggac acctcagaga    9060
ttcactgacc tagtgaaatt catctctgac aagattaaat tccttaatcc ggataggag    9120
tacgacttca gagatctcac ttggtgtatc aacccgccag agagaatcaa attggattat    9180
```

```
gatcaatact gtgcagatgt ggctgctgaa gagctcatga atgcattggt gaactcaact    9240
ctactggaga ccagaacaac caatcagttc ctagctgtct caaagggaaa ctgctcaggg    9300
cccactacaa tcagaggtca attctcaaac atgtcgctgt ccctgttaga cttgtattta    9360
ggtcgaggtt acaatgtgtc atctatagtc actatgacat cccagggaat gtatggggga    9420
acttacctag tggaaaagcc taatctgagc agcaaaaggt cagagttgtc acaactgagc    9480
atgtaccgag tgtttgaagt aggtgttatc agaaatccgg gtttggggc tccggtgttc     9540 catatgacaa actatcttga gcaaccagtc agtaatgatc tcagcaactg tatggtggct    9600
ttgggggagc tcaaactcgc agccctttgt cacggggaag attctatcac aattccctat    9660
cagggatcag ggaaaggtgt cagcttccag ctcgtcaagc taggtgtctg gaaatcccca    9720
accgacatgc aatcctgggt ccccttatca acggatgatc cagtgataga caggctttac    9780
ctctcatctc acagaggtgt tatcgctgac aatcaagcaa atgggctgt cccgacaaca     9840 cgaacagatg acaagttgcg aatggagaca tgcttccaac aggcgtgtaa gggtaaaatc    9900
caagcactct gcgagaatcc cgagtgggca ccattgaagg ataacaggat tccttcatac    9960
ggggtcttgt ctgttgatct gagtctgaca gttgagctta aaatcaaaat tgcttcggga   10020
ttcgggccat tgatcacaca cggttcaggg atggacctat acaaatccaa ccacaacaat   10080
gtgtattggc tgactatccc gccaatgaag aacctagcct taggtgtaat caacacattg   10140
gagtggatac cgagattcaa ggttagtccc tacctcttca ctgtcccaat taaggaagca   10200
ggcgaagact gccatgcccc aacataccta cctgcggagg tggatggtga tgtcaaactc   10260
agttccaatc tggtgattct acctggtcaa gatctccaat atgttttggc aacctacgat   10320
acttccaggg ttgaacatgc tgtggtttat tacgtttaca gcccaggccg ctcattttct   10380 tactttatc cttttaggtt gcctataaag ggggtcccca tcgaattaca agtggaatgc    10440
ttcacatggg accaaaaact ctggtgccgt cacttctgtg tgcttgcgga ctcagaatct   10500
ggtggacata tcactcactc tgggatggtg ggcatgggag tcagctgcac agtcacccgg   10560
gaagatggaa ccaatcgcag atagggctgc tagtgaacca atcacatgat gtcacccaga   10620
catcaggcat acccactagt gtgaaataga catcagaatt aagaaaaacg tagggtccaa   10680
gtggttcccc gttatggact cgctatctgt caaccagatc ttatacctg aagttcacct    10740 agatagcccg atagttacca ataagatagt agccatcctg gagtatgctc gagtccctca   10800
cgcttacagc ctggaggacc ctacactgtg tcagaacatc aagcaccgcc taaaaacgg    10860 attttccaac caaatgatta taaacaatgt ggaagtggg aatgtcatca gtccaagct    10920 taggagttat ccggcccact ctcatattcc atatccaaat tgtaatcagg atttatttaa   10980
catagaagac aaagagtcaa cgaggaagat ccgtgaactc ctcaaaaagg ggaattcgct   11040
gtactccaaa gtcagtgata aggttttcca atgcttaagg gacactaact cacggcttgg   11100
cctaggctcc gaattgaggg aggacatcaa ggagaaagtt attaacttgg gagttttacat  11160 gcacagctcc cagtggtttg agccctttct gttttggttt acagtcaaga ctgagatgag   11220
gtcagtgatt aaatcacaaa cccatacttg ccataggagg agacacacac ctgtattctt   11280
cactggtagt tcagttgagt tgctaatctc tcgtgacctt gttgctataa tcagtaaaga   11340
gtctcaacat gtatattacc tgacatttga actggttttg atgtattgtg atgtcataga   11400
ggggaggtta atgacagaga ccgctatgac tattgatgct aggtatacag agcttctagg   11460
aagagtcaga tacatgtgga aactgataga tggtttcttc cctgcactcg ggaatccaac   11520
```

```
ttatcaaatt gtagcaatgc tggagcctct ttcacttgct tacctgcagc tgagggatat    11580
aacagtagaa ctcagaggtg ctttccttaa ccactgcttt actgaaatac atgatgttct    11640
tgaccaaaac gggttttctg atgaaggtac ttatcatgag ttaattgaag ctctagatta    11700
cattttcata actgatgaca tacatctgac aggggagatt ttctcatttt tcagaagttt    11760
cggccacccc agacttgaag cagtaacggc tgctgaaaat gttaggaaat acatgaatca    11820
gcctaaagtc attgtgtatg agactctgat gaaaggtcat gccatatttt gtggaatcat    11880
aatcaacggc tatcgtgaca ggcacggagg cagttggcca ccgctgaccc tcccctgca    11940 tgctgcagac acaatccgga atgctcaagc ttcaggtgaa gggttaacac atgagcagtg    12000
cgttgataac tggaaatctt ttgctggagt gaaatttggc tgctttatgc ctcttagcct    12060
ggatagtgat ctgacaatgt acctaaagga caaggcactt gctgctctcc aaagggaatg    12120
ggattcagtt tacccgaaag agttcctgcg ttacgaccct cccaagggaa ccgggtcacg    12180
gaggcttgta gatgttttcc ttaatgattc gagctttgac ccatatgatg tgataatgta    12240
tgttgtaagt ggagcttacc tccatgaccc tgagttcaac ctgtcttaca gcctgaaaga    12300
aaaggagatc aaggaaacag gtagactttt tgctaaaatg acttacaaaa tgagggcatg    12360
ccaagtgatt gctgaaaatc taatctcaaa cgggattggc aaatatttta aggacaatgg    12420
gatggccaag gatgagcacg atttgactaa ggcactccac actctagctg tctcaggagt    12480
ccccaaagat ctcaaagaaa gtcacagggg ggggccagtc ttaaaaacct actcccgaag    12540
cccagtccac acaagtacca ggaacgtgag agcagcaaaa gggtttatag gttccctca    12600 agtaattcgg caggaccaag acactgatca tccggagaat atggaagctt acgagacagt    12660
cagtgcattt atcacgactg atctcaagaa gtactgcctt aattggagat atgagaccat    12720
cagcttgttt gcacagaggc taatgagat ttacggattg ccctcatttt tccagtggct    12780
gcataagagg cttgagacct ctgtcctgta tgtaagtgac cctcattgcc ccccgacct    12840 tgacgcccat atcccgttat ataaagtccc caatgatcaa atcttcatta agtaccctat    12900
gggaggtata aagggtatt gtcagaagct gtggaccatc agcaccattc cctatctata    12960
cctggctgct tatgagagcg gagtaaggat tgcttcgtta gtgcaagggg acaatcagac    13020
catagccgta acaaaaaggg tacccagcac atggccctac aaccttaaga aacgggaagc    13080
tgctagagta actagagatt actttgtaat tcttaggcaa aggctacatg atattggcca    13140
tcacctcaag gcaaatgaga caattgtttc atcacatttt tttgtctatt caaaaggaat    13200
atattatgat gggctacttg tgtcccaatc actcaagagc atcgcaagat gtgtattctg    13260
gtcagagact atagttgatg aaacaagggc agcatgcagt aatattgcta caacaatggc    13320
taaaagcatc gagagaggtt atgaccgtta ccttgcatat ccctgaacg tcctaaaagt    13380 gatacagcaa attctgatct ctcttggctt cacaatcaat tcaaccatga cccgggatgt    13440
agtcataccc ctcctcacaa caacgaccct cttaataagg atggcactgt tgcccgctcc    13500
tattgggggg atgaattatc tgaatatgag caggctgttt gtcagaaaca tcggtgatcc    13560
agtaacatca tcaattgctg atctcaagag aatgattctc gcctcactaa tgcctgaaga    13620
gaccctccat caagtaatga cacaacaacc ggggactct tcattcctag actgggctag    13680 cgaccettac tcagcaaatc ttgtatgtgt ccagagcatc actagactcc tcaagaacat    13740
aactgcaagg tttgtcctga tccatagtcc aaacccaatg ttaaaggat tattccatga    13800 tgacagtaaa gaagaggacg agggactggc ggcattcctc atggacaggc atattatagt    13860
acctagggca gctcatgaaa tcctggatca tagtgtcaca ggggcaagag agtctattgc    13920
```

```
aggcatgctg gataccacaa aaggcttgat tcgagccagc atgaggaagg ggggggttaac   13980 ctctcgagtg ataaccagat tgtccaatta tgactatgaa caattcagag cagggatggt   14040
gctattgaca ggaagaaaga gaaatgtcct cattgacaaa gagtcatgtt cagtgcagct   14100
ggcgagagct ctaagaagcc atatgtgggc gaggctagct cgaggacggc ctatttacgg   14160
ccttgaggtc cctgatgtac tagaatctat gcgaggccac cttattcggc gtcatgagac   14220
atgtgtcatc tgcgagtgtg gatcagtcaa ctacggatgg tttttttgtcc cctcgggttg   14280 ccaactggat gatattgaca aggaaacatc atccttgaga gtcccatata ttggttctac   14340
cactgatgag agaacagaca tgaagcttgc cttcgtaaga gccccaagtc gatccttgcg   14400
atctgctgtt agaatagcaa cagtgtactc atgggcttac ggtgatgatg atagctcttg   14460
gaacgaagcc tggttgttgg ctaggcaaag ggccaatgtg agcctggagg agctaagggt   14520
gatcactccc atctcaactt cgactaattt agcgcatagg ttgagggatc gtagcactca   14580
agtgaaatac tcaggtacat cccttgtccg agtggcgagg tataccacaa tctccaacga   14640
caatctctca tttgtcatat cagataagaa ggttgatact aactttatat accaacaagg   14700
aatgctccta gggttgggtg ttttagaaac attgtttcga ctcgagaaag ataccggatc   14760
atctaacacg gtattacatc ttcacgtcga aacagattgt tgcgtgatcc cgatgataga   14820
tcatcccagg atacccagct cccgcaagct agagctgagg gcagagctat gtaccaaccc   14880
attgatatat gataatgcac ctttaattga cagagatgca acaaggctat acacccagag   14940
ccataggagg caccttgtgg aatttgttac atggtccaca ccccaactat atcacatttt   15000
agctaagtcc acagcactat ctatgattga cctggtaaca aaatttgaga aggaccatat   15060
gaatgaaatt tcagctctca taggggatga cgatatcaat agtttcataa ctgagtttct   15120
gctcatagag ccaagattat tcactatcta cttgggccag tgtgcggcca tcaattgggc   15180
atttgatgta cattatcata gaccatcagg gaaatatcag atgggtgagc tgttgtcatc   15240
gttcctttct agaatgagca aaggagtgtt taaggtgctt gtcaatgctc taagccaccc   15300
aaagatctac aagaaattct ggcattgtgg tattatagag cctatccatg gtccttcact   15360
tgatgctcaa aacttgcaca caactgtgtg caacatggtt tacacatgct atatgaccta   15420
cctcgacctg ttgttaatg aagagttaga agagttcaca tttctcttgt gtgaaagcga   15480
cgaggatgta gtaccggaca gattcgacaa catccaggca aaaacttat gtgttctggc   15540 agatttgtac tgtcaaccag ggacctgccc accaattcga ggtctaagac cggtagagaa   15600
atgtgcagtt ctaaccgacc atatcaaggc agaggctatg ttatctccag caggatcttc   15660
gtggaacata aatccaatta ttgtagacca ttactcatgc tctctgactt atctccggcg   15720
aggatcgatc aaacagataa gattgagagt tgatccagga ttcatttttcg acgccctcgc   15780 tgaggtaaat gtcagtcagc caaagatcgg cagcaacaac atctcaaata tgagcatcaa   15840 ggcttttcaga ccccccacacg atgatgttgc aaaattgctc aaagatatca acacaagcaa   15900
gcacaatctt cccatttcag ggggcaatct cgccaattat gaaatccatg ctttccgcag   15960
aatcgggttg aactcatctg cttgctacaa agctgttgag atatcaacat taattaggag   16020
atgccttgag ccaggggagg acggcttgtt cttgggtgag ggatcgggtt ctatgttgat   16080
cacttataag gagatactta aactaaacaa gtgcttctat aatagtgggg tttccgccaa   16140
ttctagatct ggtcaaaggg aattagcacc ctatccctcc gaagttggcc ttgtcgaaca   16200
cagaatggga gtaggtaata ttgtcaaagt gctctttaac gggaggcccg aagtcacgtg   16260
```

```
ggtaggcagt gtagattgct tcaatttcat agttagtaat atccctacct ctagtgtggg   16320
gtttatccat tcagatatag agaccttgcc tgacaaagat actatagaga agctagagga   16380
attggcagcc atcttatcga tggctctgct cctgggcaaa ataggatcaa tactggtgat   16440
taagcttatg cctttcagcg gggattttgt tcagggattt ataagttatg tagggtctca   16500
ttatagagaa gtgaaccttg tatacccta g atacagcaac ttcatatcta ctgaatctta   16560
tttggttatg acagatctca aggctaaccg gctaatgaat cctgaaaaga ttaagcagca   16620
gataattgaa tcatctgtga ggacttcacc tggacttata ggtcacatcc tatccattaa   16680
gcaactaagc tgcatacaag caattgtggg agacgcagtt agtagaggtg atatcaatcc   16740
tactctgaaa aaacttacac ctatagagca ggtgctgatc aattgcgggt tggcaattaa   16800
cggacctaag ctgtgcaaag aattgatcca ccatgatgtt gcctcaggqc aagatggatt   16860 gcttaattct atactcatcc tctacaggga gttggcaaga ttcaaagaca accaaagaag   16920
tcaacaaggg atgttccacg cttaccccgt attggtaagt agcaggcaac gagaacttat   16980
atctaggatc acccgcaaat tttgggggca cattcttctt tactccggga acagaaagtt   17040
gataaataag tttatccaga atctcaagtc cggctatctg atactagact tacaccagaa   17100
tatcttcgtt aagaatctat ccaagtcaga gaaacagatt attatgacgg ggggtttgaa   17160
acgtgagtgg gttttttaagg taacagtcaa ggagaccaaa gaatggtata agttagtcgg   17220
atacagtgcc ctgattaagg actaattggt tgaactccgg aaccctaatc ctgccctagg   17280
tggttaggca ttatttgcaa tatattaaag aaaactttga aaatacgaag tttctattcc   17340
cagctttgtc tggtggccgg catggtccca gcctcctcgc tggcgccggc tgggcaacat   17400
tccgagggga ccgtcccctc ggtaatggcg aatgggacgc ggccgatccg gctgctaaca   17460
aagcccgaaa ggaagctgag ttggctgctg ccaccgctga gcaataacta gcataacccc   17520
ttggggcctc taaacgggtc ttgagggggtt ttttgctgaa aggaggaact atatccggat   17580
gcggccgcag gtacccagct tttgttccct ttagtgaggg ttaatttcga gcttggcgta   17640
atcatggtca tagctgtttc ctgtgtgaaa ttgttatccg ctcacaattc cacacaacat   17700
acgagccgga agcataaagt gtaaagcctg gggtgcctaa tgagtgagct aactcacatt   17760
aattgcgttg cgctcactgc ccgctttcca gtcgggaaac ctgtcgtgcc agctgcatta   17820
atgaatcggc caacgcgcgg ggagaggcgg tttgcgtatt gggcgctctt ccgcttcctc   17880
gctcactgac tcgctgcgct cggtcgttcg gctgcggcga gcggtatcag ctcactcaaa   17940
ggcggtaata cggttatcca cagaatcagg ggataacgca ggaaagaaca tgtgagcaaa   18000
aggccagcaa aaggccagga accgtaaaaa ggccgcgttg ctggcgtttt tccataggct   18060
ccgcccccct gacgagcatc acaaaaatcg acgctcaagt cagaggtggc gaaacccgac   18120
aggactataa agataccagg cgtttccccc tggaagctcc ctcgtgcgct ctcctgttcc   18180
gaccctgccg cttaccggat acctgtccgc ctttctccct tcgggaagcg tggcgctttc   18240
tcatagctca cgctgtaggt atctcagttc ggtgtaggtc gttcgctcca agctgggctg   18300
tgtgcacgaa ccccccgttc agcccgaccg ctgcgcctta tccggtaact atcgtcttga   18360
gtccaacccg gtaagacacg acttatcgcc actggcagca gccactggta acaggattag   18420
cagagcgagg tatgtaggcg gtgctacaga gttcttgaag tggtggccta actacggcta   18480
cactagaagg acagtatttg gtatctgcgc tctgctgaag ccagttacct tcggaaaaag   18540
agttggtagc tcttgatccg gcaaacaaac caccgctggt agcggtggtt ttttgttttg   18600
caagcagcag attacgcgca gaaaaaaagg atctcaagaa gatcctttga tcttttctac   18660
```

```
ggggtctgac gctcagtgga acgaaaactc acgttaaggg attttggtca tgagattatc    18720
aaaaaggatc ttcacctaga tccttttaaa ttaaaaatga agttttaaat caatctaaag    18780
tatatatgag taaacttggt ctgacagtta ccaatgctta atcagtgagg cacctatctc    18840
agcgatctgt ctatttcgtt catccatagt tgcctgactc cccgtcgtgt agataactac    18900
gatacgggag ggcttaccat ctggccccag tgctgcaatg ataccgcgag acccacgctc    18960
accggctcca gatttatcag caataaacca gccagccgga agggccgagc gcagaagtgg    19020
tcctgcaact ttatccgcct ccatccagtc tattaattgt tgccgggaag ctagagtaag    19080
tagttcgcca gttaatagtt tgcgcaacgt tgttgccatt gctacaggca tcgtggtgtc    19140
acgctcgtcg tttggtatgg cttcattcag ctccggttcc caacgatcaa ggcgagttac    19200
atgatccccc atgttgtgca aaaaagcggt tagctccttc ggtcctccga tcgttgtcag    19260
aagtaagttg gccgcagtgt tatcactcat ggttatggca gcactgcata attctcttac    19320
tgtcatgcca tccgtaagat gcttttctgt gactggtgag tactcaacca agtcattctg    19380
agaatagtgt atgcggcgac cgagttgctc ttgcccggcg tcaatacggg ataataccgc    19440
gccacatagc agaactttaa aagtgctcat cattggaaaa cgttcttcgg ggcgaaaact    19500
ctcaaggatc ttaccgctgt tgagatccag ttcgatgtaa cccactcgtg cacccaactg    19560
atcttcagca tcttttactt tcaccagcgt ttctgggtga gcaaaaacag gaaggcaaaa    19620
tgccgcaaaa aagggaataa gggcgacacg gaaatgttga atactcatac tcttcctttt    19680
tcaatattat tgaagcattt atcagggtta ttgtctcatg agcggataca tatttgaatg    19740
tatttagaaa aataaacaaa tagggggttcc gcgcacattt ccccgaaaag tgc           19793

```

<210> SEQ ID NO 2
<211> LENGTH: 19798
<212> TYPE: DNA
<213> ORGANISM: Artificial
<220> FEATURE:
<223> OTHER INFORMATION: Complete nucleotide sequence of p(+)MV3EZ-GFP

<400> SEQUENCE: 2

```
cacctaaatt gtaagcgtta atattttgtt aaaattcgcg ttaaattttt gttaaatcag      60 ctcattttt aaccaatagg ccgaaatcgg caaaatccct tataaatcaa agaatagac       120 cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca agttttttgg ggtcgaggtg ccgtaaagca ctaaatcgga acctaaagg     300 gagcccccga tttagagctt gacggggaaa gccggccatt taggccatag ggcgctggca    360
agtgtagcgg tcacgctgcg cgtaaccacc acacccgccg cgcttaatgc gccgctacag    420
ggcgcgtccc attcgccatt caggctgcgc aactgttggg aagggcgatc ggtgcgggcc    480
tcttcgctat tacgccagct ggcgaaaggg ggatgtgctg caaggcgatt aagttgggta    540
acgccagggt tttcccagtc acgacgttgt aaaacgacgg ccagtgaatt gtaatacgac    600
tcactataac caaacaaagt tgggtaagga tagttcaatc aatgatcatc ttctagtgca    660
cttaggattc aagatcctat tatcagggac aagagcagga ttagggatat ctgagatggc    720
cacactttta aggagcttag cattgttcaa aagaaacaag acaaaccac ccattacatc     780 aggatccggt ggagccatca gaggaatcaa acacattatt atagtaccaa tccctggaga    840
ttcctcaatt accactcgat ccagacttct ggaccggttg gtcaggttaa ttggaaaccc    900
```

```
ggatgtgagc gggcccaaac taacagggc actaataggt atattatcct tatttgtgga     960
gtctccaggt caattgattc agaggatcac cgatgaccct gacgttagca taaggctgtt    1020
agaggttgtc cagagtgacc agtcacaatc tggccttacc ttcgcatcaa gaggtaccaa    1080
catggaggat gaggcggacc aatacttttc acatgatgat ccaattagta gtgatcaatc    1140
caggttcgga tggttcgaga acaaggaaat ctcagatatt gaagtgcaag accctgaggg    1200
attcaacatg attctgggta ccatcctagc ccaaatttgg gtcttgctcg caaaggcggt    1260
tacggcccca gacacggcag ctgattcgga gctaagaagg tggataaagt acacccaaca    1320
aagaagggta gttggtgaat ttagattgga gagaaaatgg ttggatgtgg tgaggaacag    1380
gattgccgag gacctctcct tacgccgatt catggtcgct ctaatcctgg atatcaagag    1440
aacacccgga aacaaaccca ggattgctga aatgatatgt gacattgata catatatcgt    1500
agaggcagga ttagccagtt ttatcctgac tattaagttt gggatagaaa ctatgtatcc    1560
tgctcttgga ctgcatgaat tgctggtga gttatccaca cttgagtcct tgatgaacct    1620
ttaccagcaa atggggaaa ctgcacccta catggtaatc ctggagaact caattcagaa    1680
caagttcagt gcaggatcat accctctgct ctggagctat gccatgggag taggagtgga    1740
acttgaaaac tccatggggg gtttgaactt tggccgatct tactttgatc cagcatattt    1800
tagattaggg caagagatgg taaggaggtc agctggaaag gtcagttcca cattggcatc    1860
tgaactcggt atcactgccg aggatgcaag gcttgtttca gagattgcaa tgcatactac    1920
tgaggacaag atcagtagag cggttggacc cagacaagcc caagtatcat ttctacacgg    1980
tgatcaaagt gagaatgagc taccgagatt ggggggcaag aagatagga gggtcaaaca    2040
gagtcgagga gaagccaggg agagctacag agaaaccggg cccagcagag caagtgatgc    2100
gagagctgcc catcttccaa ccggcacacc cctagacatt gacactgcat cggagtccag    2160
ccaagatccg caggacagtc gaaggtcagc tgacgccctg cttaggctgc aagccatggc    2220
aggaatctcg gaagaacaag gctcagacac ggacacccct atagtgtaca atgacagaaa    2280
tcttctagac taggtgcgag aggccgaggg ccagaacaac atccgcctac cctccatcat    2340
tgttataaaa aacttaggaa ccaggtccac acagccgcca gcccatcaac catccactcc    2400
cacgattgga gccaatggta aagagcagg cacgccatgt caaaaacgga ctggaatgca    2460
tccgggctct caaggccgag cccatcggct cactggccat cgaggaagct atggcagcat    2520
ggtcagaaat atcagacaac ccaggacagg agcgagccac ctgcagggaa gagaaggcag    2580
gcagttcggg tctcagaaaa ccatgcctct cagcaattgg atcaactgaa ggcggtgcac    2640
ctcgcatccg cggtcaggga cctggagaga gcgatgacga cgctgaaact ttgggaatcc    2700
ccccaagaaa tctccaggca tcaagcactg ggttacagtg ttattacgtt tatgatcaca    2760
gcggtgaagc ggttaaggga atccaagatg ctgactctat catggttcaa tcaggccttg    2820
atggtgatag caccctctca ggaggagaca atgaatctga aaacagcgat gtggatattg    2880
gcgaacctga taccgaggga tatgctatca ctgaccgggg atctgctccc atctctatgg    2940
ggttcagggc ttctgatgtt gaaactgcag aaggagggga gatccacgag ctcctgagac    3000
tccaatccag aggcaacaac tttccgaagc ttgggaaaac tctcaatgtt cctccgcccc    3060
cggacccgg tagggccagc acttccggga cacccattaa aaagggcaca gacgcgagat    3120
tagcctcatt tggaacggag atccgtctct tattgacagg tggtgcaacc caatgtgctc    3180
gaaagtcacc ctcggaacca tcaggccag gtgcacctgc ggggaatgtc cccgagtgtg    3240
tgagcaatgc cgcactgata caggagtgga caccccgaatc tggtaccaca atctccccga    3300
```

```
gatcccagaa taatgaagaa gggggagact attatgatga tgagctgttc tctgatgtcc    3360
aagatattaa aacagccttg gccaaaatac acgaggataa tcagaagata atctccaagc    3420
tagaatcact gctgttattg aagggagaag ttgagtcaat taagaagcag atcaacaggc    3480
aaaatatcag catatccacc ctggaaggac acctctcaag catcatgatc gccattcctg    3540
gacttgggaa ggatcccaac gaccccactg cagatgtcga aatcaatccc gacttgaaac    3600
ccatcatagg cagagattca ggccgagcac tggccgaagt tctcaagaaa cccgttgcca    3660
gccgacaact ccaaggaatg acaaatggac ggaccagttc cagaggacag ctgctgaagg    3720
aatttcagct aaagccgatc gggaaaaaga tgagctcagc cgtcgggttt gttcctgaca    3780
ccggccctgc atcacgcagt gtaatccgct ccattataaa atccagccgg ctagaggagg    3840
atcggaagcg ttacctgatg actctccttg atgatatcaa aggagccaat gatcttgcca    3900
agttccacca gatgctgatg aagataataa tgaagtagct acagctcaac ttacctgcca    3960
accccatgcc agtcgaccca actagtacaa cctaaatcca tcataaaaaa cttaggagca    4020
aagtgattgc ctcccaagtt ccacaatgac agagatctac gacttcgaca agtcggcatg    4080
ggacatcaaa gggtcgatcg ctccgataca acccaccacc tacagtgatg gcaggctggt    4140
gccccaggtc agagtcatag atcctggtct aggcgacagg aaggatgaat gctttatgta    4200
catgtttctg ctgggggttg ttgaggacag ggattcccta gggcctccaa tcgggcgagc    4260
atttgggtcc ctgcccttag gtgttggcag atccacagca aagcccgaaa aactcctcaa    4320
agaggccact gagcttgaca tagttgttag acgtacagca gggctcaatg aaaaactggt    4380
gttctacaac aacaccccac taactctcct cacaccttgg agaaaggtcc taacaacagg    4440
gagtgtcttc aacgcaaacc aagtgtgcaa tgcggttaat ctgataccgc tcgataccc    4500
gcagaggttc cgtgttgttt atatgagcat cacccgtctt tcggataacg ggtattacac    4560
cgttcctaga agaatgctgg aattcagatc ggtcaatgca gtggccttca acctgctggt    4620
gacccttagg attgacaagg cgataggccc tgggaagatc atcgacaata cagagcaact    4680
tcctgaggca acatttatag tccacatcgg gaacttcagg agaaagaaga gtgaagtcta    4740
ctctgccgat tattgcaaaa tgaaaatcga aaagatgggc ctggttttg cacttggtgg    4800
gataggggc accagtcttc acattagaag cacaggcaaa atgagcaaga ctctcaatgc    4860
acaactcggg ttcaagaaga ccttatgtta cccgctgatg gatatcaatg aagaccttaa    4920
tcgattactc tggaggagca gatgcaagat agtaagaatc caggcagttt gcagccatc    4980
agttcctcaa gaattccgca tttacgacga cgtgatcata aatgatgacc aaggactatt    5040
caaagttctg tagaccgtag tgcccagcaa tgcccgaaaa cgaccccct cacaatgaca    5100
gccagaaggc ccgacaaaaa agcccccctc cgaaagactc cacggaccaa gcgagaggcc    5160
agccagcagc cgacggcaag cgcgaacacc aggcggcccc agcacagaac agccctgaca    5220
caaggccacc accagccacc ccaatctgca tcctcctcgt gggaccccg aggaccaacc    5280
cccaaggctg ccccgatcc aaaccaccaa ccgcatcccc accaccccg ggaaagaaac    5340
ccccagcaat tggaaggccc ctcccctct tcctcaacac aagaactcca caaccgaacc    5400
gcacaagcga ccgaggtgac ccaaccgcag gcatccgact ccctagacag atcctctctc    5460
cccggcaaac taaacaaaac ttagggccaa ggaacataca cacccaacag aacccagacc    5520
ccggcccacg gcgccgcgcc cccaaccccc gacaaccaga gggagcccc aaccaatccc    5580
gccggctccc ccggtgccca caggcaggga caccaacccc cgaacagacc cagcacccaa    5640
```

```
ccatcgacaa tccaagacgg ggggggccccc ccaaaaaaaa gcccccaggg gccgacagcc    5700
agcaccgcga ggaagcccac ccaccccaca cacgaccacg gcaaccaaac cagaacccag    5760
accaccctgg gccaccagct cccagactcg gccatcaccc cgcagaaagg aaaggccaca    5820
acccgcgcac cccagccccg atccggcggg gagccaccca acccgaacca gcacccaaga    5880
gcgatccccg aaggaccccc gaaccgcaaa ggacatcagt atcccacagc ctctccaagt    5940
cccccggtct cctcctcttc tcgaagggac caaaagatca atccaccaca cccgacgaca    6000
ctcaactccc caccccctaaa ggagacaccg ggaatcccag aatcaagact catccaatgt    6060
ccatcatggg tctcaaggtg aacgtctctg ccatattcat ggcagtactg ttaactctcc    6120
aaacacccac cggtcaaatc cattggggca atctctctaa gatagggtg gtaggaatag    6180 gaagtgcaag ctacaaagtt atgactcgtt ccagccatca atcattagtc ataaaattaa    6240
tgcccaatat aactctcctc aataactgca cgagggtaga gattgcagaa tacaggagac    6300
tactgagaac agttttggaa ccaattagag atgcacttaa tgcaatgacc cagaatataa    6360
gaccggttca gagtgtagct tcaagtagga gacacaagag aagttgcgaa tggagacatg    6420
cttccaacag gcgtgtaagg gtaaaatcca agcactctgc gagaatcccg agtgggcacc    6480
attgaaggat aacaggattc cttcatacgg ggtcttgtct gttgatctga gtctgacagt    6540
tgagcttaaa atcaaaattg cttcgggatt cgggccattg atcacacacg gttcagggat    6600
ggacctatac aaatccaacc acaacaatgt gtattggctg actatcccgc caatgaagaa    6660
cctagcctta ggtgtaatca acacattgga gtggataccg agattcaagg ttagtcccta    6720
cctcttcact gtcccaatta aggaagcagg cgaagactgc catgccccaa catacctacc    6780 tgccggaggtg gatggtgatg tcaaactcag ttccaatctg gtgattctac ctggtcaaga    6840
tctccaatat gttttggcaa cctacgatac ttccagggtt gaacatgctg tggtttatta    6900
cgtttacagc ccaggccgct cattttctta cttttatcct tttaggttgc ctataaaggg    6960
ggtccccatc gaattacaag tggaatgctt cacatgggac caaaaactct ggtgccgtca    7020
cttctgtgtg cttgcggact cagaatctgg tggacatatc actcactctg ggatggtggg    7080
catgggagtc agctgcacag tcacccggga agatggaacc aatcgcagat agggctgcta    7140
gtgaaccaat cacatgatgt cacccagaca tcaggcatac ccactagtct accctccatc    7200
attgttataa aaacttagg aaccaggtcc acacagccgc cagcccatca acgcgtatct    7260
tcaccggtga tctatcgcgt acgtagcgcg catgagtaaa ggagaagaac ttttcactgg    7320
agttgtccca attcttgttg aattagatgg tgatgttaat gggcacaaat tttctgtcag    7380
tggagagggt gaaggtgatg atttgcggga gtagtcctgg caggtgcggc cctaggcgtt    7440
gccacagctg ctcagataac ggccggcatt gcacttcacc agtccatgct gaactctcaa    7500
gccatcgaca atctgagagc gagcctggaa actactaatc aggcaattga ggcaatcaga    7560
caagcagggc aggagatgat attggctgtt cagggtgtcc aagactacat caataatgag    7620
ctgataccgt ctatgaacca actatcttgt gatttaatcg ccagaagct cgggctcaaa    7680 ttgctcagat actatacaga aatcctgtca ttatttggcc ccagtttacg ggaccccata    7740
tctgcggaga tatctatcca ggctttgagc tatgcgcttg gaggagacat caataaggtg    7800
ttagaaaagc tcggatacag tggaggtgat ttactgggca tcttagagag cagaggaata    7860
aaggcccgga taactcacgt cgacacagag tcctacttca ttgtcctcag tatagcctat    7920
ccgacgctgt ccgagattaa gggggtgatt gtccaccggc tagaggggt ctcgtacaac    7980 ataggctctc aagagtggta taccactgtg cccaagtatg ttgcaaccca agggtacctt    8040
```

```
atctcgaatt ttgatgagtc atcgtgtact ttcatgccag aggggactgt gtgcagccaa    8100
aatgccttgt acccgatgag tcctctgctc caagaatgcc tccggggta caccaagtcc     8160 tgtgctcgta cactcgtatc cgggtctttt gggaaccggt tcattttatc acaagggaac    8220
ctaatagcca attgtgcatc aatcctttgc aagtgttaca caacaggaac gatcattaat    8280
caagaccctg acaagatcct aacatacatt gctgccgatc actgcccggt agtcgaggtg    8340
aacggcgtga ccatccaagt cgggagcagg aggtatccag acgctgtgta cttgcacaga    8400
attgacctcg gtcctcccat atcattggag aggttggacg tagggacaaa tctggggaat    8460
gcaattgcta agttggagga tgccaaggaa ttgttggagt catcggacca gatattgagg    8520
agtatgaaag gtttatcgag cactagcata gtctacatcc tgattgcagt gtgtcttgga    8580
gggttgatag gatccccgc tttaatatgt tgctgcaggg ggcgttgtaa caaaaaggga    8640
gaacaagttg gtatgtcaag accaggccta agcctgatc ttacgggaac atcaaaatcc    8700
tatgtaaggt cgctctgatc ctctacaact cttgaaacac aaatgtccca caagtctcct    8760
cttcgtcatc aagcaaccac cgcacccagc atcaagccca cctgaaatta tctccggctt    8820
ccctctggcc gaacaatatc ggtagttaat taaaacttag ggtgcaagat catccacaat    8880
gtcaccacaa cgagaccgga taaatgcctt ctacaaagat aacccccatc ccaagggaag    8940
taggatagtc attaacagag aacatcttat gattgataga ccttatgttt tgctggctgt    9000
tctgtttgtc atgtttctga gcttgatcgg gttgctagcc attgcaggca ttagacttca    9060 tcggcagcc atctacaccg cagagatcca taaaagcctc agcaccaatc tagatgtaac    9120
taactcaatc gagcatcagg tcaaggacgt gctgacacca ctcttcaaaa tcatcggtga    9180
tgaagtgggc ctgaggacac ctcagagatt cactgaccta gtgaaattca tctctgacaa    9240
gattaaattc cttaatccgg atagggagta cgacttcaga gatctcactt ggtgtatcaa    9300
cccgccagag agaatcaaat tggattatga tcaatactgt gcagatgtgg ctgctgaaga    9360
gctcatgaat gcattggtga actcaactct actggagacc agaacaacca atcagttcct    9420
agctgtctca aagggaaact gctcagggcc cactacaatc agaggtcaat tctcaaacat    9480
gtcgctgtcc ctgttagact tgtatttagg tcgaggttac aatgtgtcat ctatagtcac    9540
tatgacatcc cagggaatgt atgggggaac ttacctagtg gaaaagccta atctgagcag    9600
caaaaggtca gagttgtcac aactgagcat gtaccgagtg tttgaagtag gtgttatcag    9660
aaatccgggt ttgggggctc cggtgttcca tatgacaaac tatcttgagc aaccagtcag    9720
taatgatctc agcaactgta tggtggcttt gggggagctc aaactcgcag ccctttgtca    9780
cggggaagat tctatcacaa ttccctatca gggatcaggg aaaggtgtca gcttccagct    9840
cgtcaagcta ggtgtctgga atccccaac cgacatgcaa tcctgggtcc ccttatcaac    9900
ggatgatcca gtgatagaca ggctttacct ctcatctcac agaggtgtta tcgctgacaa    9960
tcaagcaaaa tggctgtcc cgacaacacg aacagatgac caacatacgg aaaacttacc    10020
cttaaattta tttgcactac tggaaaacta cctgttccat ggccaacact tgtcactact    10080
ttcacctatg gtgttcaatg cttttcaaga tacccagatc atatgaaacg gcatgacttt    10140
ttcaagagtg ccatgcccga aggttacgta caggaaagaa ctatattttt caaagatgac    10200
gggaactaca agacacgtgc tgaagtcaag tttgaaggtg ataccttgt taatagaatc    10260 gagttaaaag gtattgattt taagaagat ggaaacattc ttggcacaa attggaatac    10320 aactataact cacacaatgt atacatcatg gcagacaaac aaaagaatgg aatcagagtt    10380
```

```
aacttcaaaa ttagacacaa cattgaagat ggaagcgttc aactagcaga ccattatcaa   10440
caaaatactc caattggcga tggccctgtc cttttaccag acaaccatta cctgtccaca   10500
caatctgccc tttcgaaaga tcccaacgaa aagagagacc acatggtcct tcttgagttt   10560
gtaacagctg ctgggattac acatggcatg gatgaactat acaaatagtg agcgcgcagc   10620
gctgacgtct cgcgatgata ctagtgtgaa atagacatca gaattaagaa aaacgtaggg   10680
tccaagtggt tccccgttat ggactcgcta tctgtcaacc agatcttata ccctgaagtt   10740
cacctagata gcccgatagt taccaataag atagtagcca tcctggagta tgctcgagtc   10800
cctcacgctt acagcctgga ggaccctaca ctgtgtcaga acatcaagca ccgcctaaaa   10860
aacggatttt ccaaccaaat gattataaac aatgtggaag ttgggaatgt catcaagtcc   10920
aagcttagga gttatccggc ccactctcat attccatatc caaattgtaa tcaggattta   10980
tttaacatag aagacaaaga gtcaacgagg aagatccgtg aactcctcaa aaaggggaat   11040
tcgctgtact ccaaagtcag tgataaggtt ttccaatgct taagggacac taactcacgg   11100
cttggcctag gctccgaatt gagggaggac atcaaggaga aagttattaa cttgggagtt   11160
tacatgcaca gctcccagtg gtttgagccc tttctgtttt ggtttacagt caagactgag   11220
atgaggtcag tgattaaatc acaaacccat acttgccata ggaggagaca cacacctgta   11280
ttcttcactg gtagttcagt tgagttgcta atctctcgtg accttgttgc tataatcagt   11340
aaagagtctc aacatgtata ttacctgaca tttgaactgg ttttgatgta ttgtgatgtc   11400
atagagggga ggttaatgac agagaccgct atgactattg atgctaggta tacagagctt   11460 ctaggaaagag tcagatacat gtggaaactg atagatggtt tcttccctgc actcgggaat   11520
ccaacttatc aaattgtagc aatgctggag cctctttcac ttgcttacct gcagctgagg   11580
gatataacag tagaactcag aggtgctttc cttaaccact gctttactga aatacatgat   11640
gttcttgacc aaaacgggtt ttctgatgaa ggtacttatc atgagttaat tgaagctcta   11700 gattacatt tcataactga tgacatacat ctgacagggg agattttctc atttttcaga   11760
agtttcggcc accccagact tgaagcagta acggctgctg aaaatgttag gaaatacatg   11820
aatcagccta aagtcattgt gtatgagact ctgatgaaag gtcatgccat attttgtgga   11880
atcataatca acggctatcg tgacaggcac ggaggcagtt ggccaccgct gaccctcccc   11940
ctgcatgctg cagacacaat ccggaatgct caagcttcag gtgaagggtt aacacatgag   12000
cagtgcgttg ataactggaa atcttttgct ggagtgaaat ttggctgctt tatgcctctt   12060
agcctggata gtgatctgac aatgtaccta aaggacaagg cacttgctgc tctccaaagg   12120
gaatgggatt cagtttaccc gaaagagttc ctgcgttacg accctcccaa gggaaccggg   12180
tcacggaggc ttgtagatgt tttccttaat gattcgagct ttgacccata tgatgtgata   12240
atgtatgttg taagtggagc ttacctccat gaccctgagt tcaacctgtc ttacagcctg   12300
aaagaaaagg agatcaagga aacaggtaga cttttttgcta aaatgactta caaaatgagg   12360
gcatgccaag tgattgctga aaatctaatc tcaaacggga ttggcaaata ttttaaggac   12420
aatgggatgg ccaaggatga gcacgatttg actaaggcac tccacactct agctgtctca   12480
ggagtcccca aagatctcaa agaaagtcac aggggggggc cagtcttaaa aacctactcc   12540
cgaagcccag tccacacaag taccaggaac gtgagagcag caaaagggtt tatagggttc   12600
cctcaagtaa ttcggcagga ccaagacact gatcatccgg agaatatgga agcttacgag   12660
acagtcagtg catttatcac gactgatctc aagaagtact gccttaattg gagatatgag   12720
accatcagct tgtttgcaca gaggctaaat gagatttacg gattgccctc attttttcag   12780
```

```
tggctgcata agaggcttga gacctctgtc ctgtatgtaa gtgaccctca ttgccccccc   12840
gaccttgacg cccatatccc gttatataaa gtccccaatg atcaaatctt cattaagtac   12900
cctatgggag gtatagaagg gtattgtcag aagctgtgga ccatcagcac cattccctat   12960
ctatacctgg ctgcttatga gagcggagta aggattgctt cgttagtgca aggggacaat   13020
cagaccatag ccgtaacaaa aagggtaccc agcacatggc cctacaacct taagaaacgg   13080
gaagctgcta gagtaactag agattacttt gtaattctta ggcaaaggct acatgatatt   13140
ggccatcacc tcaaggcaaa tgagacaatt gtttcatcac attttttttgt ctattcaaaa   13200 ggaatatatt atgatgggct acttgtgtcc caatcactca agagcatcgc aagatgtgta   13260
ttctggtcag agactatagt tgatgaaaca agggcagcat gcagtaatat tgctacaaca   13320
atggctaaaa gcatcgagag aggttatgac cgttaccttg catattccct gaacgtccta   13380
aaagtgatac agcaaattct gatctctctt ggcttcacaa tcaattcaac catgacccgg   13440
gatgtagtca tacccctcct cacaaacaac gacctcttaa taaggatggc actgttgccc   13500
gctcctattg gggggatgaa ttatctgaat atgagcaggc tgtttgtcag aaacatcggt   13560
gatccagtaa catcatcaat tgctgatctc aagagaatga ttctcgcctc actaatgcct   13620
gaagagaccc tccatcaagt aatgacacaa caaccggggg actcttcatt cctagactgg   13680
gctagcgacc cttactcagc aaatcttgta tgtgtccaga gcatcactag actcctcaag   13740
aacataactg caaggtttgt cctgatccat agtccaaacc caatgttaaa aggattattc   13800
catgatgaca gtaaagaaga ggacgaggga ctggcggcat tcctcatgga caggcatatt   13860
atagtaccta gggcagctca tgaaatcctg gatcatagtg tcacaggggc aagagagtct   13920
attgcaggca tgctggatac cacaaaaggc ttgattcgag ccagcatgag gaagggggg   13980 ttaacctctc gagtgataac cagattgtcc aattatgact atgaacaatt cagagcaggg   14040
atggtgctat tgacaggaag aaagagaaat gtcctcattg acaaagagtc atgttcagtg   14100
cagctggcga gagctctaag aagccatatg tgggcgaggc tagctcgagg acggcctatt   14160
tacggccttg aggtccctga tgtactagaa tctatgcgag gccaccttat tcggcgtcat   14220
gagacatgtg tcatctgcga gtgtggatca gtcaactacg gatggttttt tgtcccctcg   14280
ggttgccaac tggatgatat tgacaaggaa acatcatcct tgagagtccc atatattggt   14340
tctaccactg atgagagaac agacatgaag cttgccttcg taagagcccc aagtcgatcc   14400
ttgcgatctg ctgttagaat agcaacagtg tactcatggg cttacggtga tgatgatagc   14460
tcttggaacg aagcctggtt gttggctagg caaagggcca atgtgagcct ggaggagcta   14520
agggtgatca ctcccatctc aacttcgact aatttagcgc ataggttgag ggatcgtagc   14580
actcaagtga aatactcagg tacatccctt gtccgagtgg cgaggtatac cacaatctcc   14640
aacgacaatc tctcatttgt catatcagat aagaaggttg atactaactt tatataccaa   14700
caaggaatgc tcctagggtt gggtgttttta gaaacattgt ttcgactcga gaaagatacc   14760
ggatcatcta acacggtatt acatcttcac gtcgaaacag attgttgcgt gatcccgatg   14820
atagatcatc ccaggatacc cagctcccgc aagctagagc tgagggcaga gctatgtacc   14880
aacccattga tatatgataa tgcacccttta attgacagag atgcaacaag gctatacacc   14940
cagagccata ggaggcacct tgtggaattt gttacatggt ccacacccca actatatcac   15000
attttagcta agtccacagc actatctatg attgacctgg taacaaaatt tgagaaggac   15060
catatgaatg aaatttcagc tctcataggg gatgacgata tcaatagttt cataactgag   15120
```

```
tttctgctca tagagccaag attattcact atctacttgg gccagtgtgc ggccatcaat    15180
tgggcatttg atgtacatta tcatagacca tcagggaaat atcagatggg tgagctgttg    15240
tcatcgttcc tttctagaat gagcaaagga gtgtttaagg tgcttgtcaa tgctctaagc    15300
cacccaaaga tctacaagaa attctggcat tgtggtatta tagagcctat ccatggtcct    15360
tcacttgatg ctcaaaactt gcacacaact gtgtgcaaca tggtttacac atgctatatg    15420
acctacctcg acctgttgtt gaatgaagag ttagaagagt tcacatttct cttgtgtgaa    15480
agcgacgagg atgtagtacc ggacagattc gacaacatcc aggcaaaaca cttatgtgtt    15540
ctggcagatt tgtactgtca accagggacc tgcccaccaa ttcgaggtct aagaccggta    15600
gagaaatgtg cagttctaac cgaccatatc aaggcagagg ctatgttatc tccagcagga    15660
tcttcgtgga acataaatcc aattattgta gaccattact catgctctct gacttatctc    15720
cggcgaggat cgatcaaaca gataagattg agagttgatc caggattcat tttcgacgcc    15780
ctcgctgagg taaatgtcag tcagccaaag atcggcagca acaacatctc aaatatgagc    15840
atcaaggctt tcagaccccc acacgatgat gttgcaaaat tgctcaaaga tatcaacaca    15900
agcaagcaca atcttcccat ttcagggggc aatctcgcca attatgaaat ccatgctttc    15960
cgcagaatcg ggttgaactc atctgcttgc tacaaagctg ttgagatatc aacattaatt    16020
aggagatgcc ttgagccagg ggaggacggc ttgttcttgg gtgagggatc gggttctatg    16080
ttgatcactt ataaggagat acttaaacta acaagtgct tctataatag tggggttttcc    16140 gccaattcta gatctggtca aagggaatta gcaccctatc cctccgaagt tggccttgtc    16200
gaacacagaa tgggagtagg taatattgtc aaagtgctct ttaacgggag gcccgaagtc    16260
acgtgggtag gcagtgtaga ttgcttcaat ttcatagtta gtaatatccc tacctctagt    16320
gtggggttta tccattcaga tatagagacc ttgcctgaca aagatactat agagaagcta    16380
gaggaattgg cagccatctt atcgatggct ctgctcctgg gcaaaatagg atcaatactg    16440
gtgattaagc ttatgccttt cagcggggat ttgttcagg gatttataag ttatgtaggg    16500
tctcattata gagaagtgaa ccttgtatac cctagataca gcaacttcat atctactgaa    16560 tcttattttgg ttatgacaga tctcaaggct aaccggctaa tgaatcctga aaagattaag    16620
cagcagataa ttgaatcatc tgtgaggact tcacctggac ttataggtca catcctatcc    16680
attaagcaac taagctgcat acaagcaatt gtgggagacg cagttagtag aggtgatatc    16740
aatcctactc tgaaaaaact tacacctata gagcaggtgc tgatcaattg cgggttggca    16800
attaacggac ctaagctgtg caaagaattg atccaccatg atgttgcctc agggcaagat    16860
ggattgctta attctatact catcctctac agggagttgg caagattcaa agacaaccaa    16920
agaagtcaac aagggatgtt ccacgcttac cccgtattgg taagtagcag gcaacgagaa    16980
cttatatcta ggatcacccg caaattttgg gggcacattc ttctttactc cgggaacaga    17040
aagttgataa ataagtttat ccagaatctc aagtccggct atctgatact agacttacac    17100
cagaatatct tcgttaagaa tctatccaag tcagagaaac agattattat gacgggggt    17160 ttgaaacgtg agtgggtttt taaggtaaca gtcaaggaga ccaaagaatg gtataagtta    17220
gtcggataca gtgccctgat taaggactaa ttggttgaac tccggaaccc taatcctgcc    17280
ctaggtggtt aggcattatt tgcaatatat aaagaaaac tttgaaaata cgaagtttct    17340
attcccagct ttgtctggtg gccggcatgg tcccagcctc ctcgctgcg ccggctgggc    17400 aacattccga ggggaccgtc ccctcggtaa tggcgaatgg gacgcggccg atccggctgc    17460
taacaaagcc cgaaaggaag ctgagttggc tgctgccacc gctgagcaat aactagcata    17520
```

```
accccttggg gcctctaaac gggtcttgag gggttttttg ctgaaaggag gaactatatc   17580
cggatgcggc cgcaggtacc cagcttttgt tcccttagt gagggttaat ttcgagcttg    17640
gcgtaatcat ggtcatagct gtttcctgtg tgaaattgtt atccgctcac aattccacac    17700
aacatacgag ccggaagcat aaagtgtaaa gcctggggtg cctaatgagt gagctaactc    17760
acattaattg cgttgcgctc actgcccgct ttccagtcgg gaaacctgtc gtgccagctg    17820
cattaatgaa tcggccaacg cgcgggaga ggcggtttgc gtattgggcg ctcttccgct     17880
tcctcgctca ctgactcgct gcgctcggtc gttcggctgc ggcgagcggt atcagctcac    17940
tcaaaggcgg taatacggtt atccacagaa tcaggggata acgcaggaaa gaacatgtga    18000
gcaaaaggcc agcaaaaggc caggaaccgt aaaaaggccg cgttgctggc gtttttccat    18060
aggctccgcc cccctgacga gcatcacaaa aatcgacgct caagtcagag gtggcgaaac    18120
ccgacaggac tataaagata ccaggcgttt ccccctggaa gctccctcgt gcgctctcct    18180
gttccgaccc tgccgcttac cggatacctg tccgcctttc tcccttcggg aagcgtggcg    18240
ctttctcata gctcacgctg taggtatctc agttcggtgt aggtcgttcg ctccaagctg    18300
ggctgtgtgc acgaaccccc cgttcagccc gaccgctgcg ccttatccgg taactatcgt    18360
cttgagtcca acccggtaag acacgactta tcgccactgg cagcagccac tggtaacagg    18420
attagcagag cgaggtatgt aggcggtgct acagagttct tgaagtggtg cctaactac    18480 ggctacacta aaggacagt atttggtatc tgcgctctgc tgaagccagt taccttcgga    18540
aaaagagttg gtagctcttg atccggcaaa caaaccaccg ctggtagcgg tggtttttt    18600 gtttgcaagc agcagattac gcgcagaaaa aaaggatctc aagaagatcc tttgatcttt    18660
tctacggggt ctgacgctca gtggaacgaa aactcacgtt aagggatttt ggtcatgaga    18720
ttatcaaaaa ggatcttcac ctagatcctt ttaaattaaa aatgaagttt taaatcaatc    18780
taaagtatat atgagtaaac ttggtctgac agttaccaat gcttaatcag tgaggcacct    18840
atctcagcga tctgtctatt tcgttcatcc atagttgcct gactccccgt cgtgtagata    18900
actacgatac gggagggctt accatctggc cccagtgctg caatgatacc gcgagaccca    18960
cgctcaccgg ctccagattt atcagcaata aaccagccag ccggaagggc cgagcgcaga    19020
agtggtcctg caactttatc cgcctccatc cagtctatta attgttgccg ggaagctaga    19080
gtaagtagtt cgccagttaa tagtttgcgc aacgttgttg ccattgctac aggcatcgtg    19140
gtgtcacgct cgtcgtttgg tatggcttca ttcagctccg gttcccaacg atcaaggcga    19200
gttacatgat cccccatgtt gtgcaaaaaa gcggttagct ccttcggtcc tccgatcgtt    19260
gtcagaagta agttggccgc agtgttatca ctcatggtta tggcagcact gcataattct    19320
cttactgtca tgccatccgt aagatgcttt tctgtgactg gtgagtactc aaccaagtca    19380
ttctgagaat agtgtatgcg gcgaccgagt tgctcttgcc cggcgtcaat acgggataat    19440
accgcgccac atagcagaac tttaaaagtg ctcatcattg gaaaacgttc ttcggggcga    19500
aaactctcaa ggatcttacc gctgttgaga tccagttcga tgtaacccac tcgtgcaccc    19560
aactgatctt cagcatcttt tactttcacc agcgtttctg ggtgagcaaa aacaggaagg    19620
caaaatgccg caaaaaggg aataagggcg acacggaaat gttgaatact catactcttc    19680
ctttttcaat attattgaag catttatcag ggttattgtc tcatgagcgg atacatattt    19740
gaatgtattt agaaaaataa acaaataggg gttccgcgca catttccccg aaaagtgc     19798
```

<210> SEQ ID NO 3

<211> LENGTH: 5253
<212> TYPE: DNA
<213> ORGANISM: Artificial
<220> FEATURE:
<223> OTHER INFORMATION: This is artificially synthesized MSP1 d-190 3D7
      sequence ORF

<400> SEQUENCE: 3

```
atgaccgtcg cgcggccgag cgtgcccgcg gcgctgcccc tcctcgggga gctgccccgg      60
ctgctgctgc tggtgctgtt gtgcctgccg gccgtgtggg atccgtgac ccacgaatcc      120 tatcaggagc tggttaagaa actggaagct ttagaggacg ccgtattgac aggttactcc      180
ctattccaga aagaaaagat ggttttaaac gaagaagaaa ttaccacaaa gggagcatcc      240
gcccagtctg gagcatctgc tcagagcgga gcatctgctc agagtggagc aagcgcccaa      300
agtggagcgt ctgcccagtc aggcgcctca gctcaatctg gaacctctgg gccgagtggt      360
cctagcggta cttctccaag tagccggtct aatacactcc cacgttccaa cacctccagt      420
ggagcctccc cacccgccga cgcatccgac tcagacgcta gagttatgc agacctgaag      480 caccgcgtga ggaactacct tttcactatc aaagagttga agtaccctga attgttcgat      540
ttgaccaacc atatgctgac actctgtgac aacatacatg gtttcaagta tctgatagat      600
gggtatgaag aaattaacga gctgctctat aaactcaact tttacttcga cctgctgcgt      660
gccaagctga cgatgtctg tgcaaacgat tactgccaga tcccattcaa cctaaagata      720
cgtgcgaacg agctggatgt tctgaagaaa ctcgtgttcg ggtatcggaa acccttggac      780
aacattaagg acaatgtggg gaagatggag gattacatta gaaaaaataa acaacaatc      840 gctaacataa atgagcttat cgagggagc aaaaagacca tcgaccagaa caagaatgcc      900
gacaatgaag agggaaaaaa gaaactatac caagcccagt atgatttgag catctacaat      960
aagcaactag aggaagctca aacctcatc agcgtactgg aaaagagaat tgacaccctg      1020
aaaaagaatg aaaacattaa gaactcctg acaagatta cgaaattaa aaacccacct      1080 ccagcgaata gcgaaatac cccgaatacc ctgctggata gaacaaaaa gattgaagag      1140 cacgaagaga aaatcaagga aatcgccaag actattaagt tcaatataga ttctctgttc      1200
acagaccctc tggagctgga atactacctg cgcgagaaga taagaaggt cgacgtgacc      1260 ccaaagagcc aagacccaac aaagtccgtg cagatccca agtgccccta cccaaacggc      1320
atcgtgtatc ccctgcctct taccgacatc acaactctc tggcagccga taacgacaaa      1380
aacagctatg agacctgat gaaccccac actaaggaaa agataaacga aagatcatt      1440 accgataata aggagcggaa gatttttatc aacaacatca gaagaaaat cgacctggaa      1500 gagaaaaata tcaatcacac caaagagcaa aacaagaaat tactggagga ctatgagaag      1560
agcaaaaagg attatgagga actgttagag aagttctatg aaatgaaatt caacaacaat      1620
ttcgataagg atgtggtcga taaaatttc agcgcccggt acacctacaa cgtggagaag      1680
cagcggtaca caataagtt cagcagctcc aataactcgg tctacaatgt gcagaagctg      1740
aagaaagctc tgagctatct ggaagactac tcgctgagga agggattttc tgagaaggat      1800
ttcaaccact actacaccct caaaaccggc ctggaagctg acatcaagaa actcactgaa      1860
gagatcaaaa gttctgagaa taagatactg agaagaact tcagggact aacgcactct      1920 gcaaacggct ccctggaagt ctctgacatc gtgaaactgc aagtccaaaa ggtgctgctc      1980
atcaaaaaaa tcgaggatct gcgaaagatc gagctgtttc ttaagaacgc ccaactgaaa      2040
gactcaatcc acgtgcctaa catttacaaa ccgcagaaca accagaaacc atactatctg      2100
```

```
atcgtgctga agaaggaggt ggataagctg aaggaattca tcccaaaagt gaaagatatg    2160
ttaaagaaag agcaagccgt gctgagcagc ataacgcagc ctctggtggc cgcaagcgag    2220
acaaccgaag atggcgggca cagcacccac accctgtctc agtctggcga aacagaggtg    2280
acagaagaga cagaagagac cgaagaaaca gtggggcaca ccactactgt gaccatcact    2340
ttgcccccta cgcagccatc tcccccaaaa gaggtcaaag tcgtggaaaa ctccattgaa    2400
cagaagtcca acgacaactc acaggctctg acgaagaccg tctatctgaa gaaactggac    2460
gagttcctga ccaaaagcta catctgccat aaatacatcc tcgtgtctaa cagcagcatg    2520
gatcagaagc tgttggaggt gtacaaccta acgcccgaag aagagaacga gttaaaatcc    2580
tgtgatccct tagacctact gtttaacatt cagaacaaca tccccgctat gtacagctta    2640
tatgattcca tgaataacga cctccagcac ctgttcttcg agctgtacca gaaagagatg    2700
atctactatc tgcataagct gaaagaggag aatcacatca aaaagttgct ggaagagcag    2760
aaacagataa ctgggacgtc cagcacatcg tcacctggca acgacagt aaataccgcc    2820 cagtctgcta cacactccaa ctcccagaac cagcagagca acgcttctag caccaacacc    2880
cagaatgggg tagcagttag tagcggcccct gctgtggtgg aggaatcgca tgacccctc    2940 actgtattat ctatttcaaa cgacctaaaa gggattgtgt ccctcctcaa tttaggtaat    3000
aagaccaagg tccctaaccc cttgactatc agcactacgg aaatggagaa gttttatgaa    3060
aacatcctga gaacaacga cacctatttt aacgacgaca taaagcagtt cgtgaagagt    3120
aacagtaaag tgattaccgg gctgacagaa acccagaaaa atgctttaaa tgatgagatc    3180
aagaaactga agacacact ccagctctcc ttcgatctgt acaacaagta caaactaaag    3240
ctggacagat tattcaataa gaagaaggag cttgggcaag ataagatgca gattaagaag    3300
ctaactttac tgaaggagca gctcgagagc aagctcaact ccctgaataa tccacataat    3360
gtgctccaga acttttccgt attcttcaat aagaagaaag aagcagagat tgccgagacg    3420
gaaaataccc tcgaaaacac taagatatta ctgaaacact ataaagggct ggtgaagtat    3480
tacaacggag agtctagccc attgaagact cttttcagaag tgtcaattca aaccgaggat    3540
aactacgcaa acctagaaaa gttcagagtg ctgagcaaaa tcgacggcaa actcaatgat    3600
aacctacacc tcggaaaaaa aaagctgagc ttcctgtcca gtggacttca tcatttaatt    3660
accgaattga agaagttat caaaaacaaa aactacactg gaacagccc atctgaaaat    3720 aataaaaagg tcaacgaggc cctcaagtct tatgaaaatt tccttccaga agcaaaagtg    3780
acaaccgtcg tgaccccccc ccagcccgat gtcaccccca gccctctaag cgtgagagtg    3840
tctggatcaa gtggctccac aaaagaagaa acccagatcc ccacatcagg atctctactg    3900
accgagttgc agcaggtcgt ccaactccag aattatgacg aggaagacga cagcctcgtg    3960
gttttgccaa tcttcggcga atcagaagac aacgacgagt acctagacca agtggtcacc    4020
ggggaagcga ttagtgtcac tatggacaat atcctcagcg gcttcgagaa cgagtatgac    4080
gtgatctacc tcaaaccact agccggagtt tacagaagtc tcaagaagca gatcgaaaag    4140
aacatcttca cctttaatct aaacctaaac gacatcttga attcccggct gaaaaagcgg    4200
aaatacttcc tcgacgtact ggagtcggat ttgatgcagt ttaagcacat ctccagcaac    4260
gaatacatta tcgaggactc gttcaaactg ttaaactccg agcagaagaa cacctgctg    4320 aagtcctaca atatatcaa agagtcagtc gagaacgata ttaaattcgc ccaagaaggc    4380
ataagctact acgaaaaggt cctcgccaaa tacaaggacg atctggagtc tatcaaaaag    4440
gtcatcaaag aagagaaaga gaaatttccc agttctcccc ctacaacgcc gccctctcca    4500
```

```
gccaagactg atgaacagaa aaaagagtct aagttcctcc ctttcctcac taatatcgag    4560
actctctaca ataacctagt gaacaagatt gacgactacc tgatcaacct taaagccaag    4620
ataaacgact gcaatgtcga aaggatgag gctcatgtta agatcaccaa actgtccgat    4680
ctgaaagcca tcgacgacaa gatcgactta tttaaaaacc catacgattt cgaggctatc    4740
aaaaagctga tcaatgatga caccaagaaa gatatgctcg gcaagctgct gagcacgggt    4800
ctggtgcaga acttccctaa caccatcata tcaaagctca tagagggcaa gttccaagac    4860
atgctgaata tttcacagca tcagtgcgtc aagaagcagt gccccgaaaa ttctggatgc    4920
ttccggcacc tggatgagcg agaagagtgc aagtgcctgc ttaactataa acaggagggc    4980
gacaaatgtg tggagaaccc aaatccgacg tgcaacgaga caacggtgg ctgcgatgcc    5040 gacgcgactt gtacagagga agactcgggg agttctcgga aaaaaatcac gtgcgagtgc    5100
accaaacccg acagttatcc tctgttcgat gggatattct gctcctccag caacgttact    5160
acttccggca ctaccgtct tctatctggt cacacgtgtt tcacgttgac aggtttgctt    5220
gggacgctag taaccatggg cttgctgact taa                                5253
```

```
<210> SEQ ID NO 4
<211> LENGTH: 5160
<212> TYPE: DNA
<213> ORGANISM: Artificial
<220> FEATURE:
<223> OTHER INFORMATION: This is artificially synthesized MSP1 d-190*
      3D7sequence ORF

<400> SEQUENCE: 4
```

```
atgaccgtcg cgcggccgag cgtgcccgcg gcgctgcccc tcctcgggga gctgccccgg     60
ctgctgctgc tggtgctgtt gtgcctgccg gccgtgtggg gatccgtgac ccacgaatcc    120
tatcaggagc tggttaagaa actggaagct ttagaggacg ccgtattgac aggttactcc    180
ctattccaga agaaaagat ggttttaaac gaagaagaaa ttaccacaaa gggagcatcc    240
gcccagtctg gagcatctgc tcagagcgga gcatctgctc agagtggagc aagcgcccaa    300
agtggagcgt ctgcccagtc aggcgcctca gctcaatctg gaacctctgg gccgagtggt    360
cctagcggta cttctccaag tagccggtct aatacactcc cacgttccaa cacctccagt    420
ggagcctccc caccgccga cgcatccgac tcagacgcta agagttatgc agacctgaag    480
caccgcgtga ggaactacct tttcactatc aaagagttga agtaccctga attgttcgat    540
ttgaccaacc atatgctgac actctgtgac aacatacatg gttcaagta tctgatagat    600 gggtatgaag aaattaacga gctgctctat aaactcaact tttacttcga cctgctgcgt    660
gccaagctga cgatgtctg tgcaaacgat tactgccaga tcccattcaa cctaaagata    720
cgtgcgaacg agctggatgt tctgaagaaa ctcgtgttcg ggtatcggaa acccttggac    780
aacattaagg acaatgtggg gaagatggag gattacatta agaaaaataa acaacaatc    840 gctaacataa atgagcttat cgaggggagc aaaaagacca tcgaccagaa caagaatgcc    900
gacaatgaag agggaaaaaa gaaactatac caagcccagt atgatttgag catctacaat    960
aagcaactag aggaagctca acctcatc agcgtactgg aaaagagaat tgacaccctg   1020
aaaaagaatg aaaacattaa gaaactcctg gacaagatta cgaaattaa aaacccacct   1080 ccagcgaata gcgaaatac cccgaatacc ctgctggata agaacaaaaa gattgaagag   1140
cacgaagaga aaatcaagga aatcgccaag actattaagt caatatagaa ttctctgttc   1200
acagaccctc tggagctgga atactacctg cgcgagaaga ataagaaggt cgacgtgacc   1260
```

```
ccaaagagcc aagacccaac aaagtccgtg cagatcccca agtgcccta cccaaacggc    1320
atcgtgtatc ccctgcctct taccgacatc cacaactctc tggcagccga taacgacaaa    1380
aacagctatg gagacctgat gaaccccac actaaggaaa agataaacga gaagatcatt    1440
accgataata aggagcggaa gattttatc aacaacatca agaagaaaat cgacctggaa    1500
gagaaaaata tcaatcacac caaagagcaa aacaagaaat tactggagga ctatgagaag    1560
agcaaaaagg attatgagga actgttagag aagttctatg aaatgaaatt caacaacaat    1620
ttcgataagg atgtggtcga taaaattttc agcgcccggt acacctacaa cgtggagaag    1680
cagcggtaca caataagtt cagcagctcc aataactcgg tctacaatgt gcagaagctg    1740
aagaaagctc tgagctatct ggaagactac tcgctgagga agggatttc tgagaaggat    1800
ttcaaccact actacaccct caaaaccggc ctggaagctg acatcaagaa actcactgaa    1860
gagatcaaaa gttctgagaa taagatactg gagaagaact tcaagggact aacgcactct    1920
gcaaacggct ccctggaagt ctctgacatc gtgaaactgc aagtccaaaa ggtgctgctc    1980
atcaaaaaaa tcgaggatct gcgaaagatc gagctgtttc ttaagaacgc ccaactgaaa    2040
gactcaatcc acgtgcctaa catttacaaa ccgcagaaca aaccagaacc atactatctg    2100
atcgtgctga agaaggaggt ggataagctg aaggaattca tcccaaaagt gaaagatatg    2160
ttaaagaaag agcaagccgt gctgagcagc ataacgcagc ctctggtggc cgcaagcgag    2220
acaaccgaag atggcgggca cagcacccac accctgtctc agtctggcga acagaggtg    2280
acagaagaga cagaagagac cgaagaaaca gtggggcaca ccactactgt gaccatcact    2340
ttgcccccta cgcagccatc tcccccaaaa gaggtcaaag tcgtggaaaa ctccattgaa    2400
cagaagtcca cgacaactc acaggctctg acgaagaccg tctatctgaa gaaactggac    2460
gagttcctga ccaaaagcta catctgccat aaatacatcc tcgtgtctaa cagcagcatg    2520
gatcagaagc tgttggaggt gtacaaccta acgcccgaag aagagaacga gttaaaatcc    2580
tgtgatccct tagacctact gtttaacatt cagaacaaca tccccgctat gtacagctta    2640
tatgattcca tgaataacga cctccagcac ctgttcttcg agctgtacca gaaagagatg    2700
atctactatc tgcataagct gaaagaggag aatcacatca aaaagttgct ggaagagcag    2760
aaacagataa ctgggacgtc cagcacatcg tcacctggca acacgacagt aaataccgcc    2820
cagtctgcta cacactccaa ctcccagaac cagcagagca acgcttctag caccaacacc    2880
cagaatgggg tagcagttag tagcggcccct gctgtggtgg aggaatcgca tgaccccctc    2940
actgtattat ctatttcaaa cgacctaaaa gggattgtgt ccctcctcaa tttaggtaat    3000
aagaccaagg tccctaaccc cttgactatc agcactacgg aaatggagaa gttttatgaa    3060
aacatcctga gaacaacga cacctatttt aacgacgaca taaagcagtt cgtgaagagt    3120
aacagtaaag tgattaccgg gctgacagaa acccagaaaa atgctttaaa tgatgagatc    3180
aagaaactga aagacacact ccagctctcc ttcgatctgt acaacaagta caaactaaag    3240
ctggacagat tattcaataa gaagaaggag cttgggcaag ataagatgca gattaagaag    3300
ctaactttac tgaaggagca gctcgagagc aagctcaact ccctgaataa tccacataat    3360
gtgctccaga acttttccgt attcttcaat aagaagaaag aagcagagat tgccgagacg    3420
gaaaataccc tcgaaaacac taagatatta ctgaaacact ataaagggct ggtgaagtat    3480
tacaacggag agtctagccc attgaagact ctttcgaaag tgtcaattca aaccgaggat    3540
aactacgcaa acctagaaaa gttcagagtg ctgagcaaaa tcgacggcaa actcaatgat    3600
```

| | |
|---|---|
| aacctacacc tcggaaaaaa aaagctgagc ttcctgtcca gtggacttca tcatttaatt | 3660 |
| accgaattga aagaagttat caaaaacaaa aactacactg ggaacagccc atctgaaaat | 3720 |
| aataaaaagg tcaacgaggc cctcaagtct tatgaaaatt tccttccaga agcaaaagtg | 3780 |
| acaaccgtcg tgaccccccc ccagcccgat gtcacccccca gccctctaag cgtgagagtg | 3840 |
| tctggatcaa gtggctccac aaaagaagaa acccagatcc ccacatcagg atctctactg | 3900 |
| accgagttgc agcaggtcgt ccaactccag aattatgacg aggaagacga cagcctcgtg | 3960 |
| gttttgccaa tcttcggcga atcagaagac aacgacgagt acctagacca agtggtcacc | 4020 |
| ggggaagcga ttagtgtcac tatggacaat atcctcagcg gcttcgagaa cgagtatgac | 4080 |
| gtgatctacc tcaaaccact agccggagtt tacagaagtc tcaagaagca gatcgaaaag | 4140 |
| aacatcttca cctttaatct aaacctaaac gacatcttga attcccggct gaaaaagcgg | 4200 |
| aaatacttcc tcgacgtact ggagtcggat ttgatgcagt ttaagcacat ctccagcaac | 4260 |
| gaatacatta tcgaggactc gttcaaactg ttaaactccg agcagaagaa caccctgctg | 4320 |
| aagtcctaca atatatcaa agagtcagtc gagaacgata ttaaattcgc caagaaggc | 4380 |
| ataagctact acgaaaaggt cctcgccaaa tacaaggacg atctggagtc tatcaaaaag | 4440 |
| gtcatcaaag aagagaaaga gaaatttccc agttctcccc ctacaacgcc gccctctcca | 4500 |
| gccaagactg atgaacagaa aaaagagtct aagttcctcc ctttcctcac taatatcgag | 4560 |
| actctctaca ataacctagt gaacaagatt gacgactacc tgatcaacct aaagccaag | 4620 |
| ataaacgact gcaatgtcga aaggatgag gctcatgtta agatcaccaa actgtccgat | 4680 |
| ctgaaagcca tcgacgacaa gatcgactta tttaaaaacc catacgattt cgaggctatc | 4740 |
| aaaaagctga tcaatgatga caccaagaaa gatatgctcg gcaagctgct gagcacgggt | 4800 |
| ctggtgcaga acttccctaa caccatcata tcaaagctca tagagggcaa gttccaagac | 4860 |
| atgctgaata tttcacagca tcagtgcgtc aagaagcagt gccccgaaaa ttctggatgc | 4920 |
| ttccggcacc tggatgagcg agaagagtgc aagtgcctgc ttaactataa acaggagggc | 4980 |
| gacaaatgtg tggagaaccc aaatccgacg tgcaacgaga caacggtgg ctgcgatgcc | 5040 |
| gacgcgactt gtacagagga agactcgggg agttctcgga aaaaaatcac gtgcgagtgc | 5100 |
| accaaacccg acagttatcc tctgttcgat gggatattct gctcctccag caacgtttag | 5160 |

<210> SEQ ID NO 5
<211> LENGTH: 4122
<212> TYPE: DNA
<213> ORGANISM: Artificial
<220> FEATURE:
<223> OTHER INFORMATION: This is artificially synthesized MSP1
    d-83-30-38 3D7 sequence ORF

<400> SEQUENCE: 5

| | |
|---|---|
| atgaccgtcg cgcggccgag cgtgcccgcg gcgctgcccc tcctcgggga gctgccccgg | 60 |
| ctgctgctgc tggtgctgtt gtgcctgccg gccgtgtggg gatccgtgac ccacgaatcc | 120 |
| tatcaggagc tggttaagaa actggaagct ttagaggacg ccgtattgac aggttactcc | 180 |
| ctattccaga aagaaaagat ggttttaaac gaagaagaaa ttaccacaaa gggagcatcc | 240 |
| gcccagtctg agcatctgc tcagagcgga gcatctgctc agagtggagc aagcgcccaa | 300 |
| agtggagcgt ctgcccagtc aggcgcctca gctcaatctg gaacctctgg gccgagtggt | 360 |
| cctagcggta cttctccaag tagccggtct aatacactcc cacgttccaa cacctccagt | 420 |
| ggagcctccc cacccgccga cgcatccgac tcagacgcta gagttatgc agacctgaag | 480 |

```
caccgcgtga ggaactacct tttcactatc aaagagttga agtaccctga attgttcgat    540
ttgaccaacc atatgctgac actctgtgac aacatacatg gtttcaagta tctgatagat    600
gggtatgaag aaattaacga gctgctctat aaactcaact tttacttcga cctgctgcgt    660
gccaagctga acgatgtctg tgcaaacgat tactgccaga tcccattcaa cctaaagata    720
cgtgcgaacg agctggatgt tctgaagaaa ctcgtgttcg ggtatcggaa acccttggac    780
aacattaagg acaatgtggg gaagatggag gattacatta agaaaaataa acaacaatc     840
gctaacataa atgagcttat cgaggggagc aaaaagacca tcgaccagaa caagaatgcc    900
gacaatgaag agggaaaaaa gaaactatac caagcccagt atgatttgag catctacaat    960
aagcaactag aggaagctca aacctcatcg agcgtactgg aaaagagaat tgacaccctg   1020
aaaaagaatg aaaacattaa gaaactcctg gacaagatta cgaaattaa aaacccacct    1080
ccagcgaata gcggaaatac cccgaatacc ctgctggata gaacaaaaa gattgaagag    1140
cacgaagaga aaatcaagga aatcgccaag actattaagt tcaatataga ttctctgttc   1200
acagaccctc tggagctgga atactacctg cgcgagaaga ataagaaggt cgacgtgacc   1260
ccaaagagcc aagacccaac aaagtccgtg cagatcccca agtgcccta cccaaacggc   1320
atcgtgtatc ccctgcctct taccgacatc cacaactctc tggcagccga taacgacaaa   1380
aacagctatg agacctgat gaaccccac actaaggaaa agataaacga gaagatcatt    1440
accgataata aggagcggaa gatttttatc aacaacatca gaagaaaat cgacctggaa    1500
gagaaaaata tcaatcacac caaagagcaa aacaagaaat tactggagga ctatgagaag   1560
agcaaaaagg attatgagga actgttagag aagttctatg aaatgaaatt caacaacaat   1620
ttcgataagg atgtggtcga taaaattttc agcgcccggt acacctacaa cgtggagaag   1680
cagcggtaca caataagtt cagcagctcc aataactcgg tctacaatgt gcagaagctg   1740
aagaaagctc tgagctatct ggaagactac tcgctgagga aagggatttc tgagaaggat   1800
ttcaaccact actacaccct caaaaccggc ctggaagctg acatcaagaa actcactgaa   1860
gagatcaaaa gttctgagaa taagatactg gagaagaact tcaagggact aacgcactct   1920
gcaaacggct ccctggaagt ctctgacatc gtgaaactgc aagtccaaaa ggtgctgctc   1980
atcaaaaaaa tcgaggatct gcgaaagatc gagctgtttc ttaagaacgc ccaactgaaa   2040
gactcaatcc acgtgcctaa catttacaaa ccgcagaaca accagaaacc atactatctg   2100
atcgtgctga agaaggaggt ggataagctg aaggaattca tcccaaaagt gaaagatatg   2160
ttaaagaaag agcaagccgt gctgagcagc ataacgcagc ctctggtggc cgcaagcgag   2220
acaaccgaag atggcgggca cagcacccac accctgtctc agtctggcga aacagaggtg   2280
acagaagaga cagaagagac cgaagaaaca gtggggcaca ccactactgt gaccatcact   2340
ttgcccccta cgcagccatc tccccaaaa gaggtcaaag tcgtggaaaa ctccattgaa   2400
cagaagtcca acgacaactc acaggctctg acgaagaccg tctatctgaa gaaactggac   2460
gagttcctga ccaaaagcta catctgccat aaatacatcc tcgtgtctaa cagcagcatg   2520
gatcagaagc tgttggaggt gtacaaccta acgcccgaag aagagaacga gttaaaatcc   2580
tgtgatccct tagacctact gtttaacatt cagaacaaca tccccgctat gtacagctta   2640
tatgattcca tgaataacga cctccagcac ctgttcttcg agctgtacca gaaagagatg   2700
atctactatc tgcataagct gaaagaggag aatcacatca aaagttgct ggaagagcag   2760
aaacagataa ctgggacgtc cagcacatcg tcacctggca acacgacagt aaataccgcc   2820
cagtctgcta cacactccaa ctcccagaac cagcagagca acgcttctag caccaacacc   2880
```

```
cagaatgggg tagcagttag tagcggccct gctgtggtgg aggaatcgca tgacccctc    2940 actgtattat ctatttcaaa cgacctaaaa gggattgtgt ccctcctcaa tttaggtaat   3000
aagaccaagg tccctaaccc cttgactatc agcactacgg aaatggagaa gttttatgaa   3060
aacatcctga agaacaacga cacctatttt aacgacgaca taaagcagtt cgtgaagagt   3120
aacagtaaag tgattaccgg gctgacagaa acccagaaaa atgctttaaa tgatgagatc   3180
aagaaactga agacacact ccagctctcc ttcgatctgt acaacaagta caaactaaag    3240
ctggacagat tattcaataa gaagaaggag cttgggcaag ataagatgca gattaagaag   3300
ctaactttac tgaaggagca gctcgagagc aagctcaact ccctgaataa tccacataat   3360
gtgctccaga acttttccgt attcttcaat aagaagaaag aagcagagat tgccgagacg   3420
gaaaataccc tcgaaaacac taagatatta ctgaaacact ataaagggct ggtgaagtat   3480
tacaacggag agtctagccc attgaagact ctttcagaag tgtcaattca aaccgaggat   3540
aactacgcaa acctagaaaa gttcagagtg ctgagcaaaa tcgacggcaa actcaatgat   3600
aacctacacc tcggaaaaaa aaagctgagc ttcctgtcca gtggacttca tcatttaatt   3660
accgaattga aagaagttat caaaaacaaa aactacactg gaacagccc atctgaaaat    3720 aataaaaagg tcaacgaggc cctcaagtct tatgaaaatt tccttccaga agcaaaagtg   3780
acaaccgtcg tgacccccc ccagcccgat gtcaccccca gccctctaag cgtgagagtg    3840
tctggatcaa gtggctccac aaaagaagaa acccagatcc ccacatcagg atctctactg   3900
accgagttgc agcaggtcgt ccaactccag aattatgacg aggaagacga cagcctcgtg   3960
gttttgccaa tcttcggcga atcagaagac aacgacgagt acctagacca agtggtcacc   4020
aacgttacta cttccggcac tacccgtctt ctatctggtc acacgtgttt cacgttgaca   4080
ggtttgcttg ggacgctagt aaccatgggc ttgctgactt aa                      4122
```

<210> SEQ ID NO 6
<211> LENGTH: 4029
<212> TYPE: DNA
<213> ORGANISM: Artificial
<220> FEATURE:
<223> OTHER INFORMATION: This is artificially synthesized MSP1
      d-83-30-38* 3D7 sequence ORF

<400> SEQUENCE: 6

```
atgaccgtcg cgcggccgag cgtgcccgcg gcgctgcccc tcctcgggga gctgccccgg   60
ctgctgctgc tggtgctgtt gtgcctgccg gccgtgtggg gatccgtgac ccacgaatcc   120
tatcaggagc tggttaagaa actggaagct ttagaggacg ccgtattgac aggttactcc   180
ctattccaga aagaaaagat ggttttaaac gaagaagaaa ttaccacaaa gggagcatcc   240
gcccagtctg gagcatctgc tcagagcgga gcatctgctc agagtggagc aagcgcccaa   300
agtggagcgt ctgcccagtc aggcgcctca gctcaatctg gaacctctgg gccgagtggt   360
cctagcggta cttctccaag tagccggtct aatacactcc acgttccaa cacctccagt    420 ggagcctccc cacccgccga cgcatccgac tcagacgcta gagttatgc agacctgaag    480 caccgcgtga gaactacct tttcactatc aaagagttga agtaccctga attgttcgat    540
ttgaccaacc atatgctgac actctgtgac aacatacatg gtttcaagta tctgatagat   600
gggtatgaag aaattaacga gctgctctat aaactcaact tttacttcga cctgctgcgt   660
gccaagctga cgatgtctg tgcaaacgat tactgccaga tcccattcaa cctaaagata    720
cgtgcgaacg agctggatgt tctgaagaaa ctcgtgttcg ggtatcggaa acccttggac   780
```

```
aacattaagg acaatgtggg aagatggag gattacatta agaaaaataa aacaacaatc    840
gctaacataa atgagcttat cgagggagc aaaaagacca tcgaccagaa caagaatgcc    900
gacaatgaag agggaaaaaa gaaactatac caagcccagt atgatttgag catctacaat    960
aagcaactag aggaagctca caacctcatc agcgtactgg aaaagagaat tgacaccctg   1020
aaaaagaatg aaaacattaa gaaactcctg gacaagatta cgaaattaa aaacccacct   1080 ccagcgaata gcgaaatac cccgaatacc ctgctggata agaacaaaaa gattgaagag   1140
cacgaagaga aaatcaagga aatcgccaag actattaagt tcaatataga ttctctgttc   1200
acagaccctc tggagctgga atactacctg cgcgagaaga ataagaaggt cgacgtgacc   1260
ccaaagagcc aagacccaac aaagtccgtg cagatcccca aagtgcccta cccaaacggc   1320
atcgtgtatc ccctgcctct taccgacatc cacaactctc tggcagccga taacgacaaa   1380
aacagctatg agacctgat gaaccccac actaaggaaa agataaacga gaagatcatt    1440
accgataata aggagcggaa gattttatc aacaacatca gaagaaaat cgacctggaa    1500 gagaaaaata tcaatcacac caaagagcaa aacaagaaat tactggagga ctatgagaag   1560
agcaaaaagg attatgagga actgttagag aagttctatg aaatgaaatt caacaacaat   1620
ttcgataagg atgtggtcga taaaattttc agcgcccggt acacctacaa cgtggagaag   1680
cagcggtaca caataagtt cagcagctcc aataactcgg tctacaatgt gcagaagctg   1740
aagaaagctc tgagctatct ggaagactac tcgctgagga aagggatttc tgagaaggat   1800
ttcaaccact actacaccct caaaaccggc ctggaagctg acatcaagaa actcactgaa   1860
gagatcaaaa gttctgagaa taagatactg gagaagaact tcaagggact aacgcactct   1920
gcaaacggct ccctggaagt ctctgacatc gtgaaactgc aagtccaaaa ggtgctgctc   1980
atcaaaaaaa tcgaggatct gcgaaagatc gagctgtttc ttaagaacgc ccaactgaaa   2040
gactcaatcc acgtgcctaa catttacaaa ccgcagaaca aaccagaacc atactatctg   2100
atcgtgctga gaaggaggt ggataagctg aaggaattca tcccaaaagt gaaagatatg   2160
ttaaagaaag agcaagccgt gctgagcagc ataacgcagc ctctggtggc cgcaagcgag   2220
acaaccgaag atggcgggca cagcacccac accctgtctc agtctggcga acagaggtg   2280 acagaagaga cagaagagac cgaagaaaca gtggggcaca ccactactgt gaccatcact   2340 ttgccccta cgcagccatc tcccccaaaa gaggtcaaag tcgtggaaaa ctccattgaa   2400
cagaagtcca cgacaactc acaggctctg acgaagaccg tctatctgaa gaaactggac   2460
gagttcctga ccaaaagcta catctgccat aaatacatcc tcgtgtctaa cagcagcatg   2520
gatcagaagc tgttggaggt gtacaaccta acgcccgaag aagagaacga gttaaaatcc   2580
tgtgatccct tagacctact gtttaacatt cagaacaaca tccccgctat gtacagctta   2640
tatgattcca tgaataacga cctccagcac ctgttcttcg agctgtacca gaaagagatg   2700
atctactatc tgcataagct gaaagaggag aatcacatca aaagttgct ggaagagcag    2760 aaacagataa ctgggacgtc cagcacatcg tcacctggca cacgacagt aaataccgcc    2820 cagtctgcta cacactccaa ctcccagaac cagcagagca acgcttctag caccaacacc   2880
cagaatgggg tagcagttag tagcggccct gctgtggtgg aggaatcgca tgacccctc    2940 actgtattat ctatttcaaa cgacctaaaa gggattgtgt ccctcctcaa tttaggtaat   3000
aagaccaagg tccctaaccc cttgactatc agcactacgg aaatggagaa gttttatgaa   3060
aacatcctga agaacaacga cacctatttt aacgacgaca taaagcagtt cgtgaagagt   3120
```

| | |
|---|---|
| aacagtaaag tgattaccgg gctgacagaa acccagaaaa atgctttaaa tgatgagatc | 3180 |
| aagaaactga agacacact ccagctctcc ttcgatctgt acaacaagta caaactaaag | 3240 |
| ctggacagat tattcaataa gaagaaggag cttgggcaag ataagatgca gattaagaag | 3300 |
| ctaactttac tgaaggagca gctcgagagc aagctcaact ccctgaataa tccacataat | 3360 |
| gtgctccaga acttttccgt attcttcaat aagaagaaag aagcagagat tgccgagacg | 3420 |
| gaaaataccc tcgaaaacac taagatatta ctgaaacact ataaagggct ggtgaagtat | 3480 |
| tacaacggag agtctagccc attgaagact cttcagaag tgtcaattca aaccgaggat | 3540 |
| aactacgcaa acctagaaaa gttcagagtg ctgagcaaaa tcgacggcaa actcaatgat | 3600 |
| aacctacacc tcggaaaaaa aaagctgagc ttcctgtcca gtggacttca tcatttaatt | 3660 |
| accgaattga agaagttat caaaaacaaa aactacactg gaacagccc atctgaaaat | 3720 |
| aataaaaagg tcaacgaggc cctcaagtct tatgaaaatt tccttccaga agcaaaagtg | 3780 |
| acaaccgtcg tgacccccc ccagcccgat gtcaccccca gccctctaag cgtgagagtg | 3840 |
| tctggatcaa gtggctccac aaaagaagaa acccagatcc ccacatcagg atctctactg | 3900 |
| accgagttgc agcaggtcgt ccaactccag aattatgacg aggaagacga cagcctcgtg | 3960 |
| gttttgccaa tcttcggcga atcagaagac aacgacgagt acctagacca agtggtcacc | 4020 |
| ggggaataa | 4029 |

<210> SEQ ID NO 7
<211> LENGTH: 1347
<212> TYPE: DNA
<213> ORGANISM: Artificial
<220> FEATURE:
<223> OTHER INFORMATION: This is artificially synthesized MSP1 d-42 3D7 sequence ORF

<400> SEQUENCE: 7

| | |
|---|---|
| atgaccgtcg cgcggccgag cgtgcccgcg gcgctgcccc tcctcgggga gctgccccgg | 60 |
| ctgctgctgc tggtgctgtt gtgcctgccg gccgtgtggg gatccgtggt caccggggaa | 120 |
| gcgattagtg tcactatgga caatatcctc agcggcttcg agaacgagta tgacgtgatc | 180 |
| tacctcaaac cactagccgg agtttacaga agtctcaaga agcagatcga aaagaacatc | 240 |
| ttcacctta atctaaacct aaacgacatc ttgaattccc ggctgaaaaa gcggaaatac | 300 |
| ttcctcgacg tactggagtc ggatttgatg cagtttaagc acatctccag caacgaatac | 360 |
| attatcgagg actcgttcaa actgttaaac tccgagcaga agaacacccct gctgaagtcc | 420 |
| tacaaatata tcaaagagtc agtcgagaac gatattaaat cgcccaaga aggcataagc | 480 |
| tactacgaaa aggtcctcgc caaatacaag gacgatctgg agtctatcaa aaaggtcatc | 540 |
| aaagaagaga agagaaaatt tcccagttct cccctacaa cgccgccctc tccagccaag | 600 |
| actgatgaac agaaaaaaga gtctaagttc ctcccttttcc tcactaatat cgagactctc | 660 |
| tacaataacc tagtgaacaa gattgacgac tacctgatca accttaaagc caagataaac | 720 |
| gactgcaatg tcgagaagga tgaggctcat gttaagatca ccaaactgtc cgatctgaaa | 780 |
| gccatcgacg acaagatcga cttatttaaa aacccatacg atttcgaggc tatcaaaaag | 840 |
| ctgatcaatg atgacaccaa gaaagatatg ctcggcaagc tgctgagcac gggtctggtg | 900 |
| cagaacttcc ctaacaccat catatcaaag ctcatagagg gcaagttcca agacatgctg | 960 |
| aatatttcac agcatcagtg cgtcaagaag cagtgccccg aaaattctgg atgcttccgg | 1020 |
| cacctggatg agcgagaaga gtgcaagtgc ctgcttaact ataaacagga gggcgacaaa | 1080 |

```
tgtgtggaga acccaaatcc gacgtgcaac gagaacaacg gtggctgcga tgccgacgcg    1140
acttgtacag aggaagactc ggggagttct cggaaaaaaa tcacgtgcga gtgcaccaaa    1200
cccgacagtt atcctctgtt cgatgggata ttctgctcct ccagcaacgt tactacttcc    1260
ggcactaccc gtcttctatc tggtcacacg tgtttcacgt tgacaggttt gcttgggacg    1320
ctagtaacca tgggcttgct gacttaa                                        1347

<210> SEQ ID NO 8
<211> LENGTH: 1254
<212> TYPE: DNA
<213> ORGANISM: Artificial
<220> FEATURE:
<223> OTHER INFORMATION: This is artificially synthesized MSP1 d-42* 3D7
      sequence ORF

<400> SEQUENCE: 8
atgaccgtcg cgcggccgag cgtgcccgcg gcgctgcccc tcctcgggga gctgccccgg    60
ctgctgctgc tggtgctgtt gtgcctgccg gccgtgtggg gatccgtggt caccggggaa    120
gcgattagtg tcactatgga caatatcctc agcggcttcg agaacgagta tgacgtgatc    180
tacctcaaac cactagccgg agtttacaga agtctcaaga agcagatcga aaagaacatc    240 ttcacccttta atctaaacct aaacgacatc ttgaattccc ggctgaaaaa gcggaaatac    300
ttcctcgacg tactggagtc ggatttgatg cagtttaagc acatctccag caacgaatac    360
attatcgagg actcgttcaa actgttaaac tccgagcaga gaacaccct gctgaagtcc    420 tacaaatata tcaaagagtc agtcgagaac gatattaaat cgcccaaga aggcataagc    480 tactacgaaa aggtcctcgc caaatacaag gacgatctgg agtctatcaa aaaggtcatc    540
aaagaagaga aagagaaatt tcccagttct cccctacaa cgccgccctc tccagccaag    600
actgatgaac agaaaaaga gtctaagttc ctcccttcc tcactaatat cgagactctc    660
tacaataacc tagtgaacaa gattgacgac tacctgatca accttaaagc caagataaac    720
gactgcaatg tcgagaagga tgaggctcat gttaagatca ccaaactgtc cgatctgaaa    780
gccatcgacg acaagatcga cttatttaaa aacccatacg atttcgaggc tatcaaaaag    840
ctgatcaatg atgacaccaa gaaagatatg ctcggcaagc tgctgagcac gggtctggtg    900
cagaacttcc ctaacaccat catatcaaag ctcatagagg gcaagttcca agacatgctg    960
aatatttcac agcatcagtg cgtcaagaag cagtgccccg aaaattctgg atgcttccgg    1020
cacctggatg agcgagaaga gtgcaagtgc ctgcttaact ataaacagga gggcgacaaa    1080
tgtgtggaga acccaaatcc gacgtgcaac gagaacaacg gtggctgcga tgccgacgcg    1140
acttgtacag aggaagactc ggggagttct cggaaaaaaa tcacgtgcga gtgcaccaaa    1200
cccgacagtt atcctctgtt cgatgggata ttctgctcct ccagcaacgt ttag          1254

<210> SEQ ID NO 9
<211> LENGTH: 5013
<212> TYPE: DNA
<213> ORGANISM: Artificial
<220> FEATURE:
<223> OTHER INFORMATION: This is artificially synthesized MSP1 d-190
      FCB1 sequence ORF

<400> SEQUENCE: 9
atgaccgtcg cgcggccgag cgtgcccgcg gcgctgcccc tcctcgggga gctgccccgg    60
ctgctgctgc tggtgctgtt gtgcctgccg gccgtgtggg gatccgtgac ccacgaatcc    120
tatcaggagc tggttaagaa actggaagct ttggaagatg ccgtccttac cggatacagc    180
```

```
ctgttccaga aggagaagat ggtgctgaat gaagggacga gtggcacggc cgttacaacc    240
agcacacccg gttctaaagg gtctgtggct agcggtggct ccggtgggtc tgtggcctct    300
gggggttccg tcgcctccgg cggcagcgtg gcatcaggtg gctcagtggc aagcggcggt    360
tccgggaaca gtcgaagaac caatccatct gacaactcta gcgattccga cgccaagtcc    420
tacgccgacc tcaagcaccg agtgagaaac tatctcctca ctatcaagga gctgaagtac    480
ccacagttgt tcgacctcac taatcatatg ctgacactgt gtgataacat tcatggcttc    540
aaatatctga ttgacggtta cgaagagatc aatgaactcc tgtacaagtt gaatttctac    600
ttcgacttgc taagggccaa actgaatgac gtttgcgcca atgactattg tcaaattcca    660
ttcaatttga agatcagagc caacgagttg gacgtattga agaagttggt cttcggatat    720
cgcaagcctc tcgacaacat caaggacaat gtgggaaaga tggaagatta tattaaaaag    780
aataagaaga ccatcgagaa cattaacgag ctgatcgaag aatccaaaaa gaccatagac    840
aaaaataaga atgcaaccaa ggaggaagaa aagaagaagt tgtaccaggc ccagtacgac    900
ctgtccatct ataacaaaca gcttgaagaa gcccataacc tcatcagcgt actggagaag    960
cgcatagaca ccctcaagaa gaatgaaaat atcaaagaac tgctcgacaa gattaatgaa   1020
attaagaatc ctccgccagc caactctggg aacacccta acacgctgct ggacaagaac   1080
aagaagatag aggagcacga gaaagagatc aaagagatcg ccaaaaccat taagttcaac   1140
atagattctc tctttactga tccccttgag ctggagtact acttgagaga agaataag    1200 aatatagaca tctccgccaa agtcgagaca aaggaatcaa ccgaacctaa tgaatatccc   1260
aatggtgtga cgtaccctct gtcttataac gatatcaaca acgctctcaa cgagctcaat   1320
agcttcggtg acttgattaa ccccttcgat tatacgaaag aaccctctaa gaatatctac   1380
acagacaatg agagaaagaa gtttatcaac gaaatcaagg agaagatcaa aattgagaag   1440
aagaaaattg agagtgacaa gaaaagttac gaagaccgca gcaaaagtct aaacgatatc   1500
actaaagagt atgaaaagct gctgaacgag atctatgatt ccaaattcaa caataacatc   1560
gacctgacca cttcgagaa aatgatggga aaacggtact cttacaaagt ggagaaactg   1620
acacaccata taccctttgc atcctatgag aattctaagc ataatcttga aagctcacc   1680 aaagctctta gtatatggga ggactattct ctgcggaaca ttgttgtgga aaagaacta   1740 aagtattaca agaatctcat aagtaagatc gaaaacgaga tcgagacgct tgttgagaac   1800
attaagaagg atgaagaaca gttgtttgag aagaagatta caaaagacga gaataagcca   1860
gacgaaaaga tcctggaggt ctccgacatc gttaaagtcc aagtgcaaaa agtactcctc   1920
atgaacaaga ttgatgaact caagaagact caactcattc tgaagaacgt ggagttaaaa   1980
cataatatac atgtgccgaa tagttataag caggagaata gcaggaacc atactacctc   2040 atcgtactca agaaagagat agacaaactg aaagtgttca tgcccaaagt cgagagcctg   2100
atcaacgaag aagaagaa cattaaaact gaaggacagt cagataactc cgagccttcc   2160
acagaaggag agataaccgg acaggctacc accaagccc gacaacaggc cggttcagct   2220
ctcgaaggcg atagcgtgca agctcaagca caagagcaga agcaggcaca gcctccagtg   2280
ccagtgcccg ttccagaggc taaagctcaa gtgcctacac caccagctcc tgtgaataac   2340
aagaccgaga atgtcagcaa actggactac cttgagaagc tctatgagtt cctgaataca   2400
tcctacatct gccacaaata tatcctcgtc tctcacagca ctatgaacga gaagattctt   2460
aaacagtaca agataaccaa ggaagaggag agtaaactgt cctcttgtga tccactggac   2520
```

```
ctgctgttca atatccagaa caacattccc gttatgtatt ctatgttcga tagcctcaac    2580
aattctctct ctcaactgtt catggagata tatgagaagg agatggtctg caacctgtat    2640
aaactcaaag acaacgacaa gattaagaac cttctggagg aagctaagaa ggtctccacc    2700
tctgttaaaa ctctctcttc cagctccatg caaccactgt ctctcacacc tcaagacaag    2760
cccgaagtga gcgctaacga cgacacctct cactcgacca accttaataa ctcactgaaa    2820
ctgtttgaga acatcctgtc tctcggcaag aataagaaca tctaccaaga acttattgga    2880
cagaaatcgt ccgagaactt ctacgagaag atactgaaag acagcgacac attctataac    2940
gagagcttca ctaacttcgt gaaatctaaa gccgatgata tcaactctct taacgatgaa    3000
tctaaacgta agaagctgga agaggacatc aataagctga agaagacact gcaactgagc    3060
ttcgacctgt acaacaagta caaactgaaa ctggagagac tcttcgacaa gaagaagaca    3120
gtcggcaagt ataagatgca gatcaagaag ttgactctgc tcaaggagca gcttgaaagc    3180
aaactcaact cactgaacaa tccgaaacac gtactgcaga acttctcagt gttcttcaac    3240
aagaagaagg aagccgagat cgccgagaca gagaacactc tggagaacac caagattctt    3300
ctcaaacact acaaaggcct cgtcaagtat tataatggcg agtcttctcc tctgaagact    3360
ctctccgagg agagcatcca gaccgaggat aactacgcca gcctcgagaa cttcaaggtc    3420
ctgtctaagc tcgaaggcaa gctgaaggac aacctgaacc tggagaagaa gaagctcagc    3480
tacctctcta gcggactgca tcacctgatc gccgagctca aggaagtcat taagaacaag    3540
aactacaccg gcaatagccc aagcgagaat aatacagacg tgaataacgc actggaatct    3600
tataagaagt tcctgcctga aggaacagat gtcgccactg tggtgtctga atctggctcc    3660
gacacactgg agcagtctca acctaagaag cctgcatcta ctcatgtcgg agccgagtcc    3720
aatacaatta ccacatctca gaacgtcgac gatgaggtcg atgacgtcat cattgtgcct    3780
atcttcggcg agagcgagga ggactacgat gacctcggcc aggtggtcac cggagaggct    3840
gtcactcctt ccgtgattga taacattctg tccaaaatcg agaacgaata cgaagtgctc    3900
tatctgaaac tctctggcag ggtctatagg tctctcaaga acagctggag gaataacgtg    3960
atgaccttca atgtcaacgt gaaggacatt ctgaacagcc gctttaataa gagagaaaat    4020
ttcaagaacg tcttggagag cgacttgatt ccctataaag acctgacctc ctctaactat    4080
gttgtcaagg acccatacaa gttcctcaat aaagagaaga gggataaatt tctgtctagc    4140
tacaactata tcaaggactc catcgacacc gatatcaatt tcgctaatga tgtgctgggg    4200
tattacaaga tcctgagcga aaaatacaag tctgaccttg actctattaa aaagtatatc    4260
aacgataagc aaggcgagaa tgaaaaatat ctgcccttcc tgaataacat cgaaaccctg    4320
tacaagacag tgaacgacaa aatcgacctc ttcgtaattc acctggaggc caaggtcctc    4380
aactatactt acgagaagag caatgtggaa gttaaaatca aggagctgaa ctacctcaaa    4440
acaatccaag acaagctggc agatttcaag aaaaataaca atttcgtcgg aattgcagac    4500
ctgtctaccg attataacca caacaatctc ctgaccaagt ttctgtccac tggcatggtg    4560
ttcgaaaacc tcgccaaaac agtgctgagc aatctgctcg acggcaacct gcagggcatg    4620
ctgaacatct cccagcacca atgcgtgaag aaacagtgcc cccagaatag cggctgtttc    4680
aggcatctgg acgagcgcga agagtgcaag tgtctcctga actacaaaca agaaggagat    4740
aagtgcgtgg agaacccaaa ccctacctgc aatgaaaaca atggcgggtg tgacgccgat    4800
gctaaatgca ccgaggaaga cagcggctct aacgaaagaa aaatcacatg cgagtgtact    4860
aagcccgact cctatccact cttcgacggg atcttctgct ccagctctag caacgttact    4920
```

```
acttccggca ctacccgtct tctatctggt cacacgtgtt tcacgttgac aggtttgctt    4980
gggacgctag taaccatggg cttgctgact taa                                 5013
```

<210> SEQ ID NO 10
<211> LENGTH: 1119
<212> TYPE: DNA
<213> ORGANISM: Artificial
<220> FEATURE:
<223> OTHER INFORMATION: This is artificially synthesized CS sequence
      ORF

<400> SEQUENCE: 10

```
atgatgagga aactggccat cctgagcgtg agcagcttcc tgttcgtgga ggccctgttt      60
caggagtacc agtgctacgg cagcagcagc aacacccggg tgctgaacga gctgaactac     120
gacaacgccg gcaccaacct gtacaacgag ctggagatga actactacgg caagcaggag     180
aactggtaca gcctgaagaa gaacagccgg tctctgggcg agaacgacga cggcaacaac     240
aacaacggcg acaacggccg ggagggcaag gacgaggaca gcgggacgg caacaacgag      300 gacaacgaga agctgcggaa gcccaagcac aagaaactta gcagcccgc cgacggcaac      360 cccgacccca cgccaacccc caacgtggac cccaacgcca tcctaatgt cgaccccaat      420 gccaatccga acgttgatcc caatgcgaat cctaacgcta ccccaatgc caacccaaat     480 gccaatccaa atgcaaatcc caacgccaat ccaaacgcaa accctaatgc taatccaaac     540
gctaatccta atgccaatcc caatgctaac ccaaacgtcg atcctaacgc aaatccgaac     600
gctaacccca acgcaaatcc caacgctaac ccgaacgcaa accctaacgc caatccgaat     660
gccaacccaa cgccaaccc gaacgctaat ccgaatgcta acccgaatgc taatcctaac      720
gcaaacccaa acgcaaaccc caatgcaaac ccaaatgcca atcccaacgc caatcctaat     780
gccaacaaga acaatcaggg caacggccag ggccacaaca tgcccaacga ccccaaccgg     840
aacgtggacg agaacgccaa cgccaacagc gccgtgaaga caacaacaa cgaggagccc      900 agcgacaagc acatcaagga gtacctgaac aagatccaga acagcctgag caccgagtgg     960
agcccctgca gcgtgacctg cggcaacggc attcaggtgc ggatcaagcc cggcagcgcc    1020
aacaagccca aggacgagct ggactacgcc aatgacatcg agaagaagat ctgcaagatg    1080
gagaagtgca gcagcgtgtt caacgtggtg aactcctga                           1119
```

<210> SEQ ID NO 11
<211> LENGTH: 1734
<212> TYPE: DNA
<213> ORGANISM: Artificial
<220> FEATURE:
<223> OTHER INFORMATION: This is artificially synthesized DiCo 1
      complete sequence ORF

<400> SEQUENCE: 11

```
ggtaccgtca cgcgtcaccg gtgtcatcat gaccgtggcc aggccctctg tgcctgccgc      60 cctgccctg ctgggcgagc tgccccggct gctgctcctg gtgctgctgt gcctgccgc       120 cgtgtgggga tccgtgatcg agatcgtgga gcggagcaac tacatgggca acccctggac    180
cgagtacatg gccaagtacg acatcgagga agtgcacgcc agcggcatcc gggtggacct    240
gggcgaggac gccgaggtgg ccggcaccca gtacaggctg cccagcggca agtgccccgt    300
gttcggcaag ggcatcatca tcgagaacag ccagaccacc ttcctgaccc ccgtggccac    360
cgagaaccag gacctgaagg acggcggctt cgccttcccc ccaccaagc ccctgatgag     420 ccccatgacc ctggaccaga tgcggcactt ctacaaggac aacgagtacg tgaagaacct    480
```

```
ggacgagctg accctgtgca gccggcacgc cggcaacatg aaccccgaca acgacaagaa    540
cagcaactac aagtaccccg ccgtgtacga cgacaaggat aagaagtgcc acatcctgta    600
tatcgccgcc caggaaaaca acggccccag gtactgcaac aaggacgaga gcaagcggaa    660
cagcatgttc tgcttcagac ccgccaagga caagagcttc cagaactacg tgtacctgag    720
caagaacgtg gtggacaact gggagaaagt gtgcccccgg aagaatctgg aaaacgccaa    780
gttcggcctg tgggtggacg gcaactgcga ggacatcccc cacgtgaacg agttcagcgc    840
caacgacctg ttcgagtgca acaagctggt gttcgagctg tccgccagcg accagcccaa    900
gcagtacgag cagcacctga ccgactacga agatcaaa gagggcttca agaacaagaa      960
cgccgacatg atcaagagcg cctttctgcc aactggcgcc ttcaaggccg acagatacaa    1020
gagccacggc aagggctaca actggggcaa ctacaacaga aagacccaga gtgcgagat    1080 cttcaacgtg aagcccacct gcctgatcaa cgacaagtcc tatatcgcca ccaccgccct    1140
gagccacccc atcgaggtgg agcacaactt cccttgcagc ctgtacaagg atgagatcaa    1200
gaaagagatc gagcgggaga gcaagaggat caagctgaac gacaacgacg acgagggcaa    1260
caagaagatc attgcccccca ggatcttcat cagcgacgat aaggacagcc tgaagtgccc    1320
ctgcgacccc gagatcgtgt cccagagcac ctgcaatttc ttcgtgtgca aatgcgtgga    1380
gaagcgggcc gaagtgacca gcaacaacga ggtggtggtg aaagaggaat ataaggacga    1440
gtacgccgac atccccgagc acaagcccac ctacgacaag atgaagatca tcattgccag    1500
ctctgccgcc gtggccgtgc tggccaccat cctgatggtg tacctgtaca gcggaagggg    1560
caacgccgag aagtacgata agatggacca gcctcagcac tacggcaaga gcaccagccg    1620
gaacgacgag atgctggacc ccgaggccag cttctggggc gaggaaaaga gagctagcca    1680
caccaccccc gtgctgatgg aaaagcccta ctactgatga gcgcgcctga gctc          1734
```

<210> SEQ ID NO 12
<211> LENGTH: 1506
<212> TYPE: DNA
<213> ORGANISM: Artificial
<220> FEATURE:
<223> OTHER INFORMATION: This is artificially synthesized DiCo 1 ecto
      sequence ORF

<400> SEQUENCE: 12

```
ggtaccgtca cgcgtcaccg gtgtcatcat gaccgtggcc aggccctctg tgcctgccgc      60
cctgcccctg ctgggcgagc tgccccggct gctgctcctg gtgctgctgt gcctgccgc     120 cgtgtgggga tccgtgatcg agatcgtgga gcggagcaac tacatgggca accccctggac   180 cgagtacatg gccaagtacg acatcgagga agtgcacggc agcggcatcc gggtggacct    240
gggcgaggac gccgaggtgg ccggcaccca gtacaggctg cccagcggca gtgccccgt    300 gttcggcaag gcatcatca tcgagaacag ccagaccacc ttcctgaccc ccgtggccac      360
cgagaaccag gacctgaagg acggcggctt cgccttcccc cccaccaagc ccctgatgag    420
ccccatgacc ctggaccaga tgcggcactt ctacaaggac aacgagtacg tgaagaacct    480
ggacgagctg accctgtgca gccggcacgc cggcaacatg aaccccgaca acgacaagaa    540
cagcaactac aagtaccccg ccgtgtacga cgacaaggat aagaagtgcc acatcctgta    600
tatcgccgcc caggaaaaca acggccccag gtactgcaac aaggacgaga gcaagcggaa    660
cagcatgttc tgcttcagac ccgccaagga caagagcttc cagaactacg tgtacctgag    720
caagaacgtg gtggacaact gggagaaagt gtgcccccgg aagaatctgg aaaacgccaa    780
```

-continued

```
gttcggcctg tgggtggacg gcaactgcga ggacatcccc cacgtgaacg agttcagcgc    840
caacgacctg ttcgagtgca acaagctggt gttcgagctg tccgccagcg accagcccaa    900
gcagtacgag cagcacctga ccgactacga gaagatcaaa gagggcttca agaacaagaa    960
cgccgacatg atcaagagcg cctttctgcc aactggcgcc ttcaaggccg acagatacaa   1020
gagccacggc aagggctaca actggggcaa ctacaacaga aagacccaga agtgcgagat   1080
cttcaacgtg aagcccacct gcctgatcaa cgacaagtcc tatatcgcca ccaccgccct   1140
gagccacccc atcgaggtgg agcacaactt cccttgcagc ctgtacaagg atgagatcaa   1200
gaaagagatc gagcgggaga gcaagaggat caagctgaac gacaacgacg acgagggcaa   1260
caagaagatc attgccccca ggatcttcat cagcgacgat aaggacagcc tgaagtgccc   1320
ctgcgacccc gagatcgtgt cccagagcac ctgcaatttc ttcgtgtgca aatgcgtgga   1380
gaagcgggcc gaagtgacca gcaacaacga ggtggtggtg aaagaggaat ataaggacga   1440
gtacgccgac atccccgagc acaagcccac ctacgacaag atgtgatgat gagcgcgcct   1500
gagctc                                                              1506
```